US011834513B2

(12) United States Patent
Spriggs et al.

(10) Patent No.: US 11,834,513 B2
(45) Date of Patent: Dec. 5, 2023

(54) ANTIBODIES TO MUC16 AND METHODS OF USE THEREOF

(71) Applicant: Memorial Sloan Kettering Cancer Center, New York, NY (US)

(72) Inventors: David Spriggs, New York, NY (US); Dharmarao Thapi, Bayside Hills, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 177 days.

(21) Appl. No.: 16/941,348

(22) Filed: Jul. 28, 2020

(65) Prior Publication Data

US 2021/0309758 A1    Oct. 7, 2021

Related U.S. Application Data

(62) Division of application No. 15/695,311, filed on Sep. 5, 2017, now Pat. No. 10,759,869, which is a division of application No. 14/850,675, filed on Sep. 10, 2015, now Pat. No. 9,790,283, which is a division of application No. 13/635,090, filed as application No. PCT/US2011/030025 on Mar. 25, 2011, now Pat. No. 9,169,328.

(60) Provisional application No. 61/317,964, filed on Mar. 26, 2010.

(51) Int. Cl.
*A61K 39/00* (2006.01)
*C07K 16/30* (2006.01)
*G01N 33/574* (2006.01)

(52) U.S. Cl.
CPC ... *C07K 16/3092* (2013.01); *G01N 33/57488* (2013.01); *A61K 39/00117* (2018.08); *A61K 2039/505* (2013.01); *A61K 2039/5156* (2013.01); *C07K 2317/24* (2013.01); *C07K 2317/33* (2013.01); *C07K 2317/34* (2013.01); *C07K 2317/622* (2013.01); *C07K 2317/77* (2013.01); *C07K 2317/92* (2013.01); *C07K 2319/02* (2013.01); *C07K 2319/03* (2013.01); *C07K 2319/33* (2013.01); *G01N 2333/705* (2013.01)

(58) Field of Classification Search
CPC .......... C07K 16/3092; A61K 2039/505; A61K 39/00117
See application file for complete search history.

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,946,778 A | 8/1990 | Ladner et al. |
| 4,975,369 A | 12/1990 | Beavers et al. |
| 4,978,745 A | 12/1990 | Schoemaker et al. |
| 5,057,313 A | 10/1991 | Shih et al. |
| 5,225,539 A | 7/1993 | Winter |
| 5,475,092 A | 12/1995 | Chari et al. |
| 5,545,806 A | 8/1996 | Lonberg et al. |
| 5,569,825 A | 10/1996 | Lonberg et al. |
| 5,585,499 A | 12/1996 | Chari et al. |
| 5,625,126 A | 4/1997 | Lonberg et al. |
| 5,736,137 A | 4/1998 | Anderson et al. |
| 5,846,545 A | 12/1998 | Chari et al. |
| 5,976,818 A | 11/1999 | O'Brien |
| 6,333,410 B1 | 12/2001 | Vankeepuram et al. |
| 6,340,701 B1 | 1/2002 | Chari et al. |
| 6,372,738 B2 | 4/2002 | Chari et al. |
| 6,429,295 B1 | 8/2002 | Carr Perez et al. |
| 7,202,346 B2 | 4/2007 | Payne et al. |
| 7,227,002 B1 | 6/2007 | Kufer et al. |
| 7,501,123 B2 | 3/2009 | Roschke et al. |
| 7,585,952 B2 | 9/2009 | D'Alessio et al. |
| 7,632,925 B2 | 12/2009 | Kufer et al. |
| 7,662,387 B2 | 2/2010 | Law et al. |
| 7,666,425 B1 | 2/2010 | Bander |
| 7,959,923 B2 | 6/2011 | You et al. |
| 9,169,328 B2 | 10/2015 | Spriggs et al. |
| 9,790,283 B2 | 10/2017 | Spriggs et al. |
| 2004/0057952 A1 | 3/2004 | Payne et al. |
| 2004/0162413 A1 | 8/2004 | Watkins et al. |
| 2006/0094069 A1 | 5/2006 | Robertson et al. |

FOREIGN PATENT DOCUMENTS

| | | |
|---|---|---|
| JP | 2006-502110 A | 1/2006 |
| RU | 2412947 C2 | 2/2011 |
| WO | WO-90/13678 A1 | 11/1990 |
| WO | WO-92/22653 A1 | 12/1992 |

(Continued)

OTHER PUBLICATIONS

Paul, Fundamental Immunology, 3rd Edition, 1993, pp. 292-295 (Year: 1993).*

(Continued)

*Primary Examiner* — Sheela J. Huff

(74) *Attorney, Agent, or Firm* — Foley & Lardner LLP

(57) ABSTRACT

The invention provides antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

18 Claims, 67 Drawing Sheets

Specification includes a Sequence Listing.

(56) References Cited

FOREIGN PATENT DOCUMENTS

| WO | WO-02/06317 A3 | 1/2002 |
|---|---|---|
| WO | WO-2004/005470 A2 | 1/2004 |
| WO | WO-2006/034488 A2 | 3/2006 |
| WO | WO-2008/141044 A2 | 11/2008 |
| WO | WO-2015/006043 A1 | 1/2015 |
| WO | WO-2016/149368 A1 | 9/2016 |

OTHER PUBLICATIONS

Pascalis et al (The Journal of Immunology (2002) 169, 3076-3084) (Year: 2002).*
Casset et al. (2003) BBRC 307, 198-205, (Year: 2003).*
D'Angelo et al, Frontiers in Immunology vol. 9 p. 1 (2018) (Year: 2018).*
Ahmad et al., "Galectin-3 precipitates as a pentamer with synthetic multivalent carbohydrates and forms heterogeneous cross-linked complexes." J Biol Chem 279, 10841-10847 (2004 ).
Almagro & Fransson, "Humanization of antibodies", Frontiers in Bioscience 2008; 13:1619-33 (Year: 2008).
Alper et al., "Epidermal growth factor receptor signaling and the invasive phenotype of ovarian carcinoma cells." J Natl Cancer Inst 93, 1375-1384 (2001).
Badgwell and Bast, "Early detection of ovarian cancer." Dis Markers, 23(5-6):397-410 (2007).
Bafna et al., "MUC4, a multifunctional transmembrane glycoprotein, induces oncogenic transformation of NIH3T3 mouse fibroblast cells." Cancer Res., 68(22):9231-9238 (2008).
Barber et al., "Chimeric NKG2D receptor-bearing T cells as immunotherapy for ovarian cancer." Cancer Res., 67 (10):5003-5008 (2007).
Barber et al., "Immunotherapy with chimeric NKG2D receptors leads to long-term tumor-free survival and development of host antitumor immunity in murine ovarian cancer." J Immunol., 180( 1) :72-78 (2008).
Bast et al., "A radioimmunoassay using a monoclonal antibody to monitor the course of epithelial ovarian cancer." N Engl J Med 309: 883-887 (1983).
Bast et al., "CA125: the past and the future." Int. J. Biol. Markers 13, 179-187 (1998).
Bast et al., "New tumor markers: CA125 and beyond." Int J Gynecol Cancer, 15 Suppl 3:274-281 (2005).
Bast et al., "Reactivity of a monoclonal antibody with human ovarian carcinoma." J Clin Invest., 68(5): 1331-1337 (1981).
Bellone et al., "Generation of CA125-specific cytotoxic l' lymphocytes in human leukocyte antigen-A2. l-positive healthy donors and patients with advanced ovarian cancer." Am J Obstet Gynecol., 200(1):75 e71-10 (2009).
Berek, "Immunotherapy of ovarian cancer with antibodies: a focus on oregovomab." Expert Opinion on Biological Therapy, 4(7): 1159-1165 (2004).
Bernsel and Von Heijne, "Improved membrane protein topology prediction by domain assignments." Protein Sci., 14(7):1723-1728 (2005).
Blalock et al., 2007, "Functions of MUC16 in Corneal Epithelial Cells", Investigative Ophthalmology Visual Science, vol. 48, No. 10, pp. 4509-4518.
Blalock et al., 2008, "Release of Membrane-Associated Mucins from Ocular Surface Epithelia", Investigative Ophthalmology & Visual Science, vol. 49, No. 5, DD. 1564-1871.
Borghouts et al., "Current strategies for the development of peptide-based anti-cancer therapeutics." J Pevt Sci., 11(11):713-726 (2005).
Brand et al., 2006, "Prospect for anti-HER2 receptor therapy in breast cancer", Anticancer Research, 26:463-70.
Brentjens and Sadelain, "Somatic cell engineering and the immunotherapy of leukemias and lymphomas." Adv Pharmacol, 51:347-370 (2004).

Brentjens et al., "Eradication of systemic B-cell tumors by genetically targeted human T lymphocytes co-stimulated by CD80 and interleukin-15." Nat Med., 9(3):279-286 (2003).
Brentjens et al., "Genetically targeted T cells eradicate systemic acute lymphoblastic leukemia xenografts." Clin Cancer Res., 13(18 Pt 1):5426-5435 (2007).
Brentjens, "A Phase I trial for the treatment of chemo-refractory chronic lymphocytic leukemia with CD19-targeted autologous T cells." Molecular Therapy 16:SI5 (2008).
Burton and Mascola, "Antibody responses to envelope glycoproteins inHIV-1 infection." Nat Immunol 16, 571-576 (2015).
Carpenito et al., "Control of large, established tumor xenografts with genetically retargeted human T cells containing CD28 and CD137 domains." Proc Natl Acad Sci., USA, 106(9):3360-3365 (2009).
Chang et al., "A novel peptide enhances therapeutic efficacy of liposomal anti-cancer drugs in mice models of human lung cancer." PLoS One, 4(1):e4171 (2009).
Cheon et al., "CA125/MUC16 is dispensable for mouse development and reproduction." PLoS One 4: e4675 (2009).
Cohen-Anisfeld and Lansbury, "A practical, convergent method for glycopeptide synthesis." J. Am. Chem. Soc. 115, 10531-10537 (1993).
Cole et al., "The EBV-hybridoma technique and its application to human lung cancer." in Monoclonal Antibodies and Cancer Theranv (Sell, Ed.), pp. 77-96, Alan R. Liss, Inc. (1985).
Corrales et al. "Conjunctival mucin mRNA expression in contact lens wear." Optom Vis Sci 86:1051-1058 (2009).
Cote et al., "Generation of human monoclonal antibodies reactive with cellular antigens." Proc Natl Acad Sci., USA, 80(7):2026-2030 (1983).
Curiel et al., "Specific recruitment of regulatory T cells in ovarian carcinoma fosters immune privilege and predicts reduced survival." Nat Med., 10(9):942-949 (2004).
Daly et al., "Recognition of human colon cancer by T cells transduced with a chimeric receptor gene." Cancer Gene Ther., 7(2):284-291 (2000).
David and Reisfeld, "Protein iodination with solid state lactoperoxidase." Biochemistry, 13(5):1014-1021 (1974).
Davies et al., "MUC16 is produced in tracheal surface epithelium and submucosal glands and is present in secretions from normal human airway and cultured bronchial epithelial cells", Int. J. Biochem. Cell Biol., vol. 39, No. 10, pp. 1943-1954, published online May 25, 2007 (May 25, 2007).
De Genst et al., "Antibody repertoire development in camelids." Dev Comp Immunol 2006; 30: 187-98 (Year: 2006).
Diamond et al., "Somatic mutation of the TI5 heavy chain gives rise to an antibody with autoantibody specificity," Proc. Natl. Acad. Sci. USA, 81:5841-5844 (1984).
Doenecke et al., "Rapid amplification of cDNA ends (RACE) improves the PCR-based isolation of immunoglohulin variable region genes from murine and human lymphoma cells and cell lines." Leukemia, 11(10):1787-1792 (1997).
Dondelinger et al., "Understanding the Significance and Implications of Antibody /MN/ CI81 Numbering and Antigen-Binding Surface/Residue Definition," Front. Immunol., 9: 1-15 (2008).
Duraisamy et al., :Distinct evolution of the human carcinoma-associated transmembrane mucins, MUCI, MUC4 and MUC16. Gene 373: 28-34 (2006).
Elofsson and Von Heijne, "Membrane protein structure: prediction versus reality." Annu Rev BioChem., 76:125-140 (2007).
Faisal et al., "Leptasome-entrapped leptospiral antigens conferred significant higher levels of protection than those entrapped with PC-liposomes in a hamster model." Vaccine, 27(47):6537-6545 (2009).
Fendrick et al., "CA125 phosphorylation is associated with its secretion from the WISH human amnion cell line." Tumour Biol., 18(5):278-289 (1997).
Fendrick et al., "Characterization of CA 125 synthesized by the human epithelial amnion WISH cell line." Tumour Biol., 14(5):310-318 (1993).

(56) References Cited

OTHER PUBLICATIONS

Fernandez-Tejada et al., "Chemical synthesis of the ~-subunit of human luteinizing (hLH) and chorionic gonadotropin (hCG) glycoprotein hormones." J Am Chem Soc 136, 8450-8458 (2014).
Finkelstein et al. eds., Protein Physics: A Course of Lectures, 4th Edition, Academic Press, Cambridge, MA, p. 23 (2012).
Finney et al., "Activation of resting human primary T cells with chimeric receptors: costimulation from CD28, inducible costimulator, CD134, and CD137 in series with signals from the TCR zeta chain." J Immunol., 172(1):104-113 (2004).
Fritsche and Bast, "CA 125 in ovarian cancer: advances and controversy." Clin Chem.,44(7):1379-1380 (1998).
GenBank Accession No. AJ277812. I, "Mus musculus partial mRNA for immunoglobulin kappa light chain variable region (IGKV gene)." URL: http://www.ncbi.nlm.nih.gov/nuccore/7711058 (2001).
Giannakouros et al., "Transformation of NIH3T3 mouse fibroblast cells by MUC16 mucin (CA125) is driven by its cytoplasmic tail." International Journal of Oncology, 46(1):91-98 (2014).
Gong et al., "Cancer patient T cells genetically targeted to prostate-specific membrane antigen specifically lyse prostate cancer cells and release cytokines in response to prostate-specific membrane antigen." Neoplasia, 1(2):123-127 (1999).
Govindarajan and Gipson, "Membrane-tethered mucins have multiple functions on the ocular surface." Exp Eve Res 90: 655-663 (2010).
Granovsky et al., "Suppression of tumor growth and metastasis in Mgat5-deficient mice." Nat Med 6, 306-312 (2000).
Greenwood and Hunter, "Preparation of iodine-131 labelled human growth hormone of high specific activity." Nature, 194:495-496 (1962).
Gubbels et al., "Mesothelin-MUC16 binding is a high affinity, N-glycan dependent interaction that facilitates peritoneal metastasis of ovarian tumors." Molecular Cancer, 5(1):50 (2006).
Habib-Agahi et al., "4-IBBL costimulation retrieves CD28 expression in activated T cells." Cell Immunol., 256(1-2):39-46 (2009).
Habib-Agahi et al., "Co-stimulation with 4-IBB ligand allows extended T-cell proliferation, synergizes with CD80/CD86 and can reactivate anergic T cells." Int Immunol., 19(12):1383-1394 (2007).
Habib-Agahi et al., "Co-stimulation with 4-IBB ligand allows extended T-cell proliferation, synergizes with CD80/CD86 and can reactivate anergic T cells." Int Immunol., 19(12): 1383-1394, Sup. Fig. 1 (2007).
Habib-Agahi et al., "Co-stimulation with 4-IBB ligand allows extended T-cell proliferation, synergizes with CD80/CD86 and can reactivate anergic T cells." Int Immunol., 19(12): 1383-1394, Sup. Fig. 2 (2007).
Habib-Agahi et al., "Co-stimulation with 4-IBB ligand allows extended T-cell proliferation, synergizes with CD80/CD86 and can reactivate anergic T cells." Int Immunol., 19(12): 1383-1394, Sup. List (2007).
Hamanishi et al., "Programmed cell death 1 ligand 1 and tumor-infiltrating CDS T lymphocytes arc prognostic factors of human ovarian cancer." Proc Natl A cad Sci., USA, 104(9):3360-3365 (2007).
Harris et al., "A comparison of the metastatic pattern of infiltrating lobular carcinoma and infiltrating duct carcinoma of the breast." Br J Cancer, 50(1):23-30 (1984).
Hedvat et al., "Application of tissue microarray technology to the study of non-Hodgkin's and Hodgkin's lymphoma." Hum Pathol., 33(10):968-974 (2002).
Helene L Debat et al, "Overpassing an aberrant Vkappa gene to sequence an anti-idiotypic abzyme with beta-lactamase-like activity that could have a linkage with autoimmune diseases", FASEB, (Mar. 1, 2001), vol. 15, doi:10.1096/fj.00-0410com, pp. 815-822.
Heller and Vendatraman, "Resampling procedures to compare two survival distributions in the presence of right censored data." Biometrics 52: 1204-1213 (1996).
High et al., "Sec6lp is adjacent to nascent type I and type II signal-anchor proteins during their membrane insertion." J Cell Biol., 121(4):743-750 (1993).

Hirabay Ashi et al., "Oligosaccharide specificity of galectins: a search by frontal affinity chromatography." Biochim Biophvs Acta 1572, 232-254 (2002).
Hollingsworth and Swanson, "Mucins in cancer: protection and control of the cell surface." Nat Rev Cancer, 4(1):45-60 (2004).
Hollyman et al., "Manufacturing validation of biologically functional T cells targeted to CD 19 antigen for autologous adoptive cell therapy." J Immuno Ther., 32(2): 169-180 (2009).
Huang et al., "MUCI cytoplasmic domain coactivates Wnt target gene transcription and confers transformation." Cancer Biol. Ther., 2(6):702-706 (2003).
Huang et al., "MUCI oncoprotein blocks glycogen synthase kinase 3beta-mediated phosphorylation and degradation of beta-catenin." Cancer Res 65: 10413-10422 (2005).
Hung et al., "Antigen-specific immunotherapy of cervical and ovarian cancer." Immunol Rev.,222:43-69 (2008).
Huse et al., "Generation of a large combinatorial library of the immunoglobulin repertoire in phage lambda." Science, 246(4935):1275-1281 (1989).
Huwyler et al., "Tumor targeting using liposomal antineoplastic drugs." Int J Nanomedicine, 3(1):21-29 (2008).
Hwu et al., "In vivo antitumor activity of T cells redirected with chimeric antibody IT-cell receptor genes." Cancer Res., 55(15):3369-3373 (1995).
Imai et al., "Chimeric receptors with 4-IBB signaling capacity provoke potent cytotoxicity against acute lymphoblastic leukemia." Leukemia, 18(4):676-684 (2004).
International Search Report for International Application No. PCT/US2016/022643, dated Sep. 5, 2016.
International Search Report on PCT/US2011/030025 (dated 2011).
Jensen et al., "Engineered CD20-specific primary human cytotoxic T lymphocytes for targeting B-cell malignancy." Cytotherapy, 5(2):131-138 (2003).
Kabawat et al., "Tissue distribution of a coelomic-epithelium-related antigen recognized by the monoclonal antibody OC125." Int J Gynecol Pathol 2: 275-285 (1983).
Kaneko et al., "A binding domain on mesothelin for CA125/MUC16." J Biol Chem, 284(6):3739-3749 (2009).
Kang et al., "Antibody redesign by chain shuffling from random combinatorial immunoglobulin ibraries," Proc. Natl. Acad. Sci. USA, 88: 11120-11123 (1991).
Kershaw et al., "A phase I study on adoptive immunotherapy using gene-modified T cells for ovarian cancer." Clin Cancer Res., 12(20 Pt 1):6106-6115 (2006).
Kershaw et al., "Dual-specific T cells combine proliferation and antitumor activity." Nat Biotechnol., 20(12):1221-1227 (2002).
Kochenderfer et al., "Construction and preclinical evaluation of an anti-CD 19 chimeric antigen receptor." J ImmunoTher., 32(7):689-702 (2009).
Kohler et al., "Continuous cultures of fused cells secreting antibody of predefined specificity"; Nature, 1975, 256:495-497 (1975).
Kononen et al., "Tissue microarrays for high-throughput molecular profiling of tumor specimens." Nat Med., 4(7):844-847 (1998).
Kozbor and Roder, "Comparison of the specific IgM and IgG antibody response in humans induced by antigen (tetanus toxoid) or a polyclonal activator (EBV) in vitro." Int Arch Allergy Appl Immunol., 72(3):260-266 (1983).
Krivak et al., "A Gynecologic Oncology Group Study of serum CA-125 levels in patients with stage III optimally debulked ovarian cancer treated with intraperitoneal compared to intravenous chemotherapy: an analysis of patients emolled in GOG 172." Gynecol Oneal., 115(1):81-85 (2009).
Lajoie et al., "Plasma membrane domain organization regulates EGFR signaling in tumor cells." J Cell Biol 179, 341-356 (2007).
Lamers et al., "Gene-modified T cells for adoptive immunotherapy of renal cell cancer maintain transgene-specific immune functions in vivo." Cancer Immunol ImmunoTher., 56(12): 1875-1883 (2007).
Lamers et al., "Treatment of metastatic renal cell carcinoma with autologous T-lymphocytes genetically retargeted against carbonic anhydrase IX: first clinical experience." J Clin Oneal., 24(13):e20-22 (2006).

(56) References Cited

OTHER PUBLICATIONS

Latouche and Sadelain, "Induction of human cytotoxic T lymphocytes by artificial antigenpresenting cells." Nat Biotechnol., 18(4):405-409 (2000).
Lau et al., "Complex N-glycan number and degree of branching cooperate to regulate cell proliferation and differentiation." Cell 129, 123-134 (2007).
Leffers et al., "Prognostic significance of tumor-infiltrating T-lymphocytes in primary and metastatic lesions of advanced stage ovarian cancer." Cancer Immunol ImmunoTher., 58(3):449-459 (2009).
Leffers et al., "Survival of ovarian cancer patients overexpressing the tumour antigen p53 is diminished in case of MHC class I down-regulation." Gynecol Oneal., 110(3):365-373 (2008).
Li et al. "Human DF3/MUC1 carcinoma-associated protein functions as an oncogene." Oncogene 22:6107-6110 (2003).
Li et al., "4-IBB (CD137) ligand enhanced anti-tumor immune response against mouse forestomach carcinoma in vivo." Cell Mol Immunol., 5(5):379-384 (2008).
Li et al., "Interaction of human MU CI and beta-catenin is regulated by Lek and ZAP-70 in activated Jurkat Tcells." Biochem Biovhvs Res Commun., 315(2):471-476 (2004).
Likhosherstov et al., "A new simple synthesis of amino sugar B~d-glycosylamines." Carbohydr. Res. 146, CI-C5 (1986).
Liu et al., A genetically defined model for human ovarian cancer. Cancer Res 64: 1655-1663 (2004).
Lloyd & Yin, "Synthesis and secretion of the ovarian cancer antigen CA 125 by the human cancer cell line NIH:OVCAR-3." Tumour Biol 22: 77-82 (2001).
Lolli et al., "The glycopeptides CSFII4(Glc) detects serum antibodies in multiple sclerosis." Journal of Neuroimmunology, 167(1-2):131-137 (2005).
Loskog et al., "Addition of the CD28 signaling domain to chimeric T-cell receptors enhances chimeric T-cell resistance to T ree:ulatory cells." Leukemia, 20(10): 1819-1828 (2006).
Maher et al., "Human T-lymphocyte cytotoxicity and proliferation directed by a single chimeric TCRi/CD28 receptor", Nature biotechnology, vol. 20, No. 1, Jan. 2002, pp. 70-75.
Marcos-Silva et al., "A novel monoclonal antibody to a defined peptide epitope in MUC16." Glycobiolorzv, 25(11): 1172-1182 (2015).
Marcos-Silva et al., "Characterization of Binding Epitopes of CA125 Monoclonal Antibodies." Journal of Proteome Research, 13(7):3349-3359 (2014).
Markwell and Fox, "Surface-specific iodination of membrane proteins of viruses and eukaryotic cells using I,3,4,6-tetrachloro-3alpha,6alpha-diphenylglycoluril." Biochemistry, I 7(22):4807-4817 (1978).
Mascola & Haynes, "HIV-1 neutralizing antibodies: understanding nature's pathways." Immunol Rev 254, 225-244 (2013).
Mazal et al. "Monoclonal antibodies toward different Tn-amino acid backbones display distinct recognition patterns on human cancer cells. Implications for effective immuno-targeting of cancer." Cancerimmunol. Immunother. 62, 1107-1122 (2013).
Mazzoletti et al., 2010, "PBK/AKT/mTOR Inhibitors In Ovarian Cancer," Curr. Med. Chem. 17:4433-4447.
Moeller et al., "A functional role for CD28 costimulation in tumor recognition by single-chain receptor-modified T cells." Cancer Gene Ther., 11(5):371-379 (2004).
Moore et al., "Current stale of biomarker development for clinical application in epithelial ovarian cancer." Gynecol Oneal., 116(2):240-245 (2010).
Nakada et al., "Epitopic structure of Tn glycophorin A for an anti-Tn antibody (MLS 128)." Proc. Natl. Acad. Sci. USA 90, 2495-2499 (1993).
Nap et al., "Immunohistochemical characterization of 22 monoclonal antibodies against the CA125 antigen: 2nd report from the ISOBM TD-1 Workshop." Tumour Biol., 17(6):325-331 (1996).
Nelson, "The impact of T-cell immunity on ovarian cancer outcomes." Immunol Rev., 222:101-116 (2008).

Nustad et al., "Epitopes on CA 125 from cervical mucus and ascites fluid and characterization of six new antibodies. Third report from the ISOBM TD-1 workshop." Tumour Biol., 23(5):303-314 (2002).
Nygren, "Conjugation of horseradish peroxidase to Fab fragments with different homobifunctional and heterobifunctional cross-linking reagents. A comparative study." Journal of Histochemistry & Cytochemistry, 30(5):407-412 (1982).
O'Brien et al., "More than 15 years of CA 125: what is known about the antigen, its structure and its function." Int J Biol Markers, 13(4):188-195 (1998).
O'Brien et al., "The CA 125 gene: a newly discovered extension of the glycosylated N-terminal domain doubles the size of this extracellular superstructure." Tumour Biol., 23(3): 154-169 (2002).
O'Brien et al., "The CA 125 gene: an extracellular superstructure dominated by repeat sequences." Tumour Biol., 22(6):348-366 (2001).
Ohno et al., "Antigen-binding specificities of antibodies are primarily determined by seven residues of VH," Proc. Natl. Acad. Sci. USA, 82:2945-2949 (1985).
Orlandi et al., "Cloning inununoglobulin variable domains for expression by the polymerase chain reaction." Proc Natl Acad Sci., USA, 86(10):3833-3837 (1989).
Osinaga et al., "Analysis of the fine specificity of Tn-binding proteins using synthetic glycopeptide epitopes and a biosensorbased on surface plasmon resonance spectroscopy." FEBS Lett. 469, 24-28 (2000).
Pain and Suro Lia. "Preparation of protein A-peroxidase monoconjugate using a heterobifunctional reagent, and its use in enzyme inununoassays." J Immunol Methods, 40(2):219-230 (1981).
Park, "The extracellular portion of the MUC16 cytoplasmic domain is detectable in ovarian carcinoma using a novel monoclonal antibody, 4HI I." Modern pathology, 0893-3952 (21 (suppl. I)):217A-218A (Jan. 1, 2008).
Parker et al., "Expansion and characterization of T cells transduced with a chimeric receptor against ovarian cancer." Hum Gene Ther., 11(17):2377-2387 (2000).
Partridge et al., "Regulation of cytokine receptors by Golgi N-glycan processing and endocytosis." Science 306, 120-124 (2004).
Ponnusamy et al., "MUC4 activates HER2 signalling and enhances the motility of human ovarian cancer cells." Br J Cancer, 99(3):520-526 (2008).
Pule et al., "Artificial T-cell receptors," Cytotherapy, 5(3):211-226 (2003).
Pule, M.A., et al., "Virus-specific T cells engineered to coexpress tumor-specific receptors: persistence and antitumor activity in individuals with neuroblastoma," Nat. Med., 14(11):1264-1270 (2008).
Quintas-Cardama et al., "Multifactorial optimization of gammaretroviral gene transfer into human T lymphocytes for clinical application." Hum Gene Ther., 18(12): 1253-1260 (2007).
Ramsauer et al., "Muc4/sialomucin complex, the intramembrane ErbB2 ligand, translocates ErbB2 to the apical surface in polarized epithelial cells." J Biol Chem 278: 30142-30147 (2003).
Ramsauer et al., "MUC4-ErbB2 complex formation and signaling in polarized CACO-2 epithelial cells indicate that Muc4 acts as an unorthodox ligand for ErbB2." Mal Biol Cell 17(7):2931-2941 (2006).
Rao et al., "Antibodies Against Specific MUC16 Glycosylation Sites Inhibit Ovarian Cancer Growth." ACS Chem Biol. 12(8):2085-2096. Epub Jun. 28, 2017.
Rao et al., "Dual-fluorescence isogenic high-content screening for MUC16/CA125 selective agents." Mol CancerTher 10: 1939-1948 (2011).
Rao et al., "Expression of the Carboxy-Terminal Portion of MUC16/CA125 Induces Transformation and Tumor Invasion." PLoS One, 10(5):e0126633 (2015).
Rao et al., "Novel Monoclonal Antibodies Against the Proximal (Carboxy-Terminal) Portions of MUC16." Applied Immunohistochemistry & Molecular Morphology, 18(5):462-472 (2010).
Raspollini et al., "Tumour-infiltrating gamma/delta T-lymphocytes are correlated with a brief disease-free interval in advanced ovarian serous carcinoma." Ann Oneal., 16(4):590-596 (2005).

(56) References Cited

OTHER PUBLICATIONS

Ren et al., "Human MU CI carcinoma-associated protein confers resistance to genotoxic anticancer agents." Cancer Cell, 5(2):163-175 (2004).
Ren et al., "MUCI oncoprotein is targeted to mitochondria by heregulin-induced activation of c-Src and the molecular chaperone HSP90." Oncozene, 25(1):20-31 (2006).
Riviere et al., "Effects of retroviral vector design on expression of human adenosine deaminase in murine hone marrow transplant recipients engrafted with genetically modified cells." Proc Natl Acad Sci., USA, 92(15):6733-6737 (1995).
Rosen et al., "Potential markers that complement expression of CA125 in epithelial ovarian cancer." Gynecol Oneal., 99(2):267-277 (2005).
Rudikoff et al., "Single amino acid substitution altering antigen-binding specificity," Proc. Natl. Acad. Sci. USA, 79: 1979-1983 (1982).
Rustin et al., "Use of CA-125 in clinical trial evaluation of new therapeutic drugs for ovarian cancer." Clin Cancer Res., 10(11):3919-3926 (2004).
Sadelain et al., "Targeting tumours with genetically enhanced T lymphocytes." Nat Rev Cancer, 3(1):35-45 (2003).
Sadelain et al., "The basic principles of chimeric antigen receptor design," Cancer Discovery, 3:388-398 (2013).
Sadelain et al., "The promise and potential pitfalls of chimeric antigen receptors." Curr Opin Immunol., 21(2):215-223 (2009).
Salih et al., "Constitutive expression of functional 4-IBB (CD137) ligand on carcinoma cells." J Immunol., 165(5):2903-2910 (2000).
Santos et al., "Sensitive in vivo imaging of T cells using a membrane-bound Gaussia princeps luciferase." Nat Med., 15(3):338-344 (2009).
Sato et al., "Intraepithelial CD8+ tumor-infiltrating lymphocytes and a high CD8 /regulatory T cell ratio are associated with favorable prognosis in ovarian cancer." Proc Natl Acad Sci., USA, 102(51):18538-18543 (2005).
Savoldo et al., "Epstein Barr virus-specific cytotoxic T lymphocytes expressing the anti-CD3Ozeta artificial chimeric T-cell receptor for immunotherapy of Hodgkin disease." Blood, I 10(7):2620-2630 (2007).
Scholler & Urban. "CA125 in ovarian cancer. Biomark." Med. 1, 513-523 (2007).
Seelenmeyer et al., "The cancer antigen CA125 represents a novel counter receptor for galectin-1." J Cell Sci. 116(Pt 7): 1305-1318 (2003).
Shinoda et al., Kruppel-like factor 5 causes cartilage degradation through transactivation of matrix metalloproteinase 9. J Biol Chem 283: 24682-24689 (2008).
Sikkink et al., "Biochemical and aggregation analysis of Bence Jones proteins from different light chain diseases," Amyloid, 15(1):29-39 (2008).
Singer, "The structure and insertion of integral proteins in membranes." Annu Rev Cell Biol., 6:247-296, A: pp. 247-268 (1990).
Singer, "The structure and insertion of integral proteins in membranes." Annu Rev Cell Biol., 6:247-296, B: pp. 269:296 (1990).
Singh et al., "Clinical potential of mucins in diagnosis, prognosis, and therapy of ovarian cancer." Lancet Oneal., 9(11):1076-1085 (2008).
Song et al., "Peptide ligand-mediated liposome distribution and targeting to EGFR expressing tumor in vivo." Int J Pharm., 363(1-2):155-161 (2008).
Sorensen et al., "Chemoenzymatically synthesized multimeric Tn/STn MU CI glycopeptides elicit cancer-specific anti-MUCI antibody responses and override tolerance." Glycobiology, 16(2):96-107 (2006).
Soslow, "Histologic subtypes of ovarian carcinoma: an overview." Int J Gynecol Pathol., 27(2):161-174 (2008).
Stephan et al., "T cell-encoded CD8O and 4-IBBL induce auto- and transcostimulation, resulting in tumor rejection." Nat Med., 13(12):1440-1449 (2007).
Strausberg et al., "Generation and initial analysis of more than 15,000 full-length human and mouse cDNA sequences." Proc Natl Acad Sci USA 99: 16899-16903 (2002).
Strome et al., 2007, "A mechanistic perspective of monoclonal antibodies in cancer therapy beyond target-related effects.", The Oncologist, 12:1084-95.
Sun et al., "Metabolic and Functional Profiling of the Normal Rat Retina," J Comp Neural, 505: 92-113 (2007).
Sun et al., "Quality of life for patients with epithelial ovarian cancer." Nat Clin Pract Oncol, 4(1):18-29 (2007).
Taylor et al., Integrative genomic profiling of human prostate cancer. (2010) Cancer Cell 18: 11-22 (2010).
TCGA "Comprehensive genomic characterization defines human glioblastoma genes and core pathways." Nature 455: 1061-1068 (2008).
Thapi et al., "Abstract 3045: Glycosylation dependence in MUC16/CA125 expression in ovarian cancer." Proceedings: AACR 104th Annual Meeting 2013; Apr. 6-10, 2013; Washington, DC; DOI: 10.1158/1538-7445.AM2013-3045 Published Apr. 2013.
Till et al., "Adoptive immunotherapy for indolent non-Hodgkin lymphoma and mantle cell lymphoma using genetically modified autologous CD20-specific T cells." Blood, 112(6):2261-2271 (2008).
Tomsova et al., "Prognostic significance of CD3 tumor-infiltrating lymphocytes in ovarian carcinoma." Gvnecol Oneal., 108(2):415-420 (2008).
Ventura et al., Activation of the MEK-S6 pathway in high-grade ovarian cancers. (2010) Appl Immunohistochem Mol Morphol 18: 499-508 (2010).
Voinea and Simionescu, "Designing of 'intelligent' liposomes for efficient delivery of drugs." J Cell Mal Med., 6(4):465-474 (2002).
Wan et al., "Expression of co-stimulator 4-IBB molecule in hepatocellular carcinoma and adjacent non-tumor liver tissue, and its possible role in tumor immunity." World J Gastroenterol., 10(2): 195-199 (2004).
Wang et al., "A T cell-independent anti tumor response in mice with bone marrow cells retrovirally transduced with an antibody/Fe-gamma chain chimeric receptor gene recognizing a human ovarian cancer antigen." Nat Med., 4(2):168-172 (1998).
Wang et al., "Abstract 141: MUC16/CA125 and Epithelial Growth Factor Receptor functionality in ovarian cancer." Proceedings: AACR 106th Annual Meeting 2015; Apr. 18-22, 2015; Philadelphia, PA; DOI: 10.1158/1538-7445.AM2015-141 Published Aug. 2015.
Wang et al., "An advance in the chemical synthesis of homogeneous N-linked glycopolypeptides by convergent aspartylation." Angew. Chem. Int. Ed. 51, 11571-11575 (2012).
Wang et al., "Universal PCR amplification of mouse immunoglobulin gene variable regions: the design of degenerate primers and an assessment of the effect of DNA polymerase 3' to 5' exonuclease activity." J Immunol Methods, 233(1-2):167-177 (2000).
Westwood et al., "Adoptive transfer of T cells modified with a humanized chimeric receptor gene inhibits growth of Lewis-Y-expressing tumors in mice." Proc Natl Acad Sci., USA, 102(52):19051-19056 (2005).
Wilkie et al., "Retargeting of human T cells to tumor-associated MU CI: the evolution of a chimeric antigen receptor." J Immunol., 180(7):4901-4909 (2008).
Wolf et al., "The expression of the regulatory T cell-specific forkhead box transcription factor FoxP3 is associated with poor prognosis in ovarian cancer." Clin Cancer Res., I 1(23):8326-8331 (2005).
Woo et al., "Regulatory CD4( )CD25( ) T cells in tumors from patients with early-stage non-small cell lung cancer and late-stage ovarian cancer." Cancer Res., 61(12):4766-4772 (2001).
Written Opinion of the International Searching Authority for International Application No. PCT/US201I/030025, dated Feb. 8, 2012.
Written Opinion of the International Searching Authority for International Application No. PCT/US2016/022643, dated Sep. 5, 2016.
Xing & Orsulic, "A mouse model for the molecular characterization of brcal-associated ovarian carcinoma." Cancer Res 66: 8949-8953 (2006).
Yarilin, "Immunology Basics," Education material for students of medical universities, Moscow, Medicine, pp. 172-174 (1999) (English translation only).
Yin and Lloyd, "Molecular cloning of the CA125 ovarian cancer antigen: identification as a new mucin, MUC16." J. Biol Chem., 276(29):27371-27375 (2001).

(56) References Cited

OTHER PUBLICATIONS

Yin et al., "Ovarian cancer antigen CA125 is encoded by the MUC16 mucin gene." Int J Cancer, 98(5):737-740 (2002).
Yoshinaga et al.,"Ig L-chain Shuffling for Affinity Maturation of Phage Library-derived Human Anti-human MCP-1 Antibody Blocking its Chemotactic Activity" J. Biochem 2008; 143:593-601. (Year: 2006).
Zhang et al., "Intratumoral T cells, recurrence, and survival in epithelial ovarian cancer." N Engl J Med., 348(3):203-213 (2003).
Zorn et al., "The prognostic value of pretreatment CA 125 in patients with advanced ovarian carcinoma: a Gynecologic Oncology Group study." Cancer 115: 1028-1035 (2009).

\* cited by examiner

Peptide 1 near Cleavage Site:
NFSPLARRVDRVAIYEE (SEQ ID NO:01)

Peptide 2 before Transmembrane:
TLDRSSVLVDGYSPNRNE (SEQ ID NO:02)

Peptide 3 inside Transmembrane:
CGVLVTTRRRKKEGEYNVQQQ (SEQ ID NO:03)

FIG. 1

|  | Concordant | | Discordant | |
|---|---|---|---|---|
|  | OC125 staining | 4H11 staining | OC125 staining | 4H11 staining |

Tissue microarrays were scored from 0 to 3 in one-half (+) increments for cytoplasmic and/or membranous staining
0 – no staining
1 – strong or weak <5%
1+ – strong or weak 5-50%
2 – strong 51-75% or weak 51-100%
2+ – strong (76-99%)
3 – strong (100%)

| n=518 | Stain score | | |
|---|---|---|---|
|  | 0 | 1-1+ | 2-3 |
| OC125 | 60 (11%) | 122 (24%) | 336 (65%) |
| 4H11 | 129 (25%) | 116 (22%) | 273 (53%) |

Concordance between OC125 and 4H11 staining was based on the amount of difference between the scores
Concordant = 0 - ½ difference
Partially concordant = 1-1 ½ difference
Discordant = 2-3 difference Of the 39 discordant cases,
OC125 > 4H11 in 59%
4H11 > OC125 in 41%

Overall 3-4% of all ovarian serous carcinomas expressed 4H11 but not OC125

| OC125/4H11 (n=518) | |
|---|---|
| Concordant | 286 (55%) |
| Partially concordant | 193 (37%) |
| Discordant | 39 (8%) |

| OC125>4H11 | 23 (59%) |
|---|---|
| 4H11>OC125 | 16 (41%) |

FIG. 2

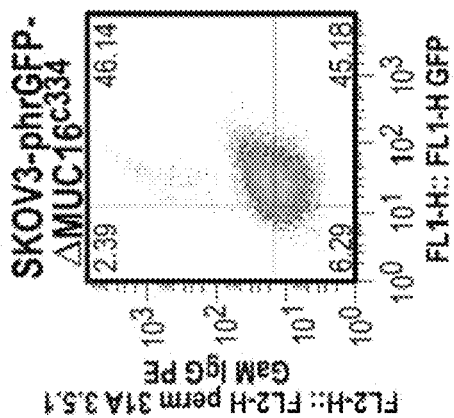
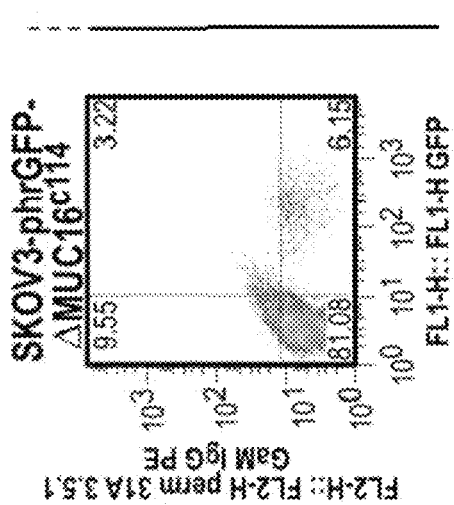
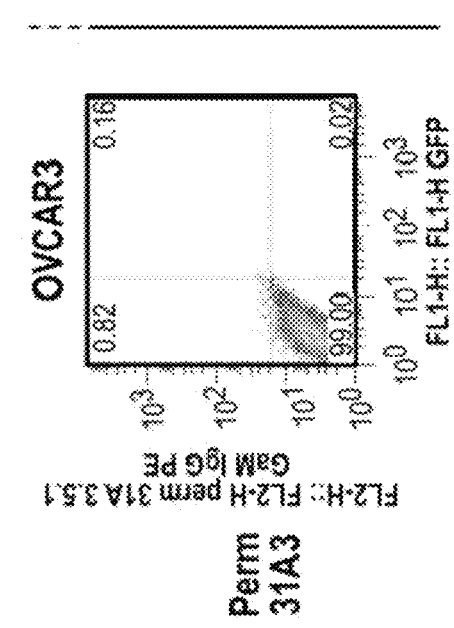
FIG. 7D (A) 4A5 VH (SEQ ID NO:04)
gtgaagctggaggagtcaggggggaggcttcgtgaagcctggagggtccctcaaaatctcctgtgcagcctctggattcac
tttcagaaactatgccatgtcctgggttcgcctgagtccggagatgaggctggagtgggtcgcaaccattagcagtgctg
gtggttacatcttctattctgacagtgtgcagggacgattcaccatttccagagacaatgccaagaacaccctccactg
caaatgggcagtctgaggtctggggacacggccatgtattactgtgcaaggcagggatttggtaactacggtgattacta
tgctatggactactggggccaagggaccacggtcaccgtctcctca (B) 4A5 VL (SEQ ID NO:05)
gacattgagctcacccagtctccatcctccctggctgtgtcagcaggagagaaggtcactatgagctgcaaatccagtca
gagtctgctcaacagtagaacccgaagaaccagttggcttggtaccagcaaaaaccaggacagtctcctgaactgctga
tctactgggcatccactcggcaatctgggtccctgatcgcttcacaggcagtggatctgggacagatttcactctcacc
atcagcagtgtgcaggctgaagacctggcagttattactgccagcaatcttataatctactcacgttcggtcctgggac
caagctggagatcaaacgg (C) 4H11 VH (SEQ ID NO:06)
gtgaagctgcaggagtcaggggggaggcttcgtgaagcctggagggtccctcaaagtctcctgtgcagcctctggattcac
tttcagtagctatgccatgtcctgggttcgcctgagtccggagatgaggctggagtgggtcgcaaccattagcagtgctg
gtggttacatcttctattctgacagtgtgcagggacgattcaccatttccagagacaatgccaagaacaccctgcacctg
caaatgggragtctgaggtctggggacacggccatgtattactgtgcaaggcagggatttggtaactacggtgattacta
tgctatggactactggggccaagggaccacggtcaccgtctcctca (D) 4H11 VL (SEQ ID NO:07)
gacattgagctcacccagtctccatcctccctggctgtgtcagcaggagagaaggtcactatgagctgcaaatccagtca
gagtctgctcaacagtagaacccgaagaaccagttggcttggtaccagcaaaaaccaggacagtctcctgaactgctga
tctactgggcatccactaggcaatctggagtccctgatcgcttcacaggcagtggatctgggacagatttcactctcacc
atcagcagtgtgcaggctgaagacctggcagttattactgccagcaatcttataatctactcacgttcggtcctgggac
caagctggaggtcaaacgg (E) 9B11 VH (SEQ ID NO:08)
gtgaagctggaggagtcaggggggagacttggtgaagcctggagggtccctgaaactctcctgtgcagtctctggattcac
tttcagtagccattccatgtcttggattcgtcagactccagagaagaggctagagtgggtcgcatccgtgagtagtggtg
gtaggatctactattcggacagtgtgaaggccgattcaccgtcaccagagaaaatgacaggaacaccctgtatttgtta
atgagtagtctgaggtctgaggacacggccatgtattattgtggaagaggacaggtattttatgctttgacaattgggg
ccaagggaccacggtcaccgtctcctca (F) 9B11 VL.A (SEQ ID NO:09)
gacattgagctcacccagtctccatcctccctggctgtgtcagcaggagagaaggtcactatgagctgcaaatccagtca
gagtctgctcaacagtagaacccgaagaaccagttggcttggtaccagcaaaaaccaggacagtctcctgaactgctga
tctactgggcatccactaggcaatctggagtccctgatcgcttcacaggcagtggatctgggacagatttcactctcacc
atcagcagtgtgcaggctgaagacctggcagttattactgccagcaatcttataatctactcacgttcggtcctgggac
caagctggaggtcaaacgg (G) 9B11 VL.B (SEQ ID NO:10)
gacattgagctcacccagtctccaaagctcctgatctacaaggtttccaaccgattttctggggtcccagacaggttcag
tggcagtggatcagggacagatttcacactcaagatcagcagagtggaggctgaggatctgggagtttattactgcttc
aaggttcacatgttccgtggacgttcggtggagggaccaagctggagatcaaacgg

FIG. 8

(H) 24B3-VH (SEQ ID NO:11)
GAGGTGAAGCTGGAGGAGTCAGGACCTGAACTGGTGAAGCCTGGGGCTTCAGTGAAGATATCCTGCAAGGCTTCTGGTTA
CTCATTTACTGGCTACTTTATGAACTGGGTGAAGCAGACCCATGGAAAGAGCCTTGAGTGGATTGGACGTATTAATCCTT
ACAATGGTGCTACTTTCTACAATCAGAAGTTCACGGGCAAGGCCACAATGACTGTAGACAAATCCTCTACCACAGCCCAC
ATGGAGCTCCTGAGCCTGACATCTGAGGACTCTGCAGTCTATTATTGTGCAAAGGGGAATTACTACGGCCCCTTTGATTA
CTGGGGCCAAGGGACCACGGTCACCGTCTCCTCA (I) 24B3-VL (SEQ ID NO:12)
GACATTGAGCTCACCCAGTCTCCATCTTATCTTGCTGCATCTCCTGAAGAAACCATTACTATTAATTGCAGGGCAAGTAA
GAGCATTAGCAAATATTTAGCCTGGTATCAAAGAAACCTGGCAAAACTAATAAGCTTCTTATCTACTCTGGATCCACTT
TGCAATCTGGAATTCCATCAAGGTTCAGTGGCAGTGGATCTGGTACAGATTTCACTCTCACCATCAGTAGCCTGGAGCCT
GAAGATTTTGCAATGTATTACTGTCAACAGCATAATGAATACCCGTGGACGTTCGGTGGAGGGACCAAGCTGGAGATCAA
ACGGGCGGCCGCA

FIG. 8 (CONTD.)

(A) Homo sapiens MUCIN-16 (GenBank NP_078966) (SEQ ID NO:13)

```
   1 mlkpsglpgs septrslmtg srstkatpem dsgltgatls pktstgaivv tehtlpfts
  61 dktlasptss vvgrttqslg vmssalpest srgmthseqr tspslspqvn gtpsrnypa
 121 omvoglsspr trtsstegnf tkeastytlt vettsgpvte kytvptetst tegdotetp
 181 dtrylpvkit spmktfadst askenapvsm tpaettvtds htpgrtnpsf gtlyssfld
 241 spkgtpnsrg etslelilst tgypfsspep gsaghsrist saplsssasv ldnklsets
 301 fsgqsltspl spgvpearas tmpnsaipfs mtlsnaetss ervrstissl gtpsistkq
 361 aetiltfhaf aetmdipsth iaktlasewl gspgrlggts tsaltttsps ttlvseetn
 421 bhstsgkete gtlntsmtpl stsapgeese mtatlvptlg fttldskirs psqvasshp
 481 relrttgsts grqssstaah gssdilratt sstskasswt sestaqqfss pqhtqwvet
 541 psmkterppa stsvaapitt svpsvvsqft tlktsstkgi wlsetsadtl igestagpt
 601 hqfavptgis mtggsstrgs qgtthlltra tassetsadl tlatngvpvs vspavskta
 661 qssppggtkp sytmvssvip etsslqssaf regtslgltp lntrhpfssp epdsaghtk
 721 stsiplissa svledkvsat stfshhkats sittgtpeis tktkpssavl ssmtlsnaa
 781 spervrnats plthpspsge etagsvltls tsaettdspn ihptgtltse ssespstls
 841 psvsgvkttf ssstpsthlf tsgeeteets npsvsqpets vsrvrttlas tsvptpvfp
 901 mdtwptrssq fssshlvsel ratsstsvtn stgsalpkis hltgtatmsq tnrdtfnds
 961 apqsttwpet spriktglps atttvstsat slssatvmvsk ftspatssms atsirepst
1021 ilttettngp gsmavastni pigkgyiteg rldtshlpig ttassetsmd ftmakesvs
1081 svspsqsmda agsstpgrts qfvdtfsddv yhltsreiti prdgtssalt pqmtathpp
1141 pdpgsarstw lgilesspss ptpkvtmsst fstqrvttsm imdtvetsrw nmpnlpstt
1201 ltpsniptsg aigkstlvpl dtpspatsle aseggiptls typestntps ihlgahass
1261 spetikltma svvkpgsytp ltfpsiethi hvstarmays sqsspemtap getntgstw
1321 ptrylttrdp kdtssaqvst phsvrtlrtt enhpktesat paaysgspkl ssspnltsp
1381 tkawtitdtt ehstqlhytk laekssgfet qsapgpvsvv iptsptigss tleltsdvp
1441 eplvlapseq ttitlpmatw lstslteema stdldisssps spmstfaifp pmstpshel
1501 kseadtsair ntdsttldqh lgirslgrtg dlttvpitpl tttwtsvieh stqaqdtls
1561 tmspthvtqs lkdqtslpas aspshltevy pelgtqgrss seattfwkps tdtlsrsie
1621 gptnlqstpp mdnttgsss sgvtlgishl pigtsspaet stnmalerrs statvsmag
1681 mgllvtsapg rslsqslgrv ssvlsestte gvtdsskgss prlntqgnta lssslepsy
1741 egsqmstslp ltsspttpdv efiggstfwt kevttvmtsd iskssartes ssatlmsta
1801 gstentgkek lrtasmdlps ptpsmsvtpw isltlsnapn ttdsldlshg vhtssagtl
1861 tdrslhtgvt rasrlengsd tasksismgn sthtsmtyte ksevsssihp rpetsapga
1921 ttlnstpgnr aisltlpfss ipvaevistg itsgpdinsa pmthspitpp tivwtstgt
1981 eqstqplhav ssekvsvqtq stpyvnsvav saspthensv ssgsstsspy ssaslesld
2041 tisrrnaits wlwdlttslp tttwpstsls ealssghsgv snpsstttef plfsaasts
2101 akgrnpetet hgpqntaast lntdassvtg lsetpvgasi ssevplpmai tsradvsgl
2161 sestanpslg tassagtklt rtislptses lvsfrmnkdp wtvsiplgsh pttntetsi
2221 vnsagppgls tvasdvidtp sdgaesiptv sfspspdtev ttishfpekt thsfrtiss
2281 theltsrvtp ipgdwmssan stkptgasps itlgerrtlt ssapttspiv ltasftets
2341 vsldnettvk tsdildarkt nelpsdssss sdlintsias stndvtktas isptsisgm
2401 assspslfss drpqvptstt stntatspsv ssntysldgg snvggtpstl ppftithpv
2461 tssallawsr pvrtfstmvs tdtasgenpt ssnsvvtsvp apgtwtsvgs ttdlpamgf
2521 ktspageahs llastlepat aftphlsaav vtgssatsea sllttseska ihsspqtpt
```

FIG. 9

```
2581 ptsganwsta atpesllvvt etsdtcltsk ilvtdtilfs tvstppskfp stgtlsgas
2641 ptllpdtpai pltateptss latsfdstpl vtiasdslgt vpsttltmss tsngdalvl
2701 tvsnpdrsip gitiqgvtes plhpsstsps kivaprntty egsitvalst lpagttgsl
2761 fsqssenset tslvdssagl ersasvmpltt geqgwassgg irsgsthstg tkttfsslpl
2821 mnpgevtams eittnrltat qstapkgipv kptsaesgll tpvsassps kafaslttsa
2881 ptwgipqstl tfefsevpsl dtksaslptp gqslntipds dsataessla kspeknpra
2941 mmtstkalsa ssfqstgfte tpegsaspsm agheprvpts gtgdpryase smsypdpsk
3001 ssamtstsla sklttlfstg qaarsgssss pialstsket efleptaste rktslflgp
3061 marqpnilvh lqtsaltlsp tstlnmsqee ppeltssqti aeeegttaet qtltftpse
3121 ptsllpvssp teptarrkss petwassisv paktslvett dgtlvttikm ssqaaqgns
3181 wpapaeetgs spagtspgsp emsttlkims skepsispei rstvrnspwk tpettvpme
3241 tvepvtlqst algsgstsls hlptgttspt ksptemmlat ervslspspp eawtnlysg
3301 pggtrqslat mssvslsespt arsitgtgqq sspelvsktt gmefsmwhgs tggttgdth
3361 sletssnils dpvtspnsvs sltdkskhkt etwvsttaip stvlnnkima aeqqtsrsv
3421 eaysstsaws sdqtsqaditl gaspdvtntl yitstaqtts lvslpsgdqg itsltnpsg
3481 ktssassvts psigletlrs nvsavksdia ptsghisqts spaevsildv ttaptpgis
3541 tittsgtnsi stttpnpevg mstmdstpat errttstehp stwsstaasd swtvtdmts
3601 lkvarspgti stmhttsfla sseteldsmst phgritvigt slvtpssdas avktetsts
3661 rtlspsdtta stpistfsrv qrmsisvpdi latswtpsst eaedvpvsmv stdhastkt
3721 pmtplstflf dslstldwdt grslssatat tsapqgattp qeltletmis patsqlpfs
3781 ghitssavtpa amarssgvtf srpdptskka eqtstqlptt tsahpgqvpr ssaartldvi
3841 htaktpdatf qrqgqtaltt ssaratsdswn ekekstpsaap witemmusvs edtikevts
3901 ssvlrtlntl dinlesgtts spswksspyc rlapssesttd kealhpstnt vettgwvts
3961 ehsshstipa hsassklttsp vvttstreqa ivsmstttwp estrartepn sfltielrd
4021 spymdtssrt qtsiisspgs taitkgprte itsskrisss flaqsmrssd spsseaitrl
4081 nfpamtssgg milamqtspp gstslsaptl dtsataswtg tplattqrft ysekttlfs
4141 gpedtsqpsp psveetsss slvplhatts psnilltsqg hspsstppvt svflsetsg
4201 gkttdmaris lepgtslppn lsstaqeals tysasrdtka ihhsadtsavt nmeatssey
4261 pipghtkpsk atsplvtshi mgditsstav fgssettele tvssvnqglq eratsqvas
4321 atetstvith vssgdatthv tktqatfssg tsissphqfi tstntftdvs tnpstslim
4381 essgvtittq tgptgsaatqg pylldtstmp yltetplavt pdfmqsektt liskgpkdv
4441 wtsppsvaet sypssltpfl vttippatst lqqgghtsspv satsvltsgl vkttdmlnt
4501 mepvtnspqn lnnpsneila tlaattdiet ihpsinkavt nsgtassahv lhstlpvss
4561 pstatspmvp assmgdalas isipgssettd iegeptsslt agrkensttlq emnsttesn
4621 ilsnvsvgai teatkmevps fdatfiptpa qstkfpdifs vassrlsnsp pmtisthmt
4681 tqtgssgats kiplaldtst letsagtpsv vtegfahski ttamnndvkd vsqtnppfq
4741 easspssqap vlvttlpssv aftpqwhsts spvsmssvlt sslvktagkv dtsletvts
4801 pqsmantldd lsvtsaattd letthpsint vvtnvgttgs afsshstvss yppepskvts
4861 nvttstmedt tisrsipkss kttrtstett ssaltpklret slsqeitsst etstvpyke
4921 tgattevsrt dvtssstsf pgpdqstvsl distetntrl stspimtssa eitittqtg
4981 hgatsqdtft mdpsnttpqa glhsamthgf sqldvttlms ripqdvswts ppsvdkrss
5041 ssflsspamt tpslisstlp edklsspmts litsglvkit dilrtrlepv tsslpnfss
5101 sdkilatskd skdtkslfps lnteetnvka rnsgheshsp aladsstpka ttqmvittt
5161 gdpapstsmp vhgssettni kreptyfltp rlretstsqs ssfptdtsfl lskvptgti
```

FIG. 9 (CONTD.)

```
5221 evsstgvnss skistpdhdk stvppdtftg eiprvftssl ktksaemtit tqasppesa
5281 hstlpldtst tlsqggthst vtqgfpysev ttlmgmgpgn vswmttppve etssvsslm
5341 spamtspspv sstspqsips splpvtalpt svlvtttdvl gttspesvts sppnlssit
5401 erpatykdta hteaamhhst ntavtnvgts gsghksqssv ladsetskat plmsttstl
5461 dtsvststpn isqtnqiqte ptsslsprlr esstsektss ttetntafsy vptgsitga
5521 rteissarts isdldrptia pdistgmltr lftspimtks aemtvttqtt tpgatsqgi
5581 pwdtsttlfq ggthstvsqg fphseittlr srtpgdvswm tppveetss gfslmspsm
5641 spspvsstsp esipssplpv talltsvlvt ttnvlgttsp epvtssppnl ssptqerlt
5701 ykdtahteam hasmhtntav anvgtsisgh esqssvpads htskatspmg itfamgdts
5761 ststpaffet riqtestssl ipglrdtrts eeintvtets tvlsevpttt ttevsrtev
5821 tssrttisgp dhskmspyis tetitrlstf pfvtgstema itnqtgpigt isqatltld
5881 sstasswegth spvtqrfphs eetttmsrst kgvswqspps veetsspssp vplpaitsh
5941 slysavsgss ptsalpvtsl ltsgrrktid mldthselvt sslpsassfs geiltseas
6001 ntetihfsen taetnmgttn smhklhssvs ihsqpsghtp pkvtgsmmed aivststpg
6061 petknvdrds tspltpelke dstalvmnst tesntvfssv sldaatevsr aevtyydpt
6121 mpasaqstks pdispeasss hsnsppltis thktiatqtg psgvtslgql tldtstiat
6181 agtpsartqd fvdsettsvm nndlndvlkt spfsaeeans lssqapllvt tspspvtst
6241 qehstsslvs vtsvptptla kitdmdtnle pvtrspqnlr ntlatseatt dthtmhpsi
6301 tavanvgtts spnefyftvs pdsdpykats avvitstsgd sivstsmprs samkkiese
6361 tfslifrlre tstsqkigss sdtstvfdka ftaattevsr teltssarts iggtekptm
6421 pdtstrsvtm lstfagltks eertlatqtg phratsqgtl twdtsirtsq agthsamth
6481 fsqldlstlt srvpeyisgt sppsvektss sssllslpai tspspvpttl pesrpsspv
6541 ltalptsglv kttdmlasva slppnlgsts hkipttsedi kdteknypst niavtnvgt
6601 tsekesysav paysseppkvt spmvtsfnir dtivstsmpg sseitrieme stfslahgl
6661 gtstsqdpiv steksavlhk lttgatetsr tevassrrts ipgpdhstes pdistevip
6721 lpislgites srmtiitrtg pplgstsqgt ftldtpttss ragthsmatq efphsemtt
6781 mnkdpeilsw tippsiekts fssslmpspa mtsppvsstl pktihttpsp mtslltpsl
6841 mttdtlgtsp epttssppnl sstsheiltt dedttaieam hpststaatn vettssghg
6901 qssvladsek tkatapmdtt stmghttvst smavssettk ikrestyslt pglretsis
6961 nasfstdtsi vlsevptgtt aevsrtevts sgrtsipgps qstvlpeist rtmtrlfas
7021 tmtesaemti ptqtgpsgst sqdtltldts ttksqakths tltqrfphse mttlmsrgp
7081 dmswqsspsl snpssipsll slpattsppp isstlpvtis sslpvtsll tsspvtttd
7141 lhtspelvts sppklshtsd erlttgkdtt nteavhpstn taasnveips sghesspssa
7201 adsetskats pmfitstqed ttvalstphf letsriqkes isslspklre tgssvetss
7261 ietsavlsev sigatteisr tevtsssrts isgsaestml peisttrkii kfptspila
7321 ssemtiktqt sppgstsest ftldtsttps lvithstmtq rlphseittl vsrgagdvp
7381 psslpveets ppssqlslsa mispspvsst lpasshsssa svtslltpgq vkttevlda
7441 aepetsspps lsstsveila tsevttdtek ihpfsntavt kvgtsssghe spssvlpds
7501 ttkatsamgt isimgdtsvs tltpalsntr kiqsepassl ttrlretsts eetslatss
7561 tvlskvstga ttevsrtsai sfsrtsmsgp eqstmsqdis igtiprisss svltesakm
7621 ittqtgpsss tlestlnint attpswveth siviqgfphp emttsmgrgp ggvswpspp
7681 vketsppssp lslpavtsph pvsttflahi ppsplpvtsl ltsgpatttd ilgtstspg
7741 ssssslstts herlttykdt ahteavhpst ntggtnvatt ssgyksqssv ladsspmct
7801 stmgdtsvlt stpafletrr iqtelasslt pglressgse gtssgtkmst vlskvptga
```

FIG. 9 (CONT'D.)

```
7861  teiskedvts  ipgpaqstis  pdistrtvsw  fstspvmtes  aeitmnthts  plgattqgt
7921  tldtsstts1  tmthstisqg  fshsqmstlm  rrgpedvswm  sppllektrp  sfslmsspa
7981  tspspvsstl  pesissssplp vtslltsgla  kttdmlhkss  epvtnspanl  sststveila
8041  sevttdtekt  hpssnrtvtd  vgtsssghes  tsfyladsqt  skvtspmvit  stmedtsvs
8101  stpgffetsr  iqteptsslt  lglrktqsse  gtgssgmst   vlsgvptgat  aevsrtevt
8161  ssrtsisgfa  qltvspetst  etitrlptss  imtesassmi  ktqtdppgst  pssthtvdi
8221  ttpnwveths  tvtqrfshse  mttlvsrspg  dniysqssv   qetssassll  slpattsps
8281  vsstlvedfp  saslpvtsll  npglvfttdr  mgfsrepgts  stsnlsstsh  erlttledt
8341  dtedmqpsth  tavnrvrtsi  sghesqssvl  sdsetpkats  pmgttytmge  tsvsistsd
8401  fetsriqlep  tssltsglre  tasserlssa  tegstvlsev  psgattevsr  tevissrgt
8461  msgpdqftis  pdisteaitr  lstspimtes  aesaitletg  spgatsegtl  tldtstttf
8521  sgthstaspg  fshsemttlm  srtpgdvpwp  slpsveeass  vssslsspam  tstsffstl
8581  esissphpv   talltlgpvk  ttdmlrtsse  petssppnls  stsaeilats  evtkdreki
8641  pssntpvvnv  gtviykhlsp  ssvladlvtt  kptspmatts  tlgntsvsts  tpafpetmm
8701  qptssltsgl  reistsqets  satersasls  gnptgattkv  srtealslgr  tstpgpaqs
8761  ispeistet1  tristptlttt gssemtitpk  tghsgassqg  tftldtssra  swpgthssa
8821  hrsphsqmtt  pmsrgpedvs  wpsrpsvekt  sppsslvsls  avtspsplys  tpsesshss
8881  lrvtslftpv  mmkttdmldt  slepvttspp  smnitsdesl  atskatmete  aiqlsenta
8941  tqmgtisarq  efyssypglp  epskvtspvv  tsstikdivs  ttipasseit  rlemsstst
9001  tptpretsts  qsihsatkps  tvpykaltsa  tiedsmtqvm  sssrgpspdq  stmsqdist
9061  vitrlstspi  ktestemtit  tqtgspgats  rgtltldtst  tfmsgthsta  sqgfshsqm
9121  almsrtpgdv  pwlshpsvee  assasfslss  pvmtssspvs  stlpdsihss  slpvtsllt
9181  glvkttellg  tssepetssp  pnlsstsaei  laitevttdt  eklemtnvvt  sgythesps
9241  vladsvttka  tssmgitypt  gdtnvltstp  afsdtsriqt  ksklsltpgl  metsiseet
9301  sstekstvls  svptgattev  srtesissr   tsipgpaqsr  mssdtsmeti  tristpltr
9361  estdmaitpk  tgpsgatsqg  tftldsssta  swpgthsatt  qrfpqsvvtt  pmsrgpedv
9421  wpsplsvekn  sppsslvsss  svtspsplys  tpsgsshssp  vpvtslftsi  mmkatdmld
9481  slepettssp  nmnitsdesl  aaskattete  aihvfentaa  shvettsate  elyssspgf
9541  eptkvispvv  tsssirdnmv  sttmpgssgi  trielesmss  ltpglretrt  sqditsste
9601  stvlykmpsg  atpevsrtev  mpssrtsipg  paqstmsldi  sdevvtrlst  spimtesae
9661  tittqtgysl  atsqvtlplg  tsmtflsgth  stmsqglshs  emtnlmsrgp  sslswtspr
9721  vettrsssl   talplttsls  pvsstlldss  psspplpvtsl ilpglvktte  vldtssepk
9781  ssspnlssts  veipatseim  tdtekihpss  ntavakvrts  ssvheshssv  ladsettit
9841  psmgitsavd  dttvftsnpa  fssetrripte ptfsltpgfr  etstseetts  itetsavly
9901  vptsattevs  mteimssnri  hipdsdqstm  spdiitevit  rlsssssmse  stqmtittq
9961  sspgataqst  ltlatttapl  arthstvppr  flhsemttlm  srspenpswk  sslfvekts
10021 ssssllslpvt tspsvsstlp  qsipsssfsv  tslltpgmvk  ttdtstepgt  slspnlsgt
10081 veilsasevt  tdtekihpss  smavtnvgtt  ssghelyssv  sihsepskat  ypvgtpssm
10141 etsistsmpa  nfettgfeae  pfshltsgfr  ktnmsldtss  vtptntpssp  gsthllqss
10201 tdftssakts  spdwppasqy  teipvdiitp  fnaspsites  tgitsfpesr  ftmsvtestl
10261 hlstdllpss  etistgtvmp  slseamtsfa  ttgvpraisg  sgspfsrtes  gpgdatlst
10321 seslpsstpv  pfssstfttt  dsstipalhe  itsssstpyr  vdtslgtess  ttegrlvmv
10381 tldtssqpgr  tsssspildtr mtesvelgtv  tsayqvpsls  trltrtdgim  ehitkipne
10441 ahrgtirpvk  gpqtstspss  pkglhtggtk  rmettttalk  ttttalktts  ratlttsvy
```

FIG. 9 (CONTD.)

```
10501 ptlgtltpln asmqmastip temmittpyv fpdvpettss latslgaets talprttps
10561 fnresettas lvsrsgaers pviqtldvss sepdttaswv ihpaetiptv skttpnffh
10621 eldtvsstat shgadvssai ptnispseld altplvtisg tdtsttfptl tksphetet
10681 ttwlthpaet satiprtipn fshhesdatp siatspgaet ssaipimtvs pgaedlvts
10741 vtssgtdrnm tiptltlspg spktiaslvt hpeaqtssai ptstispavs rlvtsmvts
10801 aaktsttnra ltnspgepat tvslvthpaq tsptvpwtts iffhsksdtt psmttshga
10861 sssavptptv stevpgvvtp lvtssravis ttipiltlsp gepettpsma tshgeesss
10921 iptptvspgv pgvvtslvts sravtsttip iltfslgepe ttpsmatshg teagssavpt
10981 lpevpgmvts lvassravts ttlptltlsp gepettpsma tshgaeesst vptvspevp
11041 vvtslvtsss gvnstsiptl ilspgelett psmatshgae assavptptv spgvsgvvt
11101 lvtssravts ttipiltlss sepettpsma tshgveassa vltvspevpg mvtslvtss
11161 avtsttiptl tissdepett tslvthseak misaiptlav sptvqglvts lvtssgset
11221 afsnltvass qpetidswva hpgteassvv ptltvstgep ftnislvthp aessstlpr
11281 tsrfshseld tmpstvtspe aesssaistt ispgipgvlt slvtssgrdi satfptvpe
11341 pheseatasw vthpavtstt vprttpnysh sepdttpsia tspgaeatsd fptitvspd
11401 pdsrvtsqvts sgtdtsiltip tltlssgeps tttsfitysa thtssaiptl pvspgaskr
11461 tslvissqtd stttfptlte tpyepettai qlihpaetnt mvprttpkfs hsksdttlp
11521 aitspgpeas savstttisp dmsdlvtslv pssgtdtstt fptlsetpye pettatwlt
11581 paetsttvsg tipnfshrgs dtapsmvtsp gvdtrsgvpt ttippsipgv vtsqvtssa
11641 dtstaiptlt pspgepetta ssathpgtqt gftvpirtvp ssepdtmasw vthppqtst
11701 vsrttssfsh sspdatpvma tsprteassa vlttispgap emvtsqitss gaatsttvp
11761 lthspgmpet tallsthprt etsktfpast vfpqvsetta sltirpgaet stalptqtt
11821 slftllvtgt srvdlsptas pgvsaktapl sthpgtstst miptstlslg llettglla
11881 sssaetstst ltltvspavs glssasittd kpqtvtswnt etspsvtsvg ppefsrtvt
11941 ttmtlipsem ptpkktshge gvsptthflrt tmvsaatnlat tgssaptvakt tttfntlag
12001 lftplttpgm stlasesvts rtsynhrswi sttssynrry wtpatstpvt stfspgist
12061 sipsstaatv pfmvpftlnf titnlqyeed mrhpgsrkfn aterelqgll kplfrnssl
12121 ylysgcrlss lrpekdssat avdaicthrp dpedlgldrs rlywelsnlt ngiqslgpy
12181 ldrnslyvng fthrssmptt stpgtstvdv gtsgtpssap spttagpllm pftlnftit
12241 lqyeedmrrt gsrkfntsss vlqgllkplf kntsvgplys gcrltllrpe kdgaatgvd
12301 icthrldpks pglnreqlyw elskltndie elgpytldrn slyvngfthq ssvsttstp
12361 tstvdlrtsg tpsslsspti maagpllvpf tlnftitnlq ygsdmghpgs rkfntterv
12421 qgllgpifkn tsvgplysgc rltslrsekd gaatgvdaic ihhldpkspg lnrerlywe
12481 sqltngikel gpytldrnsl yvngfthrts vptssstpgts tvdlgtsgtp fslpspata
12541 pllvlftlnf titnlkyeed mhrpgsrkfn ttervlqtll gpmfkntsvg llysgcrlt
12601 lrsekdgaat gvdaicthrl dpkspgvdre qlywelsqlt ngikelgpyt ldrnslyvn
12661 fthwipvpts stpgtstvdl gsgtpsslps pttagpllvp ftlnftitnl kyeedmhcp
12721 srkfntterv lqsllgpmfk ntsvgplysg crltllrsek dgaatgvdai cthrldpks
12781 gvdreqlywe lsqltngike lgpytldrns lyvngfthqt sapntstpgt stvdlgtsg
12841 psslpsptsa gpllvpftln ftitnlqyee dnhhpgsrkf nttervlqgl lgpmfknts
12901 gllysgcrlt llrpekngaa tgmdaicshr ldpkspglnr eqlywelsql thgikelgp
12961 tldrnslyvn gfthrssvap tstpgtstvd lgtsgtpssl pspttavpll vpftlnfti
13021 nlqygedmrh pgsrkfntte rvlqgllgpl fknssvgply sgcrlislrs akdgaatgv
13081 aicthhlnpq spgldreqly wqlsqmtngi kelgpytldr nslyvngfth rssglttst
```

FIG. 9 (CONT'D.)

```
13141  wtstvdlgts  gtpspvpspt  ttgpllvpft  lnftitnlqy  eenmghpgsr  kfnitesvl
13201  gllkplfkst  svgplysgcr  ltllrpekdg  vatrvdaict  hrpdpkipgl  drqqlywel
13261  qlthsitslg  pytldrdsly  vngftqrssv  pttstpgtft  vqpetsetps  slpgptatg
13321  vllpftlnft  itnlqyeedm  rrpgsrkfnt  tervlqgllm  plfkntsvss  lysgcrltl
13381  rpekdgaatr  vdavcthrpd  pkspgldrer  lywklsqlth  gitelgpytl  drhslyvng
13441  thqssmtttr  tpdtstmhla  tsrtpaslsg  pmtaspllvl  ftinftitnl  ryeenmhhp
13501  srkfntterv  lqgllrpvfk  ntsvgplysg  crltllrpkk  dgaatkvdai  ctyrpdpks
13561  gldreqlywe  lsqlthsite  lgpytldrds  lyvngftqrs  svpttsipgt  ptvdlgtsg
13621  pvskpgpsaa  spllvlftln  ftitnlryes  nmqhpgsrkf  nttervlqgl  lrslfksts
13681  gplysgcrlt  llrpekdgta  tgvdaicthh  pdpksprldr  eqlywelsql  thnitelgp
13741  aldndslfvn  gfthrssvst  tstpgtptvy  lgasktpasi  fgpsaashll  ilftlnfti
13801  nlryeenmwp  gsrkfntter  vlqgllrplf  kntsvgplys  gcrltllrpe  kdgeatgvd
13861  icthrpdptg  pgldreqlyl  elsqlthsit  elgpytldrd  slyvngfthr  ssvpttstg
13921  vseepftlnf  tinnlrymad  mgqpgslkfn  itdnvmqhll  splfqrsslg  arytgcrvi
13981  lrsvkngaet  rvdllctylq  plsgpglpik  qvfhslsqqt  hgitrlgpys  ldkdslyln
14041  ynepgpdepp  ttpkpattfl  pplseattam  gyhlktltln  ftisnlqysp  dmgkgsatf
14101  stegvlqhll  rplfqkssmg  pfylgcqlis  lrpekdgaat  gvdttctyhp  dpvgpgldi
14161  qlywelsqlt  hgvtqlgfyv  ldrdslfing  yapqnlsirg  eyqinfhivn  wnlsnpdpt
14221  seyitllrdi  qdkvttlykg  sqlhdtfrfc  lvtnltmdsv  lvtvkalfss  nldpslveq
14281  fldktlnasf  hwlgstyqlv  dihvtemess  vyqptsssst  qhfylnftit  nlpysqdka
14341  pgttnyqrnk  rniedalnql  frnssiksyf  sdcqvstfrs  vpnrhhtgvd  slcnfspla
14401  rvdrvaiyee  flrmtrngtq  lqnftldrss  vlvdgyspnr  nspltgnsdl  pfwavilig
14461  agllgvitcl  icgvlvttrr  rkkegeynvq  qqcpgyyqsh  ldledlq
```

(B) Peptide 1
14394                    14410
    nfspla r rvdrvaiyee (SEQ ID NO:01)

(C) Peptide 2
14425              14442
    tldrss vlvdgyspnr ns (SEQ ID NO:02)

(D) Peptide 3
14471                14492
    cgvlvttrr rkkegeynvq qq (SEQ ID NO:03)

(E) Transmembrane Region:
14452                       14475
    fwaviligl agllgvitcl icgvl (SEQ ID NO:14)

(F) Peptide containing the cysteine loop peptide:
14367                              14398
    ksyf sdcqvstfrs vpnrhhtgvd slcnfspl (SEQ ID NO:15)

FIG. 9 (CONTD.)

CD8 leader sequence
ATGGCTC TCCCAGTGAC TGCCCTACTG CTTCCCCTAG CGCTTCTCCT GCATGCAGAG (SEQ ID NO:32)

CD3 zeta chain intracellular domain
AGAGT GAAGTTCAGC AGGAGCGCAG AGCCCCCCGC GTACCAGCAG GGCCAGAACC AGCTCTATAA
CGAGCTCAAT CTAGGACGAA GAGAGGAGTA CGATGTTTTG GACAAGAGAC GTGGCCGGGA CCCTGAGATG
GGGGGAAAGC CGAGAAGGAA GAACCCTCAG GAAGGCCTGT ACAATGAACT GCAGAAAGAT AAGATGGCGG
AGGCCTACAG TGAGATTGGG ATGAAAGGCG AGCGCCGGAG GGGCAAGGGG CACGATGGCC TTTACCAGGG
TCTCAGTACA GCCACCAAGG ACACCTACGA CGCCCTTCAC ATGCAGGCCC TGCCCCCTCG
(SEQ ID NO:33)

(G4S)3 serine-glycine linker
GGTG GAGGTGGATC AGGTGGAGGT GGATCTGGTGGAGGTGGATC T (SEQ ID NO:34)

CD8 transmembrane domain
GCGGCCGCAC CCACCACGAC GCCAGCGCCG CGACCACCAA CCCCGGCGCC CACGATCGCG TCGCAGCCCC
TGTCCCTGCG CCCAGAGGCG TGCCGGCCAG CGGCGGGGGG CGCAGTGCAC ACGAGGGGGC TGGACTTCGC
CTGTGATATC TACATCTGGG CGCCCTTGGC CGGGACTTGT GGGGTCCTTC TCCTGTCACT GGTTATCACC
CTTTACTGCA ACCAC (SEQ ID NO:35)

CD28 transmembrane + intracellular domains (-STOP)
CAA TTGAAGTTAT GTATCCTCCT CCTTACCTAG ACAATGAGAA GAGCAATGGA ACCATTATCC
ATGTGAAAGG GAAACACCTT TGTCCAAGTC CCTATTTCC CGGACCTTCT AAGCCCTTTT GGGTGCTGGT
GGTGGTTGGT GGAGTCCTGG CTTGCTATAG CTTGCTAGTA ACAGTGGCCT TTATTATTTT CTGGGTGAGG
AGTAAGAGGA GCAGGCTCCT (SEQ ID NO:36)

```
4401  TTAATGAATC TCAAAGACAG TAATTGCAAA GGAAGGAGTC AACTGTTGTA TTTACGCGAC GACTCGTTCG GTCAAACGTA GACAGTCCTA GTTAAAGGGT
      TTATGCCAGT CATATTAATT ACTAGTCAAT TAGTTGATTT TTATTTTTGA CATATACATG TGAATGAAAG ACCCCACCTG TAGGTTTGGC AAGCTAGCTT
4501  AATACGGTCA GTATAATTAA TGATCAGTTA ATCAACTAAA AATAAAAACT GTATATGTAC ACTTACTTTC TGGGGTGGAC ATCCAAACCG TTCGATCGAA
      AAGTAACGCC ATTTTGCAAG GCATGGAAAA ATACATAACT GAGAATAGAA AAGTTCAGAT CAAGGTCAGG AACAGATGGA ACAGCTGAAT ATGGGCCAAA
4601  TTCATTGCGG TAAAACGTTC CGTACCTTTT TATGTATTGA CCCTTATCTT TTCAAGTCTA ATGGAACAGC GTTGTCTACCT TGTCGACTTA TACCCGGTTT
      CAGGATATCT GTGGTAAGCA GTTCCTGCCC CGGCTCAGGG GCCGAGTCCC CCAAGACAGC TGAATATGGG CCAAACAGGA TATCTGTGGT AAGCAGTTCC
4701  GTCCTATAGA CACCATTCGT CAAGGACGGG AACAGATGGT GGTCTTGTCG TACCTTGTCG ACTTATACCC GGTTTGTCCT ATAGACACCA TTCGTCAAGG
      TGCCCCGGCT CAGGGCCAAG GTCCCGGTTC TTGTCTACCA GGGGTTACGG CCAGGTCGGG AGTCGTCAAA GATCTCTTGG TAGTCTACAA AGGTCCCAAG
4801  ACGGGGCCGA GTCCCGGTTA CTGTGCCTTA TTTGAACTAA CCAATCAGTT CGCTTCGTCG TTCGTTCGC GCGCTATGC TCCCCGAGCT CAATAAAAGA GCCCACAACC
      TGAAATGACC CTGTGCCTTA AAACTTGATT GGTTAGTCAA GCGAAGAGCG CGGGTACCCG AAGACAAGCG CGGAATACG AGGGGCTCGA GTTATTTTCT CGGGTGTTGG
4901  ACTTTACTGG GACACGGAAT CTCCGATTGA GAGGTAACT CTGAGTCGCC GCCCATGGGC ACATAGGTTA TTTGGGAGAA CGTCAACGTA GGCTGAACAC CAGAGCGACA
      CCTCACTCGG CGCGCCAGTC GAGGTAACT CTGAGTCGCC GCCCATGGGC ACATAGGTTA TTTGGGAGAA CGTCAACGTA GGCTGAACAC CAGAGCGACA
5001  GGAGTGAGCC CCGCGGTCAG GGTCTCCTCT GAGTGATTGA CTACCGTCA GCGGGGGTCT TTCATTTGGG GGCTCGTCCG GGATCGGGAG ACCCCTGCCC AGGGACCACC
      TCCTTGGGAG GGTCTCCTCT GAGTGATTGA CTACCGTCA GCGGGGGTCT TTCATTTGGG GGCTCGTCCG GGATCGGGAG ACCCCTGCCC AGGGACCACC
5101  AGGAACCCTC CCAGAGGAGA CTCACTAACT GATGGGCAGT CGCCCCAGA AAGTAAACCC CCGAGCAGGC CCTAGCCCTC TGGGGACGGG TCCCTGGTGG
      GACCACCAC CGGGAGGTAA GCTGGCCAGC AACTTATCTG TGTCTGTCCG ATTGTCTAGT GTCTATGACT GATTTTATGC GCCTGCGTCG GTACTAGTTA
5201  CTGGGTGGTG GCCCTCCATT CGACCGGTCG TTGAATAGAC ACAGACAGC TAACAGATCA CAGATACTGA CTAAAATACG CGGACGCAGC CATGATCAAT
      GCTAACTAGC TCTGTATCTG GCGGACCCGT GGTGGAACTG ACGAGTTCGG AACACCCGGC CGCAACCCTG GGAGACGTCC CAGGGACTTC GGGGGCCGTT
5301  CGATTGATCG AGACATAGAC CGCCTGGGCA CCACCTTGAC TGCTCAAGCC TTGGGCCG GCGTTGGGAC CCTCTGCAGG GTCCCTGAAG CCCCGGCAA
      TTTGTGGCCC GACCTGAGTC CTAAATCCC GATCGTTTAG GACTCTTTGG TGCACCCCCC ACGTGGGGGG AATCTCCTCC GATATGTGGT TCTGTAGGA GACGAGAACC CTGCTCTTGG
5401  AAACACCGGG CTGGACTCAG GATTTTAGGG TCTGAATTTT TGCTTTCGGT TGGGACCGA AGCCGCGCCG CGGGTCGTGT CTGCTGCAGC ATCGTTCGT GTTCGTCTG
      TAAAACAGTT CCCGGCCTCG TCTGAATTTT TGCTTTCGGT TGGGACCGA AGCCGCGCCG CGGGTCGTGT CTGCTGCAGC ATCGTTCGT GTTCGTCTG
5501  ATTTTGTCAA GGGCGGAGGC AGACTTAAAA ACGAAAGGCA AACCCTGGCT TCGGGGCCG GCGCAACACA CTTAAGTTTG ACCTTAGGTC TAGCAAGACA CAACAGAGAC
      TCTGACTGTG TTTCTGTATT TGTCTGAAAA ACAGACTTTT ATACCCGGAC CGGATCCGGC CGGATCCGGC CGGATCCGGC ACTGGAAAGA TGTCGAGCGG
5601  AGACTGACAC AAAGACATAA ACCAGTCGGT AGATGTCAAG AGATGTCAAG CGGATCCGGC CGGATCCGGC CGGATCCGGC TGAACCTTCT ACAGCTCGCC
      ATCGCTCACA ACCAGTCGGT TGTCAGCCA TCTACAGTTC ACCAGGTTA TGGGTCCAAG GGCGTCCAGC GGCGTCCAGC GCAAATTGCA CGGATGGCCG CGAGACGGCA
5701  CCTTTAACCG AGACCTCATC ACCAGGTTA TGGGTCCAAG GGCGTCCAGC GGCGTCCAGC GGCGTCCAGC GCAAATTGCA CCAGGTCCCC TACATCGTGA CCTGGGAAGC
      GGAATTCGGC TCTGGAGTAG TGGGTCCAAG GGCGTCCAGC GGCGTCCAGC GGCGTCCAGC GCAAATTGCA CCAGGTCCCC TACATCGTGA CCTGGGAAGC
5801  CTTGGCTTTT GACCCCCCTC CCTGGGTCAA GGGGTCCAA GGCGTCCAGC GGCGTCCAGC GGCGTCCAGC GGTCCAGGGG ATGTAGCACT GGAACCTTCG
      GAACCGAAA CTGGGGGAG GGACCCCAGT GGGTCCAA GGCGTCCAGC GGCGTCCAGC GGCGTCCAGC AGGCGGGGCA GAGAGGGGGA ACTTGGAGGA
5901  CGTTCGACCC CGCCTCGATC CTCCCTTTAT GGCGTCCAAT GGCGTCCAAT GGCGTCCAAT GGCGTCCAAT GGCGTCCAAT ATATGGGGCA CCCCGCCCCC
      GCAAGCTCGG GGGAGCTAG GAGGGAAAT GGCGTCCAAT GGCGTCCAAT GGCGTCCAAT GGCGTCCAAT GGCGTCCAAT TATACCCCGT GGGGGCGGGG
```

```
6101  ACCTTCTGGCG GCAGCCTACC AAGAACAACT GGACCGACCG GTGGTACCTC ACCCTTACCG AGTCGGCGAC ACAGTGTGGG TCCGCCGACA CCAGACTAAG
      TGGAGACCGC CGTCGGATGG TTCTTGTTGA CCTGGCTGGC CACCATGGAG TGGGAATGGC TCAGCCGCTG TGTCACACCC AGGCGGCTGT GGTCTGATTC
                                                                                                        PmlI
                                                                                                        ----

6201  AACCTAGAAC CTGGCTGGAA AGGACTTGAA ACAGTCCTGC TGACCACCCC CACGGCCCTC AAAGTAGACG GCATCGCAGC GTCGGGCCAG GCCGCCCACG
      TTGGATCTTG GACCGACCTT TCCTGAACTT TGTCAGGACG ACTGGTGGGG GTGCCGGGAG TTTCATCTGC CGTAGCGTCG CAGCCCGGTC CGGCGGGTGC
                                                                                                        VH
                                                                                                        ----

CD8-Leader

6301  TGAAGGCTGC CGACCCCGGG GGTGGACCAT CCTCTAGAGT TCCCAGTGAC TGCCCAGGCT CCCAGTGGCTC TCCCAGTGAC CTTCCCCTAG CGCTTCTCCT GCATCCAGAG
      ACTTCCGACG GCTGGGGCCC CCACCTGGTA GGAGATCTGA AGGGTCACTG ACGGGTCCGA CGGGTCACTG ACGGGTCACTG AGGGTCACTG GCGAAGAGGA CGTACGTCTC
      PmlI                                        NcoI
      ----                                        ----                            VH

6401  GTGAAGCTGC AGGAGTCAGG CGGAGGCTTC GTGAAGCCTG GAGGTCCCCT CAAAGTCTCC CTGGATTCAC TTTCAGTAGC TATGCCATGT
      CACTTCGACG TCCTCAGTCC GCCTCCGAAG CACTTCGGAC CTCCAGGGGA GTTTCAGAGG GACCTAAGTG AAAGTCATCG ATACGGTACA
                                                                            VH

6501  CCTGGGTTCG CCTGAGTCCG GAGATGAGGC TGGAGTCGGT CAAAGTCTCC AGCAGTGGTA TGGGTTACAT CTTCTATTCT GACAGTGTGC AGGGACGATT
      GGACCCAAGC GGACTCAGGC CTCTACTCCG ACCTCAGCCA GTTTCAGAGG TCGTCACCAT ACCCAATGTA GAAGATAAGA CTGTCACACG TCCCTGCTAA
                                                                            VH

6601  CACCATTTCC AGAGACAATG CCAAGAACAC CCTGCACCTG TGGGGACACG GTCTGACCTTC TGGGGACAGG ACCCCTGTGC GCCATGTATT ACTGTGCAAG GCAGGGATTT
      GTGGTAAAGG TCTCTGTTAC GGTTCTTGTG GGACGTGGAC ACCCCTGTGC CAGACTGGAAG ACCCCCTGTCC TGGGGACACG CGGTACATAA TGACACGTTC CGTCCCTAAA
                                                                                                     (G4S)3 Glycine-Serine Linker
                                                                            VH 6701  GGTAACTACG GTGATTACTA TGCTATGGAC TACTGGGGCC AAGGGACCAC GGTCACCGTC TCCTCAGGTG GAGGTGGATC AGTGGAGGT GGATCTGGTG
      CCATTGATGC CACTAATGAT ACGATACCTG ATGACCCCGG TTCCCTGGTG CCAGTGGCAG AGGAGTCCAC CTCCACCTAG TCACCTCCA CCTAGACCAC
                                                                                VL
```

7701 TTGGGATGAA AGGGAGCGC CGGAGGGGCA AGGGGCACGA TGGCCTTTAC CAGGGTCTCA GTACAGCCAC CAAGGACACC TACGACGCCC TTCACATGCA
AACCCTACTT TCCGCTCGCG GCCTCCCGT TCCCCGTGCT ACCGGAAATG GTCCCAGAGT CATGTCGGTG GTTCCTGTGG ATGCTGCGGG AAGTGTACGT
CD3 zeta chain intracellular domain XhoI

7801 GGCCCTGCCC CCTCGCTAAC AGCCACTCGA G
     CCGGGACGGG GGAGCGATTG TCGGTGAGCT C

Figure 19 top strand: SEQ ID NO:39
Figure 19 bottom strand: SEQ ID NO:40

1. Mouse MUC16-CD Peptide 1 (SEQ ID NO:21):

TLDRKSVFVDGYSQNRDD  19 AA

2. Mouse 1$^{st}$ Cysteine Loop peptide 2 (SEQ ID NO:22):

KSYFSDCQVLAFRSVSNNNNHTGVDSLCNFSPL  33 AA

3. Mouse 2$^{nd}$ Cysteine Loop peptide 3 (SEQ ID NO:23):

SLYSNCRLASLRPKKNGTATGVNACSYHQN  32 AA

Fig. 20B
Alignment of mouse MUC16 (SEQ ID NO:24) and human MUC16 (SEQ ID NO:25) amino acid sequences Fig. 21
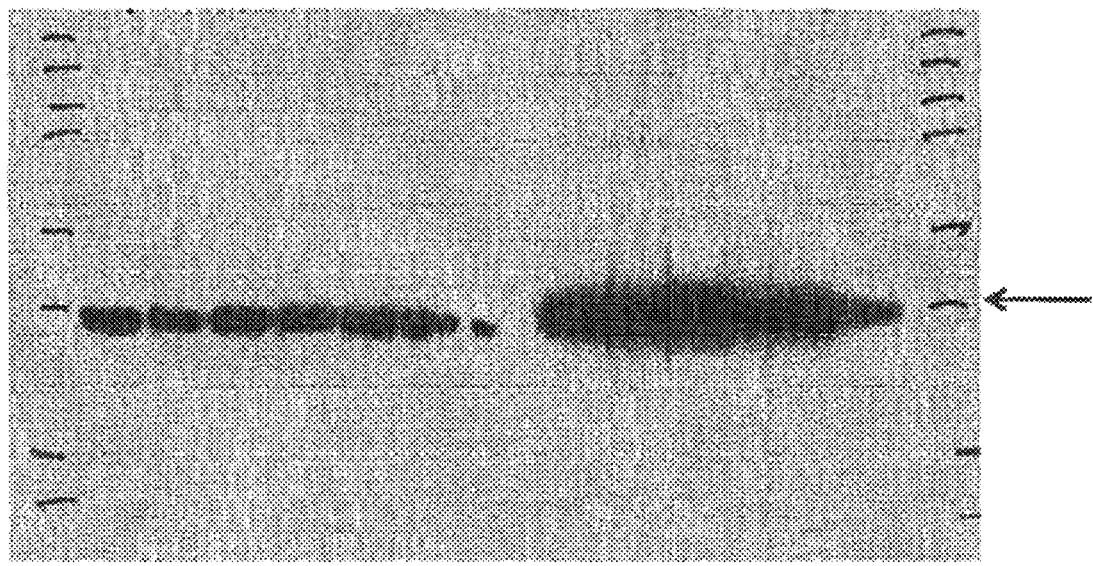
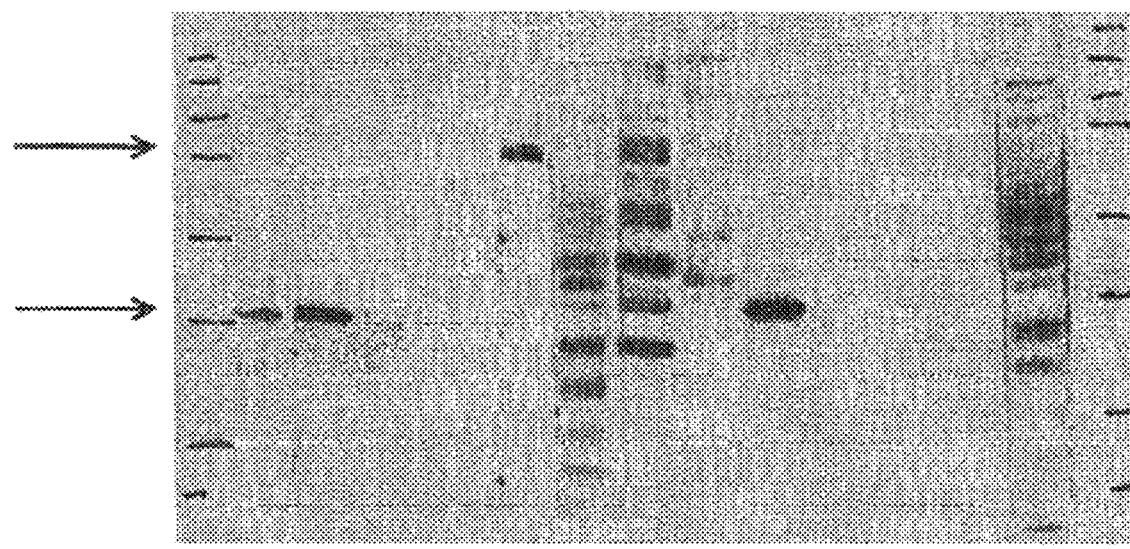

FIG. 23 (CONTD.)

A Nucleotide sequence encoding 12B10.3G10-V$_H$ (SEQ ID NO:26)

```
GAGGTGAAGCTGGAGGAGTCAGGTGGAGGATTGGTGCAACCTAAAGGATCATTGAAACTCTCTTGTGCCGCTTCT
GGTTTCACCTTCAATACCTATGCCGTGCACTGGGTCCGCCAGCCTCCAGGAAAGGGTATGGAATGGGTTGCTCGC
ATAAGAAGTAAAAGTGGAAATTATGCAACATATTATGCCGATTCAGTGAAAGACAGATTCACCATCTCCAGAAAT
GATTCACAGAGCATGCTCTATCTGCAAATGAACAACCTGAAAACTGAGGACACAGCCATATATTACTGTGTGAGA
GCGGGTAACAACGGGGCTTTTCCTTACTGGGGCCAAGGGACCACGGTCACCGTCTCCTCA
```

B 12B10.3G10-V$_H$ Amino Acid sequence (SEQ ID NO:27)

EVKLEESGGGLVQPKGSLKLSCAASGFTFNTYAVHWVRQAPGKGMEWVARIRSKSGNYAT
YYADSVKDRFTISRNDSQSMLYLQMNNLKTEDTAIYYCVRAGNNGAFPYWGQGTTVTVSS

C Nucleotide sequence encoding 12B10.3G10-V$_L$ (SEQ ID NO:28)

Note the VL has an optional NotI site added by the primer for
cloning.

```
GACATTGAGCTCACCCAGTCTCCATCCTCACTGTCTGCATCTCTGGGAGGCAGAGTCACCATCACTTGCAAGGCT
AGCCAAGATATTAAGAAGTATATAGCTTGGTACCAACACAAGCCTGGAAAAACTCCTCGACTACTCATACATTTC
ACATCTACATTACAGACAGGCATCCCATCAAGGTTCAGTGGACGTGGGTCTGGGACAGACTATTCTTCAGCATC
AGCAACCTGGAGTCTGAAGATATTGCAACTTATTATTGTCTACAGTATGATAGTCTGTACACGTTCGGAGGGGGG
ACCAAGCTGGAAATCAAACGGGCGGCCGCA
```

D 12B10.3G10-V$_L$ Amino Acid sequence (SEQ ID NO:29)

DIELTQSPSSLSASLGGRVTITCKASQDIKKYIAWYQHKPGKTPRLLIHFTSTLQTGIPS
RFSGRGSGRDYSFSISNLESEDIATYYCLQYDSLYTFGGGTKLEIKRAAA

FIGS. 24A-24D

ANTIBODIES TO MUC16 AND METHODS OF USE THEREOF

This application is a divisional of U.S. patent application Ser. No. 15/695,311, filed Sep. 5, 2017, which is a divisional of U.S. patent application Ser. No. 14/850,675, filed Sep. 10, 2015, issued as U.S. Pat. No. 9,790,283, which is a divisional of U.S. patent application Ser. No. 13/635,090, issued as U.S. Pat. No. 9,169,328, national stage of International Application No. PCT/US2011/030025, filed Mar. 25, 2011, which claims benefit of U.S. Provisional Application No. 61/317,964, filed Mar. 26, 2010, each of which are incorporated by reference herein in their entirety.

This invention was made with government support under grant number CA052477-16 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 16, 2021, 115872-2059_Sequence_Listing.txt and is 190 kilobytes in size.

FIELD OF THE INVENTION

The invention relates to antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

BACKGROUND OF THE INVENTION

Cell surface markers and shed antigens are used in the diagnosis of several cancers. For example, the CA125 antigen, recognized by the OC125 antibody, is a tissue-specific, circulating antigen expressed in ovarian cancer. The CA125 antigen is encoded by the MUC16 gene, cloned by Lloyd and Yin. The full-length gene describes a complex tethered mucin protein present primarily in a variety of gynecologic tissues, especially neoplasms. OC125 and other related antibodies react with glycosylation-dependent antigens present exclusively in the cleaved portion of the molecule.

A serum assay can detect elevated levels of the circulating CA125 antigen in many epithelial ovarian cancer patients, and this antigen, derived using the ovarian cell line OVCA433, is recognized by the OC125 antibody (1-2). The detection of circulating CA125 in scrum has proven to be a useful tool for the management of ovarian cancer patients and clinical trials (3-4). However, CA125 is neither sufficiently sensitive nor specific for general cancer screening (5-6). A variety of CA125 linked antibodies including VK8 and M11 have subsequently been defined as present on ovarian cancer cells (7-9). Although these antibodies have been used to develop serum assays and various other studies in ovarian cancer, they have significant shortcomings for clinical use in screening or tissue delivery. These antibodies are not useful as screening tools, nor can they detect the proximal residual MUC16 protein fragment after cleavage. This has limited their diagnostic and therapeutic applications.

For example, OC125, M11, and most other antibodies prepared against ovarian cancer cell extracts are directed at complex, glycosylation-dependent antigens. These antigens are exclusively present in the shed portion of MUC16 and cannot be employed to follow the biology of the proximal portion of MUC16 and may not accurately reflect tissue distribution since the glycosylation patterns can vary substantially among tissues. Because the vast majority of MUC16-reactive antibodies, including OC125, react with the glycosylation-dependent antigen present exclusively in the cleaved portion of the molecule, the true distribution of MUC16 expression is not known (21). There is currently no antibody available to track the fate of the remaining MUC16 protein fragment after cleavage and CA125 release.

Thus, there remains a need for the identification of antibodies that are directed against sequences in the peptide backbone of MUC16, and that are useful for diagnosis and treatment of cancers in which MUC16 is expressed and/or overexpressed.

SUMMARY OF THE INVENTION

The invention provides an antibody, or an antigen-binding fragment thereof, that specifically binds to a polypeptide, or antigenic portion thereof, wherein the polypeptide is selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19). In one embodiment, the antibody internalizes into a cell. While not intending to limit the invention to a particular sequence of MUC 16 ectodomain, in one embodiment, the MUC16 ectodomain polypeptide comprises a polypeptide selected from the group of Polypeptide 1 NFSPLARRVDRVAIYEE (SEQ ID NO:01) and Polypeptide 2 TLDRSSVLVDGYSPNRNE (SEQ ID NO:02). In another embodiment, the antibody lacks specific binding to a glycosylated MUC16 extracellular domain. In yet a further embodiment, the antibody specifically binds to the Polypeptide 2 (SEQ ID NO:02) of the MUC16 ectodomain polypeptide, and wherein the antibody comprises a variable heavy ($V_H$) chain encoded by SEQ ID NO:06, and a variable light ($V_L$) chain encoded by SEQ ID NO:07. In yet another alternative embodiment, the antibody specifically binds to the Polypeptide 2 (SEQ ID NO:02) of the MUC16 ectodomain polypeptide, and wherein the antibody comprises a variable heavy ($V_H$) chain encoded by SEQ ID NO:04, and a variable light ($V_L$) chain encoded by SEQ ID NO:05. In a further embodiment, the antibody specifically binds to the Polypeptide 1 (SEQ ID NO:01) of the MUC16 ectodomain polypeptide, and wherein the antibody comprises a variable heavy ($V_H$) chain encoded by SEQ ID NO:08, and a variable light ($V_L$) chain encoded by at least one of SEQ ID NO:09 and SEQ ID NO:10. In one embodiment, the MUC16 cytoplasmic domain polypeptide comprises VTTRR RKKEGEYNVQ QQ (SEQ ID NO:18). More preferably, but without limitation, the MUC16 cytoplasmic domain polypeptide comprises Polypeptide 3 CGVLVTTRRRKKEGEYNVQQQ (SEQ ID NO:03). In an alternative embodiment, the MUC16 extracellular domain polypeptide that contains a cysteine loop polypeptide comprises CQVSTFRSVPNRHHTGVDSLC (SEQ ID NO:19). More preferably, but without limitation, the MUC16 extracellular domain polypeptide comprises Polypeptide 4 KSYF SDCQVSTFRS VPNRHHTGVD SLCNFSPL (SEQ ID NO:15). In yet another alternative embodiment, the antibody specifically binds to the Polypeptide 4 (SEQ ID NO:15) of the MUC16 extracellular domain polypeptide, and wherein the antibody comprises a variable heavy ($V_H$) chain encoded by SEQ ID NO:11, and a variable light ($V_L$) chain encoded by SEQ ID NO:12. In a further alternative embodiment, the antibody is selected from the group of a chimeric antibody, a monoclonal antibody, a recombinant antibody, an antigen-binding fragment of a recombinant antibody, a humanized antibody, and an antibody displayed upon the surface of a phage. In another embodiment, the antigen-binding fragment is selected from the group of a Fab fragment, a F(ab')2 fragment, and a Fv fragment. In an alternative embodiment, the antibody, or antigen-binding fragment thereof, is covalently linked to a cytotoxic agent or a prodrug of a cytotoxic agent. In a preferred embodiment, the antibody is a monoclonal antibody produced by a hybridoma cell line.

The invention also provides an isolated monoclonal antibody, or an antigen-binding fragment thereof, produced by a hybridoma cell line, wherein the antibody specifically binds to a polypeptide, or antigenic portion thereof, wherein the polypeptide is selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19). In one embodiment, the MUC16 ectodomain polypeptide comprises Polypeptide 1 (SEQ ID NO:01) and the antibody is selected from the group of 9B11.20.16, 10A2, 2F4, 23D3, 30B1, and 31B2. In an alternative embodiment, the MUC16 ectodomain polypeptide comprises Polypeptide 2 (SEQ ID NO:02), and wherein the antibody is selected from the group of 4H11.2.5, 13H1, 29G9, 9C9.21.5.13, 28F8, 23G12, 9C7.6, 11B6, 25G4, 5C2.17, 4C7, 26B2, 4A5.37, 4A2, 25H3, and 28F7.18.10. In yet a further embodiment, the MUC16 cytoplasmic domain polypeptide comprises Polypeptide 3 CGVLVTTRRRKKEGEYNVQQQ (SEQ ID NO:03), and wherein the antibody is selected from the group of 31A3.5.1, 19D1, 10F6, 22E10, 22F1, 3H8, 22F11, 4D7, 24G12, 19G4, 9A5, 4C2, 31C8, 27G4, and 6H2. In another alternative embodiment, the MUC16 extracellular domain polypeptide comprises Polypeptide 4 KSYF SDCQVSTFRS VPNRHHTGVD SLCNFSPL (SEQ ID NO:15), and wherein the antibody is selected from the group of 24B3 and 9C7.

The invention additionally provides a composition comprising (a) any one or more of the antibodies, or antigen-binding fragments thereof, that are described herein, and (b) a pharmaceutically acceptable carrier.

Also provided by the invention is a hybridoma cell line that produces a monoclonal antibody that specifically binds to a polypeptide, or antigenic portion thereof, selected from the group of a) MUC16 ectodomain polypeptide, b) MUC16 cytoplasmic domain polypeptide, and c) MUC16 extracellular domain polypeptide that contains a cysteine loop polypeptide CQVSTFRSVPNRHHTGVDSLC (SEQ ID NO:19).

The invention additionally provides a method for detecting a disease that comprises overexpression of MUC16 in a subject, comprising a) providing i) a sample from a subject, and ii) any one or more of the antibodies, or antigen-binding fragments thereof, that are described herein, b) contacting the sample with the antibody under conditions for specific binding of the antibody with its antigen, and c) detecting an increased level of binding of the antibody to the sample compared to a control sample lacking the disease, thereby detecting the disease in the subject. In one embodiment, the disease is cancer. In a preferred embodiment, the cancer is selected from the group of ovarian cancer and breast cancer. While not intending to limit the method of detection, in one embodiment, detecting binding of the antibody to the sample is immunohistochemical, enzyme-linked immunosorbent assay (ELISA), fluorescence-activated cell sorting (FACS), Western blot, immunoprecipitation, and/or radiographic imaging.

Also provided herein is a method for treating a disease that comprises overexpression of MUC16, comprising administering to a subject having the disease a therapeutically effective amount of any one or more of the antibodies, or antigen-binding fragments thereof, that are described herein. In one embodiment, the disease is cancer, as exemplified by ovarian cancer and breast cancer.

The invention also provides an isolated antibody, or an antigen-binding fragment thereof, that specifically binds to a MUC16 polypeptide or to an antigenic portion thereof, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS, e) TLDRSSVLVDGYSQNRDD, and f) TLDRSSVLVDGYSQNRDD. In one embodiment, the antibody is selected from the group of a monoclonal antibody, a chimeric antibody, a recombinant antibody, an antigen-binding fragment of a recombinant antibody, a humanized antibody, and an antibody displayed upon the surface of a phage. In a preferred embodiment, the antibody is a monoclonal antibody produced by hybridoma cells selected from the group of 12B10-3G10, 10C4-3H5, 10C4-1F2, 10C4-2H8, 10C4-1G7, 17F2-3G5, 17F2-3F6, 17F2-2F9, 17F2-1E11, 12B10-3F7, 12B10-2F6, 12B10-2F10, 25E9-3, 25E9-5, 25E9-1, 25E9-16, 21B8-1H11, 21B8-3G6, 21B8-3H9, 21B8-1G8, 21E1-1E3, 21E1-1G9, 21E1-2G7, 21E1-3G12, 4H1-2E1, 4H1-2E3, 4H1-3E1, 4H1-3H3, 15A8-2E2, 15A8-2E10, 15A8-2E11, 15A8-3D2, 22B5-1F6, 22B5-3G9, 22B5-2G8, and 22B5-3F11. In a particular embodiment, the MUC16 polypeptide is TLDRKSVFVDGYSQNRDD (SEQ ID NO:21), and the antibody comprises a variable heavy ($V_H$) chain sequence SEQ ID NO:27, and a variable light ($V_L$) chain sequence SEQ ID NO:29, such as the monoclonal antibody produced by hybridoma cell 12B10-3G10. In an alternative embodiment, the antigen-binding fragment is selected from the group of a Fab fragment, a F(ab')2 fragment, and a Fv fragment. In a more preferred embodiment, the antibody, or antigen-binding fragment thereof, is covalently linked to a cytotoxic agent and/or to a prodrug of a cytotoxic agent. In a further embodiment, the antibody specifically binds to human MUC16 (SEQ ID NO:25). In another embodiment, the antibody internalizes into a cell. In an alternative embodiment, the antibody lacks specific binding to a glycosylated MUC16 extracellular domain.

The invention also provides a composition comprising (a) any one or more of the invention's antibodies and/or antigen-binding fragments thereof, and (b) a pharmaceutically acceptable carrier.

The invention further provides a hybridoma cell that produces an antibody, or an antigen-binding fragment thereof, that specifically binds to a MUC16 polypeptide or to an antigenic portion thereof, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNA- ICSYHQN (SEQ ID NO:23), d) KSYFSDCQVNNFRS, e) TLDRSSVLVDGYSQNRDD, and f) TLDRSSVLVDGYSQNRDD.

The invention also provides an isolated nucleotide sequence comprising a polynucleotide that encodes at least one of a variable heavy ($V_H$) chain sequence and the variable light ($V_L$) chain sequence of an antibody that specifically binds to a MUC16 polypeptide, wherein the MUC16 polypeptide is selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS, e) TLDRSSVLVDGYSQNRDD, and 0 TLDRSSVLVDGYSQNRDD. In one embodiment, the MUC16 polypeptide is TLDRKSVFVDGYSQNRDD (SEQ ID NO:21) and the polynucleotide encoding the variable heavy ($V_H$) chain sequence comprises SEQ ID NO:26, and wherein the polynucleotide encoding the variable light ($V_L$) chain sequence comprises SEQ ID NO:28.

The invention also provides a method for producing an antibody that specifically binds to a MUC16 polypeptide or to an antigenic portion thereof, comprising administering to a subject an immunologically effective amount of a MUC16 polypeptide selected from the group of a) TLDRKSVFVDGYSQNRDD (SEQ ID NO:21), b) KSYFSDCQVLAFRSVSNNNNHTGVDSLCNFSPL (SEQ ID NO:22), c) SLYSNCRLASLRPKKNGTATGVNAICSYHQN (SEQ ID NO:23), d) KSYFSDCQVNNFRS, e) TLDRSSVLVDGYSQNRDD, and f) TLDRSSVLVDGYSQNRDD.

The invention additionally provides a method for identifying a subject as having disease, comprising determining the level, in a sample from the subject, of specific binding of any one or more of the invention's antibodies and/or antigen-binding fragments thereof, with the MUC16 polypeptide or with the antigenic portion thereof, wherein detecting an altered level of the specific binding relative to a control sample identifies the subject as having disease. In one embodiment, the disease is cancer exemplified by ovarian cancer and breast cancer. In another embodiment, the method further comprises detecting an altered level of binding of the antibody to the sample compared to a control sample. Optionally, the detecting is selected from the group of immunohistochemistry, enzyme-linked immunosorbent assay (ELISA), fluorescence-activated cell sorting (FACS), Western blot, immunoprecipitation, and radiographic imaging.

The invention also provides a method for reducing one or more symptoms of disease comprising administering to a subject in need thereof a therapeutically effective amount of any one or more of the invention's antibodies and/or antigen-binding fragment thereof In one embodiment, the disease is cancer, exemplified by ovarian cancer and breast cancer. Optionally, the method further comprises detecting a reduction in one or more symptoms of the disease after the administration step.

BRIEF DESCRIPTION OF THE DRAWINGS

FIG. 1: Three MUC16 carboxy terminus peptides were synthesized at the MSKCC Microchemistry Core Facility. Polypeptide 1 is near the putative cleavage site, Polypeptide 2 is before the transmembrane, and Polypeptide 3 is the internal peptide, which is inside the transmembrane.

FIG. 2: Comparison staining of high-grade serous ovarian carcinomas using OC125 (left panel) and 4H11 (right panel)

FIG. 3A: OC125 (Score 0); FIG. 3B: OC125 (Score 1); FIG. 3C: OC125 (Score 2); FIG. 3D: OC125 (Score 3); FIG. 3E: OC125 (Score 4); FIG. 3F: OC125 (Score 5); FIG. 3G: 4H11 (Score 0); FIG. 3H: 4H11 (Score 1); FIG. 3I: 4H11 (Score 2); FIG. 3J: 4H11 (Score 3); FIG. 3K: 4H11 (Score 4); FIG. 3L: 4H11 (Score 5).

FIG. 4A: Western blot analysis of GST-$\Delta$MUC16$^{c114}$ fusion protein with monoclonal antibodies 9C9.21.5.13 and 4H11.2.5. FIG. 4B: Western blot analysis of SKOV3-phrGFP-$\Delta$MUC16$^{c114}$ and SKOV3-phrGFP-$\Delta$MUC16$^{c334}$ protein extract and probed with monoclonal antibodies 9C9.21.5.13 and 4H11.2.5.

FIGS. 7A-7D: FACS analysis as described in the Material and Methods section was performed with commercial antibodies and MUC16 carboxy terminus monoclonal antibodies on OVCAR3 wt, SKOV3-phrGFP-$\Delta$MUC16$^{c114}$ and SKOV3-phrGFP-$\Delta$MUC16$^{c334}$ stable transfected cell lines.

FIG. 8: Nucleotide sequence encoding antibody variable heavy ($V_H$) chain and antibody variable light ($V_L$) chain. (A) 4A5 $V_H$ (SEQ ID NO:04), (B) 4A5 $V_L$ (SEQ ID NO:05), (C) 4H11 $V_H$ (SEQ ID NO:06), (D) 4H11 $V_L$ (SEQ ID NO:07), (E) 9B11 $V_H$ (SEQ ID NO:08), (F) 9B11 $V_{L,A}$ (SEQ ID NO:09), (G) 9B11 $V_{L,B}$ (SEQ ID NO:10), (H) 24B3 $V_H$ (SEQ ID NO:11), (I) 24B3 $V_L$ (SEQ ID NO:12).

FIG. 9: (A) *Homo sapiens* MUC16 (GenBank NP 078966) (SEQ ID NO:13), (B) Polypeptide 1 (SEQ ID NO:01), (C) Polypeptide 2 (SEQ ID NO:02), (D) Polypeptide 3 (SEQ ID NO:03), (E) Transmembrane domain (SEQ ID NO:14), (F) Polypeptide 4 (SEQ ID NO:15) containing a cysteine loop polypeptide (SEQ ID NO: 19).

(FIG. 11A) Schematic diagram of the first generation 4H11z and second generation 4H11-28z retroviral vectors. 4H11scFv: MUC16 specific scFv derived from the heavy ($V_H$) and light ($V_L$) chain variable regions of the monoclonal antibody 4H11; CDS: CD8 hinge and transmembrane domains; CD28: CD28 transmembrane and cytoplasmic signaling domains; ζ chain: T cell receptor ζ chain cytoplasmic signaling domain; LTR: long terminal repeat; black box: CD8 leader sequence; grey box: (Gly$_4$Ser)$_3$ linker; arrows indicate start of transcription. (FIG. 11B) FACS analysis of human T cells retrovirally transduced to express either the 4H11z or 19z1 CAR. (FIG. 11C) 4H11z$^+$ but not 19z1$^+$ T cells expand on 3T3 (MUC-CD/B7.1) AAPC. CAR$^+$ were co-cultured on 3T3(MUC-CD/B7.1) AAPC monolayers at 3×10$^6$ CAR$^+$ T cells/well of a 6 well plate. Proliferation of CAR$^+$ T cells, normalized to the CAR$^+$ T cell fraction as assessed by FACS for the CAR$^+$ fraction in combination with viable T cell counts obtained on days 2, 4 and 7, as assessed by trypan blue exclusion assays.

(FIG. 12A) CAR$^+$ T cells were co-cultured on MUC-CD monolayers with (right panel) or without B7.1 (left panel). 3×10$^6$ CAR$^+$ T cells were co-cultured on AAPC monolayers in 6 well tissue culture plates in cytokine-free medium. Total viable T cell counts were assessed on days 2, 4 and 7, by trypan blue exclusion assays. 4H11-28z$^+$ T cells markedly expanded when compared to 4H11z$^+$ T cells upon co-culture with 3T3(MUC-CD) AAPCs, p=0.0023 (4H11 z compared to 4H11-28z). In contrast, both 4H11z$^+$ and 4H11-28z$^+$ T cells expanded similarly on 3T3(MUC-CD/B7.1) AAPCs, p=0.09, (4H11z compared to 4H11-28z). Control 19-28z$^+$ T cells did not proliferate on 3T3(MUC-CD), p=0.0056 (19-28z compared to 4H11z), p=0.0011 (19-28z compared to 4H11-28z), or on 3T3(MUC-CD/B7.1), p=0.0026 (19-28z compared to 4H11z), p=0.0087 (19-28z compared to 4H11-28z). (FIG. 12B) 4H11-28z$^+$ but not 4H11z$^+$ T cells secrete IL-2 upon co-culture with 3T3(MUC-CD) AAPCs. Tissue culture supernatants at day 2 following activation on 3T3(MUC-CD) AAPCs were analyzed for cytokine secretion. 4H11-28z$^+$ T cells, in contrast to 4H11z$^+$ T cells, demonstrated enhanced secretion of IL-2 consistent with T cell co-stimulation mediated through the 4H11-28z CAR. *p=0.0008 (19z1 or 19-28z compared to 4H11z), p=0.0026 (19z1 or 19-28z compared to 4H11-28z), p=0.0046 (4H11z compared to 4H11-28z). Furthermore, both 4H11-28z$^+$ and 4H11z$^+$ T cells secreted IFNγ. *p=0.011 (4H11z compared to 4H11-28z). Control 19z1 and 1928z transduced T cells failed to secrete either IL-2 or IFNγ. p=0.0034 (19z1 compared to 4H11z), p=0.036 (19-28z compared to 4H11z), ***p=0.0008 (19-28z compared to 4H11-28z). (FIG. 12C) Expansion of CAR$^+$ T cells following 3 cycles of stimulation on 3T3(MUC-CD/B7.1). Human T cells transduced to express either 4H11z or 4H11-28z CARs demonstrated a >2 log expansion over 2 cycles of stimulation on 3T3(MUC-CD/B7.1) AAPCs. Arrows indicate 1st and 2nd cycles of restimulation on AAPCs. (FIG. 12D) FACS analysis of the CAR$^+$ T cell fraction of 4H11-28z$^+$ T cells increased following each weekly cycle of stimulation. (I) FACS following initial transduction, (II) FACS at 7 days following first stimulation on AAPCs, (III) FACS at 7 days following second stimulation on AAPCs. These data are representative of one of three different experiments using three different healthy donor T cell populations, all of which demonstrated similar proliferation and cytokine secretion patterns.

(FIG. 13A) Cytotoxicity assay of 4H11z$^+$ and 4H11-28z$^+$ T cells targeting OV-CAR (MUC-CD) tumor cells demonstrates efficient cytotoxicity mediated by T cells from healthy donors modified to express the first and second generation MUC-CD targeted CARs. Control T cells modified to express the first and second generation CD19-targeted 19z1 and 19-28z CARs failed to demonstrate significant lysis of target tumor cells. (FIG. 13B) Healthy donor T cells modified to express the 4H11-28z CAR equally lyse primary patient ascites-derived MUC-CD$^+$ tumor cells when compared to T cells modified to express the control 19-28z CAR. This data represents 1 or 3 experiments targeting primary tumor cells from 3 ovarian carcinoma patients with similar results. (FIG. 13C) Autologous T cells isolated from peripheral blood, when modified with the 4H11-28z CAR, exhibit significant lysis of autologous MUC-CD$^+$ ascites-derived tumor cells when compared to control 19-28z$^+$ autologous T cells. These data represent 1 of 3 experiments utilizing T cells and autologous tumor cells from 3 different ovarian carcinoma patients with similar results. (FIG. 13D) Antigen specific proliferation of MUC-CD targeted CFSE labeled T cells after co-culture with OV-CAR3(MUC-CD) tumor cells. CFSE labeled CAR$^+$ T cells were co-cultured with MUC-CD expressing OV-CAR3 tumor cells at 1:1 ratio for 5 days. Proliferation of CFSE labeled T cells was assessed by FACS demonstrating efficient proliferation of both 4H11z$^+$ and 4H11-28z$^+$ T cells but not control 19-28z$^+$ T cells. (FIG. 13E) CFSE results were further confirmed by absolute T cell numbers assessed on days 2, 4 and 7 following co-culture with OV-CAR3(MUC-CD) tumor cells. (FIG. 13F) FACS analysis of the expression of 4-1BBL on OVCAR3(MUC-CD) cells. OV-CAR3(MUC-CD) cells were stained with anti-human 4-1BBL antibody (thick line) or with isotype control (thin line). FACS analysis demonstrated expression of 4-1BBL on OV-CAR3(MUC-CD) tumor cells. Further FACS analyses failed to reveal expression of the co-stimulatory ligands B7.1, B7.2, or OX-40L.

(FIG. 14A) intra-peritoneal injection of OV-CAR3(MUC-CD) tumors in untreated SCID-Beige mice results in abdominal distension and nodular peritoneal tumors. SCID-Beige mice were injected intraperitoneally with 3×10$^6$ OV-CAR3(MUC-CD) cells. At 5 weeks post intraperitoneal injection of OV-CAR3 (MUC-CD) tumor cells mice developed ascites as evidenced by a distended abdomen (right panel) when compared to a tumor free mouse (left panel). Post mortem visualization of the peritoneum demonstrates nodular tumor masses within the abdominal cavity. (FIG. 14B) Intraperitoneal injection of 4H11z$^+$ and 4H11-28z$^+$ T cells either delay tumor progression or fully eradicate disease. Kaplan-Meier survival curve of SCID-Beige mice treated with first or second generation of MUC-CD targeted T cells. SCID-Beige mice were infused ip with 3×10$^6$ OV-CAR3(MUC-CD) tumor cells on day 1 followed by 3×10$^7$ 4H11z$^+$ or 4H11-28z$^+$ T cells on day 2. All untreated mice or mice treated with control 19z1$^+$ T cells developed established tumors and were sacrificed by day 50. In contrast, 27% of mice treated with either 4H11z$^+$ or 4H11-28z$^+$ T cells remained without clinical evidence of disease by day 120. *p=0.01 (4H11z compared to 19z1), **p=0.0023 (4H11-28z compared to 19z1), p=0.63 (4H11z compared to 4H11-28z).

(FIG. 15A) Kaplan-Meier survival curve of SCID-Beige mice treated ip or iv with 4H11-28z$^+$ T cells. SCID-Beige mice were injected intraperitoneally with 3×10$^6$ OV-CAR3(MUC-CD/GFP-FFLuc) tumor cells followed by either iv or ip infusion of 3×10$^7$ 4H11-28z$^+$ T cells. Tumor eradication is enhanced after either ip or iv infusion of 4H11-28z$^+$ T cells when compared to control treated mice. Both ip and iv 4H11-28z$^+$ T cell treated mice exhibited statistically enhanced survival (*p<0.0001 and p=0.0038, respectively) when compared to 19-28z$^+$ T cell treated control cohorts. Conversely, difference in survival between the ip and iv 4H11-28z$^+$ T cell cohorts was not statistically significant (p=0.22). (FIG. 15B) BLI of tumor progression of representative ip and iv 4H11-28z$^+$ T cell treated mice with ultimately progressive disease following treatment compared to BLI of tumor progression in a representative control 19-28z$^+$ T cell treated mouse.

(FIG. 15C) Systemically injected CFSE stained 4H11-28z+ T cells traffic to advanced ip OV-CAR (MUC-CD) tumors. Presence of iv injected CFSE labeled 19-28z+ control T cells (left panel) and 4H11-28z+ T cells (right panel) 1 day following infusion into SCID-Beige mice with advanced OV-CAR (MUC-CD) tumors (injected 7 days earlier), as assessed by FACS analysis of single cell OV-CAR3(MUC-CD) tumor suspensions, reveals a marked population of 4H11-28z+ but not control 19-28z+ T cells within peritoneal OV-CAR3(MUC-CD) tumors.

(FIG. 16A) BLI of 4H11-28z+ T cell treated mice with either relapsed disease (middle row) or eradicated disease (bottom row) compared to a representative 19-28z+ T cell treated control mouse. (FIG. 16B) Kaplan-Meier survival curve of SCID-Beige mice with advanced OV-CAR3(MUC-CD/GFP-FFLuc) tumors treated ip with 4H11-28z+ T cells. All 4H11-28z+ T cell treated mice demonstrated enhanced survival when compared to control 19-28z+ T cell treated mice (**p=0.0011), with an overall long-term survival of 25% at day 120.

FIG. 17: CD8 leader sequence (SEQ ID NO: 32), CD3 zeta chain intracellular domain sequence (SEQ ID NO: 33), (G4S)3 serine-glycine linker sequence (SEQ ID NO: 34), CD8 transmembrane domain sequence (SEQ ID NO: 35), and CD28 transmembrane+intracellular domains (-STOP) sequence (SEQ ID NO: 36).

FIG. 18: SFG 4H11z sequence.

FIG. 19: SFG-4H11-28z sequence.

FIGS. 20A-20B: (FIG. 20A) Mouse MUC16-CD Peptide 1 (SEQ ID NO:21), Mouse first Cysteine Loop Peptide 2 (SEQ ID NO:22), and Mouse second Cysteine Loop Peptide 3 (SEQ ID NO:23). (FIG. 20B) Alignment of mouse MUC16 (SEQ ID NO:24) and human MUC16 (SEQ ID NO:25) amino acid sequences. A cysteine was added to the peptide sequence at the N terminus of Peptide 1 and Peptide 3 for better conjugation with KLH.

FIG. 21: ID8 extract with 1:10 dilution of Mouse MUC16 monoclonal Primary Supernatants.

DEFINITIONS

Figure 3A:
FIGS. 3A-3L: Immunohistochemical scoring of OC125 and 4H11 on tissue microarrays of high-grade ovarian serous carcinoma. Only membranous and/or cytoplasmic staining was considered positive. Score 0: No staining; Score 1: <5% strong or weak; Score 2: 5-50% strong or weak; Score 3: 51-75% strong or 51-100% weak; Score 4: 76-99% strong; Score 5: 100% strong.
Figure 3B:
Figure 3C:
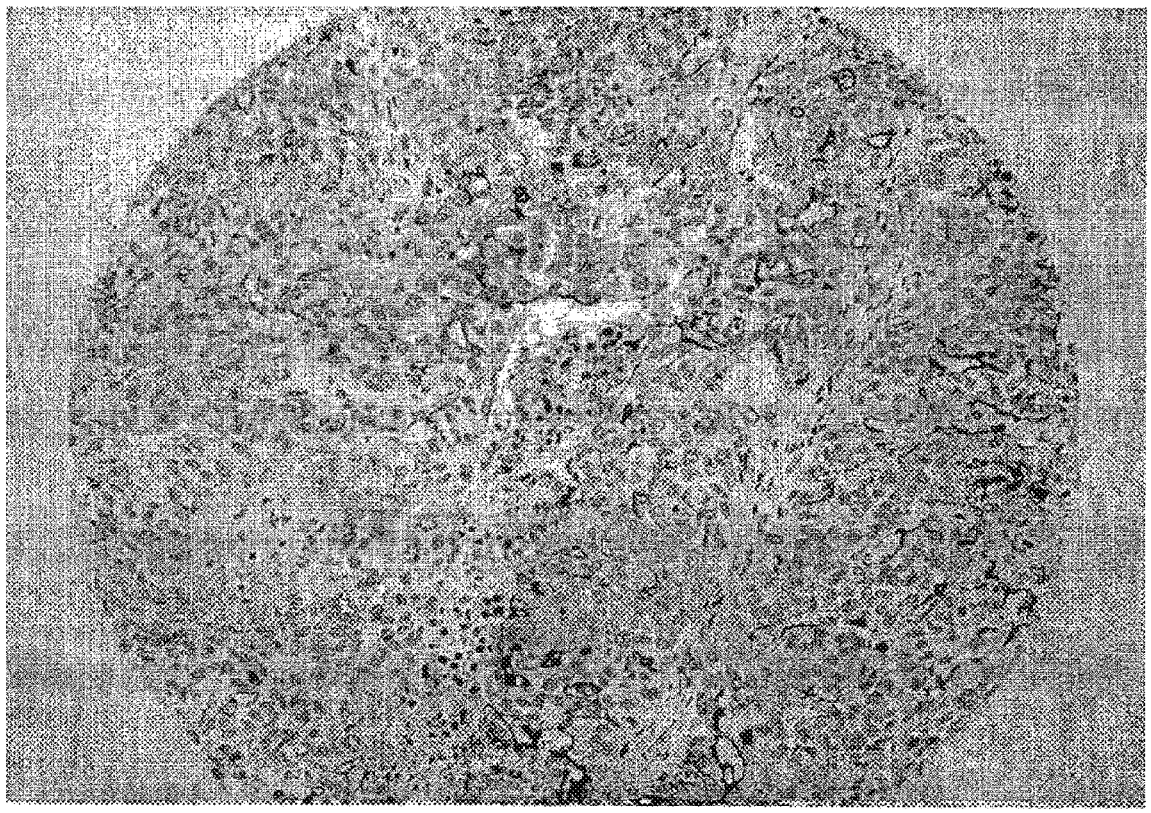
Figure 3D:
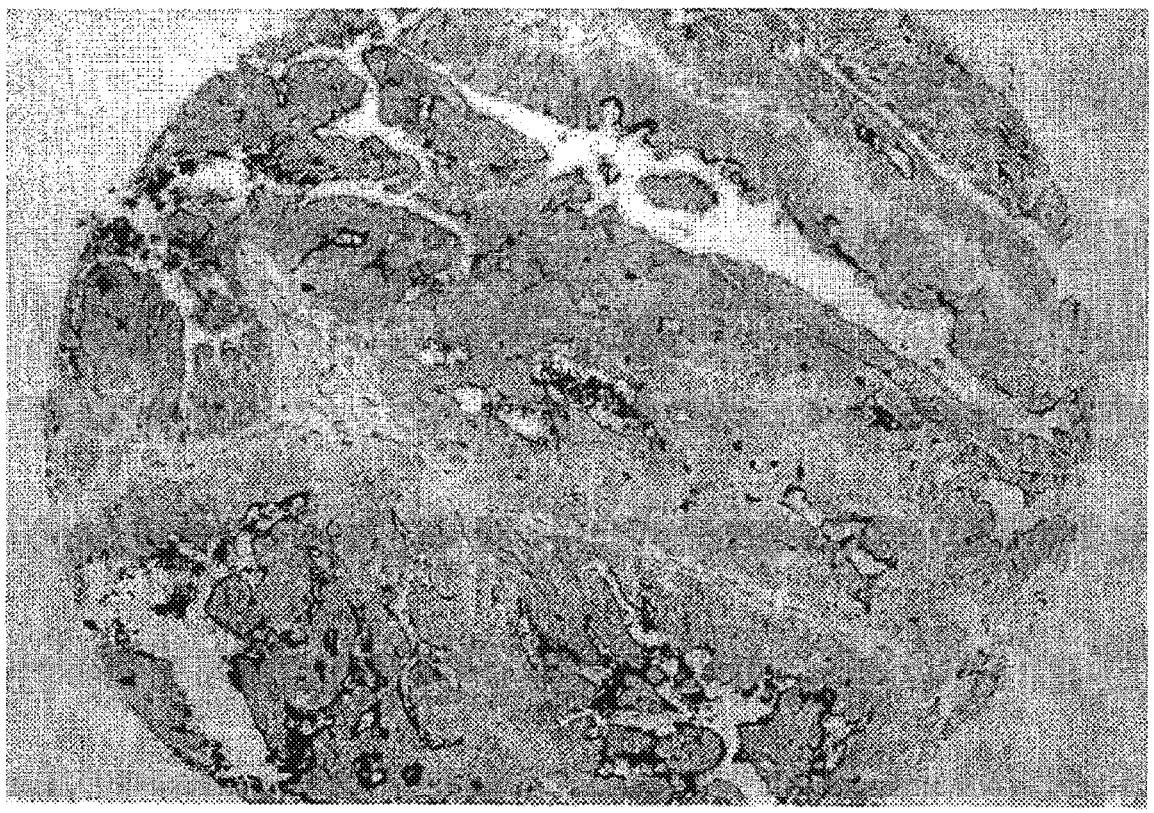
Figure 3E:
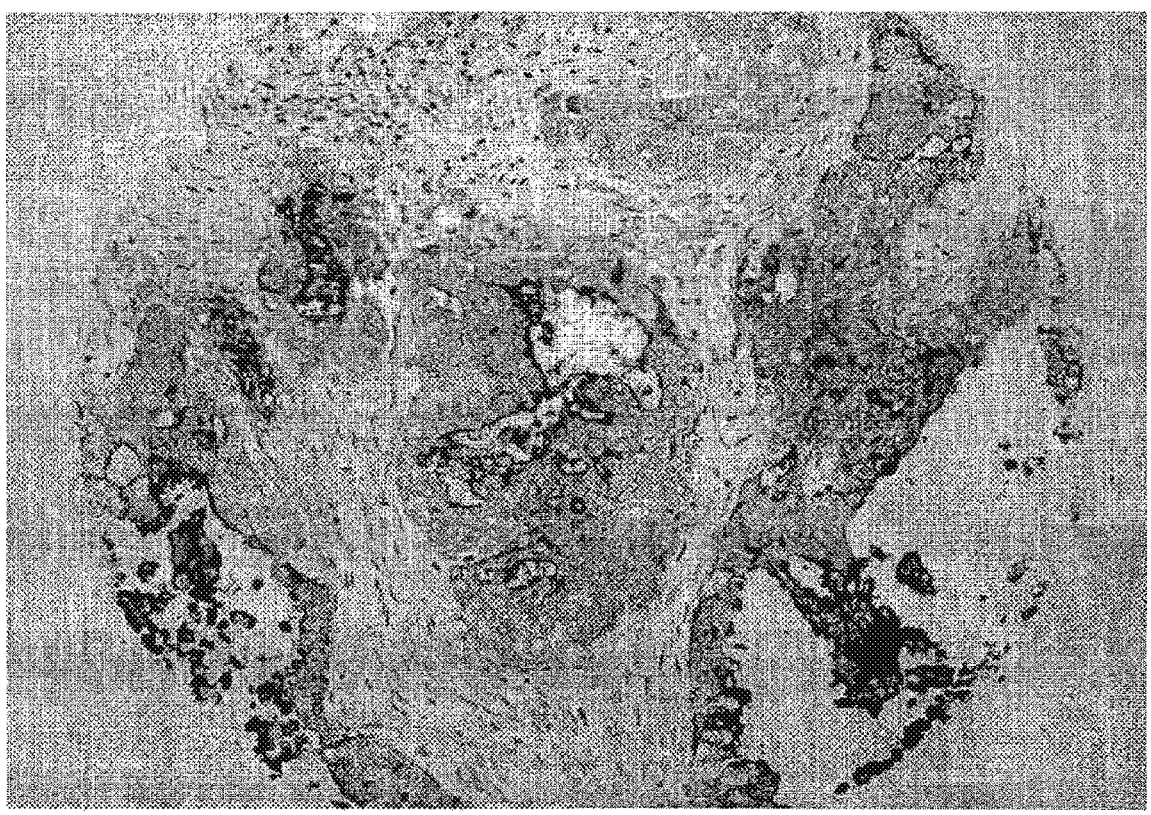
Figure 3F:
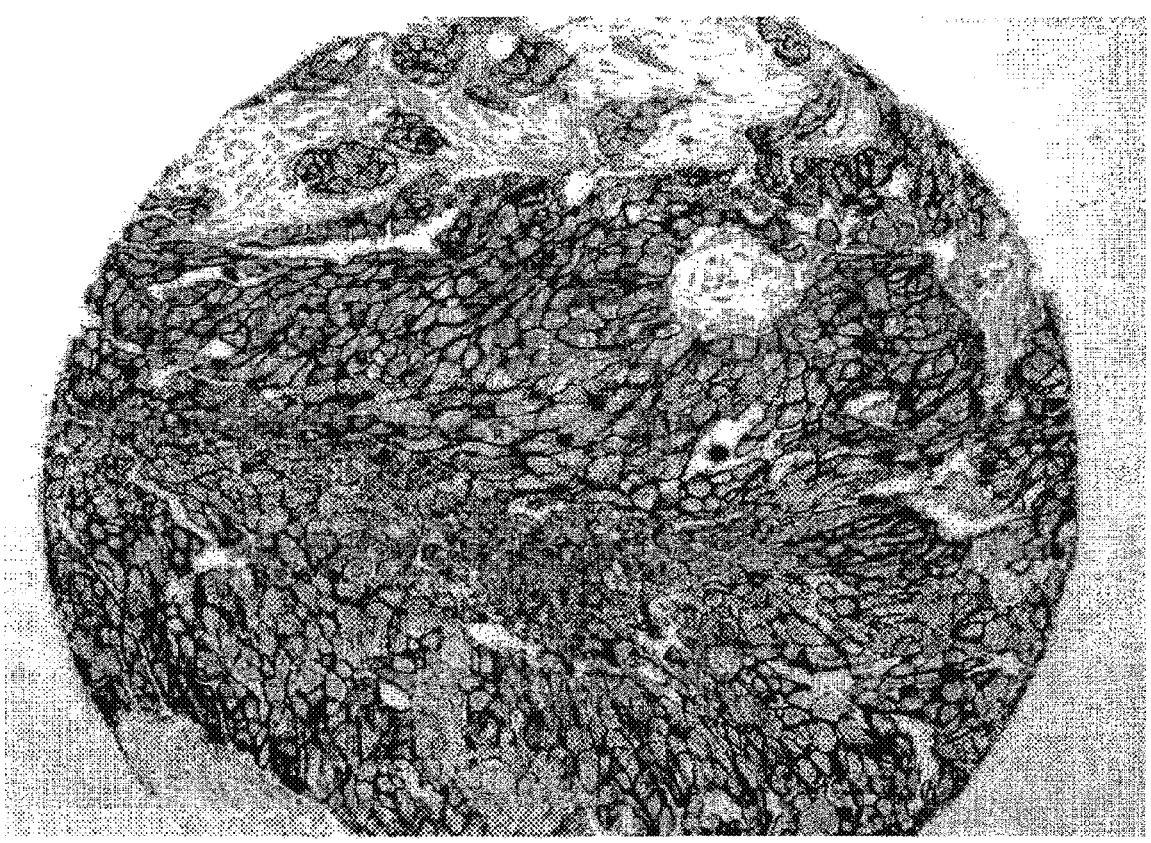
Figure 3G:
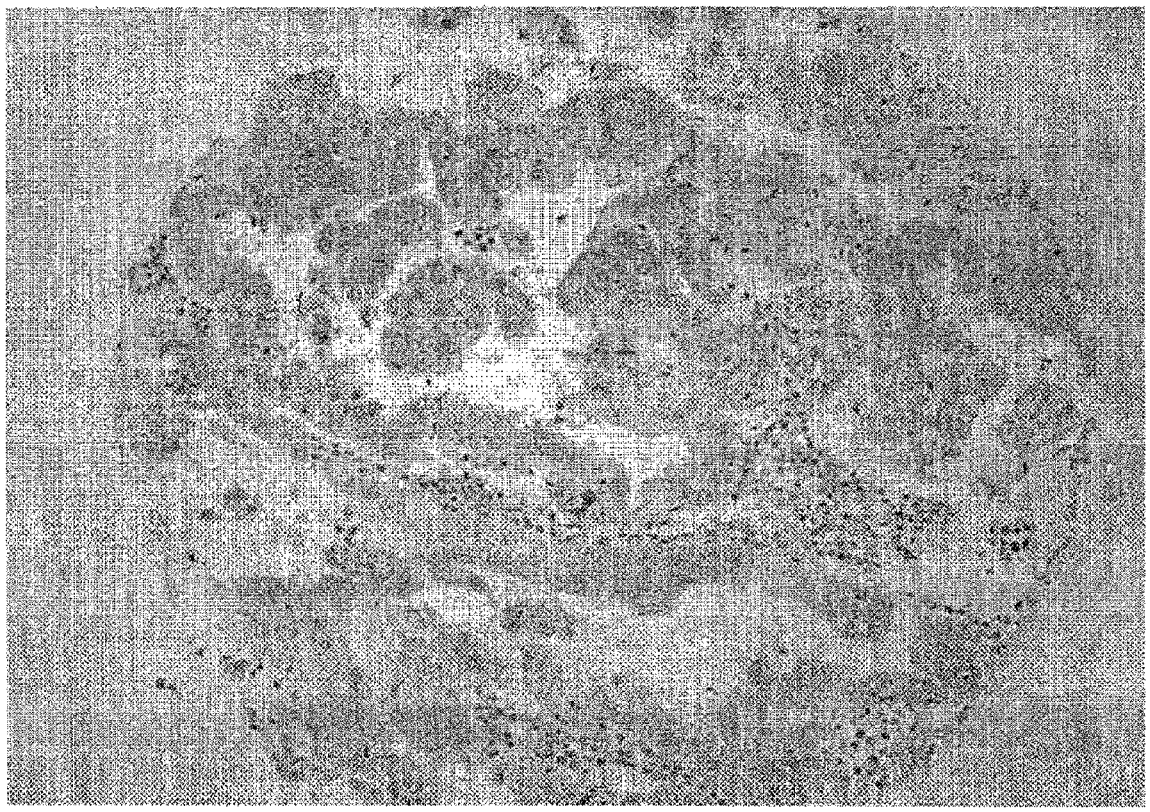
Figure 3H:
Figure 3I:
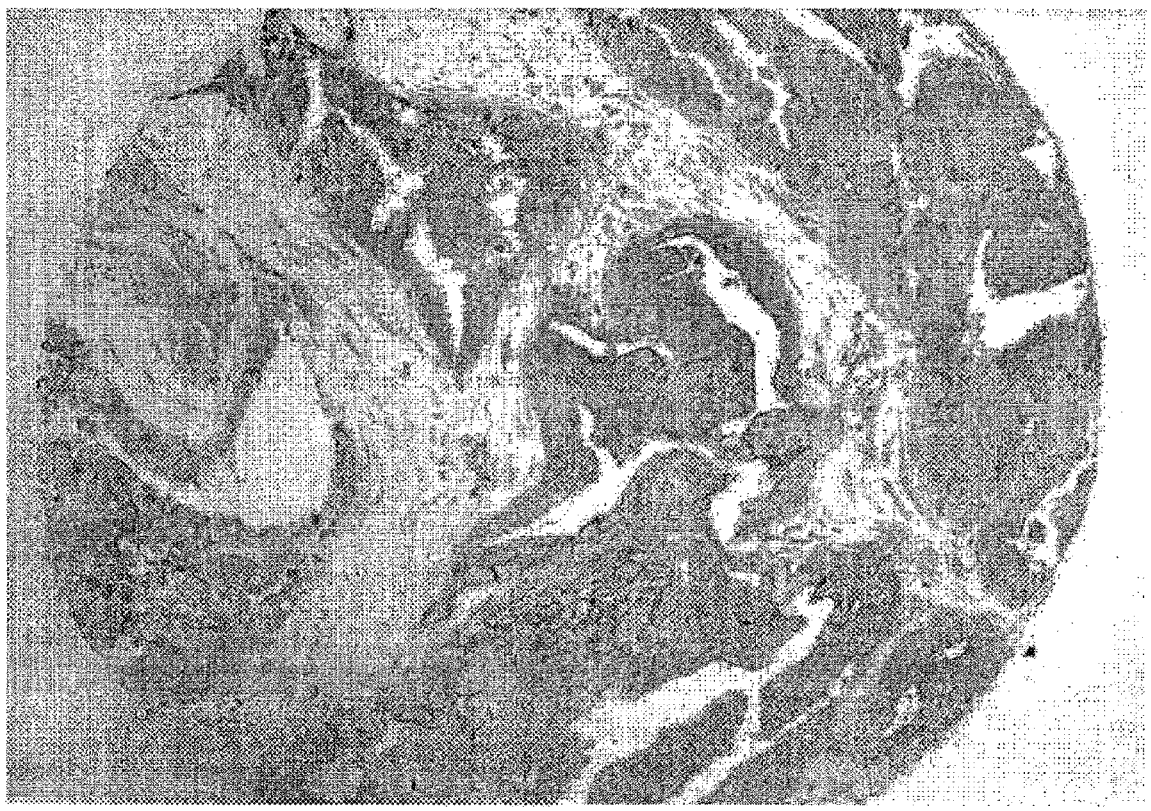
Figure 3J:
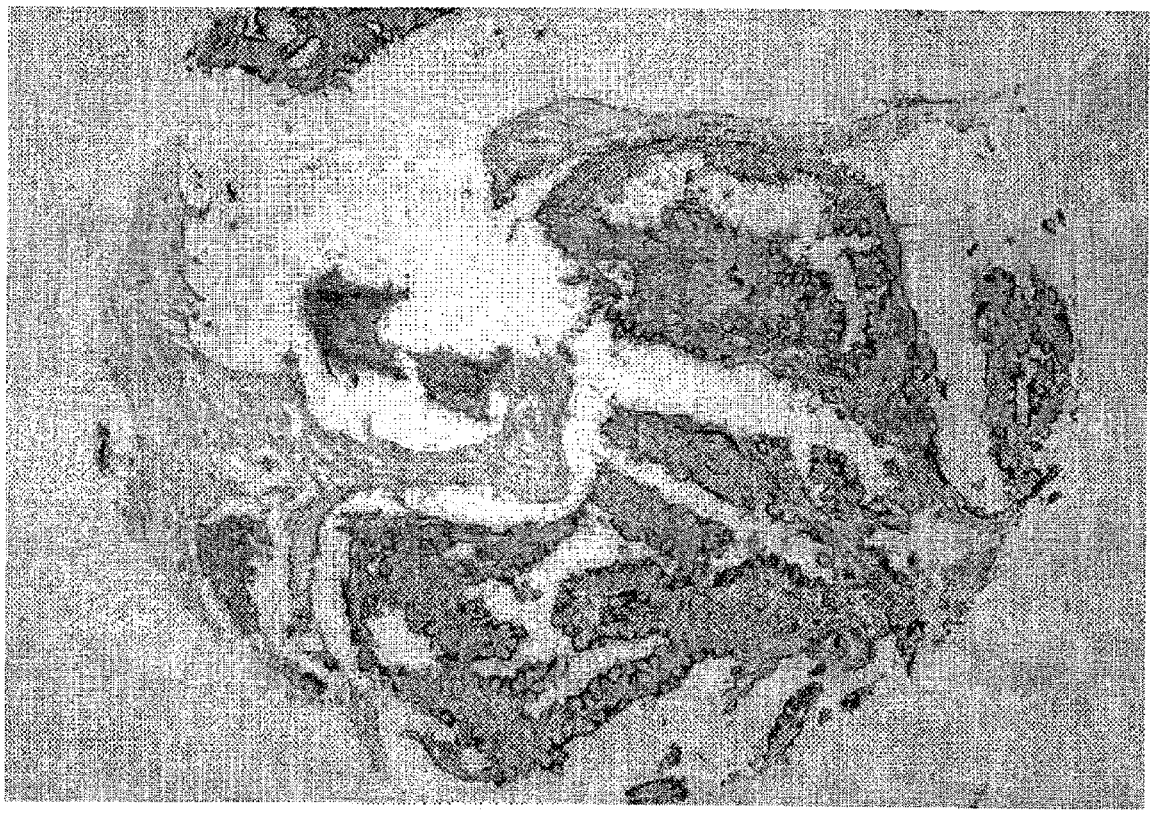
Figure 3K:
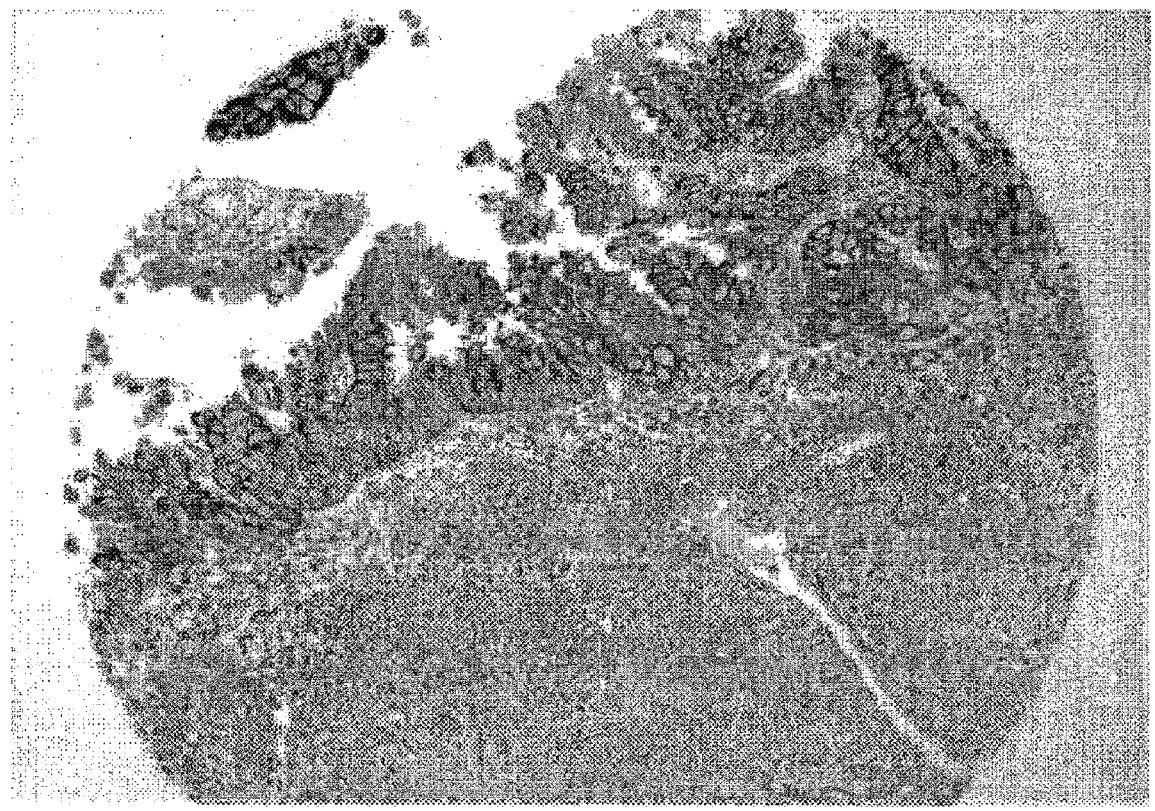
Figure 3L:
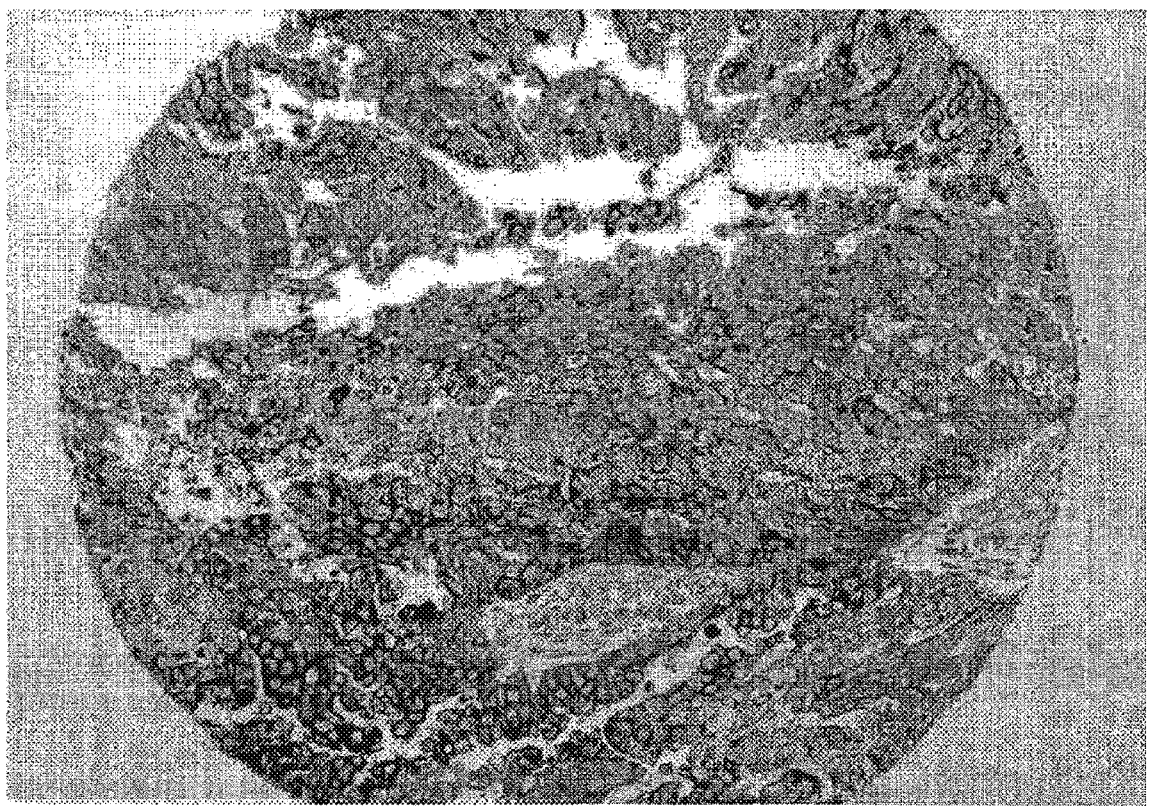

To facilitate understanding of the invention, a number of terms are defined below.

The terms "purified," "isolated," and grammatical equivalents thereof as used herein, refer to the reduction in the amount of at least one undesirable component (such as cell, protein, nucleic acid sequence, carbohydrate, etc.) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in an "enrichment," i.e., an increase in the amount of a desirable component cell, protein, nucleic acid sequence, carbohydrate, etc.).

The term "antibody" refers to an immunoglobulin (e.g., IgG, IgM, IgA, IgE, IgD, etc.). The basic functional unit of each antibody is an immunoglobulin (Ig) monomer (containing only one immunoglobulin ("Ig") unit). Included within this definition are polyclonal antibody, monoclonal antibody, and chimeric antibody.

The variable part of an antibody is its "V domain" (also referred to as "variable region"), and the constant part is its "C domain" (also referred to as "constant region") such as the kappa, lambda, alpha, gamma, delta, epsilon and mu constant regions. The "variable domain" is also referred to as the "F, region" and is the most important region for binding to antigens. More specifically, variable loops, three each on the light ($V_L$) and heavy ($V_H$) chains are responsible for binding to the antigen. These loops are referred to as the "complementarity determining regions" ("CDRs" and "idiotypes."

The immunoglobulin (Ig) monomer of an antibody is a "Y"-shaped molecule that contains four polypeptide chains: two light chains and two heavy chains, joined by disulfide bridges.

Light chains are classified as either (λ) or kappa (κ). A light chain has two successive domains: one constant domain ("CL") and one variable domain ("$V_L$"). The variable domain, $V_L$, is different in each type of antibody and is the active portion of the molecule that binds with the specific antigen. The approximate length of a light chain is 211 to 217 amino acids.

Each heavy chain has two regions, the constant region and the variable region. The There are five types of mammalian Ig heavy denoted a α, δ, ε, γ, and μ. The type of heavy chain present defines the class of antibody; these chains are found in IgA, IgD, IgE, IgG, and IgM antibodies, respectively. Distinct heavy chains differ in size and composition; α and γ contain approximately 450 amino acids, while μ and ε have approximately 550 amino acids. Each heavy chain has two regions, the constant region ("CH") and the variable ("$V_H$") region. The constant region (CH) is identical in all antibodies of the same isotype, but differs in antibodies of different isotypes. Heavy chains γ, α, and δ have a constant region composed of three tandem (in a line) Ig domains, and a hinge region for added flexibility. Heavy chains and c have a constant region composed of four immunoglobulin domains. The variable region ($V_H$) of the heavy chain differs in antibodies produced by different B cells, but is the same for all antibodies produced by a single B cell or B cell clone. The variable region of each heavy chain is approximately 110 amino acids long.

The term "specifically binds" and "specific binding" when made in reference to the binding of two molecules (e.g. antibody to an antigen, etc.) refer to an interaction of the two molecules that is dependent upon the presence of a particular structure on one or both of the molecules. For example, if an antibody is specific for epitope "A" on the molecule, then the presence of a protein containing epitope A (or free, unlabelled A) in a reaction containing labeled "A" and the antibody will reduce the amount of labeled A bound to the antibody.

The term "capable of binding" when made in reference to 'the interaction between a first molecule (such as antibody, polypeptide, glycoprotein, nucleic acid sequence, etc.) and a second molecule (such as antigen, polypeptide, glycoprotein, nucleic acid sequence, etc.) means that the first molecule binds to the second molecule in the presence of suitable concentration of salts, and suitable temperature, and pH. The conditions for binding molecules may be determined using routine and/or commercially available methods The terms "antigen," "immunogen," "antigenic," "immunogenic," "antigenically active," "immunologic," and "immunologically active" when made in reference to a molecule, refer to any substance that is capable of inducing a specific humoral immune response (including eliciting a soluble antibody response) and/or cell-mediated immune response (including eliciting a CTL response). Antigenic peptides preferably contain at least 5, at least 6, at least 7, at least 8, at least 9, and more preferably at least 10 amino acids. To elicit antibody production, in one embodiment, antigens may be conjugated to keyhole limpet hemocyanin (KLH) or fused to glutathione-S-transferase (GST).

A "cognate antigen" when in reference to an antigen that binds to an antibody, refers to an antigen that is capable of specifically binding to the antibody.

In one embodiment, the antigen comprises an epitope. The teams "epitope" and "antigenic determinant" refer to a structure on an antigen, which interacts with the binding site of an antibody or T cell receptor as a result of molecular complementarity. An epitope may compete with the intact antigen, from which it is derived, for binding to an antibody.

As used herein the terms "portion" and "fragment" when made in reference to a nucleic acid sequence or protein sequence refer to a piece of that sequence that may range in size from 2 contiguous nucleotides and amino acids, respectively, to the entire sequence minus one nucleotide and amino acid, respectively.

A "subject" that may benefit from the invention's methods includes any multicellular animal, preferably a mammal. Mammalian subjects include humans, non-human primates, murines, ovines, bovines, ruminants, lagomorphs, porcines, caprines, equines, canines, felines, aves, etc.). Thus, mammalian subjects are exemplified by mouse, rat, guinea pig, hamster, ferret and chinchilla. The invention's compositions and methods are also useful for a subject "in need of reducing one or more symptoms of a disease, e.g., in need of reducing cancer metastasis and/or in need of reducing one or more symptoms of cancer, includes a subject that exhibits and/or is at risk of exhibiting one or more symptoms of the disease. For Example, subjects may be at risk based on family history, genetic factors, environmental factors, etc. This term includes animal models of the disease. Thus, administering a composition (which reduces a disease and/or which reduces one or more symptoms of a disease) to a subject in need of reducing the disease and/or of reducing one or more symptoms of the disease includes prophylactic administration of the composition (i.e., before the disease and/or one or more symptoms of the disease are detectable) and/or therapeutic administration of the composition (i.e., after the disease and/or one or more symptoms of the disease are detectable). The invention's compositions and methods are also useful for a subject "at risk" for disease (such as cancer) refers to a subject that is predisposed to contracting and/or expressing one or more symptoms of the disease. This predisposition may be genetic (e.g., a particular genetic tendency to expressing one or more symptoms of the disease, such as heritable disorders, etc.), or due to other factors (e.g., environmental conditions, exposures to detrimental compounds, including carcinogens, present in the environment, etc.). The term subject "at risk" includes subjects "suffering from disease," i.e., a subject that is experiencing one or more symptoms of the disease. It is not intended that the present invention be limited to any particular signs or symptoms. Thus, it is intended that the present invention encompass subjects that are experiencing any range of disease, from sub-clinical symptoms to full-blown disease, wherein the subject exhibits at least one of the indicia (e.g., signs and symptoms) associated with the disease.

"Cancer cell" refers to a cell undergoing early, intermediate or advanced stages of multi-step neoplastic progression as previously described (Pitot et al., Fundamentals of Oncology, 15-28 (1978)). This includes cells in early, intermediate and advanced stages of neoplastic progression including "pre-neoplastic cells (i.e., "hyperplastic cells and dysplastic cells), and neoplastic cells in advanced stages of neoplastic progression of a dysplastic cell.

"Metastatic" cancer cell refers to a cancer cell that is translocated from a primary cancer site (i.e., a location where the cancer cell initially formed from a normal, hyperplastic or dysplastic cell) to a site other than the primary site, where the translocated cancer cell lodges and proliferates.

"Cancer" refers to a plurality of cancer cells that may or may not be metastatic, such as ovarian cancer, breast cancer, lung cancer, prostate cancer, cervical cancer, pancreatic cancer, colon cancer, stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia.

"Sample" and "specimen" as used herein are used in their broadest sense to include any composition that is obtained and/or derived from a biological source, as well as sampling devices (e.g., swabs), which are brought into contact with biological or environmental samples. "Biological samples" include those obtained from a subject, including body fluids (such as urine, blood, plasma, fecal matter, cerebrospinal fluid (CSF), semen, sputum, and saliva), as well as solid tissue. Biological samples also include a cell (such as cell lines, cells isolated from tissue whether or not the isolated cells are cultured after isolation from tissue, fixed cells such as cells fixed for histological and/or immunohistochemical analysis), tissue (such as biopsy material), cell extract, tissue extract, and nucleic acid (e.g., DNA and RNA) isolated from a cell and/or tissue, and the like. These examples are illustrative, and are not to be construed as limiting the sample types applicable to the present invention.

"Overexpression of MUC16" by a cell of interest (such as a cancer cell) refers to a higher level of MUC16 protein and/or mRNA that is expressed by the cell of interest compared to a control cell (such as a non-cancerous cell, normal cell, etc.).

"Internalize" when in reference to a cell refers to entry from the extracellular medium into the cell membrane and/or cytoplasm.

"Glycosylated" when in reference to a sequence (e.g., an amino acid sequence or nucleotide sequence) refers to a sequence that is covalently linked to one or more saccharides.

"Pharmaceutical" and "physiologically tolerable" composition refers to a composition that contains pharmaceutical molecules, i.e., molecules that are capable of administration to or upon a subject and that do not substantially produce an undesirable effect such as, for example, adverse or allergic reactions, dizziness, gastric upset, toxicity and the like, when administered to a subject. Preferably also, the pharmaceutical molecule does not substantially reduce the activity of the invention's compositions. Pharmaceutical molecules include "diluent" (i.e., "carrier") molecules and excipients.

"Immunogenically effective" and "antigenically effective" amount of a molecule interchangeably refer to an amount of the molecule that is capable of inducing a specific humoral immune response (including eliciting a soluble antibody response) and/or cell-mediated immune response (including eliciting a cytotoxic T-lymphocyte (CTL) response).

"Treating" a disease refers to reducing one or more symptoms (such as objective, subjective, pathological, clinical, sub-clinical, etc.) of the disease.

The terms "reduce," "inhibit," "diminish," "suppress," "decrease," and grammatical equivalents (including "lower," "smaller," etc.) when in reference to the level of any molecule (e.g., amino acid sequence, and nucleic acid sequence, antibody, etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of molecule, cell and/or phenomenon in the first sample (or in the first subject) is lower than in the second sample (or in the second subject) by any amount that is statistically significant using any art-accepted statistical method of analysis. In one embodiment, the quantity of molecule, cell and/or phenomenon in the first sample (or in the first subject) is at least 10% lower than, at least 25% lower than, at least 50% lower than, at least 75% lower than, and/or at least 90% lower than the quantity of the same molecule, cell and/or phenomenon in the second sample (or in the second subject). In another embodiment, the quantity of molecule, cell, and/or phenomenon in the first sample (or in the first subject) is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "increase," "elevate," "raise," and grammatical equivalents (including "higher," "greater," etc.) when in reference to the level of any molecule (e.g., amino acid sequence, and nucleic acid sequence, antibody, etc.), cell, and/or phenomenon (e.g., disease symptom, binding to a molecule, specificity of binding of two molecules, affinity of binding of two molecules, specificity to cancer, sensitivity to cancer, affinity of binding, enzyme activity, etc.) in a first sample (or in a first subject) relative to a second sample (or relative to a second subject), mean that the quantity of the molecule, cell and/or phenomenon in the first sample (or in the first subject) is higher than in the second sample (or in the second subject) by any amount that is statistically significant using any art-accepted statistical method of analysis. In one embodiment, the quantity of the molecule, cell and/or phenomenon in the first sample (or in the first subject) is at least 10% greater than, at least 25% greater than, at least 50% greater than, at least 75% greater than, and/or at least 90% greater than the quantity of the same molecule, cell and/or phenomenon in the second sample (or in the second subject). This includes, without limitation, a quantity of molecule, cell, and/or phenomenon in the first sample (or in the first subject) that is at least 10% greater than, at least 15% greater than, at least 20% greater than, at least 25% greater than, at least 30% greater than, at least 35% greater than, at least 40% greater than, at least 45% greater than, at least 50% greater than, at least 55% greater than, at least 60% greater than, at least 65% greater than, at least 70% greater than, at least 75% greater than, at least 80% greater than, at least 85% greater than, at least 90% greater than, and/or at least 95% greater than the quantity of the same molecule, cell and/or phenomenon in the second sample (or in the second subject). In one embodiment, the first subject is exemplified by, but not limited to, a subject that has been manipulated using the invention's compositions and/or methods. In a further embodiment, the second subject is exemplified by, but not limited to, a subject that has not been manipulated using the invention's compositions and/or methods. In an alternative embodiment, the second subject is exemplified by, but not limited to, a subject to that has been manipulated, using the invention's compositions and/or methods, at a different dosage and/or for a different duration and/or via a different route of administration compared to the first subject. In one embodiment, the first and second subjects may be the same individual, such as where the effect of different regimens (e.g., of dosages, duration, route of administration, etc.) of the invention's compositions and/or methods is sought to be determined in one individual. In another embodiment, the first and second subjects may be different individuals, such as when comparing the effect of the invention's compositions and/or methods on one individual participating in a clinical trial and another individual in a hospital.

The terms "alter" and "modify" when in reference to the level of any molecule and/or phenomenon refer to an increase or decrease.

Reference herein to any numerical range expressly includes each numerical value (including fractional numbers and whole numbers) encompassed by that range. To illustrate, and without limitation, reference herein to a range of "at least 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes each whole number of 5, 6, 7, 8, 9, and 10, and each fractional number such as 5.1, 5.2, 5.3, 5.4, 5.5, 5.6, 5.7, 5.8, 5.9, etc.

DESCRIPTION OF THE INVENTION

The invention provides antibodies, and antigen-binding fragments thereof, that specifically bind to a polypeptide, or antigenic portion thereof, wherein the polypeptide is selected from a) MUC16 ectodomain polypeptide, b) MUC16 cytoplasmic domain polypeptide, and c) MUC16 extracellular domain polypeptide that contains a cysteine loop polypeptide. The invention's antibodies and compositions containing them are useful in diagnostic and therapeutic applications for diseases in which MUC16 is overexpressed, such as cancer.

Using synthetic peptides, the inventors raised novel-specific antibodies to the carboxy-terminal portion of MUC16, retained by the cell, proximal to the putative cleavage site. These antibodies were characterized using fluorescence-activated cell-sorting analysis, enzyme-linked immunoassay, Western blot analysis, and immunohistochemistry. Each of the selected monoclonal antibodies was reactive against recombinant GST-ΔMUC16$^{c114}$ protein and the MUC16 transfected SKOV3 cell line. Three antibodies, 4H11, 9C9, and 4A5 antibodies demonstrated high affinities by Western blot analysis and saturation-binding studies of transfected SKOV3 cells, and displayed antibody internalization Immunohistochemical positivity with novel antibody 4H11 was similar to OC125, but with important differences, including diffuse positivity in lobular breast cancer and a small percentage of OC125-negative ovarian carcinomas which showed intense and diffuse 4H11 antibody binding.

The invention's compositions and methods are useful for diagnostic and therapeutic applications, as well as biologic studies such as membrane receptor trafficking and intracellular events. Diagnostic applications include, for example, detection of cancer using immunohistochemical, radiographic imaging, enzyme-linked immunosorbent assay (ELISA), fluorescence-activated cell sorting (FACS), Western blot, and/or immunoprecipitation detection.

The invention is further described under (A) MUC16, (B) Prior Art Antibodies, (C) Invention's Antibodies, (D) Hybridoma Cell Lines, (E) Conjugates Of The Invention's Antibodies Linked To Cytotoxic Agents And/Or Prodrugs, (F) Detecting Muc16 Portions And Diagnostic Applications, and (G) Therapeutic Applications.

A. MUC16

Figure 10:
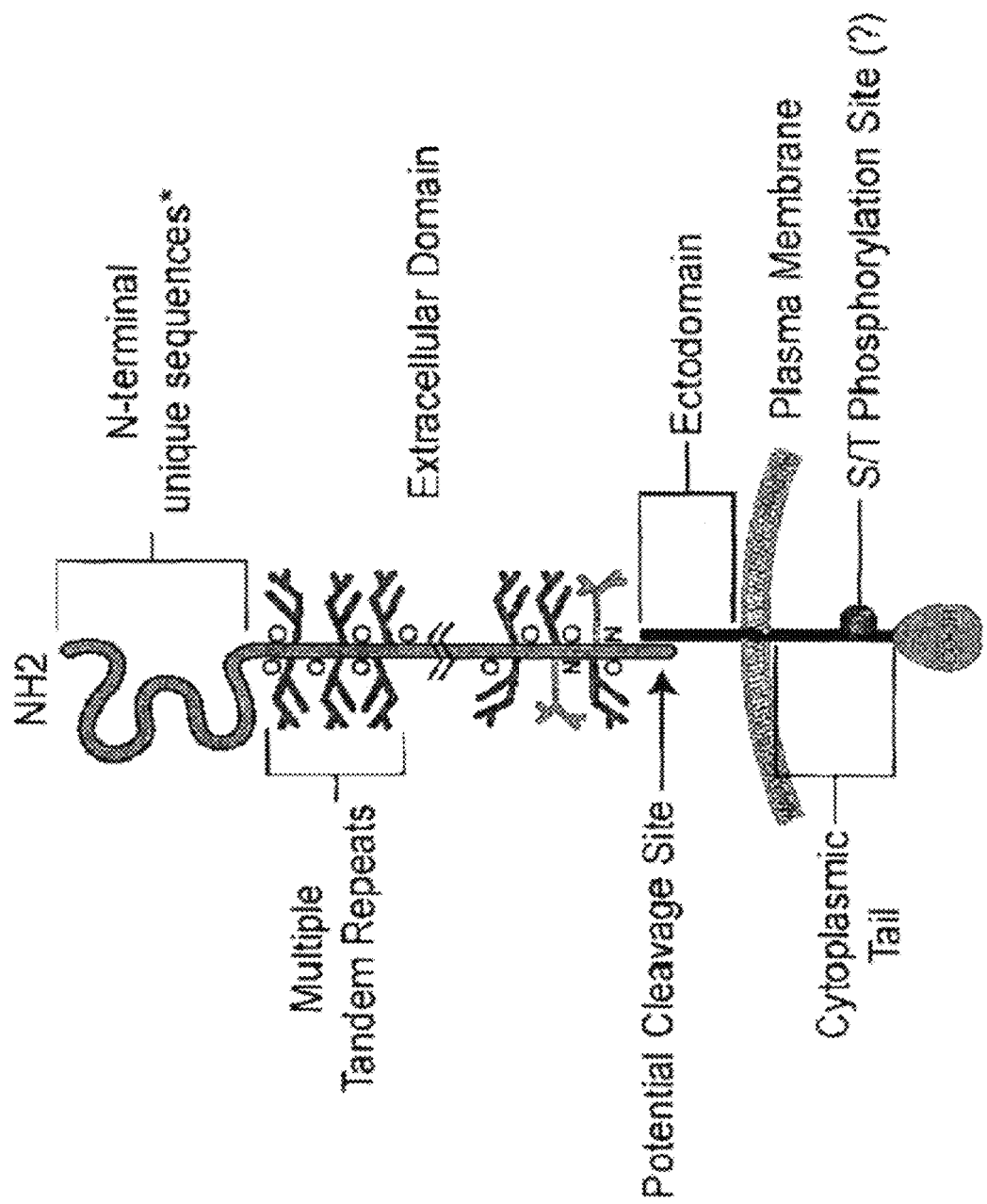
FIG. 10: Schematic of MUC16 structure.

"MUC16," "MUC-16" and "Mucin 16" interchangeably refer to a type I membrane protein that is part of a family of tethered mucins. A schematic of Muc16 is in FIG. 10, and an exemplary human Muc16 amino acid sequence (SEQ ID NO:13) is shown in FIG. 9A. An alignment of mouse MUC16 (SEQ ID NO:24) and human MUC16 (SEQ ID NO:25) amino acid sequences is shown in FIG. 20B. The term "type 1 protein" refers to a "membrane protein" that is at least partially embedded in the lipid bilayer of a cell, virus and the like, and that contains a transmembrane domain (TM) sequence embedded in the lipid bilayer of the cell, virus and the like. The portion of the protein on the NH$_2$-terminal side of the TM domain is exposed on the exterior side of the membrane, and the COOH-terminal portion is exposed on the cytoplasmic side.

Recently, the sequence of the cDNA-encoding MUC16/CA125 was described by Yin and Lloyd in 2001 and completed by O'Brien in 2002 (10-12). The complete MUC16 protein has various components consisting of a cytoplasmic tail with potential phosphorylation sites, a transmembrane domain, and an external domain proximal to an apparent cleavage site. Distal to the cleavage site, the released external domain contains 16-20 tandem repeats of 156 amino acids, each with many potential glycosylation sites (11). The overall repeat structure (FIG. 10) is well conserved across mammals, but the repeats are not completely identical in exact amino acid composition.

The MUC16 protein is part of a family of tethered mucins that includes both MUC1 and MUC4 (13). MUC1 is present in a variety of tissues and appears to signal through a beta catenin pathway, interact with EGF receptor, mediates drug resistance and can act as an oncogene (14-17). The MUC4 protein is also expressed in a variety of tissues but is common on neoplasms of the gastrointestinal track (18-20). In contrast, the CA125 antigen has been more restricted in its distribution and is present primarily in gynecologic tissues and overexpressed in Müllerian neoplasms (21). However, the CA125 antigen, recognized by the OC125 antibody, is a heavily glycosylated antigen expressed in the tandem repeat region of the larger MUC16 protein. This glycoprotein is typically shed from a putative cleavage site in the extracellular domain of the MUC16 peptide backbone.

Thus, "MUC16" protein contains (a) a "cytoplasmic domain," (b) a "transmembrane domain," and (c) a "extracellular domain." The MUC16 extracellular domain contains a cleavage site between a non-glycosylated ectodomain and a large glycosylated ectodomain of tandem repeats.

The terms "cytoplasmic domain," "cytoplasmic tail," and "CT" are used interchangeably to refer to a protein sequence, and portions thereof, that is on the cytoplasmic side of the lipid bilayer of a cell, virus and the like. Methods for determining the CT of a protein are known in the art Elofsson et al. (2007) Annu. Rev. Biochem. 76:125-140; Bernsel et al. (2005) Protein Science 14:1723-1728).

The teams "transmembrane domain" and "TM" are used interchangeably to refer to a protein sequence, and portions thereof, that spans the lipid bilayer of a cell, virus and the like. Methods for determining the TM of a protein are known in the art (Elofsson et al. (2007) Annu. Rev. Biochem. 76:125-140; Bernsel et al. (2005) Protein Science 14:1723-1728).

The terms "ectodomain" and "extracellular domain" are interchangeably used when in reference to a membrane protein to refer to the portion of the protein that is exposed on the extracellular side of a lipid bilayer of a cell, virus and the like. Methods for determining the ectodomain of a protein are known in the art (Singer (1990) Annu. Rev. Cell Biol. 6:247-296 and High et al. (1993) J. Cell Biol. 121: 743-750, and McVector software, Oxford Molecular).

The exemplary Muc16 of FIG. 9 contains (a) a "MUC16 cytoplasmic domain" from amino acid 14476 to 14507, vttrr rkkegeynvq qqcpgyyqsh ldledlq (SEQ ID NO:16), that interacts with the intracellular signal transduction machinery; (b) a "MUC16 transmembrane domain" from amino acid 14452 to 14475, fwaviligl agllgvitcl icgvl (SEQ ID NO: 14) that spans the plasma membrane; and (c) a "MUC16 extracellular domain" amino acid 1 to 14392 (SEQ ID NO:13) that contains a cleavage site between an non-glycosylated ectodomain and a large glycosylated ectodomain of tandem repeats. The "MUC 16 ectodomain" is exemplified by nfsplar rvdrvaiyee flrmtrngtq lqnftldrss vlvdgyspnr nepltgnsdl p (SEQ ID NO:17) from amino acid 14394 to 14451 of SEQ ID NO:13 of FIG. 9A.

The exemplary MUC16 ectodomain contains both Polypeptide 1 (nfsplar rvdrvaiyee (SEQ ID NO:01), which is from amino acid 14394 to 14410 of SEQ ID NO:13), and Polypeptide 2 (tldrss vlvdgyspnr ne (SEQ ID NO:02), which is from amino acid 14425 to 14442 of SEQ ID NO:13), against which the invention's exemplary antibodies were produced. Polypeptide 3, cgvlvttrr rkkegeynvq qq (SEQ ID NO:03) is from amino acid 14472 to 14492 of SEQ ID NO: 13, and contains both a transmembrane domain portion (cgvl) and a cytoplasmic domain portion (vttrr rkkegeynvq qq (SEQ ID NO:18)). Thus, the CGVL is optional in SEQ ID NO:03, as it is part of the transmembrane domain.

Polypeptide 4 (ksyf sdcqvstfrs vpnrhhtgvd slcnfspl (SEQ ID NO:15), is located in a non-glycosylated portion of the Muc16 extracellular domain, is from amino acid 14367 to 14398 of SEQ ID NO:13, and contains a cysteine loop polypeptide cqvstfrsvpnrhhtgvdslc (SEQ ID NO:13).

B. Prior Art Antibodies

The expression of the MUC16/CA125 antigen has long been associated with gynecologic tissues. "CA125," "CA-125," "Cleaved CA125," and "cleaved CA-125," interchangeably refer to the glycosylated external domain of the tethered mucin MUC16, that is distal to the cleavage site (Payne et al., U.S. Pat. No. 7,202,346). This released external domain contains 16-20 tandem repeats of 156 amino acids, each with potential glycosylation sites. An apparent cysteine-based disulfide loop of 19 amino acids is present in all repeats and the N-terminal end contains a hairbrush structure that is heavily 0-glycosylated (11). The deduced size would be 2.5 MD for the protein part, and with added carbohydrates, this could increase to 5 MD (10, 26).

CA125, though it is not sensitive or specific enough to be used as a general screening tool, is routinely used to monitor patients with ovarian carcinoma. The tests used to measure CA125 are antibody based detection methods, as are the immunohistochemical stains routinely performed for diagnostic purposes. The epitope specificity of 26 antibodies to MUC16 was studied in the first report from the International Society of Oncodevelopmental Biology and Medicine (ISOBM) TD-1 Workshop and the application of 22 antibodies to immunohistochemistry was reported in the second report from the TD-1 workshop (7, 21). The existing antibodies were grouped as OC125-like, Ml 1-like, or OV197-like and all of the known antibodies recognized CA125 epitopes in the repeating, glycosylated elements in the external domain of the tethered mucin MUC16, distal to the putative cleavage site.

The vast majority of MUC16-reactive antibodies, including OC125, react with the glycosylation-dependent antigen present exclusively in the cleaved portion of the molecule so the true distribution of MUC16 expression is not known (21). There is currently no antibody available to track the fate of the remaining MUC16 protein fragment after cleavage and CA125 release.

C. Invention's Antibodies

In order to better explore the biology of human MUC16, the inventors have derived monoclonal antibodies against the extracellular portion of the MUC16-carboxy terminus, proximal to the putative cleavage site, as well as one monoclonal antibody against the internal cytoplasmic domain. In contrast to prior antibodies, these are derived against the peptide backbone of MUC16 and are not directed at complex glycoprotein epitopes. Since these epitopes are proximal to the cleavage site, they are unlikely to be found in the circulation and provide novel targets for diagnostic methods and therapeutic interventions. Data herein demonstrate the identification and characterization of exemplary antibodies developed against the MUC16 peptide backbone.

The inventors have developed novel antibodies that are directed at the non-cleaved, non-glycosylated peptide backbone of MUC16. These are exemplified by both 4H11 and 9C9 antibodies, which react with peptide sequences in the non-cleaved ectodomain of MUC16 and are detectable on the surface of ovarian cancer cell lines and in paraffin-fixed tissues from human ovarian cancer surgical specimens. The antibodies show high affinity and are readily internalized by ovarian cancer cells when bound to the ectodomain of MUC16. This suggests that the proximal portion of MUC16 has an independent biology from the more distal, cleaved portion of the mucin. It also suggests that the proximal portions of MUC16 could provide convenient targets for diagnostic and therapeutic interventions. Targeting the peptide backbone of MUC16 provides highly specific tissue delivery for genetically engineered cells, liposomes, or antibody conjugates, including conjugates with the invention's antibodies.

The invention's antibodies, exemplified by antibody 4H11, are useful as tools in immunohistochemistry. Date herein show that 4H11 is relatively specific to high-grade ovarian serous carcinoma. Invasive lobular breast carcinoma is the major exception and shows extensive MUC16 protein as detected by 4H11. Lobular carcinoma of the breast has unique biology which is characterized by a propensity to metastasize to serosal surfaces (27). Since MUC16 is the cognate binding partner of mesothelin, this may have important implications for lobular cancer (28). The discordance rates for OC125 and 4H11 also suggest that 4H11 might provide additional, independent information from OC125 in a subset of ovarian carcinomas. Some tumors that are negative with OC125 retain cytoplasmic and extracellular portions of the MUC16 glycoprotein, portions of the molecule that are likely involved in transduction of signals potentially important in the malignant phenotype.

Thus, in one embodiment, the invention provides an isolated antibody, or an antigen-binding fragment thereof, that specifically binds to a polypeptide, or antigenic portion thereof, wherein the polypeptide is exemplified by a) MUC16 ectodomain polypeptide (exemplified by NFSPLARRVDRVAIYEE FLRMTRNGTQ LQNFTLDRSS VLVDGYSPNRNEPLTGNSDL P (SEQ ID NO:17)), b) MUC16 cytoplasmic domain polypeptide (exemplified by VTTRR RKKEGEYNVQ QQ (SEQ ID NO: 18), which is contained within each of CGVLVTTRR RKKEGEYNVQ QQ (SEQ ID NO:03) and LVTTRRRKKEGEYNVQ QQ (SEQ ID NO:20)), and c) MUC16 extracellular domain polypeptide that contains a cysteine loop polypeptide CQVSTFRSVPNRHHTGVDSLC (SEQ ID NO:19).

Figure 5A:
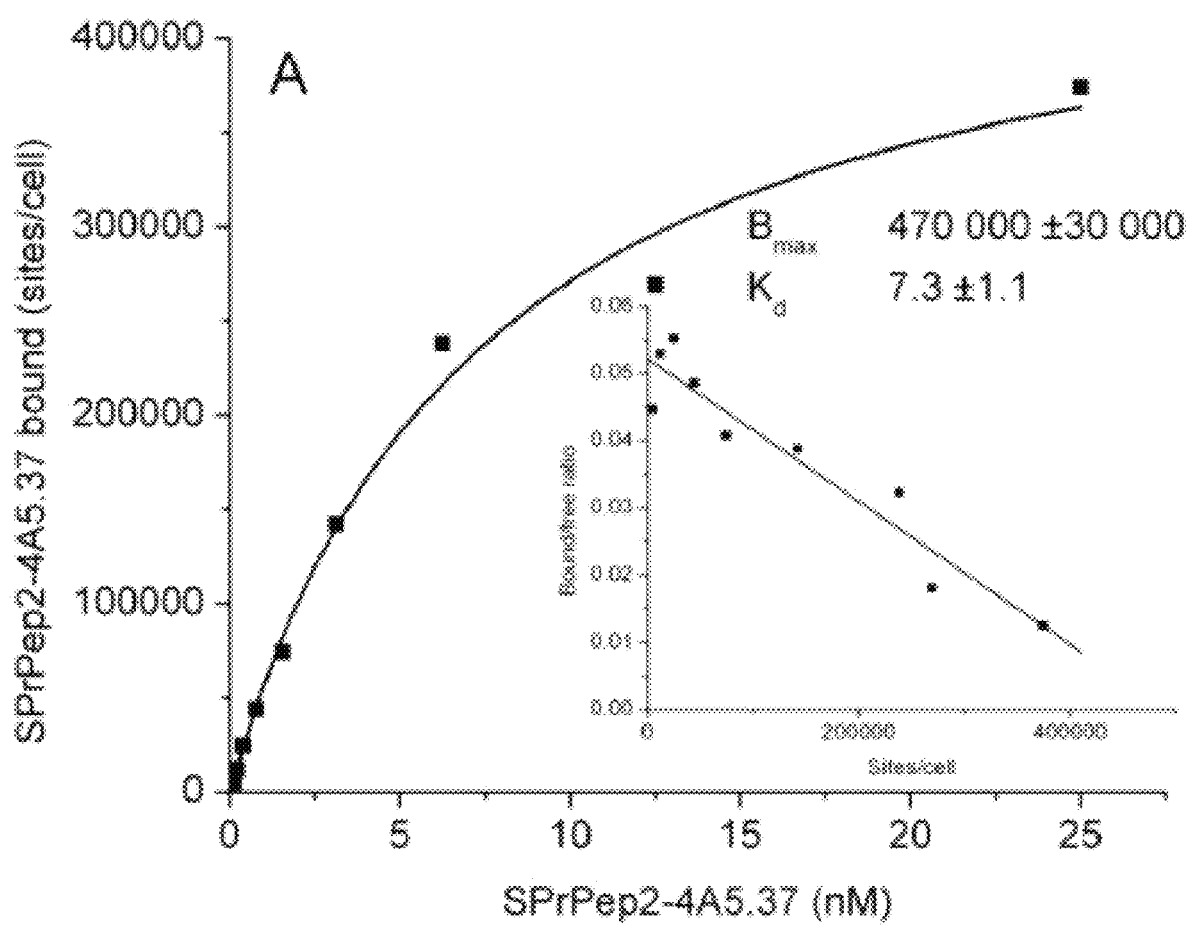
FIGS. 5A-5D: MUC16 carboxy terminus monoclonal antibodies binding affinity on OVCAR3 cells.
Figure 5B:
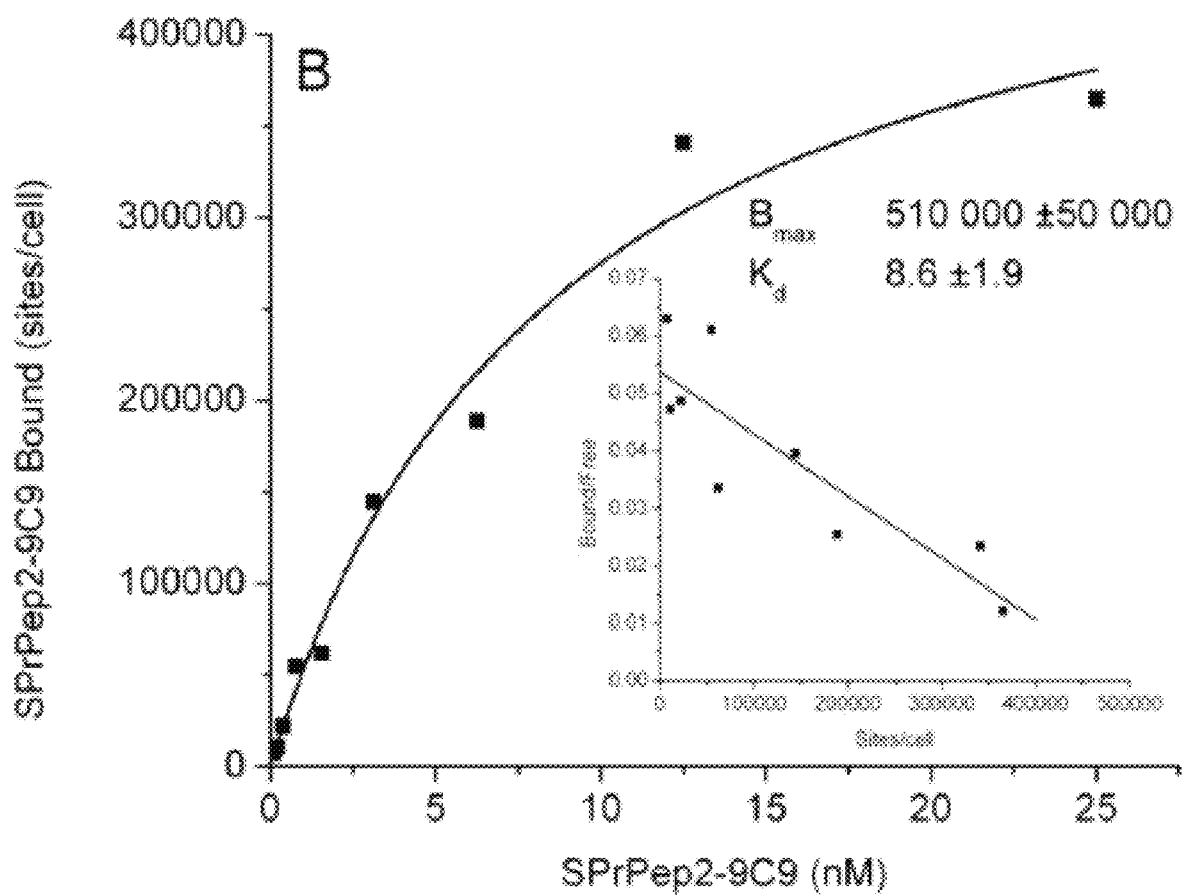
Figure 5C:
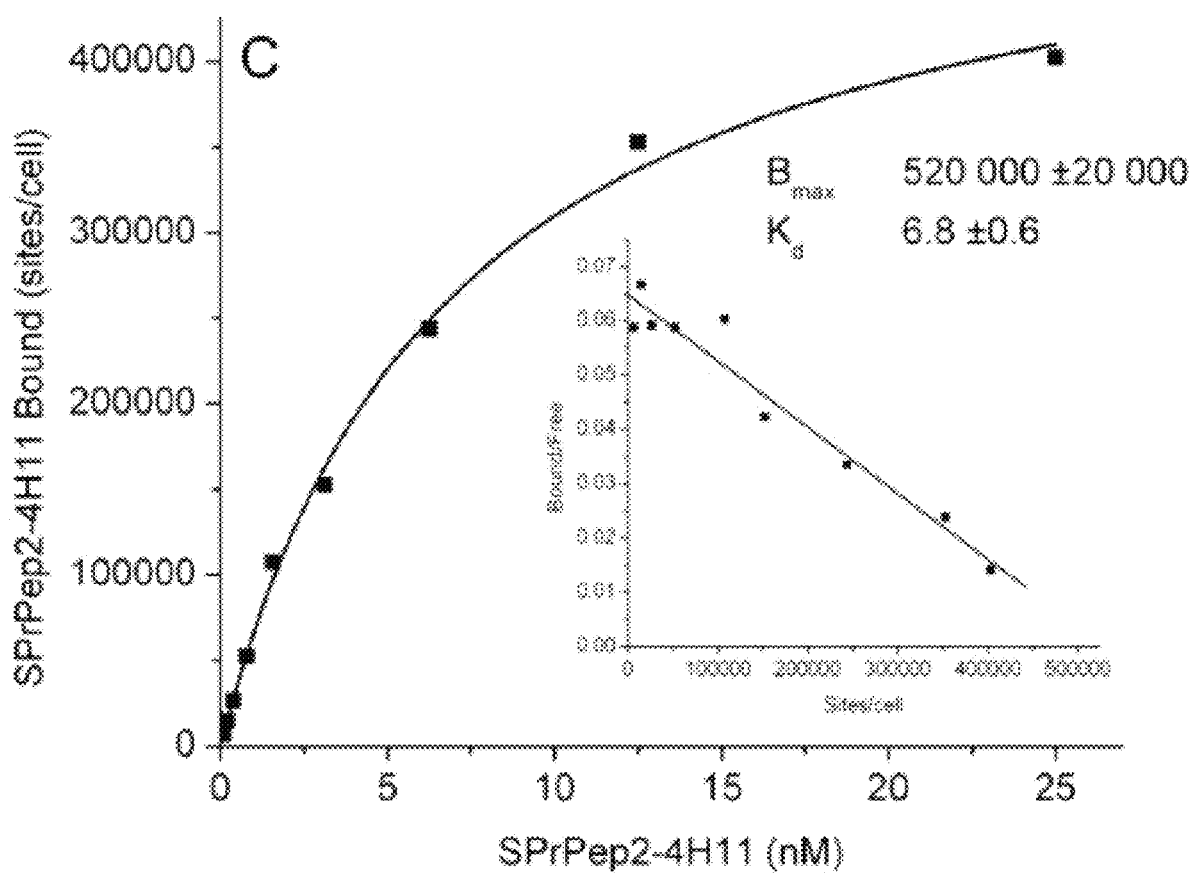
Figure 5D:
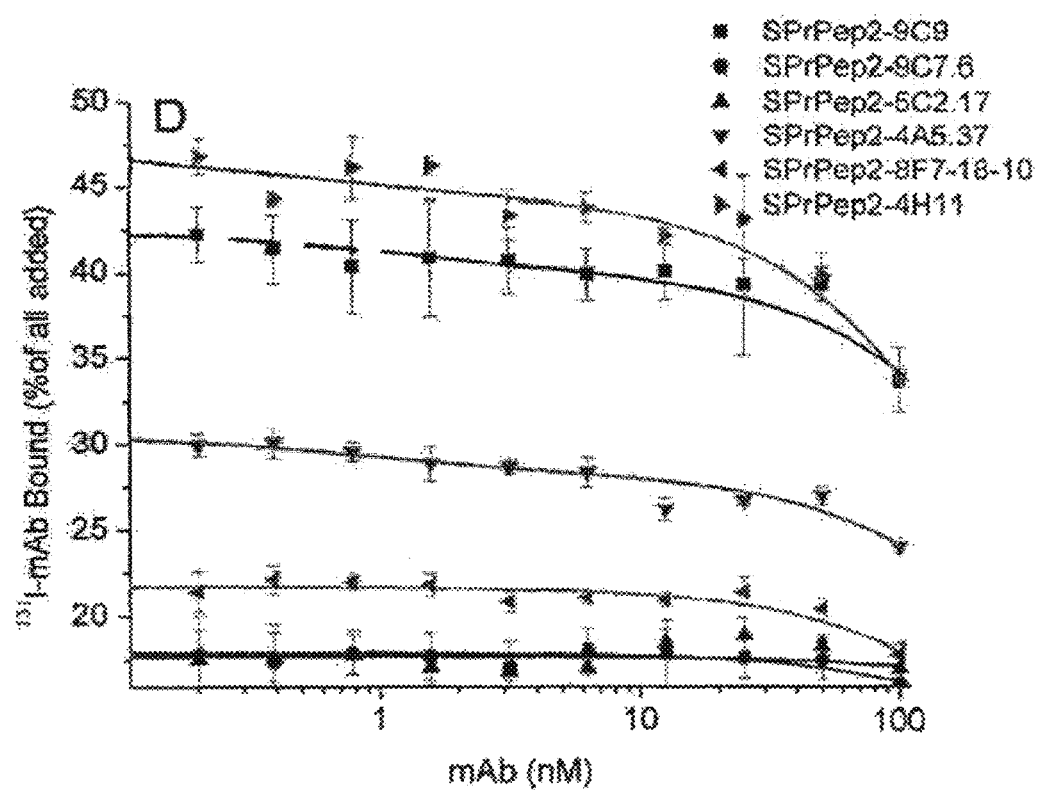
Figure 5E:
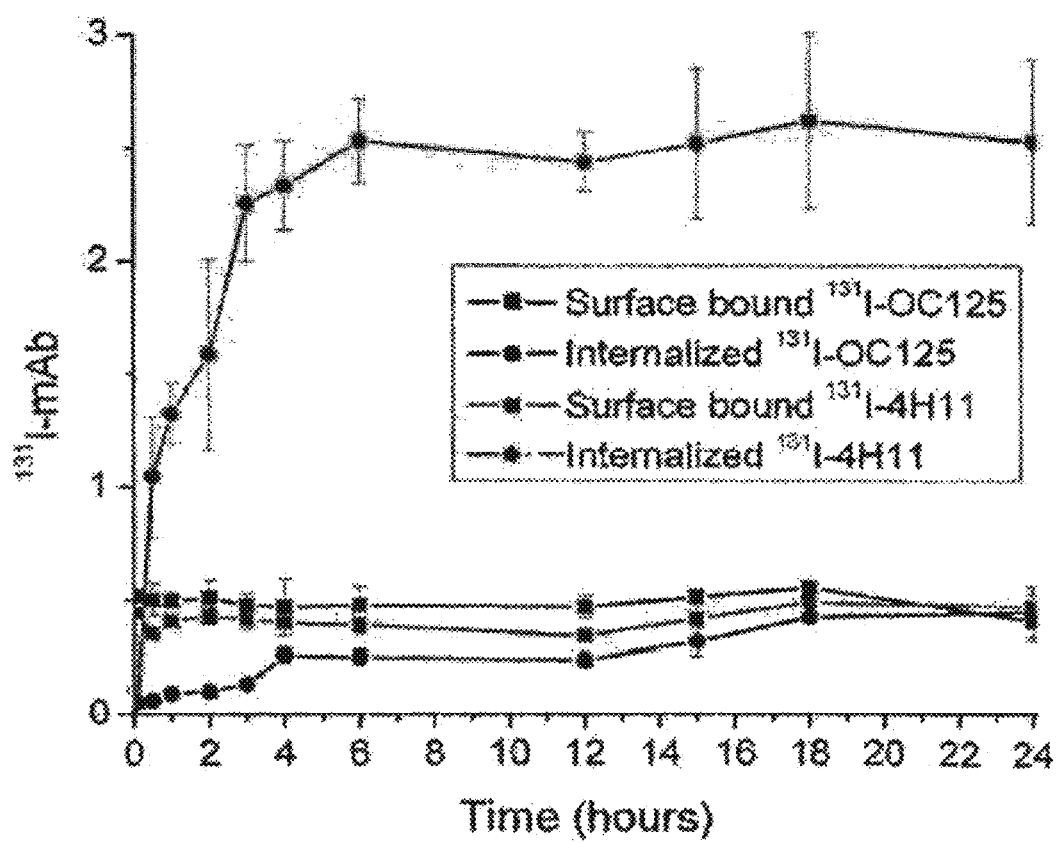
FIG. 5E: Internalization of radio-labeled 4H11 and OC125 monoclonal antibodies on SKOV3-phrGFP-$\Delta$MUC16$^{c334}$ stable transfected cells.
Figure 6A:
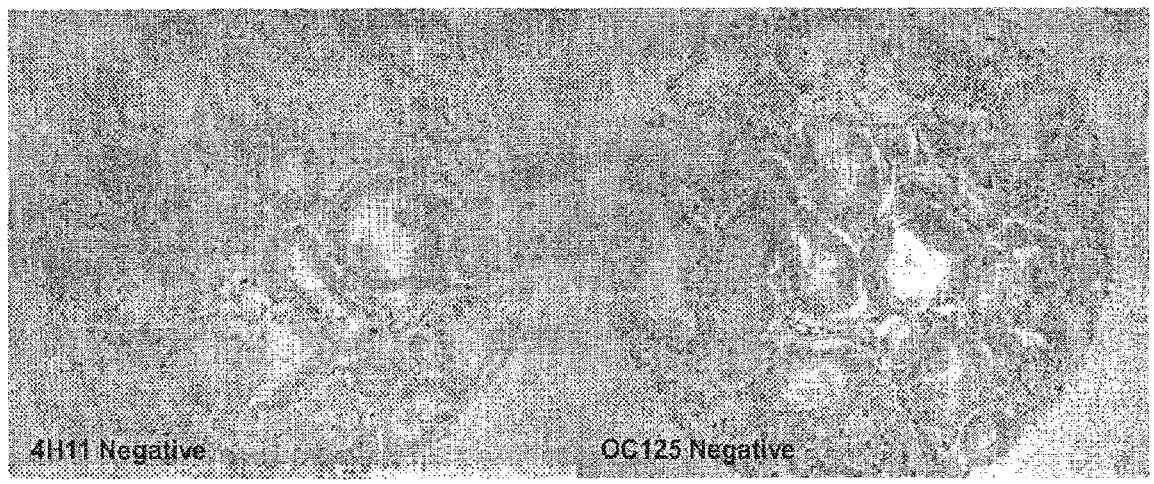
FIGS. 6A-6D: Comparison staining intensities of OC125 and 4H11 monoclonal antibodies on tissue microarrays containing cancers of the prostate (6A, concordant), lung (6B, discordant), breast (6C, discordant), and pancreas (6D, discordant).
Figure 6B:
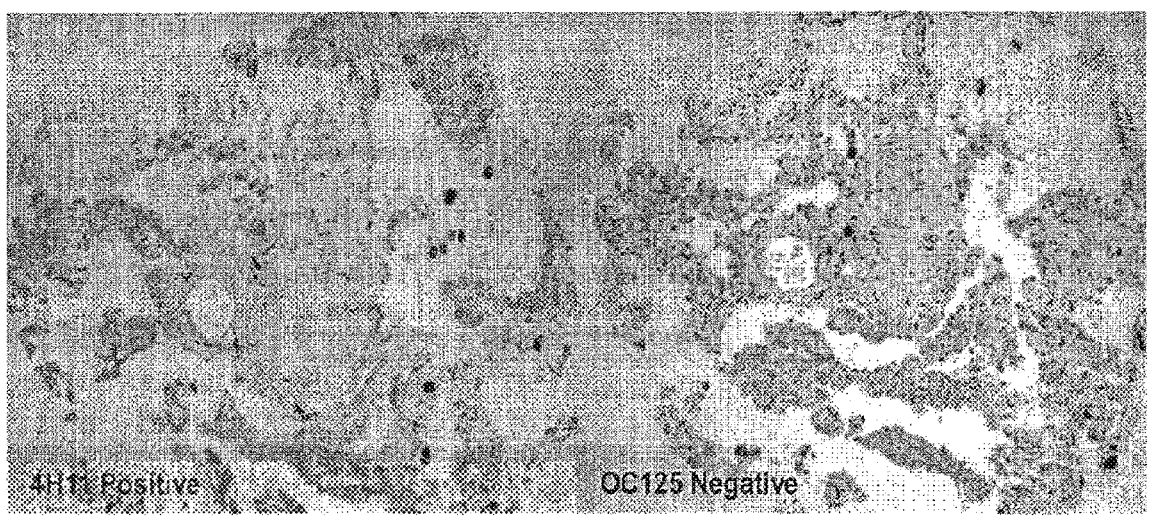
Figure 6C:
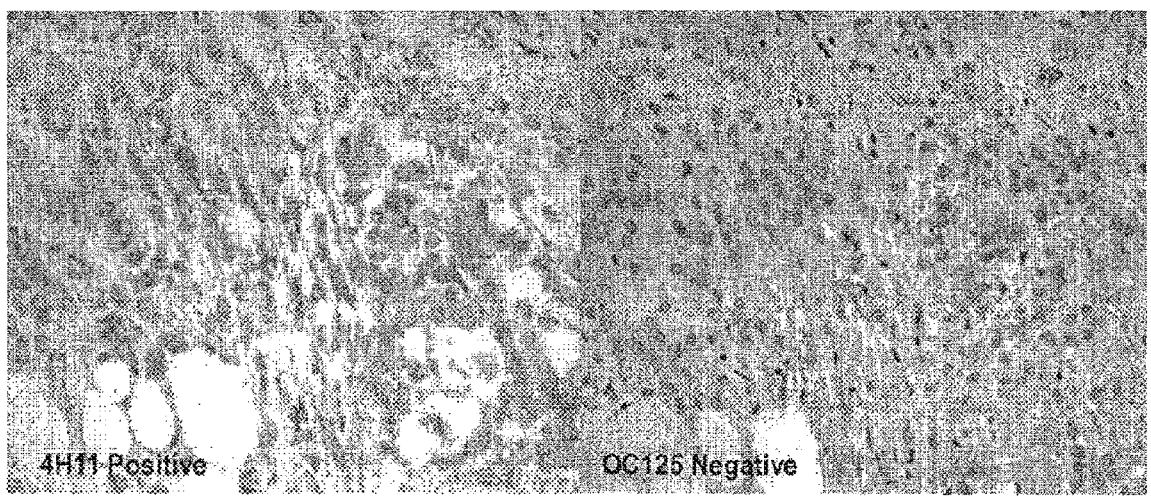
Figure 6D:
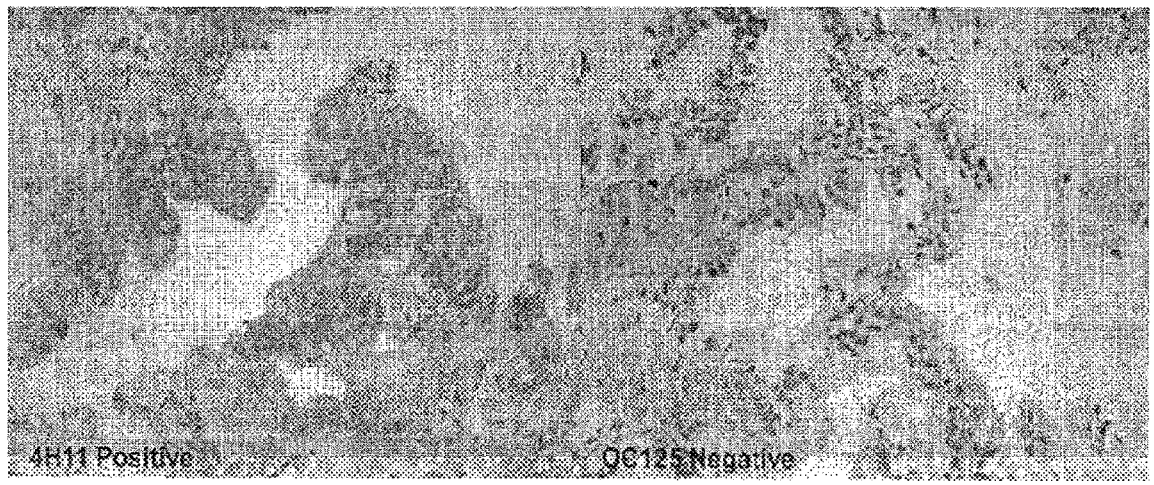

One advantage of the invention's antibodies is that the antibody internalizes into a cell, thereby being useful in applications for delivery inside a cell, such as disease therapy. "Internalized" when in reference to a molecule that is internalized by a cell refers to passage of the molecule that is in contact with the extracellular surface of a cell membrane across the cell membrane to the intracellular surface of the cell membrane and/or into the cell cytoplasm. Methods for determining internalization are disclosed herein, including the detection of radiolabeled molecule inside the cell (FIG. 5E).

In one embodiment, the invention's antibodies specifically bind to MUC16 ectodomain polypeptide that comprises a polypeptide selected from the group consisting of Polypeptide 1 NFSPLARRVDRVAIYEE (SEQ ID NO:01)

and Polypeptide 2 TLDRSSVLVDGYSPNRNE (SEQ ID NO: 02). Data herein show that the invention's antibodies specifically bind to GST-ΔMUC16$^{c114}$(Example 2, Table 1A). The specificity of the invention's antibodies is in contrast to prior art antibodies (e.g., VK8, M11 and OC125 antibodies) that did not bind to GST-ΔMUC16$^{c114}$ purified protein or cell lysates of the SKOV3-phrGFP-ΔMUC16$^{c114}$ cell line (Example 2, FIG. 2).

In a further embodiment, the invention's antibodies lack specific binding to a glycosylated MUC16 extracellular domain, exemplified by the cleaved CA-125 described in Payne et al., U.S. Pat. No. 7,202,346.

While not intending to limit the sequence of the $V_L$ and $V_H$ regions of the invention's antibodies, in one embodiment, the antibody specifically binds to the Polypeptide 2 (SEQ ID NO:02) of the MUC16 ectodomain polypeptide, wherein the antibody comprises a variable heavy ($V_H$) chain encoded by SEQ ID NO:06 (i.e., the antibody 4H111 variable heavy ($V_H$) chain amino acid sequence of FIG. 8), and a variable light ($V_L$) chain encoded by SEQ ID NO:07 (i.e., the antibody 4H11 variable light ($V_L$) chain amino acid sequence of FIG. 8). In a particular embodiment, the antibody is chimeric, wherein at least one of the $V_L$ and $V_H$ chains is fused to a human immunoglobulin constant region.

Also without intending to limit the sequence of the $V_L$ and $V_H$ regions of the invention's antibodies, in one embodiment, the antibody specifically binds to the Polypeptide 2 (SEQ ID NO:02) of the MUC16 ectodomain polypeptide, wherein the antibody comprises a variable heavy ($V_H$) chain encoded by SEQ ID NO:04 (i.e., the antibody 4A5 variable heavy ($V_H$) chain nucleotide sequence of FIG. 8), and a variable light ($V_L$) chain encoded by SEQ ID NO:05 (i.e., the antibody 4A5 variable light ($V_L$) chain nucleotide sequence of FIG. 8). In a particular embodiment, the antibody is chimeric wherein at least one of the $V_L$ and $V_H$ chains is covalently linked to a human immunoglobulin constant region.

Still without intending to limit the sequence of the $V_L$ and $V_H$ regions of the invention's antibodies, in one embodiment, the antibody specifically binds to the Polypeptide 1 (SEQ ID NO:01) of the MUC16 ectodomain polypeptide, wherein the antibody comprises a variable heavy ($V_H$) chain encoded by SEQ ID NO:08 (i.e., the antibody 9B11 variable heavy ($V_H$) chain nucleotide sequence of FIG. 8), and a variable light ($V_L$) chain encoded by at least one of SEQ ID NO:09 (i.e., antibody 9B11 variable light ($V_{L,A}$) chain nucleotide sequence of FIG. 8), and SEQ ID NO:10 (i.e., the antibody 9B11 variable light ($V_{L,B}$) chain nucleotide sequence of FIG. 8). In a particular embodiment, the antibody is chimeric wherein at least one of the $V_L$ and $V_H$ chains is covalently linked to a human immunoglobulin constant region.

While not intending to restrict the source of antigen to which the invention's antibodies bind, in one embodiment, the MUC16 ectodomain polypeptide is expressed by a cell. Data herein show that the invention's exemplary antibodies bind to SKOV3 cells transduced with phrGFP-ΔMUC16$^{c114}$ (Example 2).

While not limiting the sequence of antigen to which the invention's antibodies bind, in a further embodiment, the invention's antibodies specifically bind to a MUC16 cytoplasmic domain polypeptide that comprises VTTRR RKKEGEYNVQ QQ (SEQ ID NO:18). In a particular embodiment, the MUC16 cytoplasmic domain polypeptide comprises Polypeptide 3 CGVLVTTRRRKKEG-EYNVQQQ (SEQ ID NO:03). In some embodiment, the MUC16 cytoplasmic domain polypeptide is expressed by a cell. For example, data herein show that the invention's exemplary antibody binds to SKOV3 cells transduced with phrGFP-ΔMUC16$^{c114}$ (Example 2). In a particular embodiment, the cell is permeabilized to facilitate internalization of the antibody into the cell so that it comes into contact with its cytoplasmic antigen.

Still without limiting the sequence of antigen to which the invention's antibodies bind, in a further embodiment, the invention's antibodies bind to a MUC16 extracellular domain polypeptide that contains a cysteine loop polypeptide CQVSTFRSVPNRHHTGVDSLC (SEQ ID NO:19). In a more preferred embodiment, the MUC16 extracellular domain polypeptide comprises Polypeptide 4 KSYF SDCQVSTFRS VPNRHHTGVD SLCNFSPL (SEQ ID NO:15).

Still without intending to limit the sequence of the $V_L$ and $V_H$ regions of the invention's antibodies, in one embodiment, the antibody specifically binds to Polypeptide 4 (SEQ ID NO:15) of the MUC16 extracellular domain polypeptide, wherein the antibody comprises a variable heavy ($V_H$) chain encoded by SEQ ID NO:11 (i.e., the antibody 24B3 variable heavy ($V_H$) chain amino acid sequence of FIG. 8), and a variable light ($V_L$) chain encoded by SEQ ID NO: 12 (i.e., the antibody 24B3 variable light ($V_L$) chain amino acid sequence of FIG. 8).

The invention contemplates chimeric antibodies (see U.S. Pat. No. 7,662,387), monoclonal antibodies, recombinant antibodies, an antigen-binding fragment of a recombinant antibody, a humanized antibody, and an antibody displayed upon the surface of a phage (U.S. Pat. No. 7,202,346). In particular, the invention contemplates antibody fragments that contain the idiotype ("antigen-binding region" or "antigen-binding fragment") of the antibody molecule. For example, such antigen-binding fragments include, but are not limited to, the Fab region, F(ab')2 fragment, pFc' fragment, and Fab' fragments.

The "Fab region" and "fragment, antigen binding region," interchangeably refer to portion of the antibody arms of the immnoglobulin "Y" that function in binding antigen. The Fab region is composed of one constant and one variable domain from each heavy and light chain of the antibody. Methods are known in the art for the construction of Fab expression libraries (Huse et al., Science, 246:1275-1281 (1989)) to allow rapid and easy identification of monoclonal Fab fragments with the desired specificity. In another embodiment, Fc and Fab fragments can be generated by using the enzyme papain to cleave an immunoglobulin monomer into two Fab fragments and an Fc fragment. The enzyme pepsin cleaves below the hinge region, so a "F(ab')2 fragment" and a "pFc' fragment" is formed. The F(ab')2 fragment can be split into two "Fab' fragments" by mild reduction.

The invention also contemplates a "single-chain antibody" fragment, i.e., an amino acid sequence having at least one of the variable or complementarity determining regions (CDRs) of the whole antibody, and lacking some or all of the constant domains of the antibody. These constant domains are not necessary for antigen binding, but constitute a major portion of the structure of whole antibodies. Single-chain antibody fragments are smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies. Techniques for the production of single-chain antibodies are known (U.S. Pat. No. 4,946,778). The variable regions of the heavy and light chains can be fused together to form a "single-chain variable fragment" ("scFv fragment"), which is only half the size of the Fab fragment, yet retains the original specificity of the parent immunoglobulin.

The "Fc region" and "Fragment, crystallizable region" interchangeably refer to portion of the base of the immnoglobulin "Y" that function in role in modulating immune cell activity. The Fc region is composed of two heavy chains that contribute two or three constant domains depending on the class of the antibody. By binding to specific proteins, the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils. In an experimental setting, Fc and Fab fragments can be generated in the laboratory by cleaving an immunoglobulin monomer with the enzyme papain into two Fab fragments and an Fc fragment.

The invention contemplates polyclonal antibodies and monoclonal antibodies. "Polyclonal antibody" refers to an immunoglobulin produced from more than a single clone of plasma cells; in contrast "monoclonal antibody" refers to an immunoglobulin produced from a single clone of plasma cells. Generic methods are available for making polyclonal and monoclonal antibodies that are specific to a desirable polypeptide. For the production of monoclonal and polyclonal antibodies, various host animals can be immunized by injection with the peptide corresponding to any molecule of interest in the present invention, including but not limited to hamsters, rabbits, mice, rats, sheep, goats, etc. For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 (1975)), techniques using germ-free animals and utilizing technology such as that described in PCT/US90/02545, as well as the trioma technique, the human B-cell hybridoma technique (See e.g., Kozbor et al., Immunol. Today, 4:72 (1983)), and the EBV-hybridoma technique to produce human monoclonal antibodies (Cole et al., in Monoclonal Antibodies and Cancer Therapy, Alan R. Liss, Inc., pp. 77-96 (1985)). In some particularly preferred embodiments of the present invention, the present invention provides monoclonal antibodies.

Also contemplated are chimeric antibodies. As used herein, the Willi "chimeric antibody" contains portions of two different antibodies, typically of two different species. See, e.g.: U.S. Pat. No. 4,816,567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al. Chimeric antibodies include monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer (H2L2) formed by two HL dimers associated through at least one disulfide bridge. A polyvalent chimeric antibody can also be produced, for example, by employing a He region that aggregates (e.g., IgM H chain).

The invention also contemplates "humanized antibodies," i.e., chimeric antibodies that have constant regions derived substantially or exclusively from human antibody constant regions, and variable regions derived substantially or exclusively from the sequence of the variable region from a mammal other than a human. Humanized antibodies preferably have constant regions and variable regions other than the complement determining regions (CDRs) derived substantially or exclusively from the corresponding human antibody regions and CDRs derived substantially or exclusively from a mammal other than a human. Thus, in one embodiment, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody may also comprise at least a portion of an immunoglobulin constant region (Fc), typically that of a human immunoglobulin. Humanized antibodies may be generated using methods known in the art, e.g., U.S. Pat. No. 5,225,539 to Winter et al., including using human hybridomas (Cote et al., Proc. Natl. Acad. Sci. U.S.A. 80:2026-2030 (1983)) or by transforming human B cells with EBV virus in vitro (Cole et al., in Monoclonal Antibodies and Cancer Therapy, Alan R. Liss, pp. 77-96 (1985)). Additional methods include, for example, generation of transgenic non-human animals which contain human immunoglobulin chain genes and which are capable of expressing these genes to produce a repertoire of antibodies of various isotypes encoded by the human immunoglobulin genes (U.S. Pat. Nos. 5,545,806; 5,569,825 and 5,625,126). Humanized antibodies may also be made by substituting the complementarity determining regions of, for example, a mouse antibody, into a human framework domain (PCT Pub. No. WO92/22653).

Importantly, early methods for humanizing antibodies often resulted in antibodies with lower affinity than the non-human antibody starting material. More recent approaches to humanizing antibodies address this problem by making changes to the CDRs. See U.S. Patent Application Publication No. 20040162413, hereby incorporated by reference. In some embodiments, the invention's humanized antibodies contain an optimized heteromeric variable region (e.g. that may or may not be part of a full antibody other molecule) having equal or higher antigen binding affinity than a donor heteromeric variable region, wherein the donor heteromeric variable region comprises three light chain donor CDRs, and wherein the optimized heteromeric variable region comprises: a) a light chain altered variable region comprising; i) four unvaried human germline light chain framework regions, and ii) three light chain altered variable region CDRs, wherein at least one of the three light chain altered variable region CDRs is a light chain donor CDR variant, and wherein the light chain donor CDR variant comprises a different amino acid at only one, two, three or four positions compared to one of the three light chain donor CDRs (e.g. the at least one light chain donor CDR variant is identical to one of the light chain donor CDRs except for one, two, three or four amino acid differences).

Chimeric antibodies containing amino acid sequences that are fused to constant regions from human antibodies, or to toxins or to molecules with cytotoxic effect, are known in the art (e.g., U.S. Pat. Nos. 7,585,952; 7,227,002; 7,632,925; 7,501,123; 7,202,346; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 6,429,295; 7,666,425; and 5,057,313).

Antibodies that are specific for a particular antigen may be screened using methods known in the art (e.g., U.S. Pat. No. 7,202,346) and disclosed herein. For example, In the production of antibodies, screening for the desired antibody can be accomplished by radioimmunoassay, ELISA (enzyme-linked immunosorbent assay), "sandwich" immunoassays, immunoradiometric assays, gel diffusion precipitin reactions, immunodiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

In one embodiment, the invention's antibodies are monoclonal antibodies produced by a hybridoma cell line. In a particular embodiment, the monoclonal antibody specifically binds to a MUC16 ectodomain polypeptide that comprises Polypeptide 1 (SEQ ID NO:01), as exemplified by the antibody selected from the group consisting of 9B11.20.16, 10A2, 2F4, 23D3, 30B1, and 31B2 (Tables 1 and 2). In a preferred embodiment, the antibody is 9B11.

In another embodiment, the monoclonal antibody specifically binds to a MUC16 ectodomain polypeptide that comprises Polypeptide 2 (SEQ ID NO:02), wherein the antibody is exemplified by 4H11.2.5, 13H1, 29G9, 9C9.21.5.13, 28F8, 23G12, 9C7.6, 11B6, 25G4, 5C2.17, 4C7, 26B2, 4A5.37, 4A2, 25H3, and 28F7.18.10 (Tables 1 and 2). In a preferred embodiment, the antibody is exemplified by 4H111.2.5, 4A5.37, 9C9.21.5.13, 28F7.18.10, 9C7.6, and 5C2.17.

In a further embodiment, the monoclonal antibody specifically binds to a MUC16 cytoplasmic domain polypeptide that comprises Polypeptide 3 CGVLVTTRRRKKEGEYNVQQQ (SEQ ID NO:03), wherein the antibody is exemplified by 31A3.5.1, 19D1, 10F6, 22E10, 22F1, 3H8, 22F11, 4D7, 24G12, 19G4, 9A5, 4C2, 31C8, 27G4, and 6H2 (Tables 1 and 2). In a preferred embodiment, the antibody is 31A3.5.1.

In another embodiment, the monoclonal antibody specifically binds to a MUC16 extracellular domain polypeptide that comprises Polypeptide 4 KSYF SDCQVSTFRS VPNRHHTGVD SLCNFSPL (SEQ ID NO:15), wherein the antibody is exemplified by 24B3 and 9C7 (Table 2).

The invention's antibodies and methods for their use (both diagnostic and therapeutic) are disease specific. "Specificity" of a method and/or molecule for disease, such as "specificity for cancer" which is interchangeably used with "cancer specificity", refers to the proportion (e.g., percentage, fraction, etc.) of negatives (i.e., healthy individuals not having disease) that are correctly identified, i.e., the percentage of healthy subjects who are correctly identified as not having disease. Specificity may be calculated according to the following equation:

Specificity=number of true negatives/(number of true negatives+number of false positives).

Thus, in some embodiments, the invention's compositions and/or methods have a "cancer specificity" greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% specificity is most desirable, i.e., not predicting anyone from the healthy group as having cancer, it is not necessary. Data herein demonstrate the invention's cancer specificity (Table 3).

In alternative embodiments, specificity is expressed (together with sensitivity) as a statistical measure of the performance of a binary classification test, such as using a Receiver Operator Characteristic (ROC) curve". For any test, there is usually a trade-off between specificity and sensitivity. For example: in cancer screening tests of human subjects, it is undesirable to risk falsely identifying healthy people as having cancer (low specificity), due to the high costs. These costs are both physical (unnecessary risky procedures) and financial. This trade-off can be represented graphically using a ROC curve. "Receiver Operator Characteristic curve" and "ROC curve" refer to a plot of the true positive rate (AKA sensitivity) versus true negative rate (AKA 1-specificity). The measured result of the test is represented on the x axis while the y axis represents the number of control (e.g., healthy) or case (e.g., cancer) subjects. For any given cut point (each point along the x axis) a sensitivity and specificity of the assay can be measured. The range of sensitivity and specificity for any given assay can range from 0% to 100%, depending on the selected cut point. For this reason, in some preferred embodiments, the AUC is used as the standard measure of an assay's specificity and/or sensitivity. The "area under the curve" ("AUC") for the ROC curve plot is equal to the probability that a classifier will rank a randomly chosen positive instance higher than a randomly chosen negative one. Thus, AUC is a general measure of a tests ability to successfully discriminate between case (e.g., cancer) and control (e.g., healthy) subjects. Random chance would generate an AUC of 0.5. Therefore, in one embodiment, useful tests preferably have AUC's greater than 0.50, including any value from 0.51 to 1.00, such as from 0.55 to 1.00, from 0.60 to 1.00, from 0.65 to 1.00, from 0.70 to 1.00, from 0.75 to 1.00, from 0.80 to 1.00, from 0.85 to 1.00, from 0.90 to 1.00, from 0.95 to 1.00, and most preferably 1.00. AUC values greater than 0.50 include 0.51, 0.52, 0.52, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, and 0.99.

The invention's antibodies and methods for their use (both diagnostic and therapeutic) are disease sensitive. "Sensitivity" of a method and/or molecule for disease, such as "sensitivity for cancer" which is interchangeably used with "cancer sensitivity," refers to the proportion (e.g., percentage, fraction, etc.) of positives (i.e., individuals having cancer) that are correctly identified as such (e.g. the percentage of people with cancer who are identified as having the condition). Sensitivity may be calculated according to the following equation; Sensitivity=number of true positives/(number of true positives+number of false negatives).

Thus, in some embodiments, the invention's compositions and/or methods have a "disease sensitivity," such as "cancer sensitivity," greater than 50%, including any numerical value from 51% to 100%, such as 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. While a 100% sensitivity is most desirable (i.e., predicting all subjects from the cancer group as having cancer), it is not necessary.

In alternative embodiments, the invention's compositions and/or methods have a "disease sensitivity," such as "cancer sensitivity," equal to or lower than 50%, including any numerical value from 0% to 50%, such as 1%, 2%, 3%, 4%, 6%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, and 49%.

In some embodiments, sensitivity is expressed (together with specificity) as a statistical measure of the performance of a binary classification test, such as using AUC of a ROC curve, as discussed above with respect to specificity.

D. Hybridoma Cell Lines

In addition to the invention's novel antibodies, the invention also provides hybridoma cell lines that produce these antibodies. "Hybridoma cell" refers to a cell line produced by fusing a specific antibody-producing B cell with a myeloma (B cell cancer) cell that is selected for its ability to grow in tissue culture and for an absence of antibody chain synthesis. The antibodies produced by the hybridoma cell are all of a single specificity and are therefore monoclonal antibodies (in contrast to polyclonal antibodies).

In a particular embodiment, the invention provides hybridoma cell lines that produce a monoclonal antibody that specifically binds to a polypeptide, or antigenic portion thereof, selected from the group consisting of a) MUC16 ectodomain polypeptide (e.g., NFSPLAR RVDRVAIYEE FLRMTRNGTQ LQNFTLDRSS VLVDGYSPNR NEPLTGNSDL P (SEQ ID NO:17)), b) MUC16 cytoplasmic domain polypeptide (e.g., VTTRR RKKEGEYNVQ QQ (SEQ ID NO:18)), and c) MUC 16 extracellular domain polypeptide that contains a cysteine loop polypeptide CQVSTFRSVPNRHHTGVDSLC (SEQ ID NO:19). The MUC16 polypeptide SEQ ID NO:18 is contained within LVTTRR RKKEGEYNVQ QQ (SEQ ID NO:20). Thus, SEQ ID NO:20 contains both a transmembrane domain amino acid (L) and a cytoplasmic domain portion VTTRR RKKEGEYNVQ QQ (SEQ ID NO:18), i.e., the L is optional, as it is part of the transmembrane domain. The MUC16 polypeptide SEQ ID NO:18 is also contained within CGVLVTTRR RKKEGEYNVQ QQ (SEQ ID NO:03).

Thus, SEQ ID NO:03 contains both a transmembrane domain portion (CGVL) and a cytoplasmic domain portion VTTRR RKKEGEYNVQ QQ (SEQ ID NO:18), i.e., the CGVL is optional, as it is part of the transmembrane domain.

E. Conjugates of the Invention's Antibodies Linked to Cytotoxic Agents and/or Prodrugs The invention contemplates conjugate antibodies. A "conjugate" antibody refers to an antibody of the present invention covalently linked to a cytotoxic agent and/or a prodrug of a cytotoxic agent.

"Cytotoxic agent" refers any agent that is capable of reducing the growth of, and/or killing, a target cell. A "prodrug" represents an analog of a cytotoxic agent that substantially lacks cytotoxic activity until subjected to an activation step. Activation steps may include enzymatic cleavage, a chemical activation step such as exposure to a reductant, or a physical activation step such as photolysis.

The covalent linkage between the invention's antibodies and the cytotoxic agent or prodrug can include cleavable linkages such as disulfide bonds, which may advantageously result in cleavage of the covalent linkage within the reducing environment of the target cell. Such conjugates are useful as tumor-cell specific therapeutic agents.

In one embodiment, the cytotoxic agent is a small drug molecule (Payne et al., U.S. Pat. No. 7,202,346). In another embodiment, the cytotoxic agent a maytansinoid, an analog of a maytansinoid, a prodrug of a maytansinoid, or a prodrug of an analog of a maytansinoid (U.S. Pat. Nos. 6,333,410; 5,475,092; 5,585,499; 5,846,545; 7,202,346). In another embodiment, the cytotoxic agent may be a taxane (see U.S. Pat. Nos. 6,340,701 & 6,372,738 & 7,202,346) or CC-1065 analog (see U.S. Pat. Nos. 5,846,545; 5,585,499; 5,475,092 & 7,202,346).

In another embodiment, the cytotoxic agent is exemplified by an auristatin, a DNA minor groove binding agent, a DNA minor groove alkylating agent, an enediyne, a duocarmycin, a maytansinoid, and a vinca alkaloid (U.S. Pat. No. 7,662,387).

In a further embodiment, the cytotoxic agent is an antitubulin agent (U.S. Pat. No. 7,662,387). In yet another embodiment, the cytotoxic agent is exemplified by dimethylvaline-valine-dolaisoleuine-dolaproine-phenylalanine-p-phenylenediamine (AFP), dovaline-valine-dolaisoleunine-dolaproine-phenylalanine (MMAF), and monomethyl auristatin E (MAE) (U.S. Pat. No. 7,662,387).

In an additional embodiment the toxic agent is exemplified by radioisotope emitting radiation, immunomodulator, lectin, and toxin (U.S. Pat. No. 6,429,295). In particular, the radioisotope emitting radiation is an alpha-emitter selected from the group consisting of $^{212}$Bi, $^{213}$Bi, and $^{211}$At, or a beta-emitter selected from the group consisting of $^{186}$Re and $^{90}$Y, or a gamma-emitter $^{131}$I (U.S. Pat. No. 7,666,425).

In an alternative embodiment, the toxin is exemplified by ricin, the A-chain of ricin, and pokeweed antiviral protein (U.S. Pat. No. 5,057,13).

In yet another embodiment, the cytotoxic agent is an anti-cancer drug selected from the group consisting of methotrexate, 5-fluorouracil, cycloheximide, daunomycin, doxorubicin, chlorambucil, trenimon, phenylenediamine mustard, adriamycin, bleomycin, cytosine arabinoside or Cyclophosphamide (U.S. Pat. No. 5,057,13).

F. Detecting Muc16 Portions And Diagnostic Applications

The invention provides a method for detecting a disease that comprises overexpression of MUC16 in a subject, wherein the method comprises a) providing i) a sample from a subject, and ii) any one or more of the invention's antibodies, b) contacting the sample with the antibody under conditions for specific binding of the antibody with its cognate antigen, and c) detecting an increased level of binding of the antibody to the sample compared to a control sample lacking the disease, thereby detecting the disease in the subject. Generic methods for detecting disease using antibodies are known in the art (Payne et al., U.S. Pat. No. 7,202,346). The invention's methods are particularly useful in detecting cancer, such as ovarian cancer and breast cancer.

The invention's methods are not limited to a particular approach to detecting binding of the invention's antibodies to their antigens. In one embodiment, detecting binding to the invention's antibodies typically involves using antibodies that are labeled with a detectable moiety, such as radioisotope (e.g., $^3$H, $^{14}$C, $^{32}$P, $^{35}$S and/or $^{125}$I), fluorescent or chemiluminescent compound (e.g., fluorescein isothiocyanate, rhodamine, and/or luciferin) and/or an enzyme (e.g., alkaline phosphatase, beta-galactosidase and/or horseradish peroxidase).

Methods for conjugating antibodies to a detectable moiety arc known in the art (e.g., Hunter, et al., Nature 144:945 (1962); David, e at., Biochemistry 13:1014 (1974); Pain, et al., J. Immunol. Meth. 40:219 (1981); and Nygren, J. Histochem and Cytochem 30:407 (1982).

Thus, the invention's antibodies may be employed in immunoassays, such as competitive binding assays, direct and indirect sandwich assays, and immunoprecipitation assays, including immunohistochemistry, enzyme-linked immunosorbent assay (ELISA), fluorescence-activated cell sorting (FACS), and Western blots.

For example, with respect to immunohistochemical detection, data herein demonstrate that antibody 4H11 is useful in detecting high-grade ovarian serous carcinoma, lobular cancer (28), and a subset of ovarian carcinomas that are negative with OC125 and that retain cytoplasmic and extracellular portions of the MUC16 glycoprotein.

The antibodies of the invention also are useful for radiographic in vivo imaging, wherein an antibody labeled with a detectable moiety such as a radio-opaque agent or radioisotope is administered to a subject, preferably into the bloodstream, and the presence and location of the labeled antibody in the host is assayed. This imaging technique is useful in the staging and treatment of malignancies.

The invention's antibodies are additionally useful as affinity purification agents. In this process, the antibodies are immobilized on a suitable support, such a Sephadex resin or filter paper, using methods well known in the art, to capture and purify molecules that contain antigens that specifically bind to the invention's antibodies.

G. Therapeutic Applications

The invention provides methods for treating a disease that comprises overexpression of MUC16, comprising administering to a subject having the disease a therapeutically effective amount of any one or more of the invention's antibodies. Generic methods for treating disease with antibodies are known in the art (Payne et al., U.S. Pat. No. 7,202,346). The invention's methods are particularly useful in treating cancer, such as ovarian cancer and breast cancer. These methods are also applicable to primary cancer, metastatic cancer, and recurrent cancer.

The term "administering" to a subject means providing a molecule to a subject. This may be done using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789). The invention's compositions may be administered prophylactically (i.e., before the observation of disease symptoms) and/or therapeutically (i.e., after the observation of disease symptoms). Administration also may be concomitant with (i.e., at the same time as, or during) manifestation of one or more disease symptoms. Also, the invention's compositions may be administered before, concomitantly with, and/or after administration of another type of drug or therapeutic procedure (e.g., surgery). Methods of administering the invention's compositions include, without limitation, administration in parenteral, oral, intraperitoneal, intranasal, topical and sublingual forms. Parenteral routes of administration include, for example, subcutaneous, intravenous, intramuscular, intrasternal injection, and infusion routes.

In one embodiment, the invention's compositions comprise a lipid for delivery as liposomes. Methods for generating such compositions are known in the art (Borghouts et al. (2005). J Pept Sci 11, 713-726; Chang et al. (2009) PLoS One 4, e4171; Faisal et al. (2009) Vaccine 27, 6537-6545; Huwyler et al. (2008) Int J Nanomedicine 3, 21-29; Song et al. (2008) Int J Pharm 363, 155-161; Voinea et al. J Cell Mol Med 6, 465-474).

Antibody treatment of human beings with cancer is known in the art, for example in U.S. Pat. Nos. 5,736,137; 6,333,410; 5,475,092; 5,585,499; 5,846,545; 7,202,346; 6,340,701; 6,372,738; 7,202,346; 5,846,545; 5,585,499; 5,475,092; 7,202,346; 7,662,387; 7,662,387; 6,429,295; 7,666,425; 5,057,313.

The invention's antibodies may be administered with pharmaceutically acceptable carriers, diluents, and/or excipients. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose.

The invention's antibodies are typically administered in a therapeutic amount. The terms "therapeutic amount," "pharmaceutically effective amount," "therapeutically effective amount," and "biologically effective amount," are used interchangeably herein to refer to an amount that is sufficient to achieve a desired result, whether quantitative or qualitative. In particular, a pharmaceutically effective amount is that amount that results in the reduction, delay, and/or elimination of undesirable effects (such as pathological, clinical, biochemical and the like) that are associated with disease. For example, a "therapeutic amount that reduces cancer" is an amount that reduces, delays, and/or eliminates one or more symptoms of cancer.

For example, specific "dosages" of a ""therapeutic amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors, which those skilled in the art will recognize The dosage amount and frequency are selected to create an effective level of the compound without substantially harmful effects.

When present in an aqueous dosage form, rather than being lyophilized, the antibody typically will be formulated at a concentration of about 0.1 mg/ml to 100 mg/ml.

Depending on the type and severity of the disease, about 0.015 to 15 mg of antibody/kg of patient weight is an initial candidate dosage for administration to the patient, whether, for example, by one or more separate administrations, or by continuous infusion. For repeated administrations over several days or longer, depending on the condition, the treatment is repeated until a desired suppression of disease symptoms occurs.

The methods of the present invention can be practiced in vitro, in vivo, or ex vivo.

EXPERIMENTAL

The following examples serve to illustrate certain preferred embodiments and aspects of the present invention and are not to be construed as limiting the scope thereof.

Example 1

Materials And Methods

The following is a brief description of the exemplary materials and methods used in the subsequent Examples.

Cell Cultures:

OVCAR3, SKOV3, and A2780 cell lines were obtained through the American Type Culture Collection (ATCC, Manassas, Va.) and sustained in culture according to the ATCC literature. For the creation of MUC16+ transfected cell lines, the carboxyterminus portion of the MUC16 cDNA was introduced as green fluorescent protein fusion proteins using the Vitality phrGFP vector expression system (Stratagene, La Jolla, Calif.). Stable cell lines were selected using geneticin (G418, Invitrogen, Grand Island, N.Y.) in their respective culture media and isolated by expression of Green Fluorescence Protein. Stable transfectants were routinely maintained in G418 in their culture media respectively. The $\Delta MUC16^{c114}$ transfectants have cell surface expression of MUC16 protein from the putative cleavage site to the carboxyterminus (AA 1776 to 1890) (12).

Monoclonal Preparation:

Using the MUC16 sequence, peptide sequences encoding elements of the $\Delta MUC16^{c114}$ amino acid sequence were synthesized at the Memorial Sloan-Kettering Cancer Center (MSKCC) Microchemistry Core Facility. The inventors synthesized 3 polypeptides (FIG. 1) and modified Polypeptide 1 and Polypeptide 2 with a cysteine at the N-terminus for better conjugation to KLH. Equal concentrations of the KLH-conjugated peptides were mixed and then used as the immunogen for 5 BALB/c mice. The inventors selected 1 of the 5 mice whose serum showed the highest reactivity to individual peptides by ELISA, and the MSKCC Monoclonal Antibody Core Facility performed the fusion and selected the antibodies using standard protocols. After 10 days of fusion, supernatants were selected and screened for reactivity by ELISA against the individual synthetic peptides.

ELISA:

Sandwich ELISA was performed to see the positivity of the antibodies to individual peptides and GST-$\Delta MUC16^{c114}$ fusion protein following routine core facility protocol for ELISA assay.

FACS Analyses:

Adherent target cells were removed by 0.05% Trypsin and 0.1% EDTA, washed, and counted by a hemocytometer. Cells were distributed into multiple Eppendorf tubes with at least 0.5-1×$10^6$ cells per tube. Cells were washed with phosphate buffered saline (PBS) containing 1% FCS and 0.025% Sodium Azide (FACS buffer). For internal FACS staining, cells in the Eppendorf tubes were permeabilized with 1:10 diluted FACS Permeabilizing Solution 2 (BD BioSciences, San Jose, Calif.) for 10 minutes at room temperature and then washed twice with ice cold FACS buffer. Then they were incubated either without (for second antibody control) or with 1 µg/tube of bioreactive supernatants of mouse MUC16 monoclonals for 30 minutes on ice. For surface FACS staining, cells were incubated either without (for second antibody control) or with 1 µg/tube of bioreactive supernatants of MUC16 monoclonals (9B11.20.16, 9C9.21.5.13 and 4H11.2.5), Mouse anti-human OC125 (M3519), Mouse anti-human M11 (M3520) (DakoCytomation, Dako North America Inc., Carpinteria, Calif.) or VK8 (kindly provided by Dr. Beatrice Yin and Dr. Ken Lloyd, MSKCC, New York, N.Y.) for 30 minutes on ice. Cells in Eppendorf tubes were also surface stained with 1 µg/tube of non-specific isotype matched control mouse antibodies (13C4 for IgG1 and 4E11 for IgG2b monoclonals obtained from MSKCC Monoclonal Core Facility) and incubated on ice for 30 minutes. All cells were washed three times with FACS buffer. Cells were incubated with 1 µg/tube of second antibody Goat anti-mouse IgG1-PE or IgG2b-PE for 30 minutes on ice and then washed three times with FACS buffer. The cells were analyzed by a FACS Calibur machine at the MSKCC Flow Cytometry Core Facility.

Western Blot Analysis:

Stable cell lines were cultured in 10 cm dishes in their respective culture media and incubated with 5% $CO_2$ at 37° C. for 3 days. They were washed twice with ice cold PBS to remove the serum-containing media. Adherent cells were scraped with 1-2 ml of ice cold PBS, and the cells were spun down in an Eppendorf tube at 4° C. in an Eppendorf centrifuge. Supernatant was discarded, and the cells were lysed with 0.2 ml of modified Ripa lysis buffer (20 mM Tris-HCL; pH 7.4; 150 mM NaCl; 1% NP-40; 1 mM Na3VO4; 1 mM PMSF; 1 mM DTT; 10 µg/ml leupeptin; and 10 µg/ml aprotinin) for 30 minutes on ice and spun at 4° C. for 10 minutes. The soluble solution was separated into a tube and the debris pellet was discarded. Protein concentration was measured using the Bio-Rad Protein Assay (BioRsD Laboratories, Hercules, Calif.). Equal amounts of proteins (GST-MUC16-CD-fusion protein or stable cell line extracts) were separated by sodium dodecyl sulfate polyacrylamide gel electrophoresis (SDS-PAGE) and transferred to nitrocellulose membrane using a BioRad transfer apparatus in a cold room at 4° C. The membranes were blocked with 3% bovine serum albumin (BSA) in PBS with 0.1% Tween-20 (PBST) at 4° C. overnight. Membranes were probed with primary antibody (1:1000 dilution) for 1 hr at room temperature and then washed three times with PBST. Then the membranes were stained with corresponding second antibody, anti-Mouse IgG Horse Radish Peroxidase (HRP) linked whole antibody from sheep (GE Healthcare, UK) (1:5000 dilution), for 1 hr at room temperature. Membranes were washed three times with PBST and developed with a Western Lightning© chemiluminescence reagent (ECL, Perkin Elmer, Waltham, Mass.) for 1-5 minutes at room temperature, and the signals were developed on Kodak BioMax Film.

Binding and internalization studies with monoclonal antibodies and OVCAR3 and SKOV3 stable transfectants:

Purified monoclonal antibodies were labeled with $^{131}I$ using the iodogen method and purified by size exclusion chromatography (22). Saturation binding studies were performed with radiolabeled antibodies using substrates of intact OVCAR-3 cells. Briefly, 10 test solutions were prepared (in triplicate) and they contained increasing amounts of the radioiodinated antibodies, 3-500 000 cells in a total volume of 500 µL of PBS (0.2% BSA; pH 7.4). The cells were isolated by rapid filtration through a glass fiber membrane and washed with ice cold tris buffered saline. Cells were counted in a gamma counter with standards of total activity added. For each concentration of radiolabeled antibody, non-specific binding was determined in the presence of 100 nM of the unmodified antibody. The data were analyzed with a least squares regression method (Origin, Microcal, Software Inc., Northampton, Mass.) to determine the $K_d$ and $B_{max}$ values, and a Scatchard transformation was performed.

Antibody cell internalization studies were performed with $^{131}$I-4H11 and $^{131}$I-OC125 monoclonal antibodies and SKOV3-phrGFP-ΔMUC16$^{c334}$ stable transfected cells. Briefly, radiolabeled antibody (370 MBq/mg, 100 kcpm) in 2 mL of medium was added to SKOV3 cells plated in a 6-well plate. The plates were incubated at 37° C. for up to 24 hours. At various time points, the medium was removed from three wells and the cells washed with 2×2 mL PBS. Cell surface bound activity was then stripped and collected with 2×2 mL of an ice cold acid wash (100 mM acetic acid 100 mM glycine; pH 3.0). The cells were then dissolved with 2×1 ml 1 M NaOH and collected. At the end of the study all samples were counted with a gamma counter together with standards, representing the initial amount of radioactivity added. All the media samples were analyzed by ITLC-SG with mobile phases of 5% TCA to determine unbound $^{131}$I.

Tissue Microarray (TMA):

Tissue microarrays were either constructed within our institution or bought from a commercial laboratory if not available internally. Briefly, core-needle biopsies of pre-existing paraffin-embedded tissue were obtained from the so-called donor blocks and then relocated into a recipient paraffin-arrayed "master" block by using the techniques by Kononen et al. and subsequently modified by Hedvat et al (23-24). A manually operated Tissue Arrayer MTA-1 from Beecher Instruments Inc. (Sun Prairie, Wis.) was used to produce sample circular spots (cores) that measured 0.6 to 1.0 mm in diameter. The cores were arrayed 0.3 to 0.4 mm apart from each other. A layer of control tissues was strategically laid around the actual tissue microarrays in order to avoid edging effects. The specific composition of each tissue microarray is delineated below. Slides of tissue microarrays for ovarian cancer, prostate cancer, adenocarcinoma of the lung, mutinous neoplasms of the pancreas, and invasive ductal and invasive lobular breast carcinoma were prepared by cutting 4 um sections from formalin-fixed paraffin-embedded tissue. Normal adult and fetal tissue microarrays were obtained from a commercial source (Biomax, US). OVCAR3 cells were used as positive controls.

Immunohistochemistry:

Immunohistochemistry was performed on the tissue microarrays with both standard OC125 (Ventana, Tucson, Ariz.) and the novel monoclonal antibodies. Sections of the tissue microarrays were cut at 4 microns, placed on Superfrost/Plus microscope slides (Fisher brand) and baked in a 60° oven for at least 60 minutes. The slides were then deparaffinized and hydrated to distilled water, soaked in citrate buffer at pH 6.00 for 30 minutes at 97° C., washed in running water for 2-5 minutes, incubated for 5 minutes in 3% hydrogen peroxide diluted in distilled water. Slides were washed in distilled water for 1 minute, transferred to a bath of phosphate buffered saline (PBS), pH 7.2, for two changes of 5 minutes each and placed in 0.05% BSA diluted in PBS for a minimum of 1 minute. After drying around tissue sections, normal serum was applied at a 1:20 dilution in 2% BSA/PBS and incubated for a minimum of 10 minutes at room temperature in a humidity chamber. The serum was then suctioned off without allowing the sections to dry, and approximately 150 lambda of novel antibody at a dilution of 1:1000 was placed on the tissue. The slide was incubated overnight (approximately 15-18 hours) at 4° C. in a humidity chamber. Primary antibody was washed off using three changes of PBS for 10 minutes each. Secondary antibody, biotinylated α-mouse from Vector laboratories (Burlingame, Ca), was applied at 1:500 dilution in 1% BSA/PBS and incubated for 45-60 minutes at room temperature in humidity chamber. The antibody was washed off again using three changes of PBS as above. Slides were then transferred to a bath of diaminobenzidine (DAB), diluted in PBS for 5-15 minutes. The slides were then washed in tap water for 1 minute, counterstained using Harris modified hematoxylin (Fisher), decolorized with 1% acid alcohol and blue in ammonia water, dehydrated with 3 changes each of 95% ethanol, 100% ethanol and xylene for 2 minutes each and coverslipped with permanent mounting medium.

Immunohistochemistry Scoring:

Commercially available antibodies, such as OC125 and M11, target complex glycosylation-dependent epitopes. Our hypothesis is that glycosylation may be tissue specific; therefore, it was important to examine the utility of the peptide-directed antibodies in paraffin-fixed tissues and survey the prevalence of MUC16 expression. The three candidate antibodies, 4H11, 9C9 and 4A5, were characterized using OVCAR3 cell line pellets. Of the three, the 4H11 antibody showed the strongest, most diffuse and consistent staining pattern at multiple dilutions, with the least amount of background staining and, therefore, was optimized for use in human tissues in the pathology core facility.

Using 4H11, the inventors stained and scored positivity using tissue microarrays from high-stage, high-grade ovarian serous carcinomas (FIG. 2), these tumors being the most common type of ovarian cancer, representing approximately 80-85% of all ovarian carcinomas in Western industrialized nations (25). To test the specificity of the novel antibody, the inventors also stained tissue microarrays of cancers of the prostate, lung, breast, and pancreas and compared their staining intensities with that of OC125 monoclonal antibody (FIGS. 6A-6D). To determine whether there would be any cross-reactivity with normal human tissues, the antibodies were also tested on normal human adult and fetal TMAs.

All of the stained sections were reviewed by a reference pathologist (KJP). A subset of cores for which there was equivocal staining was also independently scored by a second pathologist (RAS) to ensure consistency in scoring methods. Only cytoplasmic and/or membranous staining was considered positive. If a portion of the cell showed membranous staining, that was considered partial staining. A scoring system was devised to provide a semiquantitative assessment of staining distribution and intensity in individual cores. At the same time, it was designed to be useful for comparing the staining distribution and intensity between OC125 and the novel antibodies. The score incorporated the percentage of cells, the intensity and pattern of the staining according to the following standards: score 0: no staining; score 1: <5% strong or weak; score 2: 5-50% strong or weak; score 3: 51-75% strong or 51-100% weak; score 4: 76-99% strong; and score 5: 100% strong staining (FIG. 3). The pathologist first reviewed all tissue microarrays stained with OC125 and scored each core. Then the same cores stained with the novel antibodies were scored 1 to several days after OC125 without reference to the previous results. Direct comparison of the scoring between the stains for each core was made only after all of the scoring was completed.

The same process was used for all non-ovarian tissue microarrays. After comparison, core staining was determined to be concordant, equivocal, or discordant based on the point differentials. Concordant cores differed by 0 to 1 point, equivocal cores differed by 2 points, and discordant cores differed by 3 to 5 points. The one exception to this rule was when the difference of 1 point was between a score of 0 and 1, in which case, the differences were considered equivocal. This was in order to truly separate negative cases from even focally positive ones.

Example 2

Generation and Characterization of Anti-MUC16 Monoclonal Antibodies

MUC16-directed monoclonal antibodies were isolated by ELISA-based screening using both the individual peptides and recombinant GST-ΔMUC16$^{c114}$ protein followed by sequential subcloning for single cell clones.

TABLE 1A and 1B

MUC16-carboxyterminus monoclonal antibodies showing their reactivity to GST-ΔMUC16$^{c114}$ western, FACS analysis on OVCAR3 wild type cells Table 1A

| Peptide 1 | | | | Peptide 2 | | | | Peptide 3 | | | |
|---|---|---|---|---|---|---|---|---|---|---|---|
| ELISA Hybridoma Sups (1:1) | (1:10) GST-MucCD Western +/− | (1:1) OVCAR3 FACS +/− | Isotype | ELISA Hybridoma Sups (1:1) | (1:10) GST-MucCD Western +/− | (1:1) OVCAR3 FACS +/− | Isotype | ELISA Hybridoma Sups (1:1) | (1:10) GST-MucCD Western +/− | (1:1) OVCAR3 FACS +/− | Isotype |
| 10A2 | + | − | IgG1, IgM | 13H1 | Weak | − | IgG1 | 22E10 | + | − | IgG2b |
| 23D4 | − | − | missing | 28F8 | + | + | IgG1, IgM | 22F11 | Weak | − | IgM |
| 2F4 | Weak | − | IgG1, IgM | 11B6 | − | − | IgM | 19G4 | Weak | − | IgG1, IgM |
| 9B11 | Weak | +/− | IgG1 | 4C7 | + | − | IgG1 | 31A3 | Weak | − | IgG1 |
| 23D3 | Weak | + | IgG1, IgG2b | 28F7 | + | + | IgG1 | 4C2 | + | − | IgG1, IgM |
| 30B1 | − | − | IgG1 | 9C7 | + | + | IgG1 | 27G4 | + | − | IgM |
| 31B2 | + | − | IgM | 9C9 | + | + | IgG1, IgG2b | 19D1 | + | − | IgG2b |
| | | | | 4H11 | + | + | IgG2b, IgM | 22F1 | + | − | IgG2b, IgM |
| | | | | 4A2 | − | − | IgG1 | 4D7 | + | − | IgG3 |
| | | | | 4A5 | + | + | IgG1 | 9A5 | − | − | IgM |
| | | | | 29G9 | + | | IgG1 | 31C8 | − | − | IgG2b |
| | | | | 5C2 | + | + | IgG1 | 6H2 | Weak | − | IgG1, IgM |
| | | | | 23G12 | − | − | IgG1, IgG2a | 10F6 | − | − | IgG1 |
| | | | | 25G4 | − | − | IgG1, IgM | 3H8 | + | − | IgG1, IgM |
| | | | | 26B2 | + | + | IgG1, IgG2b, IgM | 24G12 | − | − | IgG1, IgM |
| | | | | 25H3 | − | − | IgG1, IgM | | | | |

Table 1B

| Peptide 1 | | | Peptide 2 | | | Peptide 3 | | |
|---|---|---|---|---|---|---|---|---|
| | OVCAR3 FACS +/− | Isotype | | OVCAR3 FACS +/− | Isotype | | OVCAR3 FACS +/− | Isotype |
| 9B11.20.16 | +/− | IgG1 | 9C9.21.5.13 | + | IgG2b | 31A3.5.1 | − | IgG1 |
| | | | 4H11.2.5 | + | IgG2b | | | |
| | | | 9C7.6 | + | IgG1 | | | |
| | | | 5C2.17 | + | IgG1 | | | |
| | | | 4A5.37 | + | IgG1 | | | |
| | | | 28F7.18.10 | + | IgG1 | | | |

TABLE 2

Antibodies specific for exemplary portions of MUC16

1. Muc16 Polypeptide 1:
14394                        14410                        (MUC16 sequence)
NFSPLARRVDRVAIYEE (SEQ ID NO: 01)               17 aa
Mouse monoclonals which are specific to this peptide are:

| Clone | Isotype |
|---|---|
| 9B11.20.16 | (IgG1) |
| 10A2 | (IgG1, IgM) |
| 2F4 | (IgG1, IgM) |
| 23D3 | (IgG1, IgG2b) |
| 30B1 | (IgG1) |
| 31B2 | (IgM) |

2. Muc16 Polypeptide 2:
14425                        14442                        (MUC16 sequence)
TLDRSSVLVDGYSPNRNE (SEQ ID NO: 02)             18 aa
Mouse monoclonals which are specific to this peptide are:

| Clone | Isotype | Clone | Isotype | Clone | Isotype |
|---|---|---|---|---|---|
| 4H11.2.5 | (IgG2b) | 13H1 | (IgG1) | 29G9 | (IgG1) |
| 9C9.21.5.13 | (IgG2b) | 28F8 | (IgG1, IgM) | 23G12 | (IgG1, IgG2a) |
| 9C7.6 | (IgG1) | 11B6 | (IgM) | 25G4 | (IgG1, IgM) |
| 5C2.17 | (IgG1) | 4C7 | (IgG1) | 26B2 | (IgG1, IgG2b, IgM) |
| 4A5.37 | (IgG1) | 4A2 | (IgG1) | 25H3 | (IgG1, IgM) |
| 28F7.18.10 | (IgG1) | | | | |

3. Muc16 Polypeptide 3 (SEQ ID NO: 03)
14472                        14492                        (MUC16 sequence)
CGVLVTTRRRKKEGEYNVQQQ                      21 aa
Mouse monoclonals which are specific to this peptide are:

| Clone | Isotype | Clone | Isotype | Clone | Isotype |
|---|---|---|---|---|---|
| 31A3.5.1 | (IgG1) | 19D1 | (IgG2b) | 10F6 | (IgG1) |
| 22E10 | (IgG2b) | 22F1 | (IgG2b, IgM) | 3H8 | (IgG1, IgM) |
| 22F11 | (IgM) | 4D7 | (IgG3) | 24G12 | (IgG1, IgM) |
| 19G4 | (IgG1, IgM) | 9A5 | (IgM) | | |
| 4C2 | (IgG1, IgM) | 31C8 | (IgG2b) | | |
| 27G4 | (IgM) | 6H2 | (IgG1, IgM) | | |

14452                        14475
FWAVILIGLAGLLGLITCLICGVL (SEQ ID NO: 14) is Transmembrane region    24 aa 4. Muc 16 Polypeptide 4 (SEQ ID NO: 15) containing a cysteine loop polypeptide (SEQ ID NO: 19):
14367                        14398                        (MUC16 sequence)
KSYFSDCQVSTFRSVPNRHHTGVDSLCNFSPL (SEQ ID NO: 15)     32 aa
|_____ S - S _____|
Mouse monoclonals which are specific to this peptide are:
24B3 (IgM)
9C7 (IgM)

| Clone | Isotype |
|---|---|
| 4F12 | IgM kappa |
| 6H6 | IgM kappa |
| 25C2 | IgM kappa |
| 6E8 | IgM kappa |
| 2A3 | IgM, IgG1, IgG2b, kappa |
| 2G4 | IgM, IgG1, kappa |
| 4C8 | IgM, kappa |
| 2A6 | IgG1 kappa |
| 24G12 | IgG1 kappa |
| 15D5 | IgG1 kappa |
| 6E2 | IgM, IgG1, IgG3, IgG2a, kappa |
| 7E6 | IgM, kappa, lambda |
| 7G11 | IgM kappa |
| 20C3 | IgG1, IgG2b |
| 9A3 | IgM kappa |
| 15B6 | IgM kappa |
| 19D3 | IgM kappa |
| 5H8 | IgM, IgG1, IgG2b, kappa |
| 24A12 | IgM kappa |
| 2D10 | IgG3, IgM kappa |
| 5B2 | IgM, IgG3, IgG2b, IgG2a, IgG1, kappa |
| 8B6 | IgG2a, IgG3, kappa |
| 5A11 | IgM, kappa |
| 7D11 | light kappa only |
| 9F10 | IgM, kappa |
| 15D10 | IgM, kappa |
| 18D2 | IgM, kappa |
| 13A11 | IgM, kappa |
| 1A9 | IgM, kappa |
| 3B2 | IgM, kappa |
| 24F6 | IgM, kappa |
| 24E4 | IgM, kappa |
| 5A1 | IgG2a, IgM, kappa |
| 7B9 | IgM, kappa |
| 22F4 | IgM, kappa |

The identified monoclonal antibodies are listed in Table 1A and Table 2. Each of the selected monoclonal antibodies was reactive against GST-ΔMUC16$^{c114}$. The commercial MUC16-directed antibodies (OC125, M11, or VK8) did not bind to GST-ΔMUC16$^{c114}$ in ELISA or Western blotting. The clones were tested in FACS against OVCAR3 ovarian cancer cells and in Western blot analysis against GST-ΔMUC16$^{c114}$ (Table 1B), and selected purified monoclonal antibodies were isolated.

Figure 7A:
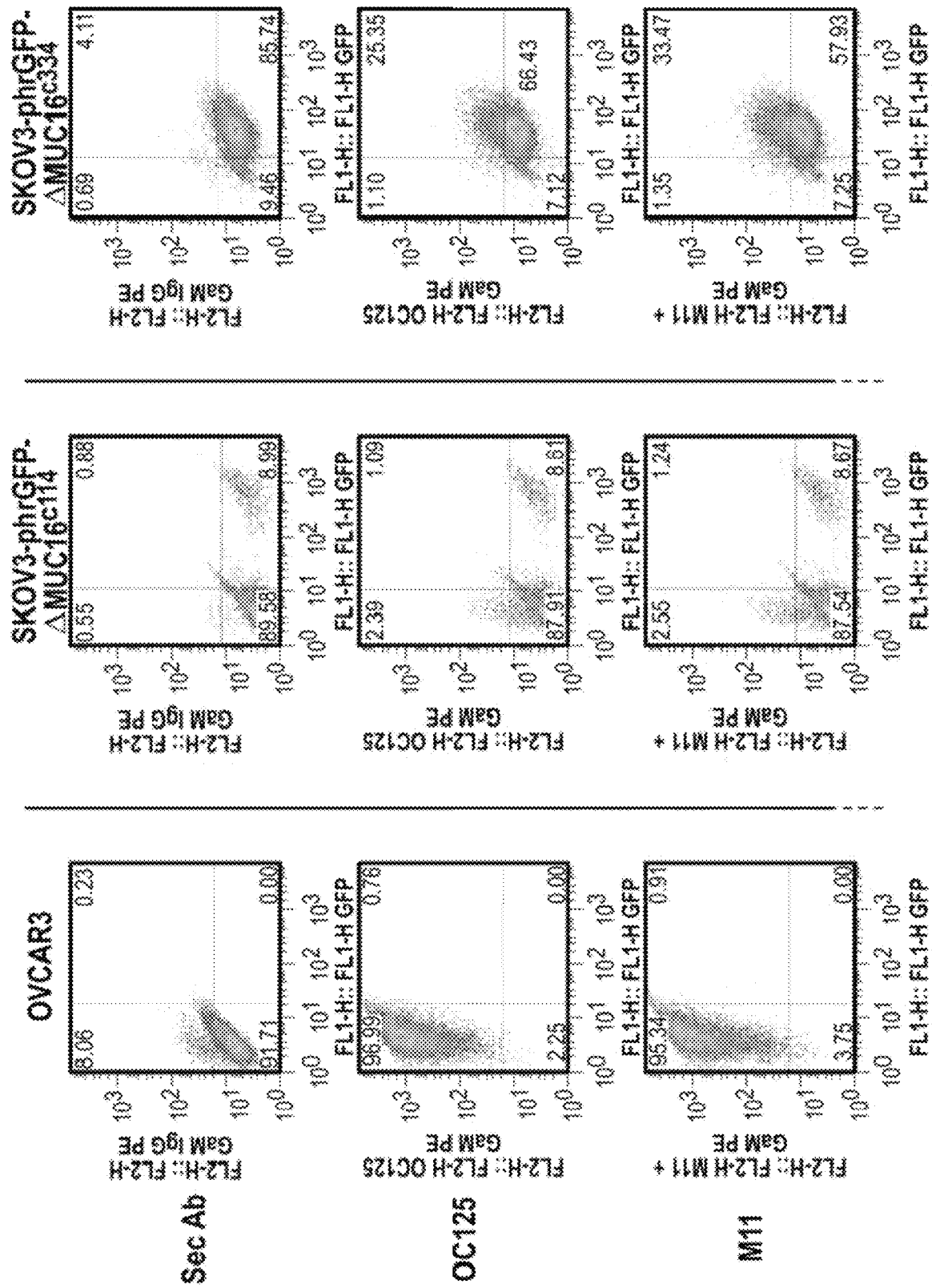
Figure 7B:
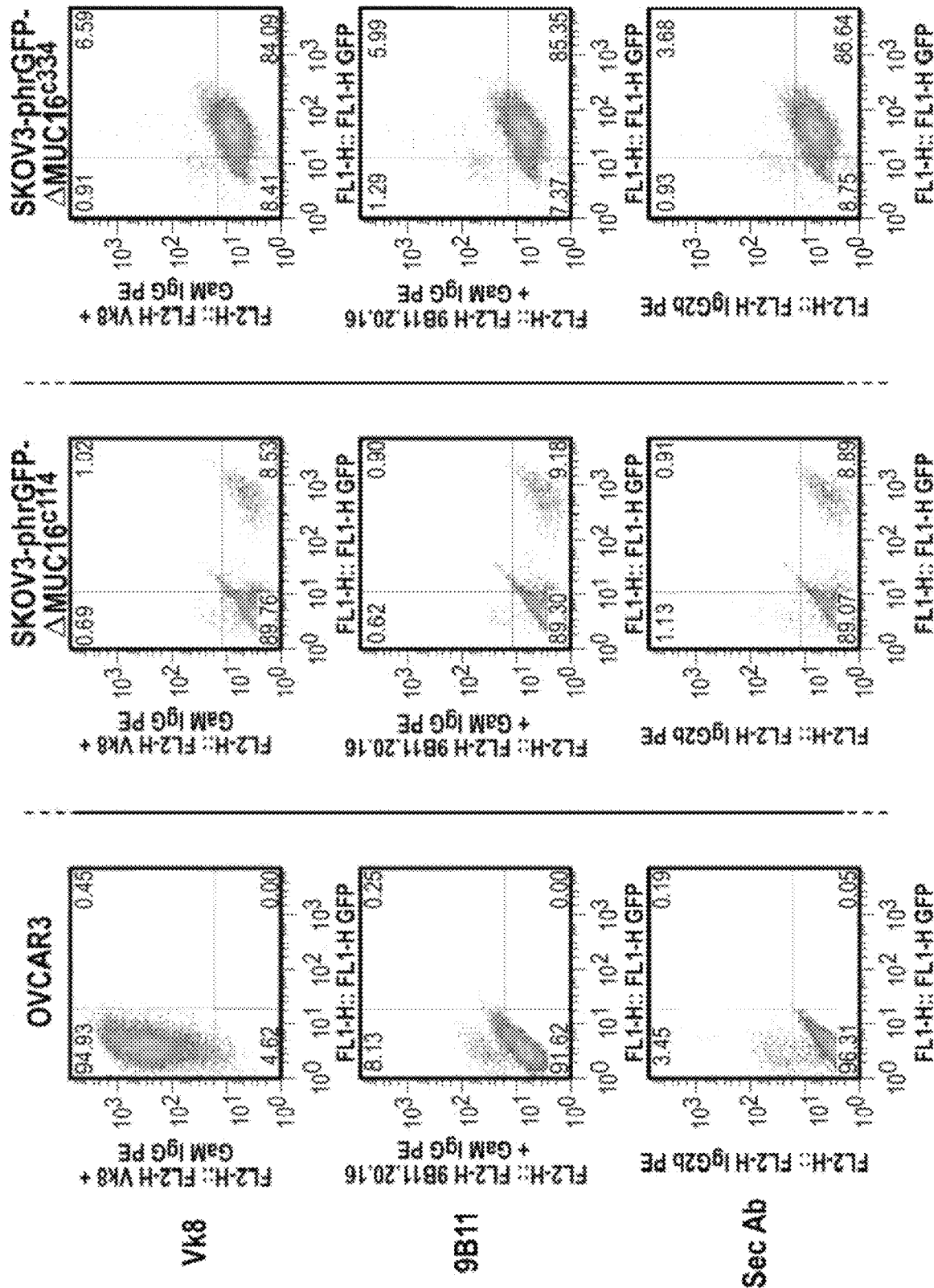
Figure 7C:
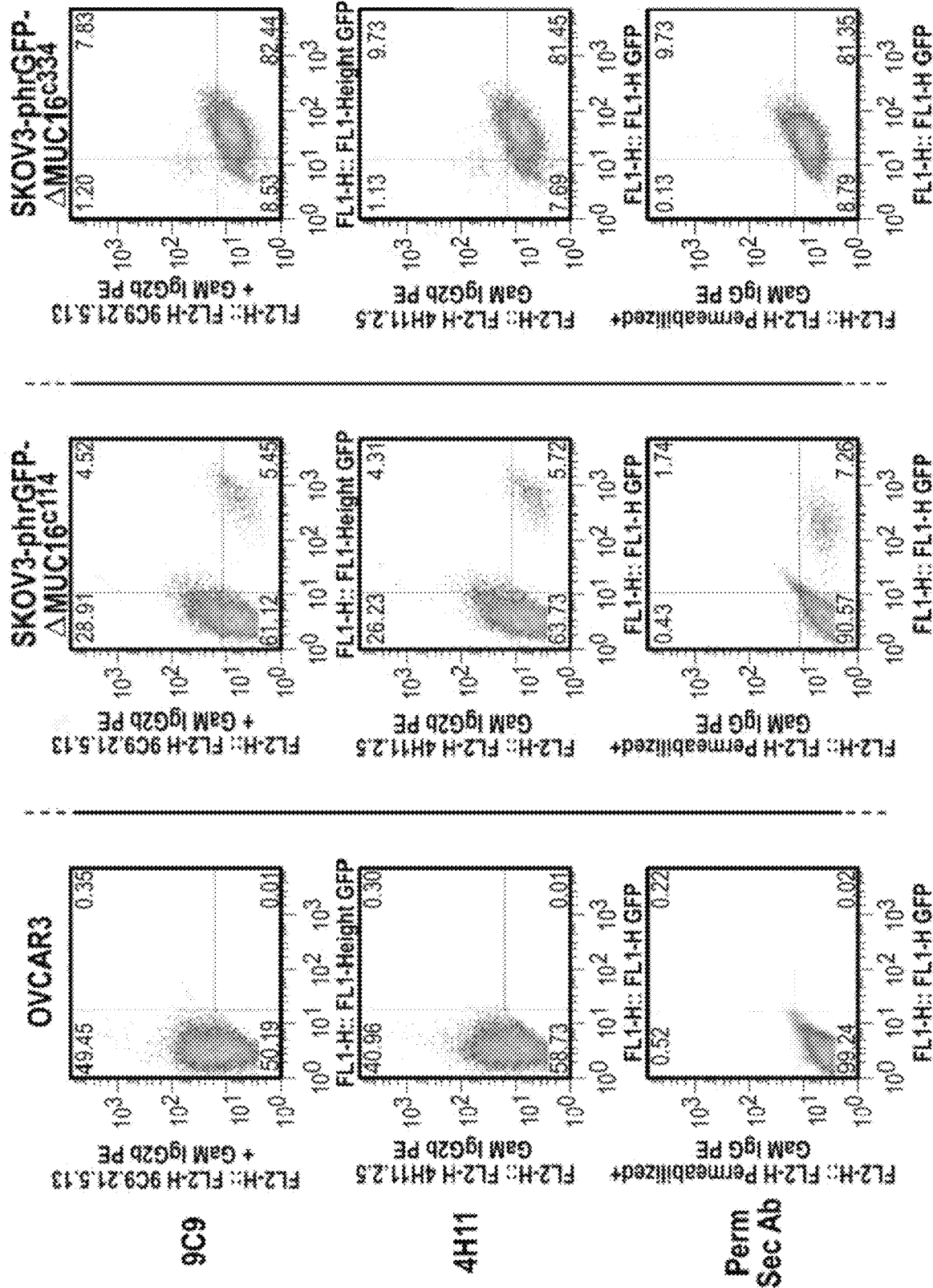

The inventors used the OVCAR3 wild type and the SKOV3 cells transduced with phrGFP-ΔMUC16$^{c114}$ to characterize the selected antibodies by FACS analysis. All of the selected monoclonal antibodies bound to both cell lines while commercial VK8, M11 and OC125 antibodies bound to the OVCAR3 cells but not to the SKOV3-phrGFP-ΔMUC16$^{c114}$ cell line. The antibodies against Polypeptide 3 required permeabilization since it is an internal epitope (FIG. 7).

Figure 4A:
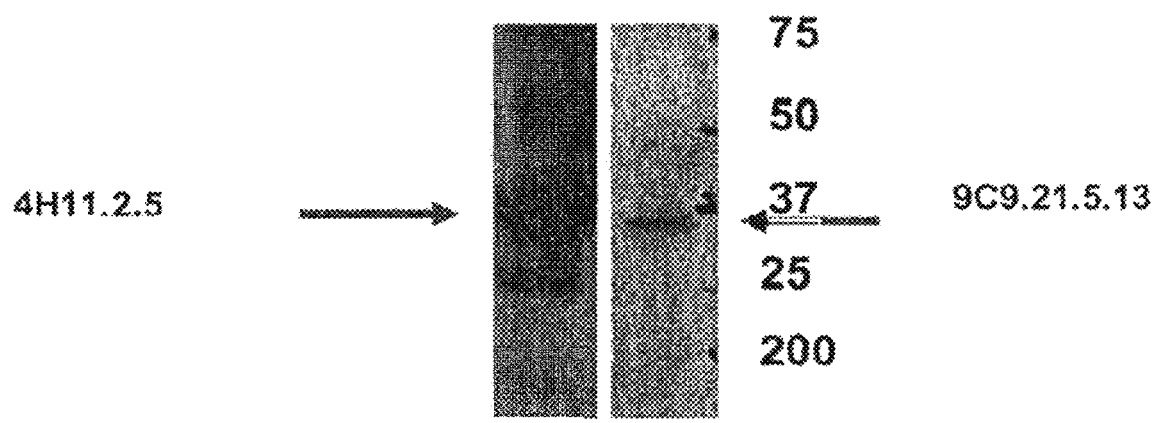
FIGS. 4A-4B: Western blot analysis.
Figure 4B:
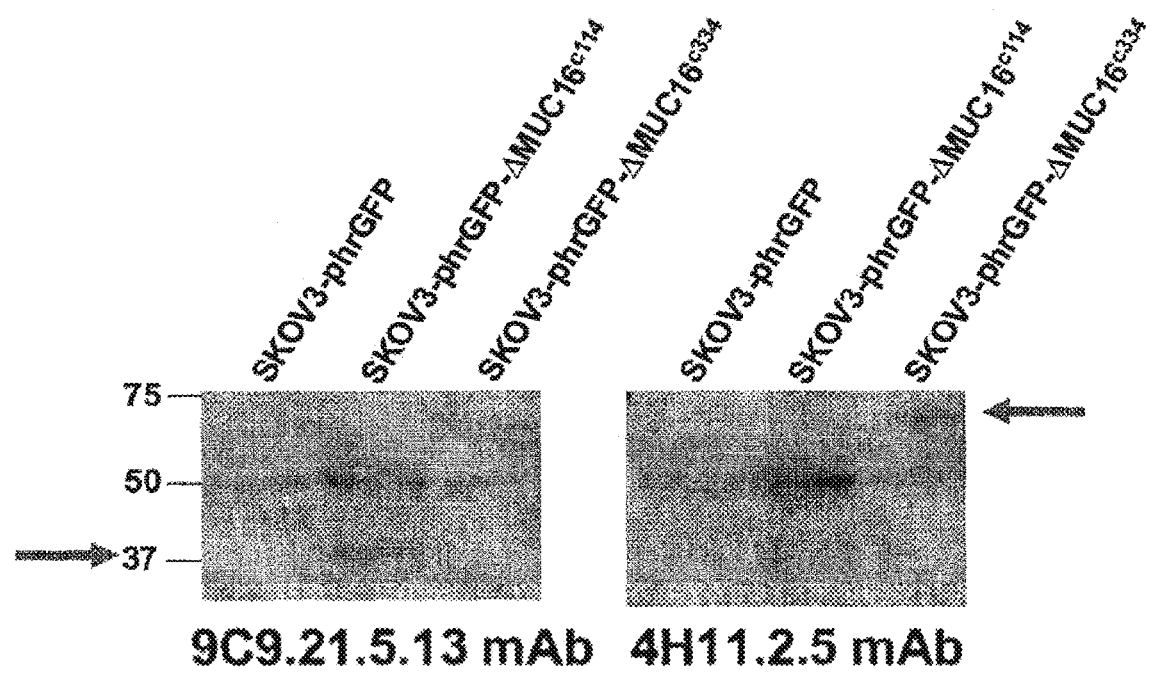

Western blot analysis using the GST-ΔMUC16$^{c114}$ purified protein showed strong binding with 4H11 and 9C9 antibodies (FIG. 4A), while the other selected antibodies showed less binding. The SKOV3-phrGFP-ΔMUC16$^{c114}$ transfectant was also positive by Western blot analysis using 4H11 and 9C9 antibodies (FIG. 4B). As before, the commercial antibodies did not interact with the GST-ΔMUC16$^{c114}$ purified protein or cell lysates of the SKOV3-phrGFP-ΔMUC16$^{c114}$ cell line.

The binding of six monoclonal antibodies against OVCAR3 MUC16 were examined in affinity binding studies. Three antibodies-9C7, 5C2 and 28F7-showed only modest levels of binding compared to the nonspecific binding of these antibodies to the OVCAR3 cells, which carry large numbers of MUC16 binding sites. In contrast, 4H11, 9C9, and 4A5 monoclonal antibodies showed highly specific binding affinity, as shown in FIGS. 5A-5D, with binding affinities of 6.8-8.6 nM against the cell surface epitopes of OVCAR3 cells. The inventors also examined the internalization of antibody bound to cell surface MUC16 protein. The inventors examined internalization in the transfected SKOV3-phrGFP-ΔMUC16$^{c334}$ cell line which bears the carboxy terminus of MUC16, including the 4H11 epitope and a single degenerate tandem repeat sequence to interact with the OC125 antibody. The commercial antibodies OC125, M11, and VK8 all bind to the cell surface of this transduced cell line. The $^{131}$I-labeled 4H11 showed rapid internalization at a high level, whereas $^{131}$I-labeled OC125 antibody was internalized at a much lower rate (FIG. 5E).

Example 3

Immunohistochemistry Results:

Given their highly specific binding affinities, the antibodies 9C9, 4A5, and 4H11 were characterized for utility in immunohistochemistry using OVCAR3 cell lines. Of the three, the 4H11 antibody was selected to be optimized for use in human tissues based on its robust, sensitive and specific staining pattern as compared to the other two antibodies.

A. Ovary

Two high-stage, high-grade ovarian serous carcinoma tissue microarray slides composed of 419 cores, representing primary, metastatic and recurrent tumors from 40 patients were stained with both OC125 and 4H11 monoclonal antibodies (FIG. 2). The OC125 tissue microarrays showed 279 (66%) cores with 3-5 staining, 99 (24%) with 1-2 staining, and 41 (10%) with no staining. The 4H11 tissue microarrays showed 236 (56%) with 3-5 staining, 91 (22%) with 1-2 staining, and 92 (22%) with no staining. The two antibodies were concordant in 233 (56%) cores, equivocal in 161 (38%), and discordant in 25 (6%). Of the 25 discordant cores, 12 (48% of discordant cases, 3% of all cases) showed greater 4H11 positivity than OC125. Nine were discordant by a difference of 4 points, and 3 were discordant by a difference of 5 points. There was a total of 186 discordant and equivocal cores together, 48 (26%) of which showed greater staining with 4H11 than OC125. The staining pattern of both 4H11 and OC125 was cytoplasmic and membranous, although the membranous pattern of OC125 was stronger and better defined than 4H11 in the majority of cases. Discordant cases demonstrated higher levels of 4H11 than other cases.

B. Breast Cancer

A variety of other tissues were also examined for 4H111 staining to test the antibody's specificity. Of the 50 cores of invasive ductal carcinomas of the breast (number of patients unavailable), only 2 (4%) showed a score of 4 or greater 4H11 staining and none had scores of 3-5 for OC125 staining. The staining pattern with OC125 was mostly apical/luminal with some granular cytoplasmic staining. Some tumors with intracytoplasmic lumina also picked up the OC125 stain. 4H11 showed a more diffuse cytoplasmic blush without membranous accentuation.

In contrast, the invasive lobular breast carcinoma tissue microarray (composed of 179 cores with viable tumor, number of patients unavailable) had frequent MUC16 staining with 4H11. In this tissue microarray, 168 cores (94%) showed no staining for OC125, 5 (3%) showed 1-2 staining, and only 6 (3%) showed a staining intensity of 3. 4H11 staining was different in its distribution pattern, with 49 (27%) showing no staining, 81 (45%) showing 1-2 staining, and 49 (27%) showing 3-4 staining. Neither OC125 nor 4H111 had cores with a staining intensity of 5. The staining pattern was of cytoplasmic, luminal/membranous, or intraluminal for both OC125 and 4H111. The intraluminal pattern was strong and intense for both stains and highlighted the intracytoplasmic lumen that is commonly present in lobular carcinomas. The concordance rates were 34% concordant, 43% equivocal, and 23% discordant. Of the equivocal and discordant cases, there was none in which the OC125 was greater than the 4H11. All 42 discordant cases and 76 of 77 equivocal cases had 4H11 greater than OC125. There was also focal luminal staining with 4H11 in benign breast ducts and lobular carcinoma in situ.

C. Lung, Pancreatic and Prostatic Adenocarcinomas

Tumors from other organs were not reactive with either antibody. The lung adenocarcinoma TMA had 237 cores from 86 patients containing viable tumor. In the pancreatic TMA there were 92 cores from 21 patients containing pancreatic mucinous tumors, including intraductal papillary mucinous neoplasms (IPMN) and invasive ductal carcinomas. In the prostate cancer TMA there were 169 cores (number of patients not available). None of these cancer tissue microarrays had significant binding to either OC125 or 4H11. This information is summarized in Table 3.

TABLE 3

Staining intensity of OC125 as compared to 4H11 in tissue microarrays

| Site | OC125 vs. 4H11 staining intensity score (%) | | | | | |
|---|---|---|---|---|---|---|
| | 0 | | 1-2 | | 3-5 | |
| | OC125 | 4H11 | OC125 | 4H11 | OC125 | 4H11 |
| Ovary high grade serous | 10 | 28 | 24 | 22 | 66 | 56 |
| Breast invasive ductal | 68 | 78 | 32 | 18 | 0 | 4 |
| Breast invasive lobular | 94 | 27 | 3 | 45 | 3 | 27 |
| Lung adenocarcinoma | 63 | 77 | 24 | 18 | 13 | 5 |
| Pancreas mucinous neoplasms | 98 | 88 | 2 | 10 | 0 | 2 |
| Prostate adenocarcinoma | 0 | 0 | 0 | 0 | 0 | 0 |

Score 0: 0% staining; 1: <5% strong or weak; 2: 5-50% strong or weak; 3: 51-75% strong or 51-100% weak; 4: 76-99% strong; 5: 100% strong D. Normal Tissues There was no staining with OC125 or 4H11 in normal adult colon, rectum, ectocervix, small intestine, ovary, liver, pancreatic ducts, spleen, kidney, and skin. OC125 and 4H111 both stained endocervical glands (OC125 luminal, 4H11 weak cytoplasmic), esophageal glands (luminal), bronchial epithelium (OC125 luminal, 4H11 intracytoplasmic granules), and thymic corpuscles (cytoplasmic). 4H11 demonstrated weak to moderate staining of the gastric glands, particularly at the crypts, with an intracytoplasmic granular pattern. Other organs that showed punctuate intracytoplasmic staining with 4H11 only were prostate, seminiferous tubules of the testes, and the islet cells of the pancreas. The staining in the pancreatic islets cells was particularly strong and consistent. There was also nonspecific staining of liver, kidney and brain with 4H11. There were no cases that stained with OC125 and not 4H11.

Similarly, there was no staining with either OC125 or 4H11 in fetal heart, gallbladder, colon, small intestine, liver, rectum, adrenal, thyroid, spleen, skin, bone, epididymis, brain, lung, muscle, smooth muscle, kidney, eye, umbilical cord, and placenta. OC125 only stained thymic corpuscles in a pattern similar to that in adult tissue. 4H111 stained both fetal pancreatic endocrine cells and endocervical glands in a similar pattern to that of their adult counterparts. Islet cells showed a granular cytoplasmic pattern, and endocervical glands showed a linear luminal pattern, which was more similar to the OC125 pattern in the adult tissue.

Example 4

Successful Eradication of Established Peritoneal Ovarian Tumors in SCID-Beige Mice Following Adoptive Transfer of T Cells Genetically Targeted to the MUC16 Antigen.

Purpose: Most patients diagnosed with ovarian cancer will ultimately die from their disease. For this reason, novel approaches to the treatment of this malignancy are needed.

Adoptive transfer of a patients own T cells, genetically modified ex vivo through the introduction of a gene encoding an chimeric antigen receptor (CAR), an artificial T cell receptor, targeted to a tumor associated antigen, is a novel and promising approach to cancer therapy applicable to the treatment of ovarian cancer.

Experimental design: We have generated several CARs targeted to the retained extracellular domain of MUC16, termed MUC-CD, an antigen highly expressed on a majority of ovarian carcinomas. We investigate the in vitro biology of human T cells retrovirally transduced to express these CARs by co-culture assays on artificial antigen presenting cells (AAPCs) generated from NIH3T3 fibroblasts genetically modified to express the target MUC-CD antigen, as well as by cytotoxicity assays utilizing the human OV-CAR3(MUC-CD) ovarian tumor cell line and primary patient tumor cells. Finally, we assess the in vivo anti-tumor efficacy of MUC-CD targeted T cells in a SCID-Beige orthotopic, xenogeneic OV-CAR3(MUC-CD) murine tumor model.

Figure 18:
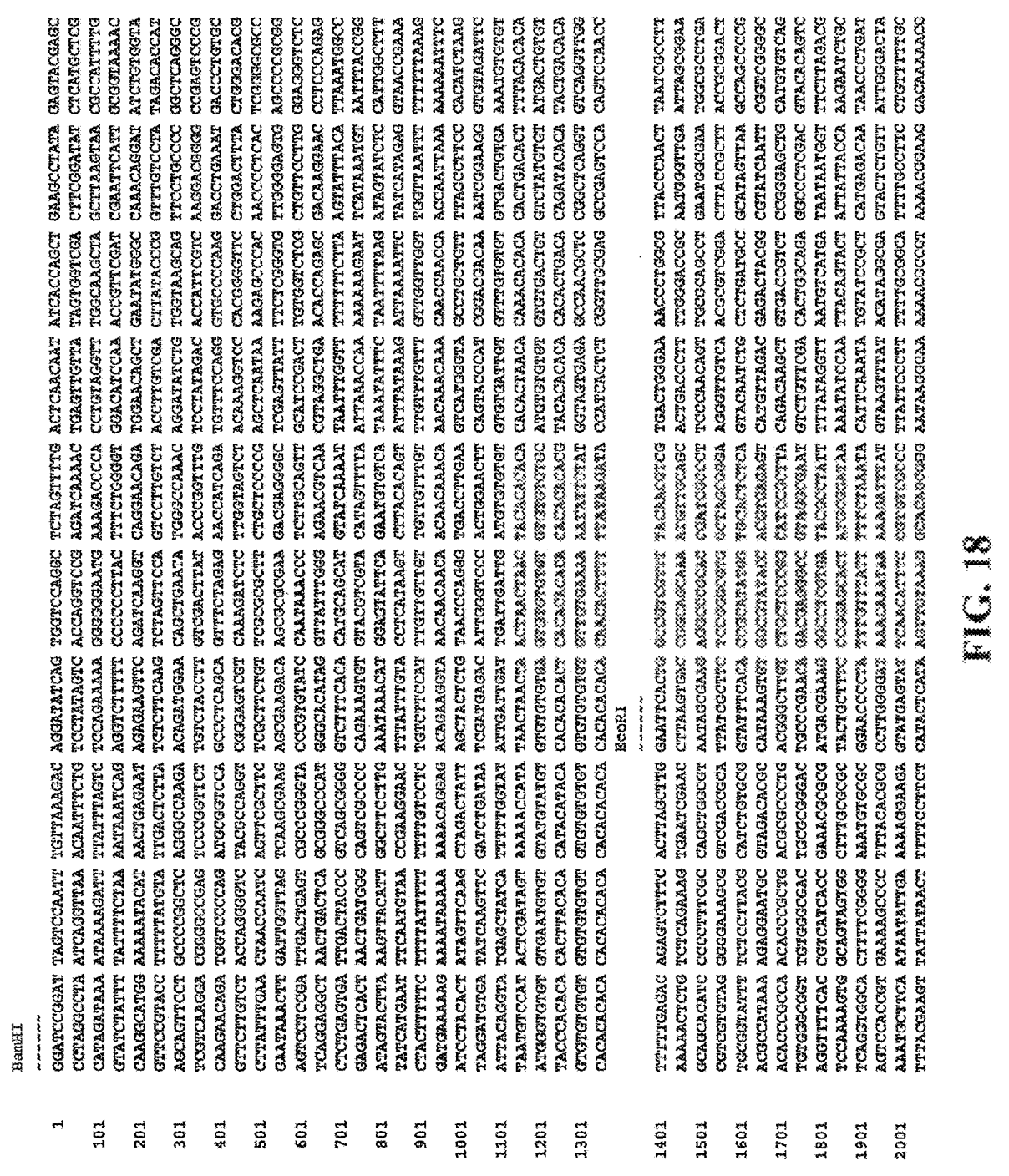
Figure 18:
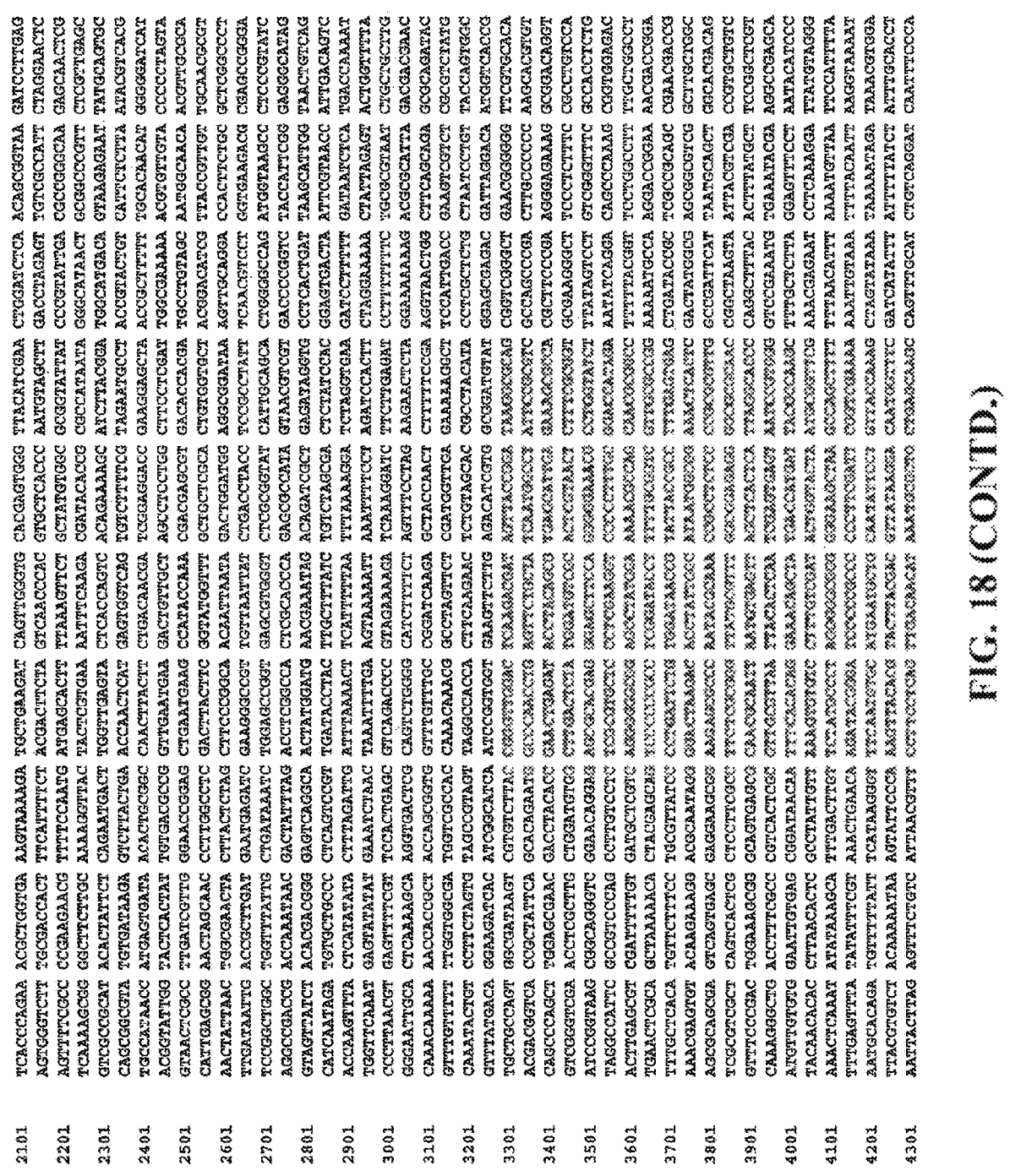
Figure 18:
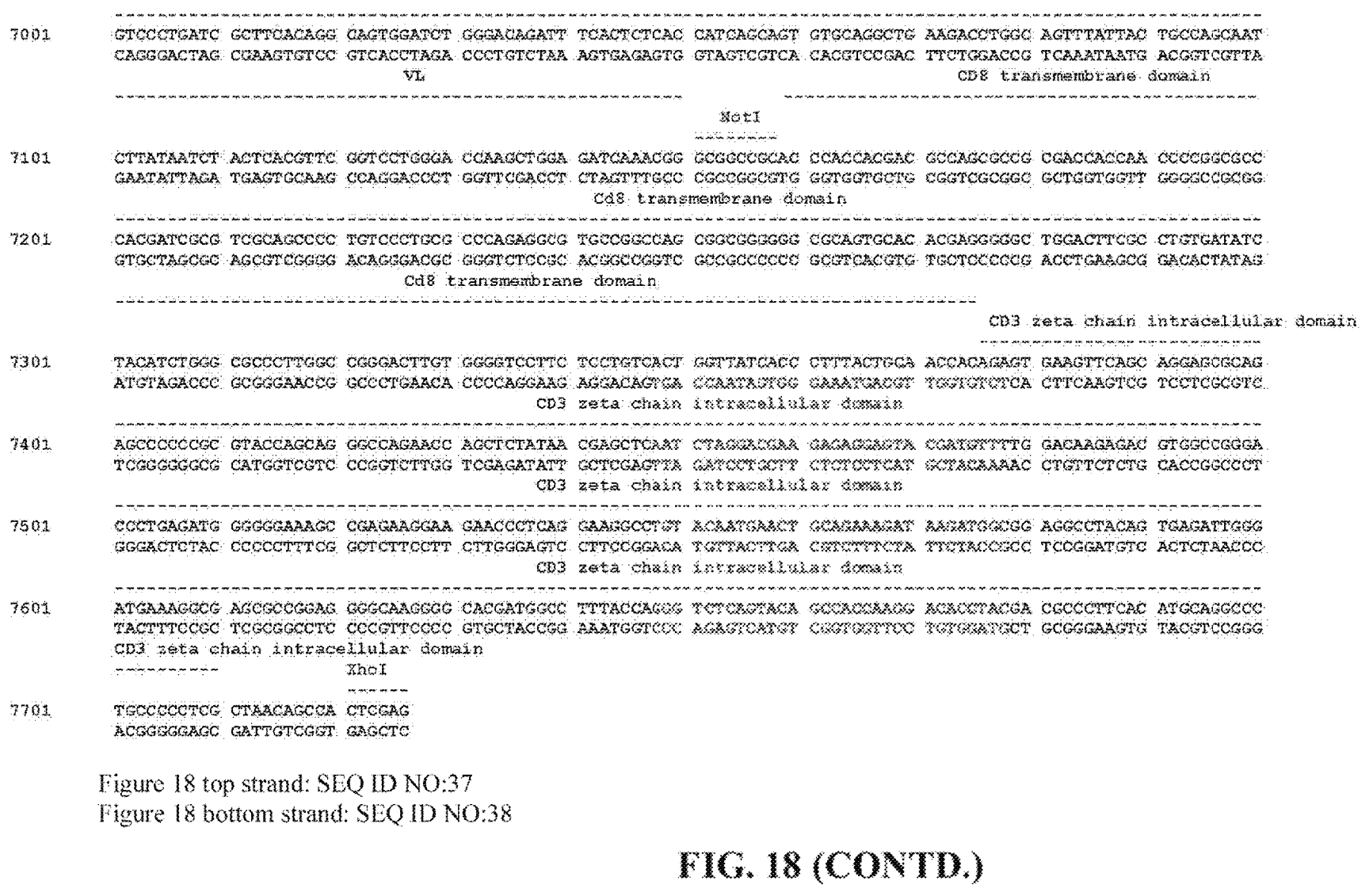
Figure 19:
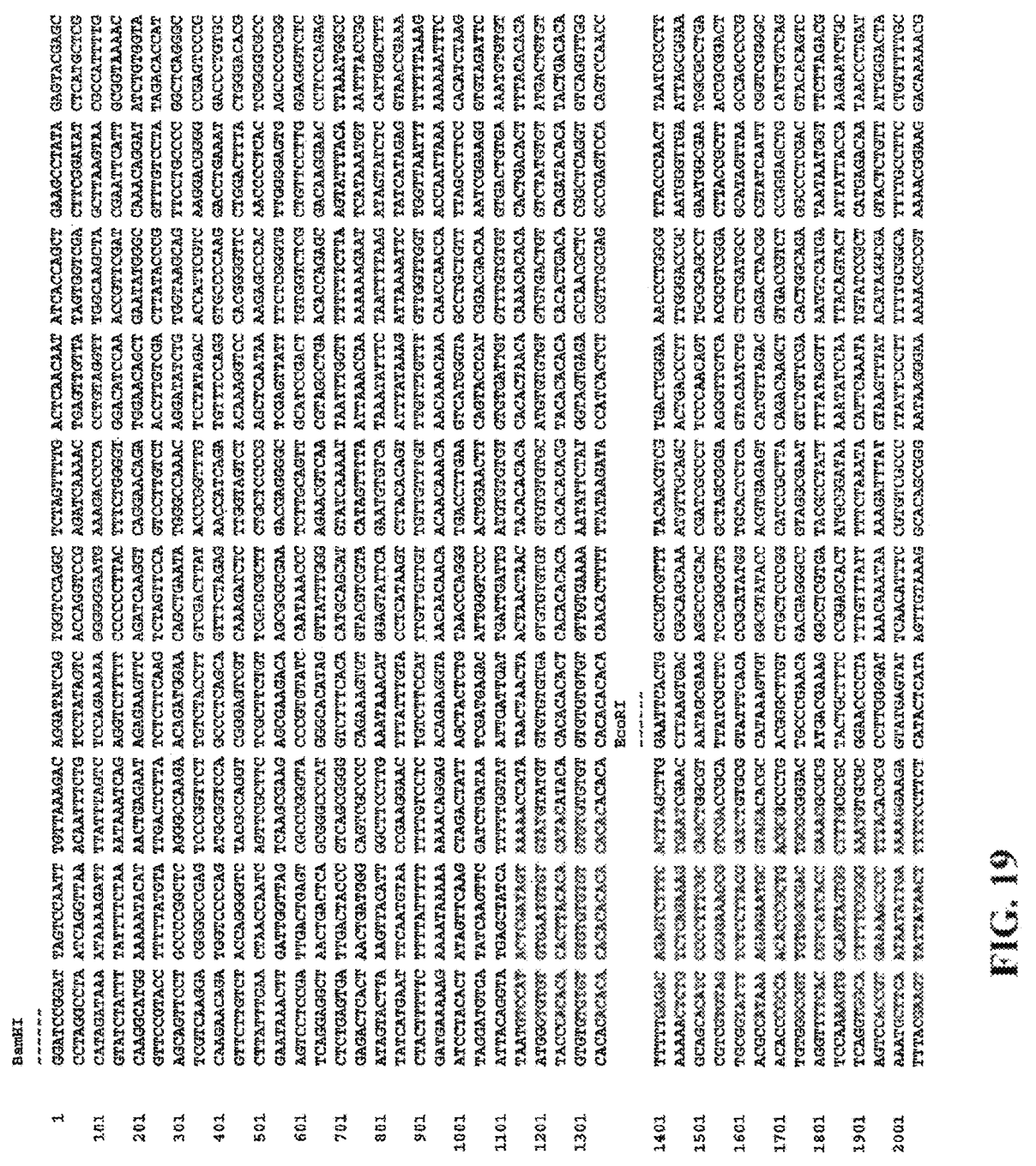
Figure 19:
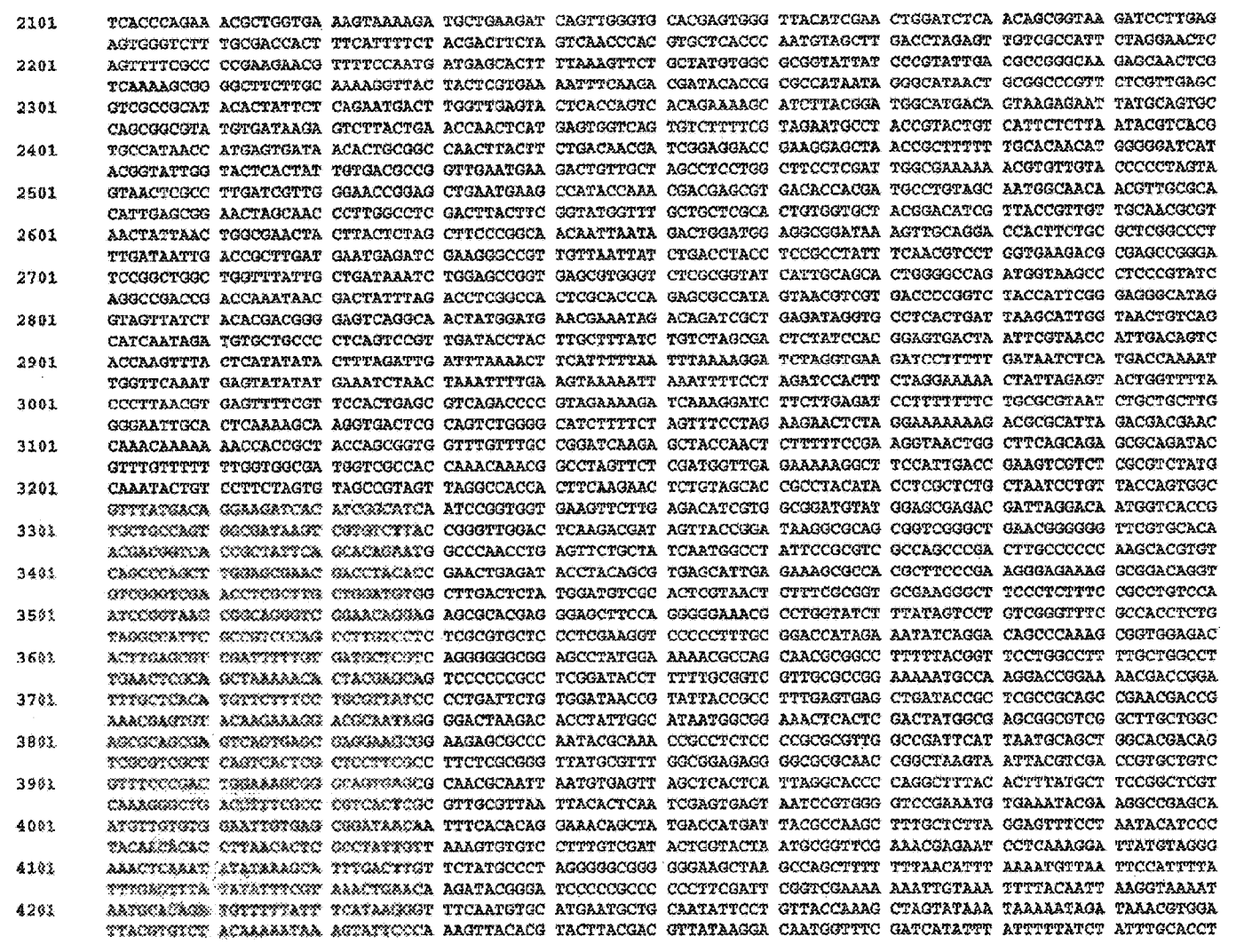
Figure 19:
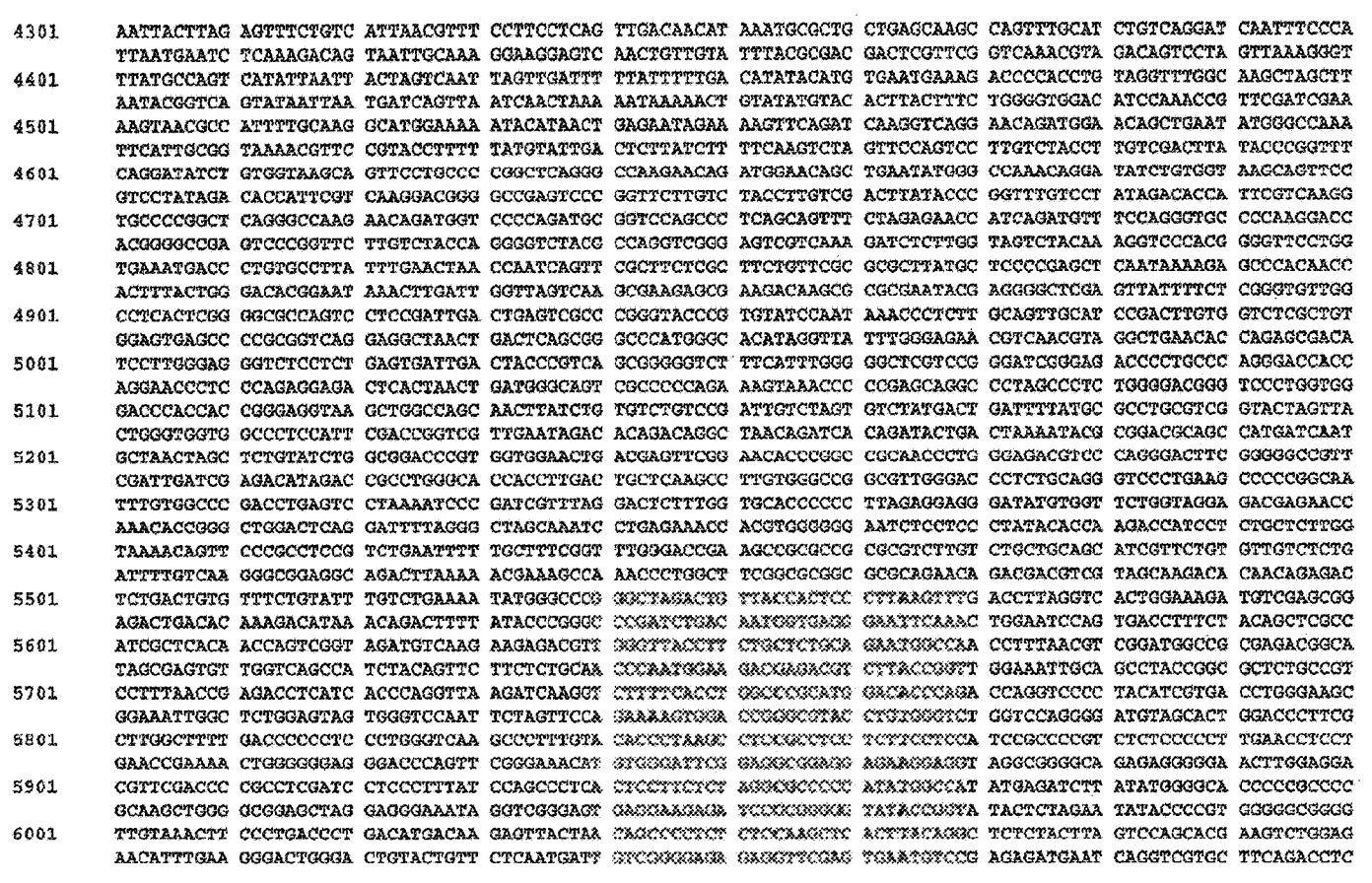

Exemplary sequences used in this work are in FIGS. 17-19.

Results: CAR modified MUC-CD targeted T cells derived from both healthy donors and ovarian cancer patients exhibited efficient in vitro cytolytic activity against both human ovarian cell lines as well as primary ovarian carcinoma cells. MUC-CD targeted T cells may be further expanded ex vivo through multiple cycles of co-culture on 3T3(MUC-CD/B7.1) AAPCs. Expanded MUC-CD targeted T cells infused into SCID-Beige mice bearing intraperitoneal human OV-CAR3(MUC-CD) tumors either delayed progression or fully eradicated tumor even in the setting of advanced disease.

Conclusion: These promising pre-clinical studies justify further investigation of MUC-CD targeted T cells as a potential therapeutic approach in the clinical setting treating patients with high risk MUC-16+ ovarian carcinomas.

Introduction

Ovarian cancer is the sixth most common cancer worldwide and the seventh leading cause of cancer-related deaths in women (1, 2). Despite multimodality therapy with surgery and chemotherapy, most patients with ovarian carcinomas have a poor prognosis. For this reason, alternative approaches to treating this disease are urgently needed.

Infusion of a patient's own T cells genetically targeted ex vivo to antigens expressed on the surface of tumor cells is a promising novel approach to the adoptive immunotherapy of cancer, and one which has only recently been explored in earnest in the clinical setting. T cells may be genetically modified to target tumor associated antigens through the retroviral introduction of genes encoding artificial T cell receptors termed chimeric antigen receptors (CARs). Genetic engineering of T cells to express artificial T cell receptors that direct cytotoxicity toward a tumor cell presents a means to enhance immune recognition and elimination of cancer cells. CARs are most commonly composed of a single chain fragment length antibody (scFv), derived from a murine monoclonal antibody targeting a given tumor associated antigen, fused to a transmembrane domain (typically CD8, CD28, OX-40, and 4-1BB), fused to the TCR ζ chain cytoplasmic signaling domain (3-13). When used to reprogram T-cell specificity, these fusion receptors permit recognition of native antigen. When expressed by the T cells, the resulting construct, upon engagement with the targeted antigen, induces T cell activation, proliferation, and lysis of targeted cells. These fusion receptors transduce a functional antigen-dependent co-stimulatory signal in primary T cells, permitting sustained T-cell proliferation when both endogenous TCR and a chimeric receptor for stimulatory signaling are engaged. To date, preclinical studies utilizing CAR-modified T cells have demonstrated promising results in a wide variety of malignancies (3, 4, 11, 14-18). More recently this approach been investigated clinically in the form of phase I trials (6, 19-21). These genetic approaches offer a means to enhance immune recognition and elimination of cancer cells.

Ovarian carcinomas appear to be relatively immunogenic tumors capable of inducing an endogenous immune response based on the fact that long-term prognosis of patients is markedly influenced by the degree and quality of the endogenous immune response to the tumor. Specifically, it has been well documented that the presence of endogenous effector T cells within the ovarian cancer tumor microenvironment directly correlates to prolonged patient survival (22-25). In contrast, increasing numbers of immune suppressive CD4$^+$ CD25$^{hi}$ regulatory T cells (Tregs) within the tumor, which in turn presumably abrogate the anti-tumor activity of infiltrating effector T cells, correlates with shorter patient survival (26-29). In fact, it appears that it is the ratio of Tregs to effector T cells within the tumor microenvironment which ultimately dictates whether the endogenous immune response to the cancer is of benefit or detriment to the patient (24, 28). In this setting, the ability to generate and subsequently expand a population of tumor targeted effector T cells ex vivo which are subsequently infused back into the patient, may in turn skew the Treg to effector T cell ratio to one more favorable to eradicating the disease.

Mucins are important biomolecules for cellular homeostasis and protection of epithelial surfaces. Changes to expression of mucins in ovarian cancer might be exploited in diagnosis, prognosis and treatment (1). MUC16 is one such mucin which is over expressed on most ovarian carcinomas and is an established surrogate serum marker (CA-125) for the detection and progression of ovarian cancers (30-33). MUC16 is a high-glycosylated mucin composed of a large cleaved and released domain, termed CA-125, consisting of multiple repeat sequences, and a retained domain (MUC-CD) which includes a residual non-repeating extracellular fragment, a transmembrane domain, and a cytoplasmic tail (34). Since the antigen is otherwise only expressed at low levels in the uterus, endometrium, fallopian tubes, ovaries, and serosa of the abdominal and thoracic cavities, MUC16 is a potentially attractive target for immune-based therapies.

However, the fact that most of the extracellular domain of MUC16 is cleaved and secreted limits the utility of MUC16 as a target antigen on ovarian carcinomas. In fact, to date, all reported MAbs to MUC16 bind to epitopes present on the large secreted CA-125 fraction of the glycoprotein, with none known to bind to the retained extra-cellular fraction (MUC-CD) of the antigen (35-37). Since the MUC-CD fraction of the antigen is retained on cell surface, generating T cells specific to this portion of MUC16 may largely overcome the limitation of MUC16 as a target for adoptive cellular immunotherapy. To this end, we have previously generated a series of murine MAbs specific to the retained MUC-CD extracellular domain (38). Utilizing a hybridoma which expresses one such MAb, 4H11, we have successfully constructed several CARs specific to the MUC-CD antigen. This invention provides a nucleic acid encoding a chimeric T cell receptor, composed of, at least a zeta chain, a signaling region and a binding element that specifically interacts with a selected target as well as the chimeric T cell receptor comprising a zeta chain portion, a signaling region and a binding element.

In this report, we demonstrate highly efficient retroviral transduction of these MUC-CD targeted CARs into human T cells with resulting T cells able to specifically target and lyse MUC-CD$^+$ tumor cells in vitro. Furthermore, we demonstrate efficient MUC-CD targeted T cell expansion in vitro through repeated co-culture on NIH (3T3) fibroblasts genetically modified to express MUC-CD and the co-stimulatory ligand B7.1 (CD80). Successful expansion of modified T cells allowed us to subsequently generate sufficient T cell numbers to conduct in vivo studies in immune compromised SCID-Beige mice bearing established intraperitoneal MUC-CD$^+$ human ovarian tumors. Significantly, in these studies we demonstrate marked anti-tumor efficacy of MUC-CD targeted T cells, both following direct intraperitoneal as well as intravenous injection when compared to either untreated mice, or mice treated with T cells bearing a CAR targeted to an irrelevant antigen. In addition, we demonstrate significant cytotoxicity of 41-111-28z$^+$ patient's T cells and healthy donor's T cells targeting primary ascites-derived ovarian carcinoma cells from cancer patients.

To our knowledge this is the first report wherein T cells genetically targeted to the MUC16 antigen demonstrate marked anti-tumor efficacy against MUC16$^+$ tumors either in vitro or in vivo. These data serve as a rationale for proposing future clinical trials utilizing this approach in patients with high risk ovarian carcinomas.

Materials and Methods

Cell Lines and T Cells

The OV-CAR3 tumor cell line was cultured in RPMI 1640 (Invitrogen, Grand Island, N.Y.) supplemented with 10% heat-inactivated FBS, nonessential amino acids, HEPES buffer, pyruvate, and BME (Invitrogen). The PG13 and gpg29 retroviral producer cell lines were cultured in DMEM (Invitrogen) supplemented with 10% FCS, and NIH-3T3 artificial antigen-presenting cells (AAPC), described previously (3), were cultured in DMEM supplemented with 10% heat-inactivated donor calf serum. T cells were obtained from peripheral blood of healthy donors under IRB approved protocol #95-054, in BD Vacutainer CPT tubes (Becton Dickinson, Franklin Lakes, N.J.) as per the manufacturers instructions. All media were supplemented with 2 mmol/L L-glutamine (Invitrogen), 100 units/mL penicillin, and 100 µg/mL streptomycin (Invitrogen). T cells were cultured RPMI 1640 media as above supplemented with 20 IU/ml IL-2 (Novartis Pharmaceuticals, East Hanover, N.J.) and where indicated, medium was supplemented with 10 ng/mL interleukin 15 (R&D Systems, Minneapolis, Minn.).

Isolation of patients ascites-derived cancer cells Primary human ascites-derived cancer cells were obtained from ovarian cancer patients undergoing surgery for newly diagnosed advanced serous ovarian carcinoma under IRB approved protocol #97-134. The tumor cells were isolated from ascitic fluid of patients by centrifugation at 600 g for 10 min at room temperature. Cells were washed once with 1×PBS and cultured in RPMI 1640 media supplemented with 10% FBS for future analysis.

Generation of the MUC-CD Targeted 4H11z and 4H11-28z CARs

The heavy and light chain variable regions of the 4H11 monoclonal antibody were derived from the hybridoma cell line 4H11. Utilizing cDNA generated from 4H11 RNA we isolated the $V_H$ coding region by RACE PCR utilizing modified primers as described elsewhere (39, 40). The $V_L$ chain variable region was cloned by standard PCR utilizing modified primers as described by Orlandi et al (41, 42). The resulting $V_H$ and $V_L$ fragments were subCloned into the TopoTA PCR 2.1 cloning vector (Invitrogen) and sequenced. The $V_H$ and $V_L$ fragments were subsequently ligated to a (Gly$_4$Ser)$_3$ spacer domain, generating the 4H11 scFv and fused to the human CD8 leader peptide (CD8L) by overlapping PCR (9, 41). In order to construct the MUC-CD targeted 4H11 CARs, the coding region of the CD8L-4H11 scFv was fused to the human CD8 hinge and transmembrane domains (to generate the 4H11z CAR), or alternatively to the CD28 transmembrane and cytoplasmic signaling domains (to generate the 4H11-28z CAR), fused to the T cell receptor CD3ζ-signaling domain (3, 9, 43). The resulting CAR constructs were subsequently sub-cloned into the modified MMLV retroviral vector SFG (44). VSV-G pseudotyped retroviral supernatants derived from transduced gpg29 fibroblasts were used to construct stable PG13 gibbon ape leukemia virus (GaLV) envelope-pseudotyped retroviral producing cell lines (41).

Retroviral Gene Transfer

Isolated healthy donor peripheral blood mononuclear cells (PBMCs) were activated with phytohemagglutinin (PHA) at 2 μg/ml (Sigma. St. Louis, Mo.) and retrovirally transduced on retronectin coated non-tissue culture plates (45). Briefly, six-well non-tissue culture plates (BD Biosciences, San Jose, Calif.) were coated with RetroNectin (RN) (Takara Biomedicals, Otsu, Japan) as per manufacturer's instructions. Forty-eight hours after PHA activation, aliquots of $1\times10^6$ T cells in 1 ml of supplemented RPMI medium were placed in each well of the RN-coated plates, along with 1 ml of SFG retroviral supernatant. T cells were centrifuged daily for 3 consecutive days with fresh retroviral supernatant added daily at 2000 g at 30° C. for 1 hr (45). Gene transfer was assessed on day 7 by FACS.

In order to generate the relevant NIII-3T3 murine fibroblast artificial antigen presenting cells, a MUC-CD construct encoding the retained extracellular, transmembrane and cytoplasmic domains of the MUC-16 antigen was initially subcloned into SFG retroviral vector, SFG (MUC-CD). 3T3(MUC-CD) AAPCs were generated by retroviral transduction of SFG (MUC-CD) into wild-type NTH-3T3 fibroblasts, while 3T3(MUC-CD/B7.1) AAPCs were generated by retroviral transduction of previously established 3T3 (B7.1) fibroblasts (41, 46). Highly enriched cell lines were isolated by FACS.

To generate the OV-CAR3(MUC-CD) and OV-CAR3 (MUC-CD/GFP-FFLuc) cell lines, we retrovirally transduced the WT OV-CAR3 human ovarian cancer cell line with SFG (GFP-FFLuc) as described previously (47) and/or SFG (MUC-CD) VSV-G pseudotyped retroviral supernatants derived from gpg29 fibroblasts as described elsewhere (44). Resulting tumor cells were sorted by FACS for either MUC-CD expression alone for the OVCAR3(MUC-CD) cell line, or dual MUC-CD and GFP expression for the OVCAR3(MUC-CD/GFP-FFLuc) cell line. MUC-CD expression by FACS was assessed using the 4H111 MAb.

In Vitro Analyses of CAR$^+$ Human T Cells

To assess in vitro expansion and cytokine release upon stimulation, transduced T cells were co-cultured for 7 days after retroviral transduction in 6-well tissue culture plates (BD Biosciences) on confluent NIH 3T3 AAPCs in RPMI medium supplemented with 10% FBS in the absence of supplemented cytokines. In order to generate sufficient numbers of CAR-modified T cells for in vivo studies, transduced T cells were co-cultured on B7.1$^+$ AAPCs (3T3(MUC-CD/B7.1)) in RPMI medium supplemented with 20 IU IL-2/mL and 10 ng/mL IL-15 as described previously (3, 43). Patients T cells were activated and expanded with human CD3/CD28 beads (DYNAL®, Invitrogen, Carlsbad, Calif.) following manufacturer's recommendations.

Western Blot Analysis of CAR Expression

Western blot analysis of T-cell lysates under reducing conditions with 0.1 mol/L DTT (Sigma) was performed as previously described (46). Briefly, transduced T cells were washed in PBS and resuspended in radioimmunoprecipitation assay (RIPA) buffer (Boston BioProducts, Worcester, Mass.) with mini complete protease inhibitor as per the manufacturer's instructions (Roche Diagnostics, Indianapolis, Ind.). Resulting proteins were separated on 12% SDS-PAGE mini gels (Bio-Rad, Hercules, Calif.) after the addition of 6× reducing loading buffer (Boston BioProducts, Worcester, Mass.) and heating at 100° C. for 10 min. Separated proteins were subsequently transferred to Immobilon membranes and probed using an anti-human CD3 chain monoclonal antibody (BD Biosciences). Antibody binding was detected by probing the blot with goat anti-mouse horse radish peroxidase-conjugated antibody followed by luminescent detection using Western Lighting Chemiluminescence Reagent Plus (Perkin-Elmer Life Sciences, Boston, Mass.) as per the manufacturer's instructions.

Cytotoxicity Assays

In vitro modified T cell cytotoxicity was assessed using the DELFIA® EuTDA assay (PerkinElmer LAS, Inc, Boston, Mass.) following manufacturer's recommendations. Cytotoxocity was assessed at 2 hours at effector T cell to target OV-CAR3(MUC-CD) or primary tumor cells (E:T) at indicated ratios. Effector T cells in these assays represent the number of CD8$^+$ CAR$^+$ T cells.

Cytokine Detection Assays

Cytokine assays were performed as per manufacturer's specifications using a multiplex Human Cytokine Detection assay to detect IL-2 and IFNγ (Millipore Corporation, Billerica, Mass.) utilizing the Luminex IS100 system. Cytokine concentrations were assessed using IS 2.3 software (Luminex Corp., Austin, Tex.).

In Vivo SCID-Beige Mouse Tumor Models

In all in vivo studies, 8-12 week-old FOX CHASE C.B.-17 (SCID-Beige mice) (Taconic, Hudson, N.Y.) were initially injected ip with either $3\times10^6$ OV-CAR3(MUC-CD), or for bioluminescent imaging (BLI) studies $3\times10^6$ OV-CAR3(MUC-CD/GFP-FFLuc) tumor cells. Subsequently, $3\times10^7$ CAR$^+$ T cells were injected ip or iv on day 1 or 7 following tumor injection as indicated. Mice were monitored for distress as assessed by increasing abdominal girth, ruffled fur, and decreased response to stimuli. Distressed mice were euthanized. All murine studies were done in context of an Institutional Animal Care and Use Committee-approved protocol (#00-05-065).

Bioluminescent Imaging (BLI) of OVCAR3(MUC-CD/GFP-FFLuc) Tumor Cells in SCID-Beige Mice BLI was performed using Xenogen IVIS imaging system with Living Image software (Xenogen; Alameda, Calif.). Briefly, OVCAR3(MUC-CD/GFP-FFLuc) tumor bearing mice were injected by ip with D-luciferin (150 mg/kg; Xenogen) suspended in 200 μl PBS and imaged under 2% isoflurane anesthesia after 10 min. Image acquisition was done on a 25-cm field of view at medium binning level for 0.5-min exposure time (3, 43).

Flow Cytometry

All flow cytometric analyses of T cells and tumor cells was performed using a FACScan cytometer with Cellquest software (BD Biosciences). T cells were analyzed using CAR-specific polyclonal goat Alexa Fluor 647 antibody (Molecular probes, Eugene, Oreg.) phycoerythrin-labeled anti-human CD4, CD8, B7.1 (Caltag Laboratories, Burlingame, Calif.), B7.2 (Invitrogen, Camarillo, Calif.), 4-1BBL, and OX40 antibodies (Ancell Corporation, Bayport, Minn.). 3T3(MUC-CD) and OV-CAR3(MUC-CD) cells were stained with Alexa Fluor 647 labeled 4H11 antibody (generated and labeled in the MSKCC monoclonal antibody core facility).

CFSE Labeling of CAR$^+$ T Cells

CAR$^+$ T cells were stained with CFSE using the CellTrace™ CFSE cell proliferation kit following manufacturer's recommendations (Molecular Probes, Eugene, Oreg.). Proliferation of CFSE labeled T cells was analyzed by FACS. For detection of CFSE labeling T cells in vivo, ovarian tumors were macerated through 40 μm cell strainer (BD Falcon, Franklin Lakes, N.J.) and washed twice with 2% FBS/PBS before antibody staining and FACS analysis.

Statistics

Survival data assessed by log-rank analysis using GraphPad Prism software (GraphPad Prism software, San Diego, Calif.). Cytokine data were analyzed by Student's one-tailed t-test.

Results

Figure 11A:
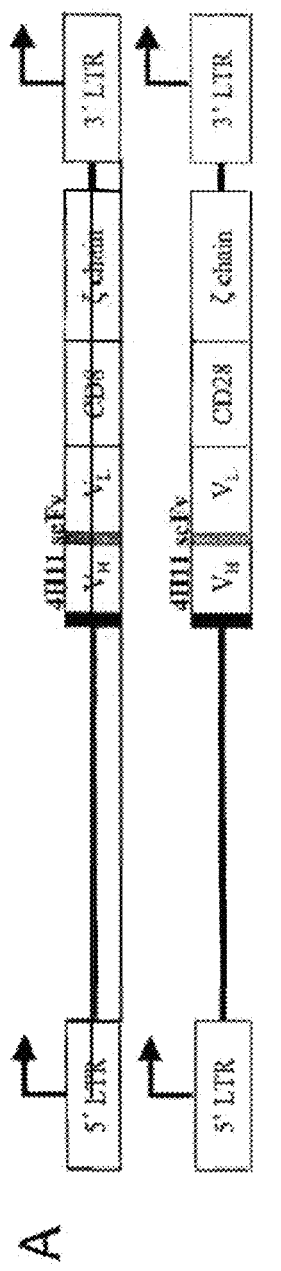
FIGS. 11A-11C. Design and in vitro analysis of MUC-CD targeted CARs.

We have constructed SFG retroviral vectors encoding first (4H11z) and second generation (4H11-28z) CARs targeted to the MUC-CD antigen using the 4H11 hybridoma which generates a MAb specific to the MUC-CD antigen (FIG. 11A). We confirmed expression of appropriately sized CAR proteins by Western blot analysis of resulting PG-13 retroviral producer cells (SFG-4H11z and SFG-4H11-28z) probed with a ζ-chain specific antibody (data not shown).

Figure 11B:
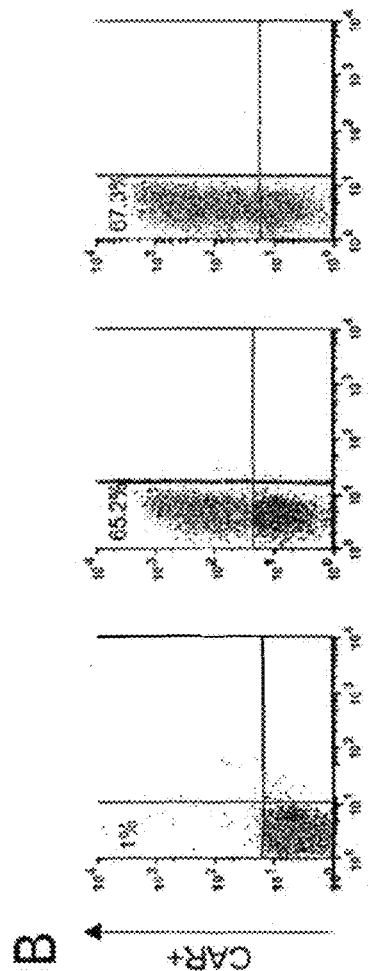
Figure 11C:
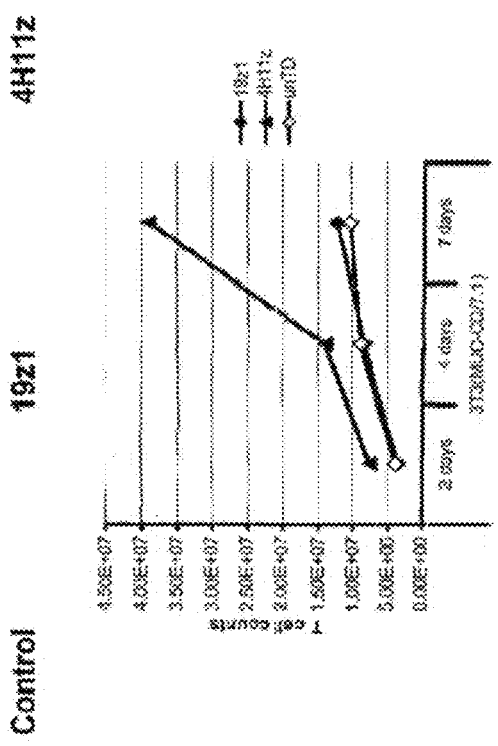

In order to assess the function of the first generation 4H11z CAR, healthy donor T cells isolated from peripheral blood were retrovirally transduced to express the 4H11z and control 19z1 CARs (FIG. 11B). Function of the 4H11 z CAR was assessed by proliferation of 4H11z transduced T cells following co-culture on 3T3(MUC-CD/B7.1) AAPCs. Results demonstrate specific proliferation of 4H11z transduced T cells, when compared to 19z1 modified T cells (FIG. 11C). These data are consistent 4H1z CAR mediated specific binding to the MUC-CD antigen and subsequent T cell activation.

Figures 12A, 12B, 12C, 12D:
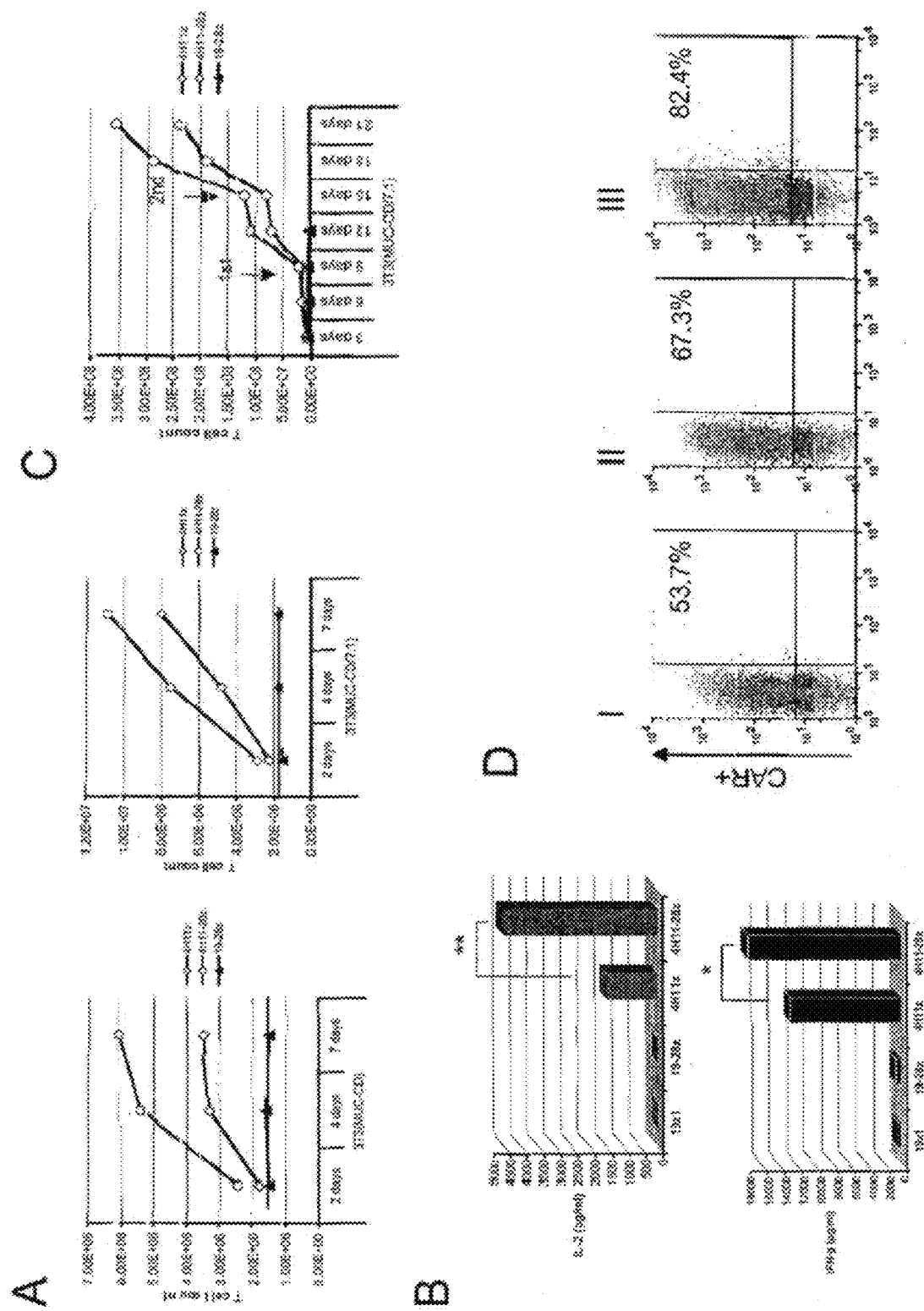
FIGS. 12A-12D. In vitro comparison of T cells modified to express the first generation 4H11z CAR to T cells modified to express the second generation co-stimulatory 4H11-28z CAR.

Since most malignancies fail to express co-stimulatory ligands, we further modified the 4H11z CAR to express the CD28 transmembrane and cytoplasmic co-stimulatory signaling domains, constructing the second generation 4H11-28z CAR (FIG. 11A). To assess whether the 4H11-28z CAR, when expressed by human T cells, was capable of generating both a primary activating signal (termed "signal 1") through the (chain, as well as a co-stimulatory signal (termed "signal 2") through the CD28 cytoplasmic domain, which in turn allows for efficient T cell proliferation in the absence of exogenous co-stimulatory ligands, we compared T cell proliferation following co-culture on either 3T3(MUC-CD) or 3T3(MUC-CD/B7.1) AAPCs in the absence of exogenous cytokines. As expected, the second generation 4H11-28z$^+$ T cells markedly expanded when compared to 4H11z$^+$ T cells upon co-culture with 3T3(MUC-CD) AAPCs. In contrast, both 4H11z$^+$ and 4H11-28z$^+$ T cells expanded similarly on 3T3(MUC-CD/B7.1) AAPCs (FIG. 12A). Co-stimulation mediated by the 4H11-28z CAR was further verified by analysis of day 2 tissue culture supernatants from co-culture experiments on 3T3(MUC-CD) AAPCs demonstrating enhanced IL-2 secretion, a cytokine typically secreted in the context of T cell co-stimulation, when compared to control 19z1 and 19-28z$^+$ T cells and first generation 4H11z$^+$ T cells (FIG. 12B). Secretion of IFNγ was comparable between 4H111z$^+$ and 4H11-28z$^+$ activated T cells.

We next assessed the ability of MUC-CD targeted T cells to expand following weekly re-stimulations through co-culture on 3T3(MUC-CD/B7.1) AAPCs in the context of exogenous IL-2 and IL-15 (3). Both 4H11z$^+$ and 4H11-28z$^+$ T cells expanded greater than 2 logs over 3 weeks (FIG. 12C). T cells transduced with the 4H11-28z were further analyzed by FACS for CAR expression 7 days after initial activation on AAPCs and following two subsequent co-stimulations on AAPCs demonstrating an expected enrichment of the CAR$^+$ T cell fraction (FIG. 12D). Similar data was generated with expanded 4H11z$^+$ T cells (data not shown).

In Vitro Cytotoxicity and Proliferation of MUC-CD Targeted T Cells Following Co-Culture with OV-CAR3(MUC-CD) and Freshly Isolated Ascites Derived Ovarian Tumor Cells.

Figures 13A, 13B, 13C, 13D, 13E, 13F:
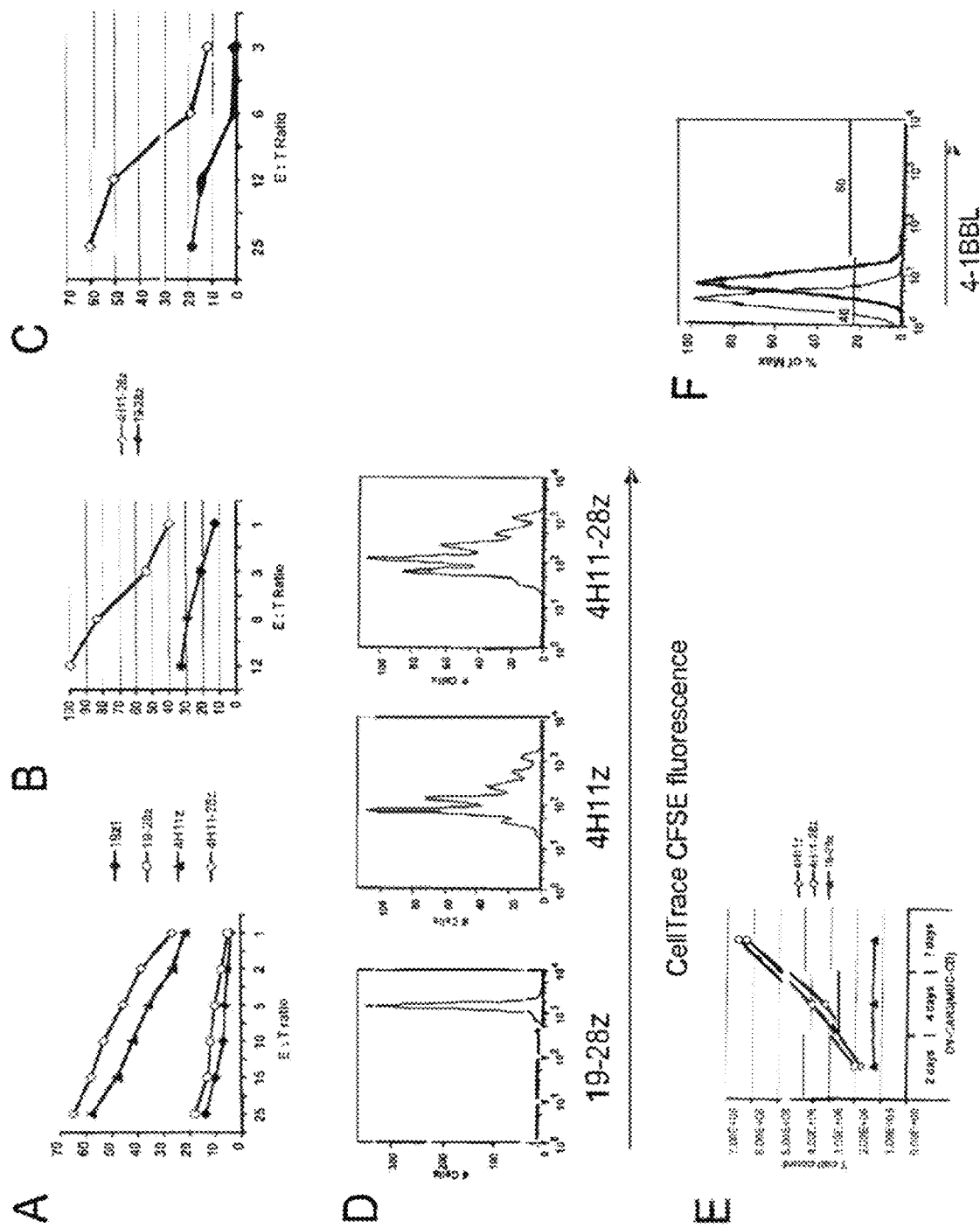
FIGS. 13A-13F. MUC-CD targeted T cells specifically expand and lyse MUC-CD$^+$ tumor cells.

In order to assess the ability of 4H11z$^+$ and 4H11-28z$^+$ T cells to target and lyse human ovarian carcinoma tumors, we utilized the human OV-CAR3 cell line which was genetically modified to express the MUC-CD antigen thereby better reflecting the majority of clinical ovarian tumor samples which express the 4H11-targeted MUC-CD antigen (48). We initially verified specific lysis by MUC-CD targeted T cells demonstrating similar significant cytotoxic activity of 4H11z and 4H11-28z CAR modified T cells targeting OV-CAR3(MUC-CD) tumor cells when compared control T cells expressing the irrelevant first and second generation CD19-targeted 19z1 and 1928z CARs (FIG. 13A). Healthy donor T cells modified to express the 4H11-28z CAR similarly exhibited lysis of freshly isolated ascites derived MUC-CD$^+$ ovarian carcinoma cells when compared to 19-28z transduced T cells (FIG. 13B). Moreover, patient's peripheral blood T cells modified to express the 4H11-28z CAR similarly lysed autologous primary MUC-CD$^+$ tumor cells derived from the same ascites sample when compared to T cells modified to express the control 19-28z CAR (FIG. 13C).

We further assessed the ability of 4H11z$^+$ and 4H11-28z$^+$ T cells from healthy donors to proliferate following co-culture on OV-CAR3(MUC-CD) as assessed by FACS of CFSE labeled T cells, as well as absolute T cells numbers over 7 days following co-culture with tumor (FIGS. 13D and 13E). Surprisingly, we found that both 4H11z$^+$ and 4H11-28z$^+$ T cells expanded equally well following co-culture with OV-CAR3(MUC-CD) tumor cells suggesting the ability of this tumor cell line to co-stimulate T cells through expression of a co-stimulatory ligand. To address this possibility, we conducted further FACS analyses of OV-CAR3 (MUC-CD) tumor cells demonstrating expression of the co-stimulatory 4-1BBL ligand (FIG. 13F), but not the B7.1, B7.2, or OX-40L co-stimulatory ligands (data not shown).

In Vivo Anti-Tumor Activity of MUC-CD Targeted T Cells in SCID-Beige Mice.

Figure 14A:
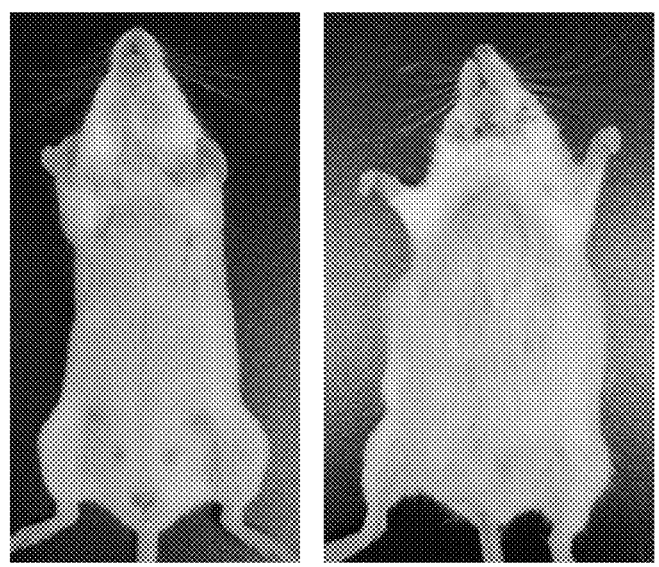
FIGS. 14A-14B. Eradication of OV-CAR3(MUC-CD) tumors after intra-peritoneal treatment with first and second generation of MUC-CD targeted T cells.

To assess the in vivo anti-tumor activity of 4H11z$^+$ and 4H11-28z$^+$ T cells, we next generated an orthotopic xenotransplant ovarian cancer tumor model by ip injection of OV-CAR3(MUC-CD) tumor cells into SCID-Beige mice. If left untreated, these mice developed marked ascites and multiple nodular peritoneal tumors by 3 weeks following tumor cell injection (FIG. 14A). All untreated tumor bearing mice had to be euthanized by 7 weeks following tumor cell injection due to evidence of distress.

Figure 14B:
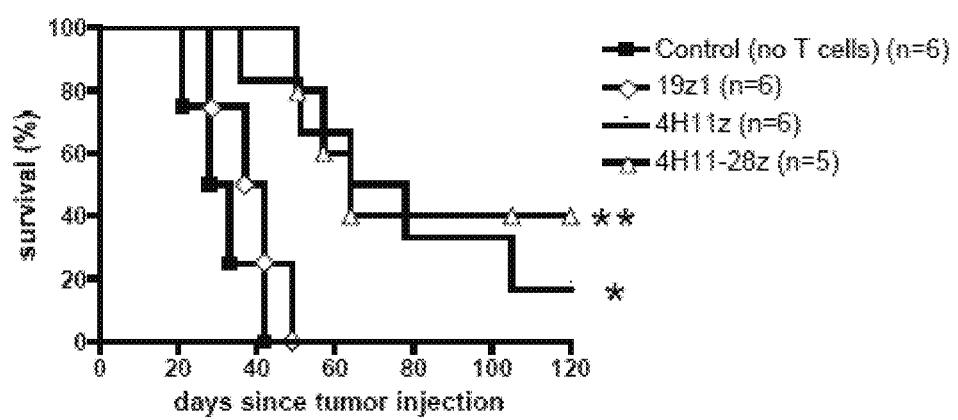

To assess the in vivo anti-tumor efficacy of MUC-CD-targeted T cells, SCID-Beige mice were injected ip with OV-CAR3(MUC-CD/GFP-FFLuc) tumor cells on day 1 followed by ip injection of 4H11z$^+$ or 4H11-28z$^+$ T cells on day 2. For negative controls, tumor bearing mice were either untreated or treated with T cells modified to express the irrelevant CD19-targeted CAR. Collectively, we found that 27% of all mice treated with MUC-CD targeted T cells (3/11 mice) remained alive without clinical evidence of disease 120 days out from tumor injection with no statistically significant difference in survival when comparing the 4H11z$^+$ and 4H11-28z$^+$ T cell treated cohorts (FIG. 14B). In contrast, both MUC-CD-targeted T cell treated cohorts demonstrated statistically significant enhanced survival when compared to untreated and 19z1 T cell treated control cohorts.

Figure 15A:
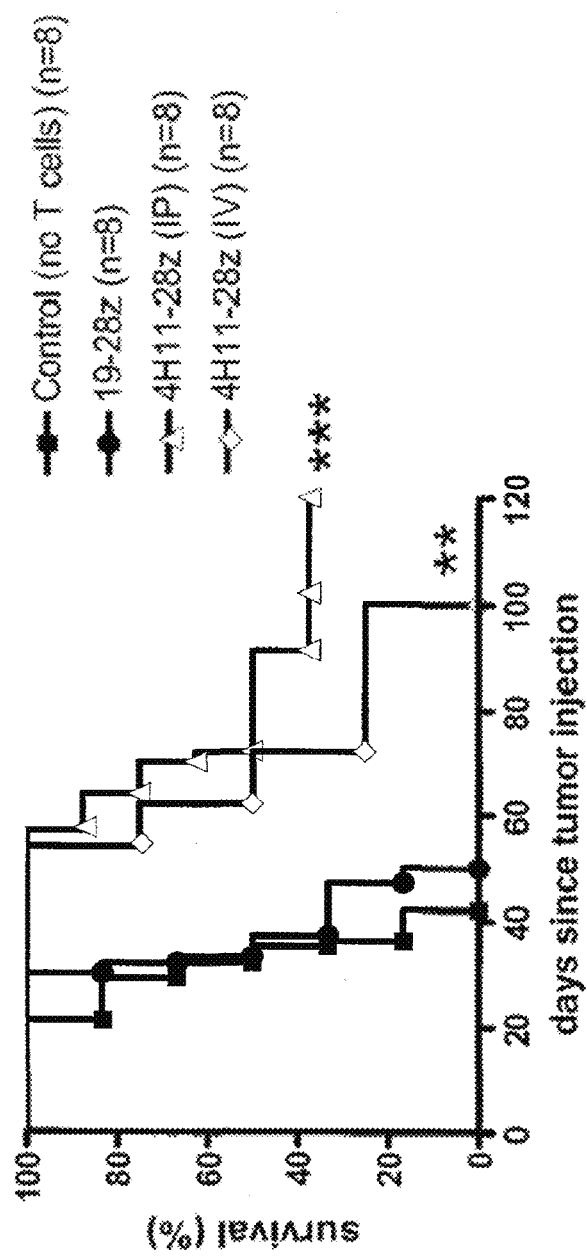
FIGS. 15A-15C. MUC-CD targeted 4H11-28z$^+$ T cells successfully traffic to ip OV-CAR3(MUC-CD/GFP-FFLuc) tumors following systemic intravenous infusion resulting in equally efficient anti-tumor efficacy when compared to ip 4H11-28z$^+$ treated tumor bearing mice.
Figure 15B:
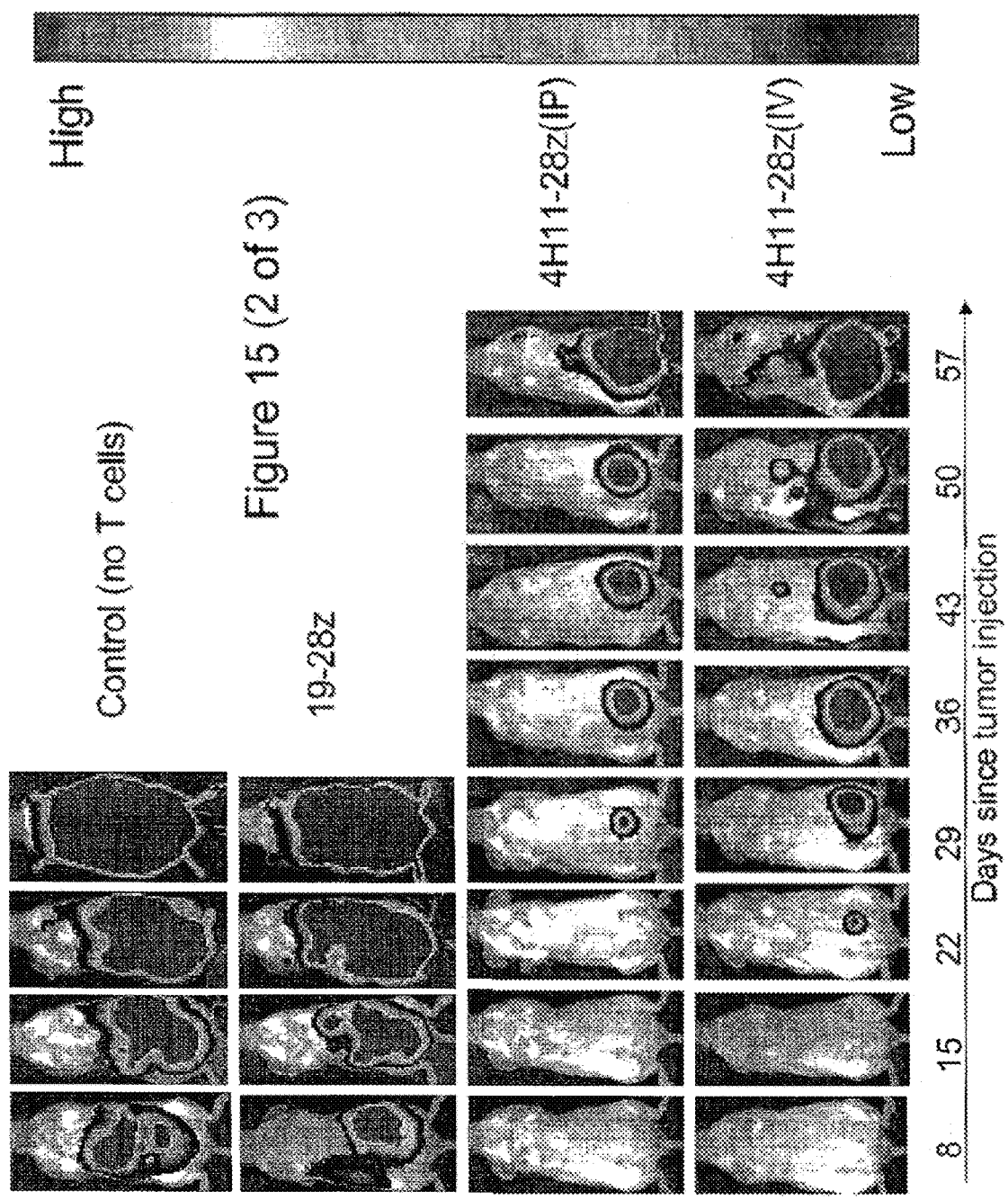
Figure 15C:
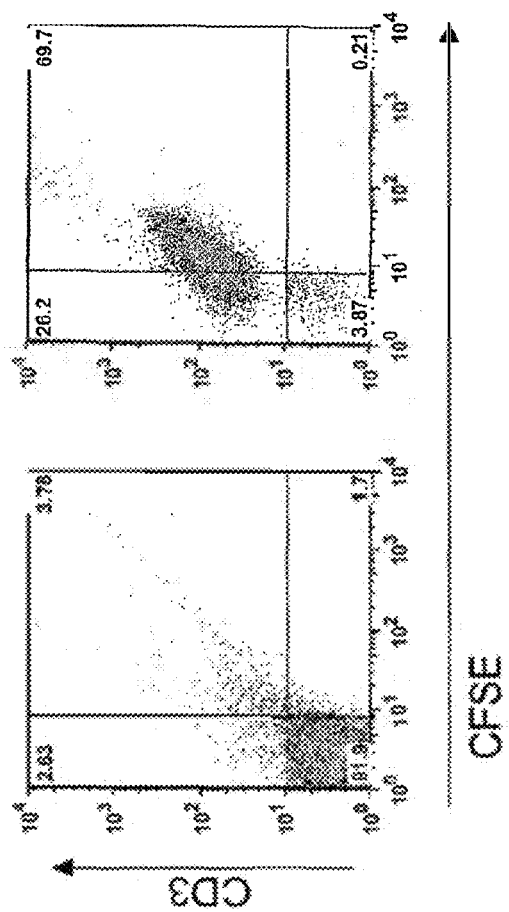

To assess whether systemically infused MUC-CD-targeted T cells successfully traffic to ip tumors, we next compared ip to iv infusion of 4H11-28z$^+$ T cells in SCID-Beige mice bearing ip OV-CAR3(MUC-CD/GFP-FFLuc) tumors. Both ip and iv 4H11-28z$^+$ T cell treated mice exhibited statistically enhanced survival when compared to untreated or 19-28z$^+$ T cell treated control cohorts as assessed by overall survival (FIG. 15A) as well as by BLI of tumor progression (FIG. 15B). Furthermore, we found overall survival between the ip and iv treated groups to be statistically equivalent by log rank analysis. These data imply successful trafficking of iv infused 4H11-28z$^+$ T cells to peritoneal tumors. We further confirmed trafficking of iv infused CFSE labeled 4H11-28z$^+$ T cells to the peritoneum by FACS analysis of single cell suspensions of macerated OV-CAR3(MUC-CD) tumors (FIG. 15C).

In Vivo Anti-Tumor Activity of MUC-CD Targeted T Cells in SCID-Beige Mice Bearing Well Established OV-CAR3(MUC-CD GFP-FFLuc) Tumors.

Figure 16A:
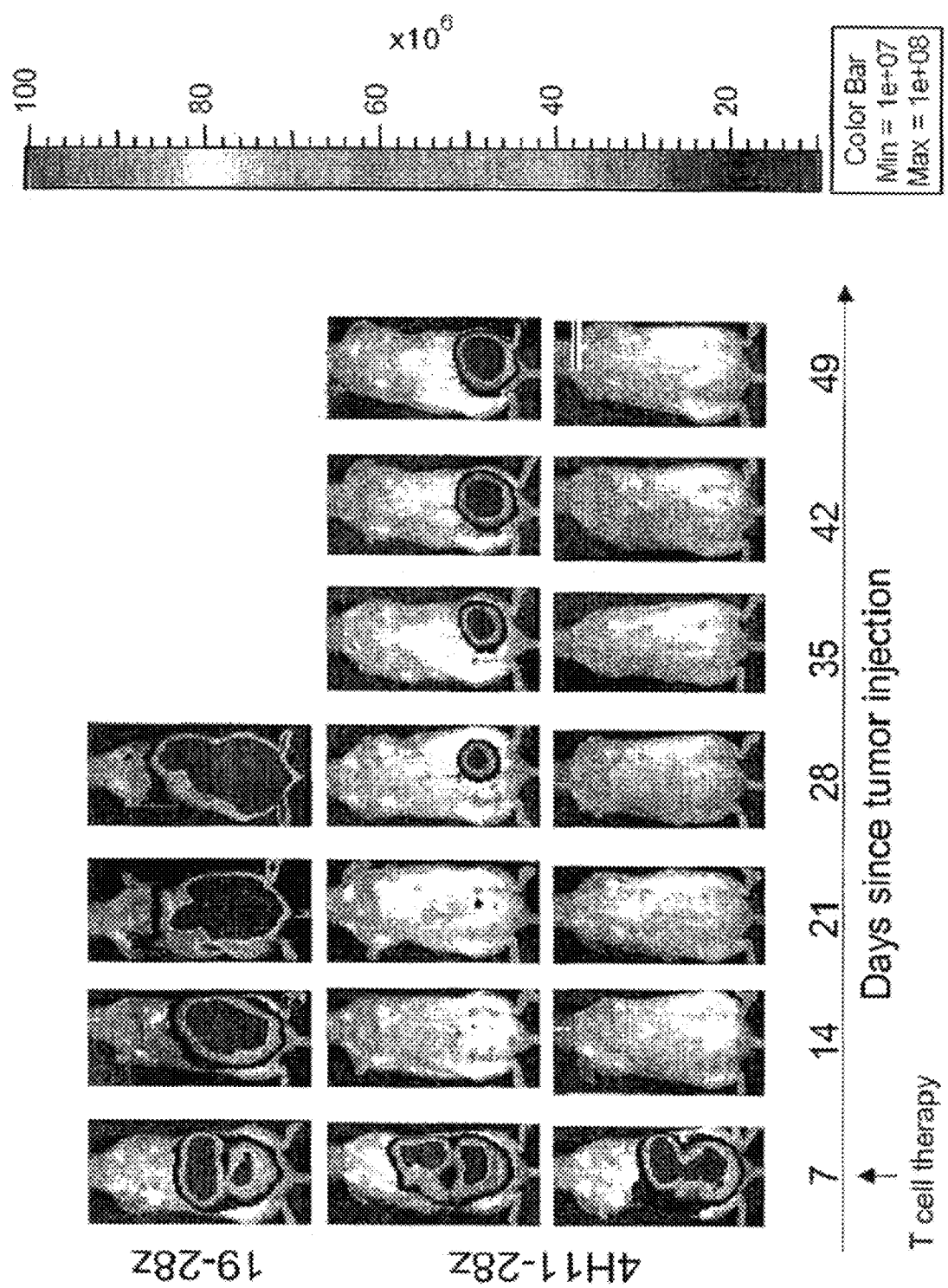
FIGS. 16A-16B. Eradication of advanced OV-CAR3 (MUC-CD) tumors in SCID-Beige mice by ip infusion of 4H11-28z+ T cells. SCID-Beige mice were injected ip with $3 \times 10^6$ OV-CAR3(MUC-CD/GFP-FFLuc) tumor cells 7 days prior to ip treatment with $3 \times 10^7$ 4H11-28z+ T cells.
Figure 16B:
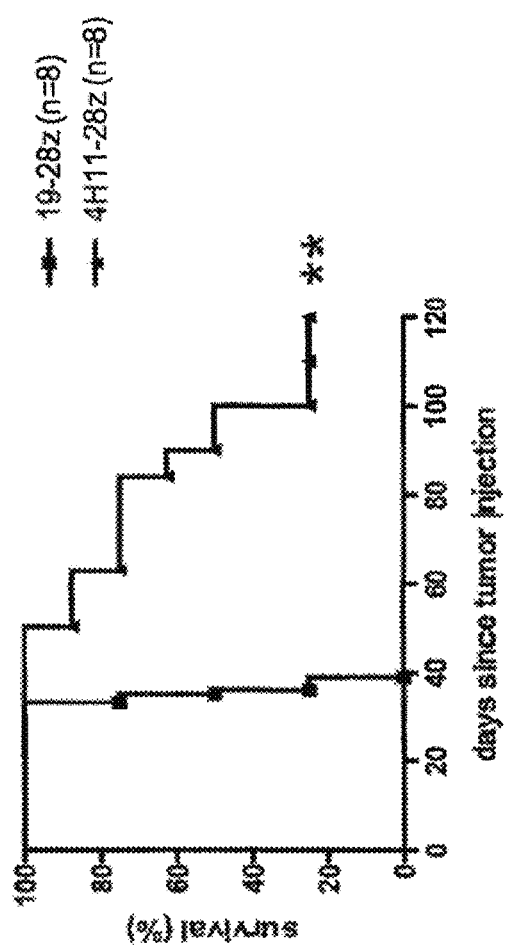

To further assess whether 4H11-28z$^+$ T cells were able to eradicate more clinically relevant tumor burdens, we next treated SCID-Beige mice bearing well established ip OV-CAR3(MUC-CD/GFP-FFLuc) tumor injected 7 days prior to adoptive T cell therapy. Once more, we found that therapy with MUC-CD targeted T cells markedly eradicated BLI evident disease in all treated mice (FIG. 16A) with 5 of 8 treated mice eventually developing relapsed progressive disease, and 3 mice remaining disease free as assessed by BLI imaging (not shown) out to 120 days post-tumor cell infusion (FIG. 16B). These data demonstrate potent in vivo anti-tumor activity mediated by MUC-CD targeted T cells even in the setting of advanced disease.

Discussion

Based on extensive analyses of patient tumor samples, ovarian carcinomas appear to be relatively immunogenic tumors. Specifically, researchers have found there to be a direct correlation between prognosis following surgery and chemotherapy and the quantity of tumor infiltrating effector T cells (TILs) in pretreatment tumor samples (25, 49, 50). Furthermore, others have described an inverse correlation between prognosis following therapy and pre-treatment levels of Tregs within the tumor, which in turn presumably inhibit the anti-tumor function of tumor specific effector TILs (26, 28, 51). Both of these findings imply a role for an endogenous effector T cell response to tumor in controlling disease progression both prior to and following initial therapy and strongly support the contention that ovarian carcinomas may be susceptible to killing by adoptive infusion of autologous T cells targeted to ovarian tumor cell antigens.

While endogenous effector TILs are one source for presumably tumor specific T cells, an alternative approach to adoptive T cell therapy is to isolate autologous peripheral blood T cells which in turn may be genetically modified ex vivo to target tumor cell antigens. One such genetic approach is to retrovirally transduce patient T cells with CARs targeted to surface exposed antigens either unique to or over-expressed by the tumor. To this end, promising preclinical studies utilizing this approach in other malignancies have recently been translated into the clinical setting (6, 16, 19, 52). Similarly, we have previously generated CARs targeted to the CD19 antigen expressed on normal B cells as well as most B cell malignancies and are currently conducting clinical trials treating patients with relapsed B cell chronic lymphocytic leukemia and acute lymphoblastic leukemias with autologous T cell modified to express a CD19 specific CAR (53).

Application of this approach to ovarian carcinomas requires the identification to suitable target antigens expressed on the tumor cell surface. Significantly, other investigators have studied this approach in both the pre-clinical and clinical setting (4, 11, 54-57). Specifically, several groups have demonstrated significant anti-tumor responses to subcutaneous human ovarian carcinoma cell line tumors in immune compromised mice following intra-tumoral and/or intravenous infusion of T cells expressing CARs specific to the mesothelin and Lewis-Y antigens overexpressed on these tumor cell lines (56, 58, 59). Furthermore, Kershaw et al recently published the results of a phase I clinical trial treating patients with relapsed ovarian carcinomas with autologous T cells modified to express a CAR specific to the alpha-folate receptor (6). The authors of this study found that therapy with targeted T cells was well tolerated, but noted a lack of anti-tumor response in these studies related to poor persistence of modified T cells over time as well as a yet undefined T cell inhibitory factor in the serum of several treated patients.

In our studies, we have chosen to target the MUC-16 glycoprotein which is over-expressed on a majority of ovarian carcinomas (1, 30, 32, 33). The utility of MUC-16 as a target antigen for adoptive T cell therapy is compromised by the fact that most of the extracellular portion of this molecule is cleaved by the tumor cell, secreted, and may be detected in the serum as the CA-125 tumor marker. However, following cleavage of this secreted fraction of MUC-16, there remains a residual extracellular fraction of the glycoprotein, termed MUC-CD, which is retained on the tumor surface and is therefore an attractive target for immune-based therapies. To this end, we utilized a series of murine hybridomas generated to the MUC-CD antigen to construct CARs specific to MUC-CD. Of these CARs, we identified a CAR generated from the 4H11 murine hybridoma termed 4H11z, which, when expressed in human T cells, following co-culture on 3T3(MUC-CD/B7.1) AAPCs, resulted in rapid destruction of AAPC monolayers as well as marked modified T cell expansion. Significantly, the antigen to the 4H11 antibody is highly expressed on a majority of pre-treatment ovarian carcinoma surgical tumor samples obtained from patients treated at our institution as assessed by immuno-histochemistry (48).

Optimal T cell activation requires both a primary T cell receptor mediated signal, "signal 1," along with a co-stimulatory "signal 2." Classically, this co-stimulatory signal may be provided by ligation of either B7.1 (CD80) or B7.2 (CD86) on the target cell with the T cell co-stimulatory receptor CD28. Alternatively, co-stimulation may be generated by ligation of 4-1BBL or OX-40L on the target cell with the respective 4-1BB or OX40 co-stimulatory receptors on the T cell (12, 60, 61). Since most tumor cells fail to express co-stimulatory ligands, we and others have previously demonstrated that second generation CARs further incorporating the cytoplasmic signaling domains the co-stimulatory receptors CD28, 4-1BB, and/or OX40 resulted in CARs capable of providing both signal 1 and signal 2 to the T cell upon binding to cognate antigen in the absence of exogenous co-stimulatory ligands (7-10, 12, 13, 15, 16, 62-65). To this end, we constructed a second generation CAR from the 4H11z CAR incorporating the transmembrane and cytoplasmic signaling domain of CD28 as described elsewhere (3, 9, 43). Consistent with previous studies, we found that T cells transduced to express the resulting 4H11-28z CAR, but not the first generation 4H11z CAR, efficiently expanded upon co-culture with 3T3(MUC-CD) fibroblasts in the absence of exogenous co-stimulation consistent with the ability of the 4H11-28z CAR to deliver both signal 1 and signal 2 to the T cell. This conclusion is further supported by the finding that 4H11-28z$^+$ T cells secreted significantly higher levels of IL-2, a cytokine indicative of T cell co-stimulation, upon co-culture on 3T3(MUC-CD) fibroblasts when compared to T cells transduced to express the first generation 4H11z CAR.

We next assessed the ability of 4H11z$^+$ and 4H11-28z$^+$ T cells to target and lyse human ovarian carcinoma tumor cells. To this end, we initially utilized the OV-CAR3 human ovarian cancer cell line. Since the OV-CAR3 tumor cell line binds the 4H11 antibody weakly, we further genetically modified the cell line to express MUC-CD (OV-CAR3 (MUC-CD)) to better mimic the clinical setting wherein a majority of clinical ovarian carcinoma tumor specimens highly express the 4H11 MUC-CD antigen (48). We demonstrated that human T cells modified to express either 4H11z or 4H11-28z eradicated OV-CAR3(MUC-CD) tumor cells in vitro, and surprisingly observed that both 4H11z$^+$ and 4H11-28z$^+$ T cells expanded following co-culture with tumor in vitro. To define the etiology of this unanticipated 4H11z$^+$ T cell expansion, we further assessed whether OV-CAR3(MUC-CD) tumor cells expressed co-stimulatory ligands, and found that this tumor cell line expressed 4-1BBL, consistent with our experimental findings as well as with previously published reports demonstrating 4-1BBL expression by a variety of carcinoma cell lines (66-68). In order to further validate the clinical relevance of these findings, we subsequently demonstrated specific in vitro lysis of primary ascites-derived tumor cells isolated from untreated ovarian carcinoma patients by both healthy donor allogeneic 4H11-28z$^+$ T cells as well as more significantly autologous 4H11-28z patient peripheral blood T cells. These data strongly support the contention that treatment with autologous 4H11-based CAR$^+$ T cells have promise in future clinical applications.

In order to assess the in vivo relevance of our in vitro findings, we next generated a murine orthotopic OV-CAR3 (MUC-CD) tumor model in SCID-Beige mice. We injected mice i.p. with OV-CAR3(MUC-CD) tumor cells and the following day infused 4H11z$^+$, 4H11-28z$^+$, and control 19z1$^-$ T cells i.p. This treatment approach resulted in a significant but similar delay to tumor progression and long-term survival in both the 4H11z$^+$ and 4H11-28z$^+$ T cell treated cohorts when compared to untreated mice or mice treated with control T cells targeted to the irrelevant CD19 antigen. We next compared ip to iv treatment with 4H11-28z$^+$ T cells of orthotopic OV-CAR3(MUC-CD/GFP-FFLuc) bearing mice, and found similar statistically significant survivals of mice over time with either direct ip infusion of T cells or systemic iv infusion of targeted T cells. Significantly, iv treated mice by day 1 following treatment, exhibited successful trafficking of targeted T cells to the peritoneum. These data suggests that adoptive therapy with targeted T cells may be equally efficacious following either a direct infusion into the peritoneum or through systemic iv infusion. These findings further support the future clinical potential of this approach in treating patients both with local relapse of disease as well as metastatic relapse to sites outside of the peritoneum.

Finally, we assessed the ability of 4H11-28z$^+$ T cells to eradicate more established disease by delaying modified T cell ip infusion by 7 days, when mice had greater established tumor burdens as assessed by bioluminescent imaging. This experimental setting better reflects the initial clinical setting wherein this adoptive T cell approach would be utilized. Significantly, despite the setting of markedly established disease, 4H11-28z$^+$ T cells retained the ability to lyse larger tumor burdens, delay relapse of tumor, and in a significant percentage of mice, fully eradicate disease.

In the studies presented here, we have consistently utilized mixed populations of CD4$^-$ and CD8$^+$ CAR$^+$ T cells to assess both in vitro and in vivo anti-tumor activity. To this end, ongoing studies will address the role of isolated CD4$^+$ and CD8$^+$ CAR$^+$ T cell subsets in the successful eradication of disease in this SCID-Beige OV-CAR3(MUC-CD) tumor model. The results of these studies may have implications to translating this therapeutic approach to the clinical setting. Furthermore, we acknowledge the limitations associated with the presented SCID-Beige tumor model. Namely, this is a xenotransplant model in an immune compromised mouse. To this end, ongoing studies in or laboratory are focused on generating a more clinically relevant syngeneic immune competent tumor model to better define the biology and anti-tumor efficacy of MUC-CD targeted CAR-modified T cells in the context of an intact immune system.

In conclusion, herein we present the first published data demonstrating the feasibility of targeting MUC-16, an antigen over-expressed on a majority of ovarian carcinomas, through adoptive therapy with genetically modified T cells targeted to the retained MUC-CD portion of the MUC-16 antigen. Further, this report is the first to demonstrate efficient targeting of T cells in an orthotopic, clinically relevant, murine model of ovarian cancer, demonstrating efficacy both by ip and iv infusion of modified T cells. Finally, these data support the further translation of this approach to the clinical setting in the form of a phase I clinical trial in patients with persistent or relapsed ovarian carcinomas following initial therapy with surgery and chemotherapy. [fi]

Example 5

Raising Mouse MUC16 Monoclonal Antibodies in Mice and Hamsters.

We selected 3 different regions of mouse MUC16 genome for which monoclonal antibodies were generated in mouse and hamster. The selected regions of the mouse MUC16 are Peptide 1 (SEQ ID NO:21, ecto region of cytoplasmic domain), Peptide 2 (SEQ ID NO:22, first cysteine loop) and Peptide 3 (SEQ ID NO:23, second cysteine loop) (FIG. 20A) and its comparison with human MUC16 is shown in FIG. 20B. A cysteine was added to the peptide sequence at the N terminus of Peptide 1 (SEQ ID NO:21) and Peptide 3 (SEQ ID NO:23) for better conjugation with KLH. Individual peptides were conjugated to KLH using Promega kit. These 3 conjugated peptides were pooled and immunized into 5 mice and 4 hamsters. 5 immunizations with a 3 week interval for each immunization were administered. Sera from these animals were tested by ELISA for their specific reactivity with individual peptides (SEQ ID NO:21, 22 and 23). Positive selected animals were allowed to rest for a month and then i.v. boosted with pooled peptides immunogen (SEQ ID NO:21, 22 and 23) and harvested the spleens after 4 days. Splenocytes were mixed with hybridoma partners and plated into microtiter plates at various clonal densities. Plates were cultured at 37° C. 5% $CO_2$ for 10 days and then selected the clones. Supernatants from these selected clones were tested by ELISA for their specific reactivity with individual peptides (SEQ ID NO:21, 22 and 23). Positive clonal sups were tested by FACS, western blot and imaging using 2 mouse cell lines (ID8 and BR5-FVB1) and a human cell line (OVCAR-3).

Table 4 shows the summary of mouse and hamster monoclonal antibodies against mouse MUC16 peptide antigens Peptide 1 (SEQ ID NO: 21), Peptide 2 (SEQ ID NO: 22), and Peptide 3 (SEQ ID NO: 23). A very strong antigenic response was seen with Peptide 1 (SEQ ID NO: 21).

TABLE 4

| Mouse MUC16 | Mouse mAbs | Frozen Mouse mAb | |
|---|---|---|---|
| Peptide 1 | 46 | 16 (3-IgG1; 8-IgG2b; 1-IgM; 4-Unkown isotype) | Animals not iv boosted with peptide 2 |
| Peptide 2 | 0 | 0 | |
| Peptide 3 | 6 | 6 (4-IgG1; 2-IgM) | |
| Peptide 1, 2, 3 | 0 | 0 | |
| Peptide 1, 2 | 0 | 0 | |
| Peptide 2, 3 | 0 | 0 | |
| No Peptide | 0 | 0 | |

| Mouse MUC16 | Hamster mAbs | Frozen Hamster mAb |
|---|---|---|
| Peptide 1 | 69 | 21 |
| Peptide 2 | 6 | 6 |
| Peptide 3 | 7 | 7 |
| Peptide 1, 2, 3 | 2 | 1 |
| Peptide 1, 2 | 1 | 1 |
| Peptide 2, 3 | 1 | 0 |
| No Peptide | 10 | 2 |

5 Details of mouse and hamster mAbs against Peptide 1 (SEQ ID NO: 21), Peptide 2 (SEQ ID NO: 22), and Peptide 3 (SEQ ID NO: 23 are listed in Table 5 and Table 6 respectively.

TABLE 5

| isotype | PEPTIDE | Fusion Well | Cloned | Clones | | | |
|---|---|---|---|---|---|---|---|
| — | 1 | 01D01 | | | | | |
| — | 1 | 09F07 | | | | | |
| IgG 1 | 1 | 16A09 | no success | | | | |
| — | 1 | 21A07 | | | | | |
| — | 1 | 24G10 | | | | | |
| IgG 1 | 1 | 10C04 | yes | 10C4-3H5 | 10C4-1F2 | 10C4-2H8 | 10C4-1G7 |
| IgG 1 | 1 | 17F02 | yes | 17F2-3G5 | 17F2-3F6 | 17F2-2F9 | 17F2-1E11 |
| IgG 2b | 1 | 01A08 | | | | | |
| IgG 2b | 1 | 01F08 | | | | | |
| IgG 2b | 1 | 12B10 | yes | 12B10-3F7 | 12B10-3G10 | 12B10-2F6 | 12B10-2F10 |
| IgG 2b | 1 | 17H10 | | | | | |
| IgG 2b | 1 | 18D05 | | | | | |
| IgG 2b | 1 | 23B12 | | | | | |
| IgG 2b | 1 | 25E09 | | 25E9-3 | 25E9-5 | 25E9-13 | 25E9-16 |
| IgM | 1 | 16F12 | | | | | |
| IgG 1 | 3 | 04A06 | no success | | | | |
| IgG 1 | 3 | 05D01 | no success | | | | |
| IgG 1 | 3 | 21B08 | yes | 21B8-1H11 | 21B8-3G6 | 21B8-3H9 | 21B8-1G8 |
| IgG 1 | 3 | 21E01 | yes | 21E1-1E3 | 21E1-1G9 | 21E1-2G7 | 21E1-3G12 |
| IgM | 3 | 08A02 | | | | | |
| IgM | 3 | 13E05 | | | | | |

TABLE 6

| Hamster mAb | Peptide | Cloned | | | |
|---|---|---|---|---|---|
| 01H03 | | | | | |
| 02F02 | 1 | | | | |
| 04E 4 | | | | | |
| 04G07 | 1 | | | | |
| 04H01 | 3 | 4H1-2E1 | 4H1-2E3 | 4H1-3E1 | 4H1-3H3 |
| 06A08 | 1 | | | | |
| 06F02 | 1 | | | | |
| 07F08 | 3 | | | | |
| 07H05 | 2 | | | | |
| 09A05 | | | | | |
| 09E 1 | 3 | | | | |
| 09F08 | 1 | | | | |
| 09H10 | | | | | |
| 10G06 | 1 | | | | |
| 10H11 | 1 | | | | |
| 11B10 | 1 | | | | |
| 12F09 | 2 | | | | |
| 15A08 | 1 | 15A8-2E2 | 15A8-2E10 | 15A8-2E11 | 15A8-3D2 |
| 15H08 | 3 | | | | |
| 19B05 | 1 | | | | |
| 21H04 | 3 | | | | |
| 22B05 | 2 | 22B5-1F6 | 22B5-3G9 | 22B5-2G8 | 22B5-3F11 |
| 22D11 | 3 | | | | |
| 23G12 | 1 | | | | |
| 25E 8 | 1 | | | | |
| 27H09 | 3 | | | | |
| 28B12 | 1&2&3 | | | | |
| 28C12 | 2 | | | | |
| 30H02 | 1 | | | | |
| 31A11 | 2 | | | | |
| 31C01 | 2 | | | | |
| 33H06 | 1&2 | | | | |
| 34F10 | 1 | | | | |
| 34H05 | 1 | | | | |
| 36C01 | 1 | | | | |
| 36C11 | | | | | |
| 36E 4 | 1 | | | | |
| 37E 10 | 1 | | | | |
| 10H11 | 1 | | | | |

Hamster antibody 22B05 recognizes mouse (SEQ ID NO:22) and also the corresponding human sequence (SEQ ID NO: 15).

Figure 22:
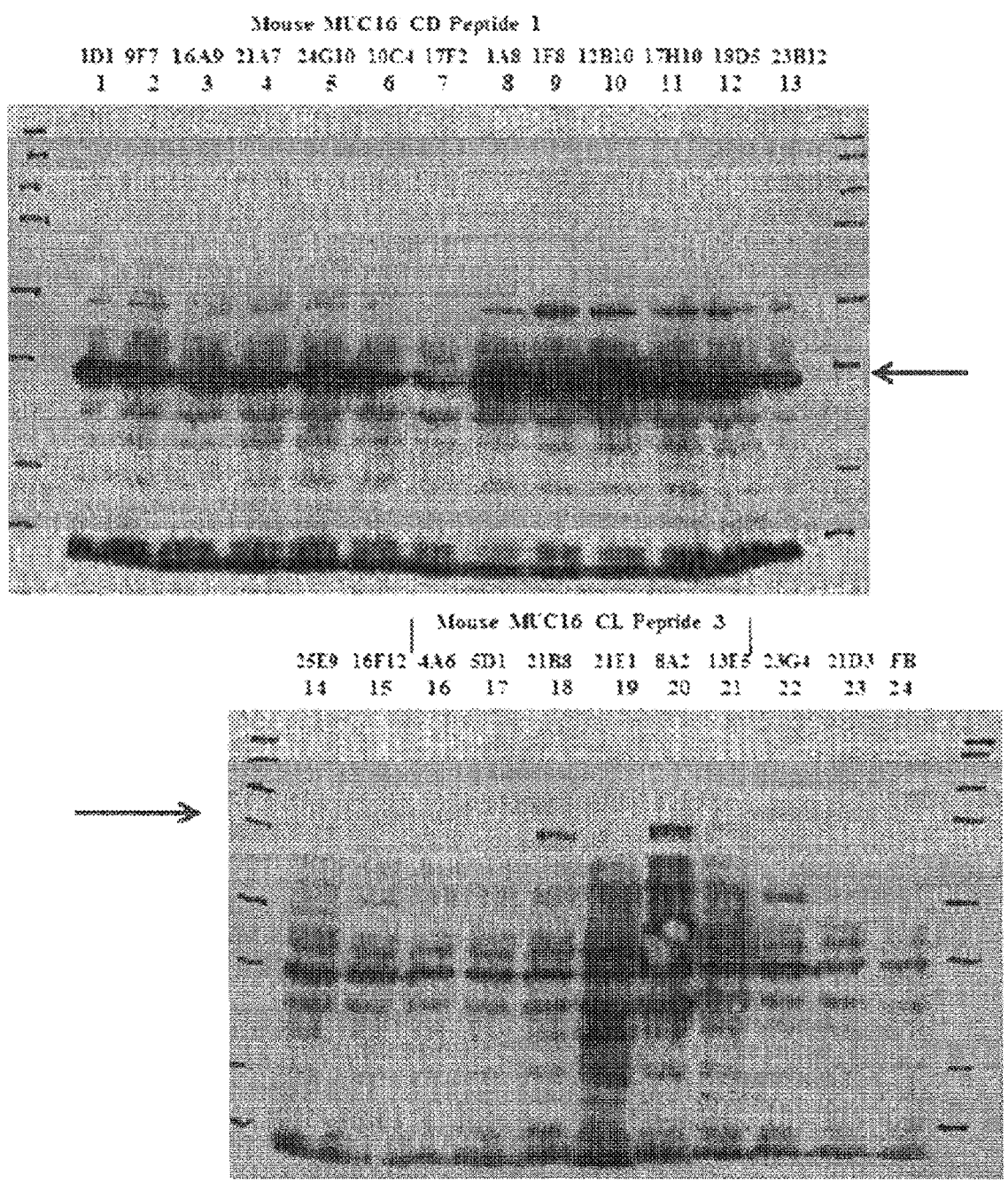
FIG. 22: BR5-FVB1 extract with 1:10 dilution of Mouse MUC16 monoclonal Primary Supernatants

Western blot analysis using mouse ID8 and BR5-FVB1 cell extracts were also performed for all the selected monoclonal antibodies as shown in FIG. 21 and FIG. 22 respectively.

Among the mouse MUC16 monoclonal antibodies, we selected 12B10-3G10 subclone mouse mAb for further screening. Similarly, hamster monoclonal antibodies, 15A8-2E10, 22B5-2G8 and 4H1-2E1 subclones were selected for further screening.

Figure 23:
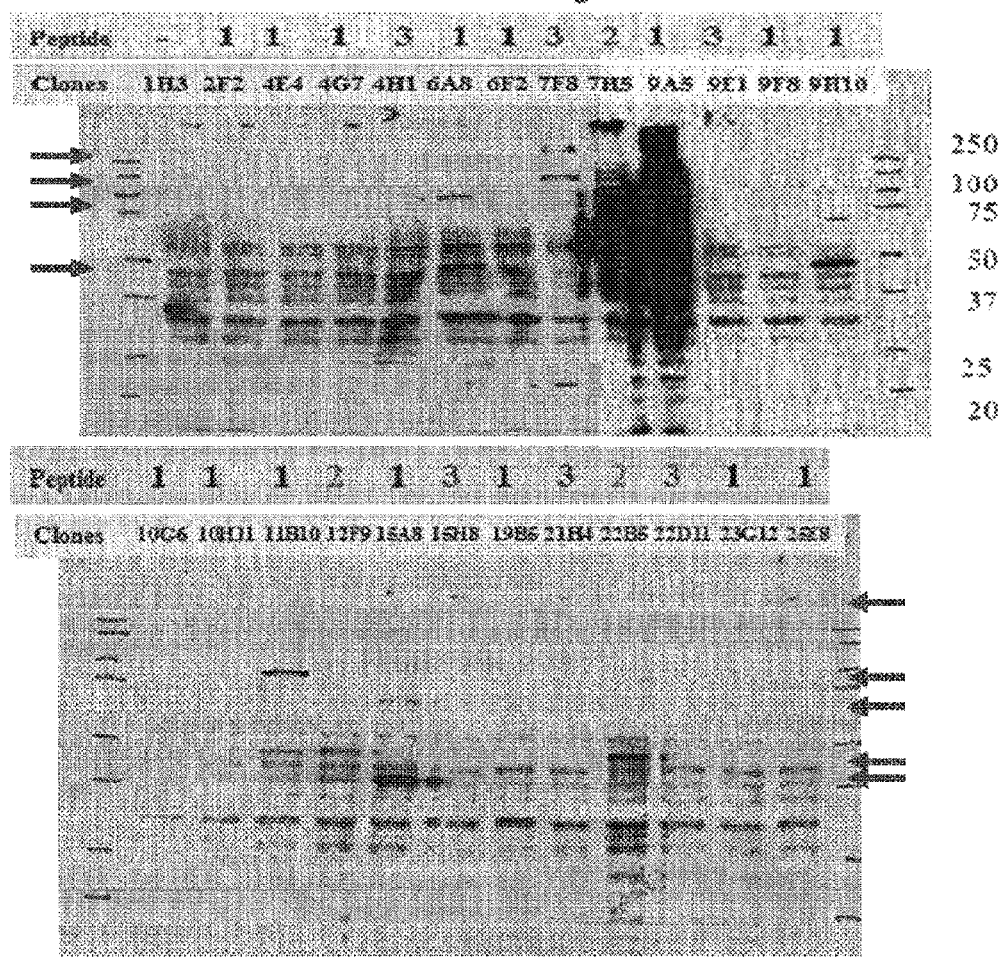
FIG. 23: Western Blot showing 38 hamster's monoclonal antibody Supernatants on ID8 cell extracts.
Figure 24:
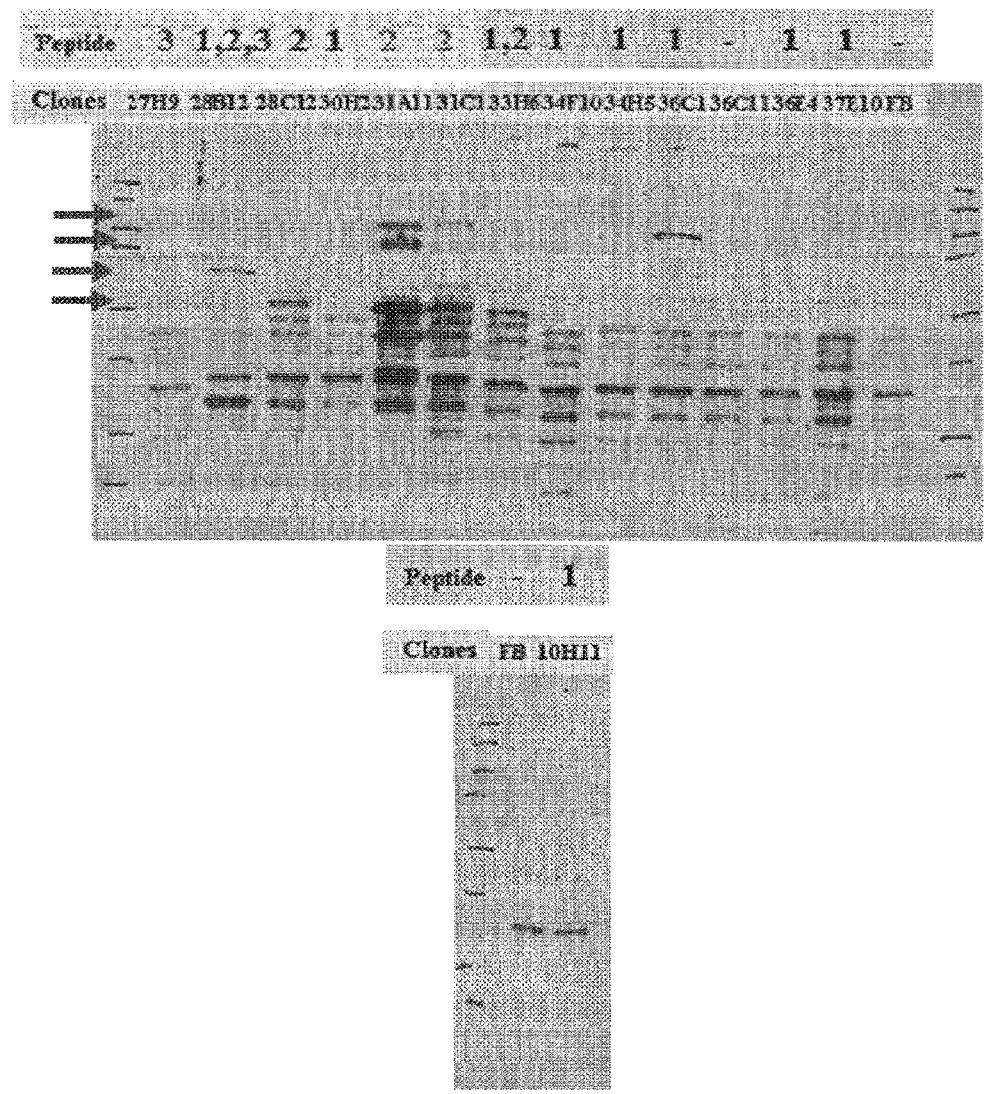
FIG. 24A: Nucleotide sequence encoding 12B10-3G10-$V_H$ (SEQ ID NO:26)
FIG. 24B: 12B10-3G10-$V_H$ Amino Acid sequence (SEQ ID NO:27)
FIG. 24C: Nucleotide sequence encoding 12B10-3G10-$V_L$(SEQ ID NO:28) (Note the $V_L$ has an optional NotI site added by the primer for cloning, and FIG. 24D: 12B10-3G10-$V_L$ Amino Acid sequence (SEQ ID NO:29).
Figure 25:
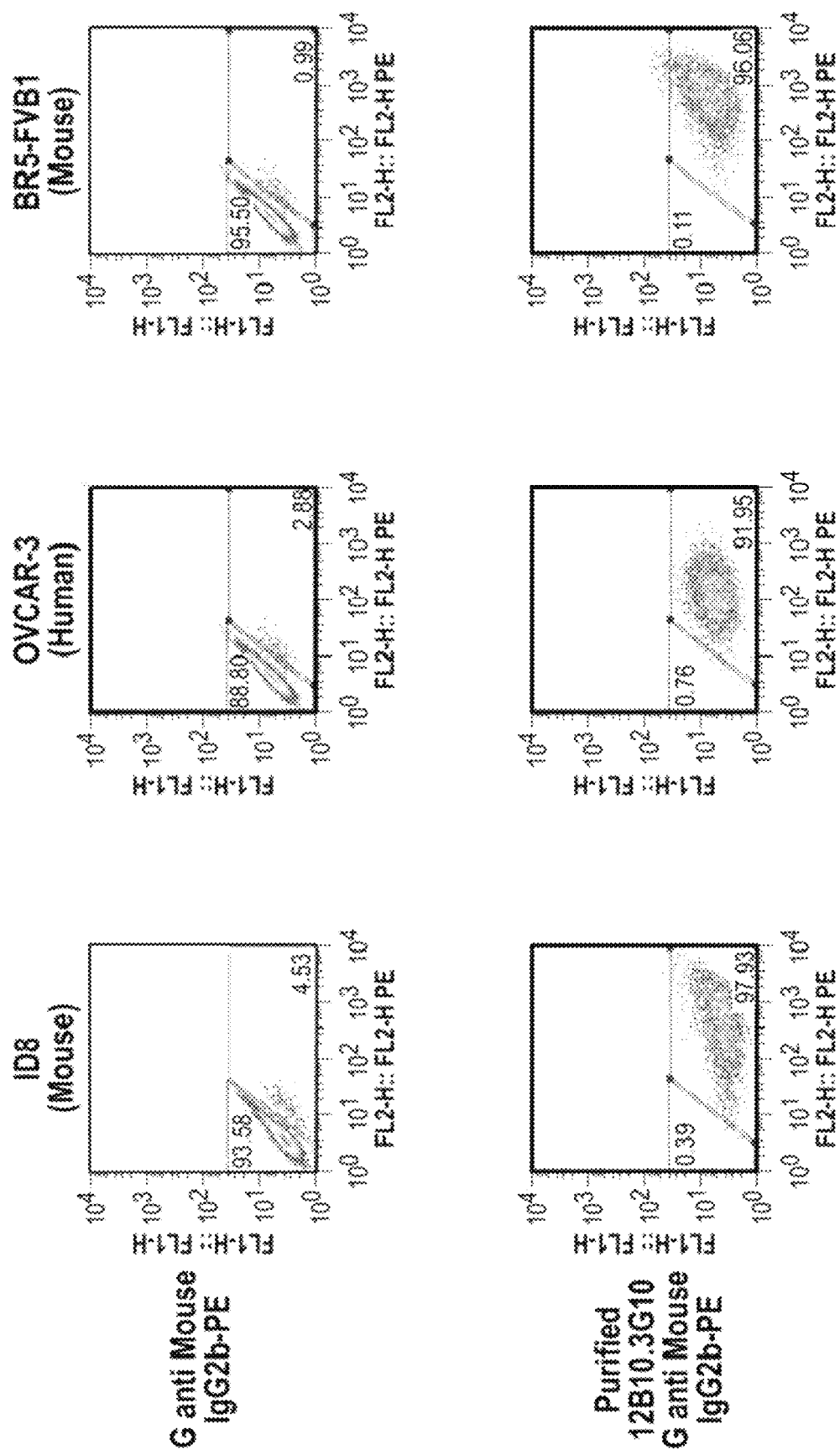
FIG. 25: FACS Analysis with Purified 12B10-3G10 mAb on ID8 (mouse), OVCAR-3 (human) and BR5-FVB1 (mouse) cell lines.

Immunohistochemical analysis was performed with paraffin and cryosections of ID8 (mouse), OVCAR-3 (human), BR5-FVB1 (mouse) cell lines and 13.5 days of Embryo. Paraffin or cryosections were probed with mouse 12B10 mAb, hamster 15A8, hamster 22B5 and hamster 4E1 mAbs to see the early development of mouse MUC16 (FIGS. 23A-23B) 12B10-3G10 sub clone were further analyzed for single chain Fv fragments. FIG. 24 show 12B10-3G10 $V_H$ and $V_L$ DNA and Amino Acids sequences. Bioreactive supernatants and purified 12B10-3G10 were generated for animal studies and other characterization studies. FACS analysis was performed with purified 12B10-3G10 on ID8, OVCAR3 and BR5-FVB1 cells showing over 90% positivity to both mouse and human MUC16 ecto-domain fragment (FIG. 25).

REFERENCES CITED IN THE SPECIFICATION AND EXAMPLES 1-3

1. Bast R C, Jr., Feeney M, Lazarus H, Nadler L M, Colvin R B, Knapp R C. Reactivity of a monoclonal antibody with human ovarian carcinoma. J Clin Invest 1981; 68(5): 1331-7.
2. Bast R C, Jr., Klug T L, St John E, Jenison E, Niloff J M, Lazarus H, et al. A radioimmunoassay using a monoclonal antibody to monitor the course of epithelial ovarian cancer. N Engl J Med 1983; 309(15):883-7.
3. Rustin G J, Bast R C, Jr., Kelloff G J, Barrett J C, Carter S K, Nisen P D, et al. Use of CA-125 in clinical trial evaluation of new therapeutic drugs for ovarian cancer. Clin Cancer Res 2004; 10(11):3919-26.
4. Rosen D G, Wang L, Atkinson I N, Yu Y, Lu K H, Diamandis E P, et al. Potential markers that complement expression of CA125 in epithelial ovarian cancer. Gynecol Oncol 2005; 99(2):267-77.
5. Bast R C, Jr., Badgwell D, Lu Z, Marquez R, Rosen D, Liu J, et al. New tumor markers: CA125 and beyond. Int J Gynecol Cancer 2005; 15 Suppl 3:274-81.
6. Moore R G, Maclaughlan S, Bast R C, Jr. Current state of biomarker development for clinical application in epithelial ovarian cancer. Gynecol Oncol 2009.
7. Nustad K, Lebedin Y, Lloyd K O, Shigemasa K, de Bruijn H W, Jansson B, et al. Epitopes on CA 125 from cervical mucus and ascites fluid and characterization of six new antibodies. Third report from the ISOBM TD-1 workshop. Tumour Biol 2002; 23(5):303-14.
8. Fendrick J L, Konishi I, Geary S M, Parmley T H, Quirk J G, Jr., O'Brien T J. CA125 phosphorylation is associated with its secretion from the WISH human amnion cell line. Tumour Biol 1997; 18(5):278-89.
9. Fendrick J L, Staley K A, Gee M K, McDougald S R, Quirk J G, Jr., O'Brien T J. Characterization of CA 125 synthesized by the human epithelial amnion WISH cell line. Tumour Biol 1993; 14(5):310-8.
10. O'Brien T J, Beard J B, Underwood L J, Shigemasa K. The CA 125 gene: a newly discovered extension of the glycosylated N-terminal domain doubles the size of this extracellular superstructure. Tumour Biol 2002; 23(3): 154-69.
11. Yin B W, Dnistrian A, Lloyd K O. Ovarian cancer antigen CA125 is encoded by the MUC16 mucin gene. Int J Cancer 2002; 98(5):737-40.
12. Yin B W, Lloyd K O. Molecular cloning of the CA125 ovarian cancer antigen: identification as a new mucin, MUC16. J Biol Chem 2001; 276(29):27371-5.
13. Hollingsworth M, Swanson B. Mucins in Cancer: protection and control of the cell surface. Nature Reviews: Cancer 2004; 4(1):45-60.
14. Huang L, Ren J, Chen D, Li Y, Kharbanda S, Kufe D. MUC1 cytoplasmic domain coactivates Wnt target gene transcription and confers transformation. Cancer Biol Ther 2003; 2(6):702-6.
15. Li Q, Ren J, Kufe D. Interaction of human MUC1 and beta-catenin is regulated by Lek and ZAP-70 in activated Jurkat T cells. Biochem Biophys Res Commun 2004; 315(2):471-6.
16. Ren J, Agata N, Chen D, Li Y, Yu W H, Huang L, et al. Human MUC1 carcinoma-associated protein confers resistance to genotoxic anticancer agents. Cancer Cell 2004; 5(2):163-75.
17. Ren J, Bharti A, Raina D, Chen W, Ahmad R, Kufe D. MUC1 oncoprotein is targeted to mitochondria by heregulin-induced activation of c-Src and the molecular chaperone HSP90. Oncogene 2006; 25(1):20-31.
18. Ramsauer V P, Pino V, Farooq A, Carothers Carraway C A, Salas P J, Carraway K L. Muc4-ErbB2 Complex Formation and Signaling in Polarized CACO-2 Epithelial Cells Indicate That Muc4 Acts as an Unorthodox Ligand for ErbB2. Mol Biol Cell 2006.
19. Bafna S, Singh A P, Moniaux N, Eudy J D, Meza J L, Batra S K. MUC4, a multifunctional transmembrane glycoprotein, induces oncogenic transformation of NIH3T3 mouse fibroblast cells. Cancer Res 2008; 68(22): 9231-8.
20. Ponnusamy M P, Singh A P, Jain M, Chakraborty S, Moniaux N, Batra S K. MUC4 activates HER2 signalling and enhances the motility of human ovarian cancer cells. Br J Cancer 2008; 99(3):520-6.
21. Nap M, Vitali A, Nustad K, Bast R C, Jr., O'Brien T J, Nilsson O, et al. Immunohistochemical characterization of 22 monoclonal antibodies against the CA125 antigen: 2nd report from the ISOBM TD-1 Workshop. Tumour Biol 1996; 17(6):325-31.
22. Markwell M A, Fox C F. Surface-specific iodination of membrane proteins of viruses and eucarytic cells using 1,3,4, 6-tetrachloro-3alpha,6alpha-diphenylglycouril. Biochemistry 1978; 17:4807-4817.
23. Kononen J, Bubendorf L, Kallioniemi A, Barlund M, Schraml P, Leighton S, et al. Tissue microarrays for high-throughput molecular profiling of tumor specimens. Nat Med 1998; 4(7):844-7.
24. Hedvat C V, Hegde A, Chaganti R S, Chen B, Qin J, Filippa D A, et al. Application of tissue microarray technology to the study of non-Hodgkin's and Hodgkin's lymphoma. Hum Pathol 2002; 33(10):968-74.
25. Soslow R A. Histologic subtypes of ovarian carcinoma: an overview. Int J Gynecol Pathol 2008; 27(2):161-74.
26. O'Brien T J, Beard J B, Underwood L J, Dennis R A, Santin A D, York L. The CA 125 gene: an extracellular superstructure dominated by repeat sequences. Tumour Biol 2001; 22(6):348-66.

27. Harris M, Howell A, Chrissohou M, Swindell R I, Hudson M, Sellwood R A. A comparison of the metastatic pattern of infiltrating lobular carcinoma and infiltrating duct carcinoma of the breast. Br J Cancer 1984; 50(1):23-30.
28. Kaneko O, Gong L, Zhang J, Hansen J K, Hassan R, Lee B, et al. A binding domain on mesothelin for CA125/MUC16. J Biol Chem 2009; 284(6):3739-49.

REFERENCES CITED IN EXAMPLE 4

1. Singh A P, Senapati S, Ponnusamy M P, et al. Clinical potential of mucins in diagnosis, prognosis, and therapy of ovarian cancer. Lancet Oncol 2008; 9(11):1076-85.
2. Sun C C, Ramirez P T, Bodurka D C. Quality of life for patients with epithelial ovarian cancer. Nat Clin Pract Oncol 2007; 4(1):18-29.
3. Brentjens R J, Latouche J B, Santos E, et al. Eradication of systemic B-cell tumors by genetically targeted human T lymphocytes co-stimulated by CD80 and interleukin-15. Nat Med 2003; 9(3):279-86.
4. Hwu P, Yang J C, Cowherd R, et al. In vivo antitumor activity of T cells redirected with chimeric antibody/T-cell receptor genes. Cancer Res 1995; 55(15):3369-73.
5. Imai C, Mihara K, Andreansky M, et al. Chimeric receptors with 4-1BB signaling capacity provoke potent cytotoxicity against acute lymphoblastic leukemia. Leukemia 2004; 18(4):676-84.
6. Kershaw M H, Westwood J A, Parker L L, et al. A phase I study on adoptive immunotherapy using gene-modified T cells for ovarian cancer. Clin Cancer Res 2006; 12(20 Pt 1):6106-15.
7. Kochenderfer J N, Feldman S A, Zhao Y, et al. Construction and preclinical evaluation of an anti-CD19 chimeric antigen receptor. J Immunother 2009; 32(7):689-702.
8. Loskog A, Giandomenico V, Rossig C, Pule M, Dotti G, Brenner M K. Addition of the CD28 signaling domain to chimeric T-cell receptors enhances chimeric T-cell resistance to T regulatory cells. Leukemia 2006; 20(10):1819-28.
9. Maher J, Brentjens R J, Gunset G, Riviere I, Sadelain M. Human T-lymphocyte cytotoxicity and proliferation directed by a single chimeric TCRzeta/CD28 receptor. Nat Biotechnol 2002; 20(1):70-5.
10. Moeller M, Haynes N M, Trapani J A, et al. A functional role for CD28 costimulation in tumor recognition by single-chain receptor-modified T cells. Cancer Gene Ther 2004; 11(5):371-9.
11. Parker L L, Do M T, Westwood J A, et al. Expansion and characterization of T cells transduced with a chimeric receptor against ovarian cancer. Hum Gene Ther 2000; 11(17):2377-87.
12. Sadelain M, Brentjens R, Riviere I. The promise and potential pitfalls of chimeric antigen receptors. Curr Opin Immunol 2009; 21(2):215-23.
13. Stephan M T, Ponomarev V, Brentjens R J, et al. T cell-encoded CD80 and 4-1BBL induce auto- and trans-costimulation, resulting in potent tumor rejection. Nat Med 2007; 13(12):1440-9.
14. Daly T, Royal R E, Kershaw M H, et al. Recognition of human colon cancer by T cells transduced with a chimeric receptor gene. Cancer Gene Ther 2000; 7(2):284-91.
15. Jensen M C, Cooper L J, Wu A M, Forman S J, Raubitschek A. Engineered CD20-specific primary human cytotoxic T lymphocytes for targeting B-cell malignancy. Cytotherapy 2003; 5(2):131-8.
16. Pule M A, Savoldo B, Myers G D, et al. Virus-specific T cells engineered to coexpress tumor-specific receptors: persistence and antitumor activity in individuals with neuroblastoma. Nat Med 2008; 14(11):1264-70.
17. Savoldo B, Rooney C M, Di Stasi A, et al. Epstein Barr virus specific cytotoxic T lymphocytes expressing the anti-CD30zeta artificial chimeric T-cell receptor for immunotherapy of Hodgkin disease. Blood 2007; 110(7):2620-30.
18. Wang G, Chopra R K, Royal R E, Yang J C, Rosenberg S A, Hwu P. A T cell-independent antitumor response in mice with bone marrow cells retrovirally transduced with an antibody/Fc-gamma chain chimeric receptor gene recognizing a human ovarian cancer antigen. Nat Med 1998; 4(2):168-72.
19. Hollyman D, Stefanski J, Przybylowski M, et al. Manufacturing validation of biologically functional T cells targeted to CD19 antigen for autologous adoptive cell therapy. J Immunother 2009; 32(2):169-80.
20. Lamers C H, Sleijfer S, Vulto A G, et al. Treatment of metastatic renal cell carcinoma with autologous T-lymphocytes genetically retargeted against carbonic anhydrase IX: first clinical experience. J Clin Oncol 2006; 24(13):e20-2.
21. Till B G, Jensen M C, Wang J, et al. Adoptive immunotherapy for indolent non-Hodgkin lymphoma and mantle cell lymphoma using genetically modified autologous CD20-specific T cells.
Blood 2008; 112(6):2261-71.
22. Hamanishi J, Mandai M, Iwasaki M, et al. Programmed cell death 1 ligand 1 and tumor-infiltrating CD8+ T lymphocytes are prognostic factors of human ovarian cancer. Proc Natl Acad Sci USA 2007; 104(9):3360-5.
23. Leffers N, Gooden M J, de Jong R A, et al. Prognostic significance of tumor-infiltrating T-lymphocytes in primary and metastatic lesions of advanced stage ovarian cancer. Cancer Immunol Immunother 2009; 58(3):449-59.
24. Sato E, Olson S H, Ahn J, et al. Intraepithelial CD8+ tumor-infiltrating lymphocytes and a high CD8+/regulatory T cell ratio are associated with favorable prognosis in ovarian cancer. Proc Natl Acad Sci USA 2005; 102(51):18538-43.
25. Zhang L, Conejo-Garcia J R, Katsaros D, et al. Intratumoral T cells, recurrence, and survival in epithelial ovarian cancer. N Engl J Med 2003; 348(3):203-13.
26. Curiel T J, Coukos G, Zou L, et al. Specific recruitment of regulatory T cells in ovarian carcinoma fosters immune privilege and predicts reduced survival. Nat Med 2004; 10(9):942-9.
27. Leffers N, Lambeck A J, de Graeff P, et al. Survival of ovarian cancer patients overexpressing the tumour antigen p53 is diminished in case of MHC class I down-regulation. Gynecol Oncol 2008; 110(3):365-73.
28. Nelson B H. The impact of T-cell immunity on ovarian cancer outcomes. Immunol Rev 2008; 222:101-16.
29. Wolf D, Wolf A M, Rumpold H, et al. The expression of the regulatory T cell-specific forkhead box transcription factor FoxP3 is associated with poor prognosis in ovarian cancer. Clin Cancer Res 2005; 11(23):8326-31.
30. Badgwell D, Bast R C, Jr. Early detection of ovarian cancer. Dis Markers 2007; 23(5-6):397-410.
31. Bast R C, Jr., Badgwell D, Lu Z, et al. New tumor markers: CA125 and beyond. Int J Gynecol Cancer 2005; 15 Suppl 3:274-81.

32. Fritsche H A, Bast R C. CA 125 in ovarian cancer: advances and controversy. Clin Chem 1998; 44(7):1379-80.
33. Krivak T C, Tian C, Rose G S, Armstrong D K, Maxwell G L. A Gynecologic Oncology Group Study of serum CA-125 levels in patients with stage III optimally debulked ovarian cancer treated with intraperitoneal compared to intravenous chemotherapy: an analysis of patients enrolled in GOG 172. Gynecol Oncol 2009; 115(1):81-5.
34. O'Brien T J, Beard J B, Underwood L J, Dennis R A, Santin A D, York L. The CA 125 gene: an extracellular superstructure dominated by repeat sequences. Tumour Biol 2001; 22(6):348-66.
35. Bellone S, Anfossi S, O'Brien T J, et al. Generation of CA125-specific cytotoxic T lymphocytes in human leukocyte antigen-A2.1-positive healthy donors and patients with advanced ovarian cancer. Am J Obstet Gynecol 2009; 200(1):75 e1-10.
36. Berek J S. Immunotherapy of ovarian cancer with antibodies: a focus on oregovomab. Expert Opin Biol Ther 2004; 4(7):1159-65.
37. O'Brien T J, Tanimoto H, Konishi I, Gee M. More than 15 years of CA 125: what is known about the antigen, its structure and its function. Int J Biol Markers 1998; 13(4):188-95.
38. Rao T D, Park K J, Smith-Jones P, et al. Novel monoclonal antibodies against proximal (carboxy-terminal) portions of MUC16 (submitted to Applied Immunohistochemistry and Molecular Morphometry).
39. Wang Z, Raifu M, Howard M, et al. Universal PCR amplification of mouse immunoglobulin gene variable regions: the design of degenerate primers and an assessment of the effect of DNA polymerase 3' to 5' exonuclease activity. J Immunol Methods 2000; 233(1-2):167-77.
40. Doenecke A, Winnacker E L, Hallek M. Rapid amplification of cDNA ends (RACE) improves the PCR-based isolation of immunoglobulin variable region genes from murine and human lymphoma cells and cell lines. Leukemia 1997; 11(10):1787-92.
41. Gong M C, Latouche J B, Krause A, Heston W D, Bander N H, Sadelain M. Cancer patient T cells genetically targeted to prostate-specific membrane antigen specifically lyse prostate cancer cells and release cytokines in response to prostate-specific membrane antigen. Neoplasia 1999; 1(2):123-7.
42. Orlandi R, Gussow D H, Jones P T, Winter G. Cloning immunoglobulin variable domains for expression by the polymerase chain reaction. Proc Natl Acad Sci USA 1989; 86(10):3833-7.
43. Brentjens R J, Santos E, Nikhamin Y, et al. Genetically targeted T cells eradicate systemic acute lymphoblastic leukemia xenografts. Clin Cancer Res 2007; 13(18 Pt 1):5426-35.
44. Riviere I, Brose K, Mulligan R C. Effects of retroviral vector design on expression of human adenosine deaminase in murine bone marrow transplant recipients engrafted with genetically modified cells. Proc Natl Acad Sci USA 1995; 92(15):6733-7.
45. Quintas-Cardama A, Yeh R K, Hollyman D, et al. Multifactorial optimization of gammaretroviral gene transfer into human T lymphocytes for clinical application. Hum Gene Ther 2007; 18(12):1253-60.
46. Latouche J B, Sadelain M. Induction of human cytotoxic T lymphocytes by artificial antigen-presenting cells. Nat Biotechnol 2000; 18(4):405-9.
47. Santos E B, Yeh R, Lee J, et al. Sensitive in vivo imaging of T cells using a membrane-bound *Gaussia princeps* luciferase. Nat Med 2009; 15(3):338-44.
48. Park K J, Soslow R, Linkov I, Rao T D, D S. The extracellular portion of the MUC16 cytoplasmic domain is detectable in ovarian carcinomas using novel monoclonal antibody, 4H11. Mod Pathol, 2008; 21(1s):217A-218A.
49. Raspollini M R, Castiglione F, Rossi Degl'innocenti D, et al. Tumour-infiltrating gamma/delta T-lymphocytes are correlated with a brief disease-free interval in advanced ovarian serous carcinoma. Ann Oncol 2005; 16(4):590-6.
50. Tomsova M, Melichar B, Sedlakova I, Steiner I. Prognostic significance of CD3+ tumor-infiltrating lymphocytes in ovarian carcinoma. Gynecol Oncol 2008; 108(2):415-20.
51. Woo E Y, Chu C S, Goletz T J, et al. Regulatory CD4(+)CD25(+) T cells in tumors from patients with early-stage non-small cell lung cancer and late-stage ovarian cancer. Cancer Res 2001; 61(12):4766-72.
52. Lamers C H, Langeveld S C, Groot-van Ruijven C M, Debets R, Sleijfer S, Gratama J W. Gene-modified T cells for adoptive immunotherapy of renal cell cancer maintain transgene-specific immune functions in vivo. Cancer Immunol Immunother 2007; 56(12):1875-83.
53. Brentjens R, Hollyman D, Weiss M, et al. A Phase I trial for the treatment of chemo-refractory chronic lymphocytic leukemia with CD19-targeted autologous T cells. Molecular Therapy 2008; 16:S15.
54. Barber A, Zhang T, DeMars L R, Conejo-Garcia J, Roby K F, Sentman C L. Chimeric NKG2D receptor-bearing T cells as immunotherapy for ovarian cancer. Cancer Res 2007; 67(10):5003-8.
55. Barber A, Zhang T, Sentman C L. Immunotherapy with chimeric NKG2D receptors leads to long-term tumor-free survival and development of host antitumor immunity in murine ovarian cancer. J Immunol 2008; 180(1):72-8.
56. Carpenito C, Milone M C, Hassan R, et al. Control of large, established tumor xenografts with genetically retargeted human T cells containing CD28 and CD137 domains. Proc Natl Acad Sci USA 2009; 106(9):3360-5.
57. Kershaw M H, Westwood J A, Hwu P. Dual-specific T cells combine proliferation and antitumor activity. Nat Biotechnol 2002; 20(12):1221-7.
58. Hung C F, Wu T C, Monie A, Roden R. Antigen-specific immunotherapy of cervical and ovarian cancer. Immunol Rev 2008; 222:43-69.
59. Westwood J A, Smyth M J, Teng M W, et al. Adoptive transfer of T cells modified with a humanized chimeric receptor gene inhibits growth of Lewis-Y-expressing tumors in mice. Proc Natl Acad Sci USA 2005; 102(52):19051-6.
60. Habib-Agahi M, Jaberipour M, Searle P F. 4-1BBL costimulation retrieves CD28 expression in activated T cells. Cell Immunol 2009; 256(1-2):39-46.
61. Habib-Agahi M, Phan T T, Searle P F. Co-stimulation with 4-1BB ligand allows extended T-cell proliferation, synergizes with CD80/CD86 and can reactivate anergic T cells. Int Immunol 2007; 19(12):1383-94.
62. Brentjens R J, Sadelain M. Somatic cell engineering and the immunotherapy of leukemias and lymphomas. Adv Pharmacol 2004; 51:347-70.
63. Finney H M, Akbar A N, Lawson A D. Activation of resting human primary T cells with chimeric receptors: costimulation from CD28, inducible costimulator, CD134, and CD137 in series with signals from the TCR zeta chain. J Immunol 2004; 172(1):104-13.

64. Sadelain M, Riviere I, Brentjens R. Targeting tumours with genetically enhanced T lymphocytes. Nat Rev Cancer 2003; 3(1):35-45.
65. Wilkie S, Picco G, Foster J, et al. Retargeting of human T cells to tumor-associated MUC1: the evolution of a chimeric antigen receptor. J Immunol 2008; 180(7):4901-9.
66. Li Q, Ai J, Song Z, Liu J, Shan B. 4-1BB (CD137) ligand enhanced anti-tumor immune response against mouse forestomach carcinoma in vivo. Cell Mol Immunol 2008; 5(5):379-84.
67. Salih H R, Kosowski S G, Haluska V F, et al. Constitutive expression of functional 4-1BB (CD137) ligand on carcinoma cells. J Immunol 2000; 165(5):2903-10.
68. Wan Y L, Zheng S S, Zhao Z C, Li M W, Jia C K, Zhang H. Expression of co-stimulator 4-1BB molecule in hepatocellular carcinoma and adjacent non-tumor liver tissue, and its possible role in tumor immunity. World J Gastroenterol 2004; 10(2):195-9.

MICROORGANISM DEPOSIT

A hybridoma designated huMUC16Pep3-31A3.5, which produces the antibody designated 31A3 (also designated 31A3.5.1) in this specification, was deposited with the American Type Culture Collection (ATCC), located at 10801 University Boulevard, Manassas, Va. 20110-2209, on Mar. 25, 2011, in compliance with the Budapest Treaty on the International Recognition of the Deposit of Microorganisms for the Purposes of Patent Procedure, and was assigned ATCC Accession No. PTA-11773.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

We claim:

1. An antibody or an antigen-binding fragment thereof, that specifically binds to a MUC16 polypeptide or to an antigenic portion thereof, wherein the amino acid sequence of the MUC16 polypeptide is:

NFSPLARRVDRVAIYEE (SEQ ID NO: 1), and wherein the antibody comprises a variable heavy ("$V_H$") chain encoded by SEQ ID NO: 08 and a variable light ("$V_L$") chain encoded by SEQ ID NO: 09 or SEQ ID NO: 10.

2. The antibody or antigen-binding fragment thereof of claim 1, wherein the antibody is a chimeric antibody.

3. The antibody or antigen-binding fragment thereof of claim 1, wherein the antibody is a humanized antibody.

4. The antibody or antigen-binding fragment thereof of claim 1, wherein the antigen-binding fragment thereof is a Fab fragment, a F(ab')2 fragment, or a Fv fragment.

5. The antibody or antigen-binding fragment thereof of claim 1, wherein the antibody lacks specific binding to a glycosylated MUC16 extracellular domain.

6. The antibody or antigen-binding fragment thereof of claim 1, wherein the antibody, or antigen-binding fragment thereof, is covalently linked to a cytotoxic agent or a prodrug of a cytotoxic agent.

7. The antibody or antigen-binding fragment thereof of claim 1, wherein the antibody internalizes into a cell or wherein the antibody is an IgG.

8. A single chain variable fragment (scFv) comprising a variable heavy (VH) chain and a variable light (VL) chain, wherein the VH chain and the VL chain are of an antibody that specifically binds to a MUC16 polypeptide or to an antigenic portion thereof, wherein the amino acid sequence of the MUC16 polypeptide is NFSPLARRVDRVAIYEE (SEQ ID NO: 1), and wherein the VH chain is encoded by SEQ ID NO:08 and the VL chain is encoded by SEQ ID NO: 09 or SEQ ID NO: 10.

9. The scFv of claim 8, which is covalently linked to a cytotoxic agent or a prodrug of a cytotoxic agent.

10. A composition comprising (a) an antibody, or antigen-binding fragment thereof, of claim 1, and (b) a pharmaceutically acceptable carrier.

11. A hybridoma cell that produces an antibody of claim 1.

12. A method for identifying a subject as having a cancer in which MUC16 is expressed, wherein said method comprises:
  (a) contacting a sample obtained from the subject with the antibody or antigen binding fragment thereof, of claim 1; and
  (b) detecting an increased level of binding of the antibody or antigen binding fragment thereof to the sample as compared to a control sample lacking the cancer.

13. The method of claim 12, wherein the cancer is ovarian cancer or breast cancer.

14. The method of claim 12, wherein the detecting is selected from the group consisting of immunohistochemistry, enzyme-linked immunosorbent assay (ELISA), fluorescence-activated cell sorting (FACS), Western blot, immunoprecipitation, and radiographic imaging.

15. A method for treating a MUC16-expressing cancer in a subject in need thereof comprising administering to the subject a therapeutically effective amount of the antibody or antigen binding fragment thereof, of claim 1.

16. The method of claim 15, wherein the cancer is ovarian cancer or breast cancer.

17. A method for treating a MUC16 expressing cancer in a subject in need thereof comprising administering to the subject a therapeutically effective amount of the scFv of claim 8.

18. The method of claim 17, wherein the cancer is ovarian cancer or breast cancer.

* * * * *

SEQUENCE LISTING

```
<160> NUMBER OF SEQ ID NOS: 40

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Asn Phe Ser Pro Leu Ala Arg Arg Val Asp Arg Val Ala Ile Tyr Glu
1               5                   10                  15
Glu

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Thr Leu Asp Arg Ser Ser Val Leu Val Asp Gly Tyr Ser Pro Asn Arg
1               5                   10                  15
Asn Glu

<210> SEQ ID NO 3
<211> LENGTH: 21
<212> TYPE: PRT
<213> ORGANISM: Artificial Sequence
<220> FEATURE:
<223> OTHER INFORMATION: Synthetic

<400> SEQUENCE: 3

Cys Gly Val Leu Val Thr Thr Arg Arg Lys Lys Glu Gly Glu Tyr
1               5                   10                  15
Asn Val Gln Gln Gln
            20
```

```
<210> SEQ ID NO 4
<211> LENGTH: 366
<212> TYPE: DNA
<213> ORGANISM: Artificial Sequence
<220> FEATURE:
<223> OTHER INFORMATION: Synthetic

<400> SEQUENCE: 4
gtgaagctgg aggagtcagg gggaggcttc gtgaagcctg gagggtccct caaaatctcc      60
tgtgcagcct ctggattcac tttcagaaac tatgccatgt cctgggttcg cctgagtccg     120
gagatgaggc tggagtgggt cgcaaccatt agcagtgctg gtggttacat cttctattct     180
gacagtgtgc agggacgatt caccatttcc agagacaatg ccaagaacac cctccacttg     240
caaatgggca gtctgaggtc tggggacacg gccatgtatt actgtgcaag gcagggattt     300
ggtaactacg gtgattacta tgctatggac tactggggcc aagggaccac ggtcaccgtc     360
tcctca                                                                366

<210> SEQ ID NO 5
<211> LENGTH: 339
<212> TYPE: DNA
<213> ORGANISM: Artificial Sequence
<220> FEATURE:
<223> OTHER INFORMATION: Synthetic

<400> SEQUENCE: 5
gacattgagc tcacccagtc tccatcctcc ctggctgtgt cagcaggaga gaaggtcact      60
atgagctgca atccagtca gagtctgctc aacagtagaa cccgaaagaa ccagttggct     120
tggtaccagc aaaaaacagg acagtctcct gaactgctga tctactgggc atccactcgg     180
caatctgggg tccctgatcg cttcacaggc agtggatctg ggacagattt cactctcacc     240
atcagcagtg tgcaggctga agacctggca gtttattact gccagcaatc ttataatcta     300
ctcacgttcg gtcctgggac caagctggag atcaaacgg                            339

<210> SEQ ID NO 6
<211> LENGTH: 366
<212> TYPE: DNA
<213> ORGANISM: Artificial Sequence
<220> FEATURE:
<223> OTHER INFORMATION: Synthetic

<400> SEQUENCE: 6
gtgaagctgc aggagtcagg gggaggcttc gtgaagcctg gagggtccct caaagtctcc      60
tgtgcagcct ctggattcac tttcagtagc tatgccatgt cctgggttcg cctgagtccg     120
gagatgaggc tggagtgggt cgcaaccatt agcagtgctg gtggttacat cttctattct     180
gacagtgtgc agggacgatt caccatttcc agagacaatg ccaagaacac cctgcacctg     240
caaatgggca gtctgaggtc tggggacacg gccatgtatt actgtgcaag gcagggattt     300
ggtaactacg gtgattacta tgctatggac tactggggcc aagggaccac ggtcaccgtc     360
tcctca                                                                366

<210> SEQ ID NO 7
<211> LENGTH: 339
<212> TYPE: DNA
<213> ORGANISM: Artificial Sequence
<220> FEATURE:
<223> OTHER INFORMATION: Synthetic

<400> SEQUENCE: 7
```

```
gacattgagc tcacccagtc tccatcctcc ctggctgtgt cagcaggaga gaaggtcact    60
atgagctgca atccagtca gagtctgctc aacagtagaa cccgaaagaa ccagttggct   120
tggtaccagc aaaaaccagg acagtctcct gaactgctga tctactgggc atccactagg   180
caatctggag tccctgatcg cttcacaggc agtggatctg ggacagattt cactctcacc   240
atcagcagtg tgcaggctga agacctggca gtttattact gccagcaatc ttataatcta   300
ctcacgttcg gtcctgggac caagctggag gtcaaacgg                          339
```

<210> SEQ ID NO 8
<211> LENGTH: 348
<212> TYPE: DNA
<213> ORGANISM: Artificial Sequence
<220> FEATURE:
<223> OTHER INFORMATION: Synthetic

<400> SEQUENCE: 8

```
gtgaagctgg aggagtcagg gggagacttg gtgaagcctg agggtccct gaaactctcc     60 tgtgcagtct ctggattcac tttcagtagc cattccatgt cttggattcg tcagactcca   120
gagaagaggc tagagtgggt cgcatccgtg agtagtggtg gtaggatcta ctattcggac   180
agtgtgaagg gccgattcac cgtcaccaga gaaaatgaca ggaacaccct gtatttgtta   240
atgagtagtc tgaggtctga ggacacggcc atgtattatt gtggaagagg acaggtattt   300
tatgctttgg acaattgggg ccaagggacc acggtcaccg tctcctca                348
```

<210> SEQ ID NO 9
<211> LENGTH: 339
<212> TYPE: DNA
<213> ORGANISM: Artificial Sequence
<220> FEATURE:
<223> OTHER INFORMATION: Synthetic

<400> SEQUENCE: 9

```
gacattgagc tcacccagtc tccatcctcc ctggctgtgt cagcaggaga gaaggtcact    60
atgagctgca atccagtca gagtctgctc aacagtagaa cccgaaagaa ccagttggct   120
tggtaccagc aaaaaccagg acagtctcct gaactgctga tctactgggc atccactagg   180
caatctggag tccctgatcg cttcacaggc agtggatctg ggacagattt cactctcacc   240
atcagcagtg tgcaggctga agacctggca gtttattact gccagcaatc ttataatcta   300
ctcacgttcg gtcctgggac caagctggag gtcaaacgg                          339
```

<210> SEQ ID NO 10
<211> LENGTH: 216
<212> TYPE: DNA
<213> ORGANISM: Artificial Sequence
<220> FEATURE:
<223> OTHER INFORMATION: Synthetic

<400> SEQUENCE: 10

```
gacattgagc tcacccagtc tccaaagctc ctgatctaca aggtttccaa ccgatttct     60 ggggtcccag acaggttcag tggcagtgga tcagggacag atttcacact caagatcagc   120
agagtggagg ctgaggatct gggagtttat tactgctttc aaggttcaca tgttccgtgg   180
acgttcggtg gagggaccaa gctggagatc aaacgg                              216
```

<210> SEQ ID NO 11
<211> LENGTH: 354
<212> TYPE: DNA
<213> ORGANISM: Artificial Sequence

```
<220> FEATURE:
<223> OTHER INFORMATION: Synthetic

<400> SEQUENCE: 11
gaggtgaagc tggaggagtc aggacctgaa ctggtgaagc ctggggcttc agtgaagata      60
tcctgcaagg cttctggtta ctcatttact ggctacttta tgaactgggt gaagcagacc     120
catggaaaga gccttgagtg gattggacgt attaatcctt acaatggtgc tactttctac     180
aatcagaagt tcacgggcaa ggccacaatg actgtagaca atcctctac acagcccac       240 atggagctcc tgagcctgac atctgaggac tctgcagtct attattgtgg aaaggggaat     300
tactacggcc cctttgatta ctggggccaa gggaccacgg tcaccgtctc ctca           354

<210> SEQ ID NO 12
<211> LENGTH: 333
<212> TYPE: DNA
<213> ORGANISM: Artificial Sequence
<220> FEATURE:
<223> OTHER INFORMATION: Synthetic

<400> SEQUENCE: 12
gacattgagc tcacccagtc tccatcttat cttgctgcat ctcctgaaga aaccattact      60
attaattgca gggcaagtaa gagcattagc aaatatttag cctggtatca aagaaaacct     120
gggaaaacta ataagcttct tatctactct ggatccactt tgcaatctgg aattccatca     180
aggttcagtg gcagtggatc tggtacagat ttcactctca ccatcagtag cctggagcct     240
gaagattttg caatgtatta ctgtcaacag cataatgaat accgtggac gttcggtgga     300 gggaccaagc tggagatcaa acgggcggcc gca                                  333

<210> SEQ ID NO 13
<211> LENGTH: 14507
<212> TYPE: PRT
<213> ORGANISM: Homo sapiens

<400> SEQUENCE: 13

Met Leu Lys Pro Ser Gly Leu Pro Gly Ser Ser Pro Thr Arg Ser
1               5                   10                  15

Leu Met Thr Gly Ser Arg Ser Thr Lys Ala Thr Pro Glu Met Asp Ser
                20                  25                  30

Gly Leu Thr Gly Ala Thr Leu Ser Pro Lys Thr Ser Gly Ala Ile
            35                  40                  45

Val Val Thr Glu His Thr Leu Pro Phe Thr Ser Pro Asp Lys Thr Leu
        50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
                100                 105                 110

Pro Ser Arg Asn Tyr Pro Ala Thr Ser Met Val Ser Gly Leu Ser Ser
            115                 120                 125

Pro Arg Thr Arg Thr Ser Ser Thr Glu Gly Asn Phe Thr Lys Glu Ala
        130                 135                 140

Ser Thr Tyr Thr Leu Thr Val Glu Thr Thr Ser Gly Pro Val Thr Glu
145                 150                 155                 160

Lys Tyr Thr Val Pro Thr Glu Ser Thr Thr Glu Gly Asp Ser Thr
                165                 170                 175
```

```
Glu Thr Pro Trp Asp Thr Arg Tyr Ile Pro Val Lys Ile Thr Ser Pro
            180                 185                 190

Met Lys Thr Phe Ala Asp Ser Thr Ala Ser Lys Glu Asn Ala Pro Val
            195                 200                 205

Ser Met Thr Pro Ala Glu Thr Thr Val Thr Asp Ser His Thr Pro Gly
    210                 215                 220

Arg Thr Asn Pro Ser Phe Gly Thr Leu Tyr Ser Ser Phe Leu Asp Leu
225                 230                 235                 240

Ser Pro Lys Gly Thr Pro Asn Ser Arg Gly Glu Thr Ser Leu Glu Leu
                245                 250                 255

Ile Leu Ser Thr Thr Gly Tyr Pro Phe Ser Ser Pro Glu Pro Gly Ser
            260                 265                 270

Ala Gly His Ser Arg Ile Ser Thr Ser Ala Pro Leu Ser Ser Ser Ala
            275                 280                 285

Ser Val Leu Asp Asn Lys Ile Ser Glu Thr Ser Ile Phe Ser Gly Gln
    290                 295                 300

Ser Leu Thr Ser Pro Leu Ser Pro Gly Val Pro Glu Ala Arg Ala Ser
305                 310                 315                 320

Thr Met Pro Asn Ser Ala Ile Pro Phe Ser Met Thr Leu Ser Asn Ala
                325                 330                 335

Glu Thr Ser Ala Glu Arg Val Arg Ser Thr Ile Ser Ser Leu Gly Thr
            340                 345                 350

Pro Ser Ile Ser Thr Lys Gln Thr Ala Glu Thr Ile Leu Thr Phe His
            355                 360                 365

Ala Phe Ala Glu Thr Met Asp Ile Pro Ser Thr His Ile Ala Lys Thr
    370                 375                 380

Leu Ala Ser Glu Trp Leu Gly Ser Pro Gly Thr Leu Gly Gly Thr Ser
385                 390                 395                 400

Thr Ser Ala Leu Thr Thr Thr Ser Pro Ser Thr Thr Leu Val Ser Glu
                405                 410                 415

Glu Thr Asn Thr His His Ser Thr Ser Gly Lys Glu Thr Glu Gly Thr
            420                 425                 430

Leu Asn Thr Ser Met Thr Pro Leu Glu Thr Ser Ala Pro Gly Glu Glu
            435                 440                 445

Ser Glu Met Thr Ala Thr Leu Val Pro Thr Leu Gly Phe Thr Thr Leu
    450                 455                 460

Asp Ser Lys Ile Arg Ser Pro Ser Gln Val Ser Ser Ser His Pro Thr
465                 470                 475                 480

Arg Glu Leu Arg Thr Thr Gly Ser Thr Ser Gly Arg Gln Ser Ser Ser
                485                 490                 495

Thr Ala Ala His Gly Ser Ser Asp Ile Leu Arg Ala Thr Thr Ser Ser
            500                 505                 510

Thr Ser Lys Ala Ser Ser Trp Thr Ser Glu Ser Thr Ala Gln Gln Phe
            515                 520                 525

Ser Glu Pro Gln His Thr Gln Trp Val Glu Thr Ser Pro Ser Met Lys
    530                 535                 540

Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590
```

```
Glu Ser Thr Ala Gly Pro Thr Thr His Gln Phe Ala Val Pro Thr Gly
            595                 600                 605

Ile Ser Met Thr Gly Gly Ser Ser Thr Arg Gly Ser Gln Gly Thr Thr
            610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Gly Gly Thr Lys Pro Ser Tyr
                660                 665                 670

Thr Met Val Ser Ser Val Ile Pro Glu Thr Ser Ser Leu Gln Ser Ser
            675                 680                 685

Ala Phe Arg Glu Gly Thr Ser Leu Gly Leu Thr Pro Leu Asn Thr Arg
            690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
            740                 745                 750

Thr Thr Gly Thr Pro Glu Ile Ser Thr Lys Thr Lys Pro Ser Ser Ala
            755                 760                 765

Val Leu Ser Ser Met Thr Leu Ser Asn Ala Ala Thr Ser Pro Glu Arg
            770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
                820                 825                 830

Glu Ser Pro Ser Thr Leu Ser Leu Pro Ser Val Ser Gly Val Lys Thr
            835                 840                 845

Thr Phe Ser Ser Ser Thr Pro Ser Thr His Leu Phe Thr Ser Gly Glu
            850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
            915                 920                 925

Thr Asn Ser Thr Gly Ser Ala Leu Pro Lys Ile Ser His Leu Thr Gly
930                 935                 940

Thr Ala Thr Met Ser Gln Thr Asn Arg Asp Thr Phe Asn Asp Ser Ala
945                 950                 955                 960

Ala Pro Gln Ser Thr Thr Trp Pro Glu Thr Ser Pro Arg Phe Lys Thr
                965                 970                 975

Gly Leu Pro Ser Ala Thr Thr Val Ser Thr Ser Ala Thr Ser Leu
                980                 985                 990

Ser Ala Thr Val Met Val Ser Lys Phe Thr Ser Pro Ala Thr Ser Ser
            995                 1000                1005

Met Glu Ala Thr Ser Ile Arg Glu Pro Ser Thr Thr Ile Leu Thr
```

```
                    1010                1015                1020
Thr Glu Thr Thr Asn Gly Pro Gly Ser Met Ala Val Ala Ser Thr
        1025                1030                1035
Asn Ile Pro Ile Gly Lys Gly Tyr Ile Thr Glu Gly Arg Leu Asp
        1040                1045                1050
Thr Ser His Leu Pro Ile Gly Thr Thr Ala Ser Ser Glu Thr Ser
        1055                1060                1065
Met Asp Phe Thr Met Ala Lys Glu Ser Val Ser Met Ser Val Ser
        1070                1075                1080
Pro Ser Gln Ser Met Asp Ala Ala Gly Ser Ser Thr Pro Gly Arg
        1085                1090                1095
Thr Ser Gln Phe Val Asp Thr Phe Ser Asp Asp Val Tyr His Leu
        1100                1105                1110
Thr Ser Arg Glu Ile Thr Ile Pro Arg Asp Gly Thr Ser Ser Ala
        1115                1120                1125
Leu Thr Pro Gln Met Thr Ala Thr His Pro Pro Ser Pro Asp Pro
        1130                1135                1140
Gly Ser Ala Arg Ser Thr Trp Leu Gly Ile Leu Ser Ser Ser Pro
        1145                1150                1155
Ser Ser Pro Thr Pro Lys Val Thr Met Ser Ser Thr Phe Ser Thr
        1160                1165                1170
Gln Arg Val Thr Thr Ser Met Ile Met Asp Thr Val Glu Thr Ser
        1175                1180                1185
Arg Trp Asn Met Pro Asn Leu Pro Ser Thr Thr Ser Leu Thr Pro
        1190                1195                1200
Ser Asn Ile Pro Thr Ser Gly Ala Ile Gly Lys Ser Thr Leu Val
        1205                1210                1215
Pro Leu Asp Thr Pro Ser Pro Ala Thr Ser Leu Glu Ala Ser Glu
        1220                1225                1230
Gly Gly Leu Pro Thr Leu Ser Thr Tyr Pro Glu Ser Thr Asn Thr
        1235                1240                1245
Pro Ser Ile His Leu Gly Ala His Ala Ser Ser Glu Ser Pro Ser
        1250                1255                1260
Thr Ile Lys Leu Thr Met Ala Ser Val Val Lys Pro Gly Ser Tyr
        1265                1270                1275
Thr Pro Leu Thr Phe Pro Ser Ile Glu Thr His Ile His Val Ser
        1280                1285                1290
Thr Ala Arg Met Ala Tyr Ser Ser Gly Ser Ser Pro Glu Met Thr
        1295                1300                1305
Ala Pro Gly Glu Thr Asn Thr Gly Ser Thr Trp Asp Pro Thr Thr
        1310                1315                1320
Tyr Ile Thr Thr Thr Asp Pro Lys Asp Thr Ser Ser Ala Gln Val
        1325                1330                1335
Ser Thr Pro His Ser Val Arg Thr Leu Arg Thr Glu Asn His
        1340                1345                1350
Pro Lys Thr Glu Ser Ala Thr Pro Ala Ala Tyr Ser Gly Ser Pro
        1355                1360                1365
Lys Ile Ser Ser Ser Pro Asn Leu Thr Ser Pro Ala Thr Lys Ala
        1370                1375                1380
Trp Thr Ile Thr Asp Thr Glu His Ser Thr Gln Leu His Tyr
        1385                1390                1395
Thr Lys Leu Ala Glu Lys Ser Ser Gly Phe Glu Thr Gln Ser Ala
        1400                1405                1410
```

```
Pro Gly Pro Val Ser Val Val Ile Pro Thr Ser Pro Thr Ile Gly
    1415                1420                1425

Ser Ser Thr Leu Glu Leu Thr Ser Asp Val Pro Gly Glu Pro Leu
    1430                1435                1440

Val Leu Ala Pro Ser Glu Gln Thr Thr Ile Thr Leu Pro Met Ala
    1445                1450                1455

Thr Trp Leu Ser Thr Ser Leu Thr Glu Glu Met Ala Ser Thr Asp
    1460                1465                1470

Leu Asp Ile Ser Ser Pro Ser Pro Met Ser Thr Phe Ala Ile
    1475                1480                1485

Phe Pro Pro Met Ser Thr Pro Ser His Glu Leu Ser Lys Ser Glu
    1490                1495                1500

Ala Asp Thr Ser Ala Ile Arg Asn Thr Asp Ser Thr Thr Leu Asp
    1505                1510                1515

Gln His Leu Gly Ile Arg Ser Leu Gly Arg Thr Gly Asp Leu Thr
    1520                1525                1530

Thr Val Pro Ile Thr Pro Leu Thr Thr Thr Trp Thr Ser Val Ile
    1535                1540                1545

Glu His Ser Thr Gln Ala Gln Asp Thr Leu Ser Ala Thr Met Ser
    1550                1555                1560

Pro Thr His Val Thr Gln Ser Leu Lys Asp Gln Thr Ser Ile Pro
    1565                1570                1575

Ala Ser Ala Ser Pro Ser His Leu Thr Glu Val Tyr Pro Glu Leu
    1580                1585                1590

Gly Thr Gln Gly Arg Ser Ser Ser Glu Ala Thr Thr Phe Trp Lys
    1595                1600                1605

Pro Ser Thr Asp Thr Leu Ser Arg Glu Ile Glu Thr Gly Pro Thr
    1610                1615                1620

Asn Ile Gln Ser Thr Pro Pro Met Asp Asn Thr Thr Thr Gly Ser
    1625                1630                1635

Ser Ser Ser Gly Val Thr Leu Gly Ile Ala His Leu Pro Ile Gly
    1640                1645                1650

Thr Ser Ser Pro Ala Glu Thr Ser Thr Asn Met Ala Leu Glu Arg
    1655                1660                1665

Arg Ser Ser Thr Ala Thr Val Ser Met Ala Gly Thr Met Gly Leu
    1670                1675                1680

Leu Val Thr Ser Ala Pro Gly Arg Ser Ile Ser Gln Ser Leu Gly
    1685                1690                1695

Arg Val Ser Ser Val Leu Ser Glu Ser Thr Thr Glu Gly Val Thr
    1700                1705                1710

Asp Ser Ser Lys Gly Ser Ser Pro Arg Leu Asn Thr Gln Gly Asn
    1715                1720                1725

Thr Ala Leu Ser Ser Ser Leu Glu Pro Ser Tyr Ala Glu Gly Ser
    1730                1735                1740

Gln Met Ser Thr Ser Ile Pro Leu Thr Ser Ser Pro Thr Thr Pro
    1745                1750                1755

Asp Val Glu Phe Ile Gly Gly Ser Thr Phe Trp Thr Lys Glu Val
    1760                1765                1770

Thr Thr Val Met Thr Ser Asp Ile Ser Lys Ser Ser Ala Arg Thr
    1775                1780                1785

Glu Ser Ser Ser Ala Thr Leu Met Ser Thr Ala Leu Gly Ser Thr
    1790                1795                1800
```

```
Glu Asn Thr Gly Lys Glu Lys Leu Arg Thr Ala Ser Met Asp Leu
1805                1810                1815

Pro Ser Pro Thr Pro Ser Met Glu Val Thr Pro Trp Ile Ser Leu
1820                1825                1830

Thr Leu Ser Asn Ala Pro Asn Thr Thr Asp Ser Leu Asp Leu Ser
1835                1840                1845

His Gly Val His Thr Ser Ser Ala Gly Thr Leu Ala Thr Asp Arg
1850                1855                1860

Ser Leu Asn Thr Gly Val Thr Arg Ala Ser Arg Leu Glu Asn Gly
1865                1870                1875

Ser Asp Thr Ser Ser Lys Ser Leu Ser Met Gly Asn Ser Thr His
1880                1885                1890

Thr Ser Met Thr Tyr Thr Glu Lys Ser Glu Val Ser Ser Ser Ile
1895                1900                1905

His Pro Arg Pro Glu Thr Ser Ala Pro Gly Ala Glu Thr Thr Leu
1910                1915                1920

Thr Ser Thr Pro Gly Asn Arg Ala Ile Ser Leu Thr Leu Pro Phe
1925                1930                1935

Ser Ser Ile Pro Val Glu Glu Val Ile Ser Thr Gly Ile Thr Ser
1940                1945                1950

Gly Pro Asp Ile Asn Ser Ala Pro Met Thr His Ser Pro Ile Thr
1955                1960                1965

Pro Pro Thr Ile Val Trp Thr Ser Thr Gly Thr Ile Glu Gln Ser
1970                1975                1980

Thr Gln Pro Leu His Ala Val Ser Ser Glu Lys Val Ser Val Gln
1985                1990                1995

Thr Gln Ser Thr Pro Tyr Val Asn Ser Val Ala Val Ser Ala Ser
2000                2005                2010

Pro Thr His Glu Asn Ser Val Ser Ser Gly Ser Ser Thr Ser Ser
2015                2020                2025

Pro Tyr Ser Ser Ala Ser Leu Glu Ser Leu Asp Ser Thr Ile Ser
2030                2035                2040

Arg Arg Asn Ala Ile Thr Ser Trp Leu Trp Asp Leu Thr Thr Ser
2045                2050                2055

Leu Pro Thr Thr Thr Trp Pro Ser Thr Ser Leu Ser Glu Ala Leu
2060                2065                2070

Ser Ser Gly His Ser Gly Val Ser Asn Pro Ser Ser Thr Thr Thr
2075                2080                2085

Glu Phe Pro Leu Phe Ser Ala Ala Ser Thr Ser Ala Ala Lys Gln
2090                2095                2100

Arg Asn Pro Glu Thr Glu Thr His Gly Pro Gln Asn Thr Ala Ala
2105                2110                2115

Ser Thr Leu Asn Thr Asp Ala Ser Ser Val Thr Gly Leu Ser Glu
2120                2125                2130

Thr Pro Val Gly Ala Ser Ile Ser Ser Glu Val Pro Leu Pro Met
2135                2140                2145

Ala Ile Thr Ser Arg Ser Asp Val Ser Gly Leu Thr Ser Glu Ser
2150                2155                2160

Thr Ala Asn Pro Ser Leu Gly Thr Ala Ser Ser Ala Gly Thr Lys
2165                2170                2175

Leu Thr Arg Thr Ile Ser Leu Pro Thr Ser Glu Ser Leu Val Ser
2180                2185                2190

Phe Arg Met Asn Lys Asp Pro Trp Thr Val Ser Ile Pro Leu Gly
```

-continued

```
              2195                2200                2205

Ser His Pro Thr Thr Asn Thr Glu Thr Ser Ile Pro Val Asn Ser
    2210                2215                2220

Ala Gly Pro Pro Gly Leu Ser Thr Val Ala Ser Asp Val Ile Asp
    2225                2230                2235

Thr Pro Ser Asp Gly Ala Glu Ser Ile Pro Thr Val Ser Phe Ser
    2240                2245                2250

Pro Ser Pro Asp Thr Glu Val Thr Thr Ile Ser His Phe Pro Glu
    2255                2260                2265

Lys Thr Thr His Ser Phe Arg Thr Ile Ser Ser Leu Thr His Glu
    2270                2275                2280

Leu Thr Ser Arg Val Thr Pro Ile Pro Gly Asp Trp Met Ser Ser
    2285                2290                2295

Ala Met Ser Thr Lys Pro Thr Gly Ala Ser Pro Ser Ile Thr Leu
    2300                2305                2310

Gly Glu Arg Arg Thr Ile Thr Ser Ala Ala Pro Thr Thr Ser Pro
    2315                2320                2325

Ile Val Leu Thr Ala Ser Phe Thr Glu Thr Ser Thr Val Ser Leu
    2330                2335                2340

Asp Asn Glu Thr Thr Val Lys Thr Ser Asp Ile Leu Asp Ala Arg
    2345                2350                2355

Lys Thr Asn Glu Leu Pro Ser Asp Ser Ser Ser Ser Asp Leu
    2360                2365                2370

Ile Asn Thr Ser Ile Ala Ser Ser Thr Met Asp Val Thr Lys Thr
    2375                2380                2385

Ala Ser Ile Ser Pro Thr Ser Ile Ser Gly Met Thr Ala Ser Ser
    2390                2395                2400

Ser Pro Ser Leu Phe Ser Ser Asp Arg Pro Gln Val Pro Thr Ser
    2405                2410                2415

Thr Thr Glu Thr Asn Thr Ala Thr Ser Pro Ser Val Ser Ser Asn
    2420                2425                2430

Thr Tyr Ser Leu Asp Gly Gly Ser Asn Val Gly Gly Thr Pro Ser
    2435                2440                2445

Thr Leu Pro Pro Phe Thr Ile Thr His Pro Val Glu Thr Ser Ser
    2450                2455                2460

Ala Leu Leu Ala Trp Ser Arg Pro Val Arg Thr Phe Ser Thr Met
    2465                2470                2475

Val Ser Thr Asp Thr Ala Ser Gly Glu Asn Pro Thr Ser Ser Asn
    2480                2485                2490

Ser Val Val Thr Ser Val Pro Ala Pro Gly Thr Trp Thr Ser Val
    2495                2500                2505

Gly Ser Thr Thr Asp Leu Pro Ala Met Gly Phe Leu Lys Thr Ser
    2510                2515                2520

Pro Ala Gly Glu Ala His Ser Leu Leu Ala Ser Thr Ile Glu Pro
    2525                2530                2535

Ala Thr Ala Phe Thr Pro His Leu Ser Ala Ala Val Val Thr Gly
    2540                2545                2550

Ser Ser Ala Thr Ser Glu Ala Ser Leu Leu Thr Thr Ser Glu Ser
    2555                2560                2565

Lys Ala Ile His Ser Ser Pro Gln Thr Pro Thr Thr Pro Thr Ser
    2570                2575                2580

Gly Ala Asn Trp Glu Thr Ser Ala Thr Pro Glu Ser Leu Leu Val
    2585                2590                2595
```

-continued

```
Val Thr Glu Thr Ser Asp Thr Thr Leu Thr Ser Lys Ile Leu Val
    2600                2605                2610

Thr Asp Thr Ile Leu Phe Ser Thr Val Ser Thr Pro Pro Ser Lys
    2615                2620                2625

Phe Pro Ser Thr Gly Thr Leu Ser Gly Ala Ser Phe Pro Thr Leu
    2630                2635                2640

Leu Pro Asp Thr Pro Ala Ile Pro Leu Thr Ala Thr Glu Pro Thr
    2645                2650                2655

Ser Ser Leu Ala Thr Ser Phe Asp Ser Thr Pro Leu Val Thr Ile
    2660                2665                2670

Ala Ser Asp Ser Leu Gly Thr Val Pro Glu Thr Thr Leu Thr Met
    2675                2680                2685

Ser Glu Thr Ser Asn Gly Asp Ala Leu Val Leu Lys Thr Val Ser
    2690                2695                2700

Asn Pro Asp Arg Ser Ile Pro Gly Ile Thr Ile Gln Gly Val Thr
    2705                2710                2715

Glu Ser Pro Leu His Pro Ser Ser Thr Ser Pro Ser Lys Ile Val
    2720                2725                2730

Ala Pro Arg Asn Thr Thr Tyr Glu Gly Ser Ile Thr Val Ala Leu
    2735                2740                2745

Ser Thr Leu Pro Ala Gly Thr Thr Gly Ser Leu Val Phe Ser Gln
    2750                2755                2760

Ser Ser Glu Asn Ser Glu Thr Thr Ala Leu Val Asp Ser Ser Ala
    2765                2770                2775

Gly Leu Glu Arg Ala Ser Val Met Pro Leu Thr Thr Gly Ser Gln
    2780                2785                2790

Gly Met Ala Ser Ser Gly Gly Ile Arg Ser Gly Ser Thr His Ser
    2795                2800                2805

Thr Gly Thr Lys Thr Phe Ser Ser Leu Pro Leu Thr Met Asn Pro
    2810                2815                2820

Gly Glu Val Thr Ala Met Ser Glu Ile Thr Thr Asn Arg Leu Thr
    2825                2830                2835

Ala Thr Gln Ser Thr Ala Pro Lys Gly Ile Pro Val Lys Pro Thr
    2840                2845                2850

Ser Ala Glu Ser Gly Leu Leu Thr Pro Val Ser Ala Ser Ser Ser
    2855                2860                2865

Pro Ser Lys Ala Phe Ala Ser Leu Thr Thr Ala Pro Pro Thr Trp
    2870                2875                2880

Gly Ile Pro Gln Ser Thr Leu Thr Phe Glu Phe Ser Glu Val Pro
    2885                2890                2895

Ser Leu Asp Thr Lys Ser Ala Ser Leu Pro Thr Pro Gly Gln Ser
    2900                2905                2910

Leu Asn Thr Ile Pro Asp Ser Asp Ala Ser Thr Ala Ser Ser Ser
    2915                2920                2925

Leu Ser Lys Ser Pro Glu Lys Asn Pro Arg Ala Arg Met Met Thr
    2930                2935                2940

Ser Thr Lys Ala Ile Ser Ala Ser Ser Phe Gln Ser Thr Gly Phe
    2945                2950                2955

Thr Glu Thr Pro Glu Gly Ser Ala Ser Pro Ser Met Ala Gly His
    2960                2965                2970

Glu Pro Arg Val Pro Thr Ser Gly Thr Gly Asp Pro Arg Tyr Ala
    2975                2980                2985
```

```
Ser Glu Ser Met Ser Tyr Pro Asp Pro Ser Lys Ala Ser Ser Ala
    2990             2995             3000

Met Thr Ser Thr Ser Leu Ala Ser Lys Leu Thr Thr Leu Phe Ser
3005             3010             3015

Thr Gly Gln Ala Ala Arg Ser Gly Ser Ser Ser Pro Ile Ser
3020             3025             3030

Leu Ser Thr Glu Lys Glu Thr Ser Phe Leu Ser Pro Thr Ala Ser
3035             3040             3045

Thr Ser Arg Lys Thr Ser Leu Phe Leu Gly Pro Ser Met Ala Arg
3050             3055             3060

Gln Pro Asn Ile Leu Val His Leu Gln Thr Ser Ala Leu Thr Leu
3065             3070             3075

Ser Pro Thr Ser Thr Leu Asn Met Ser Gln Glu Glu Pro Pro Glu
3080             3085             3090

Leu Thr Ser Ser Gln Thr Ile Ala Glu Glu Gly Thr Thr Ala
3095             3100             3105

Glu Thr Gln Thr Leu Thr Phe Thr Pro Ser Glu Thr Pro Thr Ser
3110             3115             3120

Leu Leu Pro Val Ser Ser Pro Thr Glu Pro Thr Ala Arg Arg Lys
3125             3130             3135

Ser Ser Pro Glu Thr Trp Ala Ser Ser Ile Ser Val Pro Ala Lys
3140             3145             3150

Thr Ser Leu Val Glu Thr Thr Asp Gly Thr Leu Val Thr Thr Ile
3155             3160             3165

Lys Met Ser Ser Gln Ala Ala Gln Gly Asn Ser Thr Trp Pro Ala
3170             3175             3180

Pro Ala Glu Glu Thr Gly Ser Ser Pro Ala Gly Thr Ser Pro Gly
3185             3190             3195

Ser Pro Glu Met Ser Thr Thr Leu Lys Ile Met Ser Ser Lys Glu
3200             3205             3210

Pro Ser Ile Ser Pro Glu Ile Arg Ser Thr Val Arg Asn Ser Pro
3215             3220             3225

Trp Lys Thr Pro Glu Thr Thr Val Pro Met Glu Thr Thr Val Glu
3230             3235             3240

Pro Val Thr Leu Gln Ser Thr Ala Leu Gly Ser Gly Ser Thr Ser
3245             3250             3255

Ile Ser His Leu Pro Thr Gly Thr Thr Ser Pro Thr Lys Ser Pro
3260             3265             3270

Thr Glu Asn Met Leu Ala Thr Glu Arg Val Ser Leu Ser Pro Ser
3275             3280             3285

Pro Pro Glu Ala Trp Thr Asn Leu Tyr Ser Gly Thr Pro Gly Gly
3290             3295             3300

Thr Arg Gln Ser Leu Ala Thr Met Ser Ser Val Ser Leu Glu Ser
3305             3310             3315

Pro Thr Ala Arg Ser Ile Thr Gly Thr Gly Gln Gln Ser Ser Pro
3320             3325             3330

Glu Leu Val Ser Lys Thr Thr Gly Met Glu Phe Ser Met Trp His
3335             3340             3345

Gly Ser Thr Gly Gly Thr Thr Gly Asp Thr His Val Ser Leu Ser
3350             3355             3360

Thr Ser Ser Asn Ile Leu Glu Asp Pro Val Thr Ser Pro Asn Ser
3365             3370             3375

Val Ser Ser Leu Thr Asp Lys Ser Lys His Lys Thr Glu Thr Trp
```

-continued

```
              3380              3385              3390

Val  Ser  Thr  Thr  Ala  Ile  Pro  Ser  Thr  Val  Leu  Asn  Asn  Lys  Ile
    3395                 3400                 3405

Met  Ala  Ala  Glu  Gln  Gln  Thr  Ser  Arg  Ser  Val  Asp  Glu  Ala  Tyr
    3410                 3415                 3420

Ser  Ser  Thr  Ser  Ser  Trp  Ser  Asp  Gln  Thr  Ser  Gly  Ser  Asp  Ile
    3425                 3430                 3435

Thr  Leu  Gly  Ala  Ser  Pro  Asp  Val  Thr  Asn  Thr  Leu  Tyr  Ile  Thr
    3440                 3445                 3450

Ser  Thr  Ala  Gln  Thr  Thr  Ser  Leu  Val  Ser  Leu  Pro  Ser  Gly  Asp
    3455                 3460                 3465

Gln  Gly  Ile  Thr  Ser  Leu  Thr  Asn  Pro  Ser  Gly  Gly  Lys  Thr  Ser
    3470                 3475                 3480

Ser  Ala  Ser  Ser  Val  Thr  Ser  Pro  Ser  Ile  Gly  Leu  Glu  Thr  Leu
    3485                 3490                 3495

Arg  Ala  Asn  Val  Ser  Ala  Val  Lys  Ser  Asp  Ile  Ala  Pro  Thr  Ala
    3500                 3505                 3510

Gly  His  Leu  Ser  Gln  Thr  Ser  Ser  Pro  Ala  Glu  Val  Ser  Ile  Leu
    3515                 3520                 3525

Asp  Val  Thr  Thr  Ala  Pro  Thr  Pro  Gly  Ile  Ser  Thr  Thr  Ile  Thr
    3530                 3535                 3540

Thr  Met  Gly  Thr  Asn  Ser  Ile  Ser  Thr  Thr  Thr  Pro  Asn  Pro  Glu
    3545                 3550                 3555

Val  Gly  Met  Ser  Thr  Met  Asp  Ser  Thr  Pro  Ala  Thr  Glu  Arg  Arg
    3560                 3565                 3570

Thr  Thr  Ser  Thr  Glu  His  Pro  Ser  Thr  Trp  Ser  Thr  Ala  Ala
    3575                 3580                 3585

Ser  Asp  Ser  Trp  Thr  Val  Thr  Asp  Met  Thr  Ser  Asn  Leu  Lys  Val
    3590                 3595                 3600

Ala  Arg  Ser  Pro  Gly  Thr  Ile  Ser  Thr  Met  His  Thr  Thr  Ser  Phe
    3605                 3610                 3615

Leu  Ala  Ser  Ser  Thr  Glu  Leu  Asp  Ser  Met  Ser  Thr  Pro  His  Gly
    3620                 3625                 3630

Arg  Ile  Thr  Val  Ile  Gly  Thr  Ser  Leu  Val  Thr  Pro  Ser  Ser  Asp
    3635                 3640                 3645

Ala  Ser  Ala  Val  Lys  Thr  Glu  Thr  Ser  Thr  Ser  Glu  Arg  Thr  Leu
    3650                 3655                 3660

Ser  Pro  Ser  Asp  Thr  Thr  Ala  Ser  Thr  Pro  Ile  Ser  Thr  Phe  Ser
    3665                 3670                 3675

Arg  Val  Gln  Arg  Met  Ser  Ile  Ser  Val  Pro  Asp  Ile  Leu  Ser  Thr
    3680                 3685                 3690

Ser  Trp  Thr  Pro  Ser  Ser  Thr  Glu  Ala  Glu  Asp  Val  Pro  Val  Ser
    3695                 3700                 3705

Met  Val  Ser  Thr  Asp  His  Ala  Ser  Thr  Lys  Thr  Asp  Pro  Asn  Thr
    3710                 3715                 3720

Pro  Leu  Ser  Thr  Phe  Leu  Phe  Asp  Ser  Leu  Ser  Thr  Leu  Asp  Trp
    3725                 3730                 3735

Asp  Thr  Gly  Arg  Ser  Leu  Ser  Ser  Ala  Thr  Ala  Thr  Thr  Ser  Ala
    3740                 3745                 3750

Pro  Gln  Gly  Ala  Thr  Thr  Pro  Gln  Glu  Leu  Thr  Leu  Glu  Thr  Met
    3755                 3760                 3765

Ile  Ser  Pro  Ala  Thr  Ser  Gln  Leu  Pro  Phe  Ser  Ile  Gly  His  Ile
    3770                 3775                 3780
```

```
Thr Ser Ala Val Thr Pro Ala Met Ala Arg Ser Ser Gly Val
    3785            3790            3795

Thr Phe Ser Arg Pro Asp Pro Thr Ser Lys Lys Ala Glu Gln Thr
    3800            3805            3810

Ser Thr Gln Leu Pro Thr Thr Thr Ser Ala His Pro Gly Gln Val
    3815            3820            3825

Pro Arg Ser Ala Ala Thr Thr Leu Asp Val Ile Pro His Thr Ala
    3830            3835            3840

Lys Thr Pro Asp Ala Thr Phe Gln Arg Gln Gly Gln Thr Ala Leu
    3845            3850            3855

Thr Thr Glu Ala Arg Ala Thr Ser Asp Ser Trp Asn Glu Lys Glu
    3860            3865            3870

Lys Ser Thr Pro Ser Ala Pro Trp Ile Thr Glu Met Met Asn Ser
    3875            3880            3885

Val Ser Glu Asp Thr Ile Lys Glu Val Thr Ser Ser Ser Val
    3890            3895            3900

Leu Arg Thr Leu Asn Thr Leu Asp Ile Asn Leu Glu Ser Gly Thr
    3905            3910            3915

Thr Ser Ser Pro Ser Trp Lys Ser Ser Pro Tyr Glu Arg Ile Ala
    3920            3925            3930

Pro Ser Glu Ser Thr Thr Asp Lys Glu Ala Ile His Pro Ser Thr
    3935            3940            3945

Asn Thr Val Glu Thr Thr Gly Trp Val Thr Ser Ser Glu His Ala
    3950            3955            3960

Ser His Ser Thr Ile Pro Ala His Ser Ala Ser Ser Lys Leu Thr
    3965            3970            3975

Ser Pro Val Val Thr Thr Ser Thr Arg Glu Gln Ala Ile Val Ser
    3980            3985            3990

Met Ser Thr Thr Thr Trp Pro Glu Ser Thr Arg Ala Arg Thr Glu
    3995            4000            4005

Pro Asn Ser Phe Leu Thr Ile Glu Leu Arg Asp Val Ser Pro Tyr
    4010            4015            4020

Met Asp Thr Ser Ser Thr Thr Gln Thr Ser Ile Ile Ser Ser Pro
    4025            4030            4035

Gly Ser Thr Ala Ile Thr Lys Gly Pro Arg Thr Glu Ile Thr Ser
    4040            4045            4050

Ser Lys Arg Ile Ser Ser Ser Phe Leu Ala Gln Ser Met Arg Ser
    4055            4060            4065

Ser Asp Ser Pro Ser Glu Ala Ile Thr Arg Leu Ser Asn Phe Pro
    4070            4075            4080

Ala Met Thr Glu Ser Gly Gly Met Ile Leu Ala Met Gln Thr Ser
    4085            4090            4095

Pro Pro Gly Ala Thr Ser Leu Ser Ala Pro Thr Leu Asp Thr Ser
    4100            4105            4110

Ala Thr Ala Ser Trp Thr Gly Thr Pro Leu Ala Thr Thr Gln Arg
    4115            4120            4125

Phe Thr Tyr Ser Glu Lys Thr Thr Leu Phe Ser Lys Gly Pro Glu
    4130            4135            4140

Asp Thr Ser Gln Pro Ser Pro Ser Val Glu Glu Thr Ser Ser
    4145            4150            4155

Ser Ser Ser Leu Val Pro Ile His Ala Thr Thr Ser Pro Ser Asn
    4160            4165            4170
```

```
Ile Leu Leu Thr Ser Gln Gly His Ser Pro Ser Ser Thr Pro Pro
        4175                4180                4185

Val Thr Ser Val Phe Leu Ser Glu Thr Ser Gly Leu Gly Lys Thr
        4190                4195                4200

Thr Asp Met Ser Arg Ile Ser Leu Glu Pro Gly Thr Ser Leu Pro
        4205                4210                4215

Pro Asn Leu Ser Ser Thr Ala Gly Glu Ala Leu Ser Thr Tyr Glu
        4220                4225                4230

Ala Ser Arg Asp Thr Lys Ala Ile His His Ser Ala Asp Thr Ala
        4235                4240                4245

Val Thr Asn Met Glu Ala Thr Ser Ser Glu Tyr Ser Pro Ile Pro
        4250                4255                4260

Gly His Thr Lys Pro Ser Lys Ala Thr Ser Pro Leu Val Thr Ser
        4265                4270                4275

His Ile Met Gly Asp Ile Thr Ser Ser Thr Ser Val Phe Gly Ser
        4280                4285                4290

Ser Glu Thr Thr Glu Ile Glu Thr Val Ser Ser Val Asn Gln Gly
        4295                4300                4305

Leu Gln Glu Arg Ser Thr Ser Gln Val Ala Ser Ser Ala Thr Glu
        4310                4315                4320

Thr Ser Thr Val Ile Thr His Val Ser Ser Gly Asp Ala Thr Thr
        4325                4330                4335

His Val Thr Lys Thr Gln Ala Thr Phe Ser Ser Gly Thr Ser Ile
        4340                4345                4350

Ser Ser Pro His Gln Phe Ile Thr Ser Thr Asn Thr Phe Thr Asp
        4355                4360                4365

Val Ser Thr Asn Pro Ser Thr Ser Leu Ile Met Thr Glu Ser Ser
        4370                4375                4380

Gly Val Thr Ile Thr Thr Gln Thr Gly Pro Thr Gly Ala Ala Thr
        4385                4390                4395

Gln Gly Pro Tyr Leu Leu Asp Thr Ser Thr Met Pro Tyr Leu Thr
        4400                4405                4410

Glu Thr Pro Leu Ala Val Thr Pro Asp Phe Met Gln Ser Glu Lys
        4415                4420                4425

Thr Thr Leu Ile Ser Lys Gly Pro Lys Asp Val Ser Trp Thr Ser
        4430                4435                4440

Pro Pro Ser Val Ala Glu Thr Ser Tyr Pro Ser Ser Leu Thr Pro
        4445                4450                4455

Phe Leu Val Thr Thr Ile Pro Pro Ala Thr Ser Thr Leu Gln Gly
        4460                4465                4470

Gln His Thr Ser Ser Pro Val Ser Ala Thr Ser Val Leu Thr Ser
        4475                4480                4485

Gly Leu Val Lys Thr Thr Asp Met Leu Asn Thr Ser Met Glu Pro
        4490                4495                4500

Val Thr Asn Ser Pro Gln Asn Leu Asn Asn Pro Ser Asn Glu Ile
        4505                4510                4515

Leu Ala Thr Leu Ala Ala Thr Asp Ile Glu Thr Ile His Pro
        4520                4525                4530

Ser Ile Asn Lys Ala Val Thr Asn Met Gly Thr Ala Ser Ser Ala
        4535                4540                4545

His Val Leu His Ser Thr Leu Pro Val Ser Ser Glu Pro Ser Thr
        4550                4555                4560

Ala Thr Ser Pro Met Val Pro Ala Ser Ser Met Gly Asp Ala Leu
```

```
              4565                4570               4575
Ala Ser Ile Ser Ile Pro Gly Ser Glu Thr Thr Asp Ile Glu Gly
              4580                4585               4590
Glu Pro Thr Ser Ser Leu Thr Ala Gly Arg Lys Glu Asn Ser Thr
              4595                4600               4605
Leu Gln Glu Met Asn Ser Thr Thr Glu Ser Asn Ile Ile Leu Ser
              4610                4615               4620
Asn Val Ser Val Gly Ala Ile Thr Glu Ala Thr Lys Met Glu Val
              4625                4630               4635
Pro Ser Phe Asp Ala Thr Phe Ile Pro Thr Pro Ala Gln Ser Thr
              4640                4645               4650
Lys Phe Pro Asp Ile Phe Ser Val Ala Ser Ser Arg Leu Ser Asn
              4655                4660               4665
Ser Pro Pro Met Thr Ile Ser Thr His Met Thr Thr Thr Gln Thr
              4670                4675               4680
Gly Ser Ser Gly Ala Thr Ser Lys Ile Pro Leu Ala Leu Asp Thr
              4685                4690               4695
Ser Thr Leu Glu Thr Ser Ala Gly Thr Pro Ser Val Val Thr Glu
              4700                4705               4710
Gly Phe Ala His Ser Lys Ile Thr Thr Ala Met Asn Asn Asp Val
              4715                4720               4725
Lys Asp Val Ser Gln Thr Asn Pro Pro Phe Gln Asp Glu Ala Ser
              4730                4735               4740
Ser Pro Ser Ser Gln Ala Pro Val Leu Val Thr Thr Leu Pro Ser
              4745                4750               4755
Ser Val Ala Phe Thr Pro Gln Trp His Ser Thr Ser Ser Pro Val
              4760                4765               4770
Ser Met Ser Ser Val Leu Thr Ser Ser Leu Val Lys Thr Ala Gly
              4775                4780               4785
Lys Val Asp Thr Ser Leu Glu Thr Val Thr Ser Ser Pro Gln Ser
              4790                4795               4800
Met Ser Asn Thr Leu Asp Asp Ile Ser Val Thr Ser Ala Ala Thr
              4805                4810               4815
Thr Asp Ile Glu Thr Thr His Pro Ser Ile Asn Thr Val Val Thr
              4820                4825               4830
Asn Val Gly Thr Thr Gly Ser Ala Phe Glu Ser His Ser Thr Val
              4835                4840               4845
Ser Ala Tyr Pro Glu Pro Ser Lys Val Thr Ser Pro Asn Val Thr
              4850                4855               4860
Thr Ser Thr Met Glu Asp Thr Thr Ile Ser Arg Ser Ile Pro Lys
              4865                4870               4875
Ser Ser Lys Thr Thr Arg Thr Glu Thr Glu Thr Thr Ser Ser Leu
              4880                4885               4890
Thr Pro Lys Leu Arg Glu Thr Ser Ile Ser Gln Glu Ile Thr Ser
              4895                4900               4905
Ser Thr Glu Thr Ser Thr Val Pro Tyr Lys Glu Leu Thr Gly Ala
              4910                4915               4920
Thr Thr Glu Val Ser Arg Thr Asp Val Thr Ser Ser Ser Ser Thr
              4925                4930               4935
Ser Phe Pro Gly Pro Asp Gln Ser Thr Val Ser Leu Asp Ile Ser
              4940                4945               4950
Thr Glu Thr Asn Thr Arg Leu Ser Thr Ser Pro Ile Met Thr Glu
              4955                4960               4965
```

```
Ser Ala Glu Ile Thr Ile Thr Thr Gln Thr Gly Pro His Gly Ala
    4970            4975                4980
Thr Ser Gln Asp Thr Phe Thr Met Asp Pro Ser Asn Thr Thr Pro
    4985            4990                4995
Gln Ala Gly Ile His Ser Ala Met Thr His Gly Phe Ser Gln Leu
    5000            5005                5010
Asp Val Thr Thr Leu Met Ser Arg Ile Pro Gln Asp Val Ser Trp
    5015            5020                5025
Thr Ser Pro Pro Ser Val Asp Lys Thr Ser Ser Pro Ser Ser Phe
    5030            5035                5040
Leu Ser Ser Pro Ala Met Thr Thr Pro Ser Leu Ile Ser Ser Thr
    5045            5050                5055
Leu Pro Glu Asp Lys Leu Ser Ser Pro Met Thr Ser Leu Leu Thr
    5060            5065                5070
Ser Gly Leu Val Lys Ile Thr Asp Ile Leu Arg Thr Arg Leu Glu
    5075            5080                5085
Pro Val Thr Ser Ser Leu Pro Asn Phe Ser Ser Thr Ser Asp Lys
    5090            5095                5100
Ile Leu Ala Thr Ser Lys Asp Ser Lys Asp Thr Lys Glu Ile Phe
    5105            5110                5115
Pro Ser Ile Asn Thr Glu Glu Thr Asn Val Lys Ala Asn Asn Ser
    5120            5125                5130
Gly His Glu Ser His Ser Pro Ala Leu Ala Asp Ser Glu Thr Pro
    5135            5140                5145
Lys Ala Thr Thr Gln Met Val Ile Thr Thr Thr Val Gly Asp Pro
    5150            5155                5160
Ala Pro Ser Thr Ser Met Pro Val His Gly Ser Ser Glu Thr Thr
    5165            5170                5175
Asn Ile Lys Arg Glu Pro Thr Tyr Phe Leu Thr Pro Arg Leu Arg
    5180            5185                5190
Glu Thr Ser Thr Ser Gln Glu Ser Ser Phe Pro Thr Asp Thr Ser
    5195            5200                5205
Phe Leu Leu Ser Lys Val Pro Thr Gly Thr Ile Thr Glu Val Ser
    5210            5215                5220
Ser Thr Gly Val Asn Ser Ser Ser Lys Ile Ser Thr Pro Asp His
    5225            5230                5235
Asp Lys Ser Thr Val Pro Pro Asp Thr Phe Thr Gly Glu Ile Pro
    5240            5245                5250
Arg Val Phe Thr Ser Ser Ile Lys Thr Lys Ser Ala Glu Met Thr
    5255            5260                5265
Ile Thr Thr Gln Ala Ser Pro Pro Glu Ser Ala Ser His Ser Thr
    5270            5275                5280
Leu Pro Leu Asp Thr Ser Thr Leu Ser Gln Gly Gly Thr His
    5285            5290                5295
Ser Thr Val Thr Gln Gly Phe Pro Tyr Ser Glu Val Thr Thr Leu
    5300            5305                5310
Met Gly Met Gly Pro Gly Asn Val Ser Trp Met Thr Thr Pro Pro
    5315            5320                5325
Val Glu Glu Thr Ser Ser Val Ser Ser Leu Met Ser Ser Pro Ala
    5330            5335                5340
Met Thr Ser Pro Ser Pro Val Ser Ser Thr Ser Pro Gln Ser Ile
    5345            5350                5355
```

```
Pro Ser Ser Pro Leu Pro Val Thr Ala Leu Pro Thr Ser Val Leu
    5360                5365                5370

Val Thr Thr Thr Asp Val Leu Gly Thr Thr Ser Pro Glu Ser Val
    5375                5380                5385

Thr Ser Ser Pro Pro Asn Leu Ser Ser Ile Thr His Glu Arg Pro
    5390                5395                5400

Ala Thr Tyr Lys Asp Thr Ala His Thr Glu Ala Ala Met His His
    5405                5410                5415

Ser Thr Asn Thr Ala Val Thr Asn Val Gly Thr Ser Gly Ser Gly
    5420                5425                5430

His Lys Ser Gln Ser Ser Val Leu Ala Asp Ser Glu Thr Ser Lys
    5435                5440                5445

Ala Thr Pro Leu Met Ser Thr Ser Thr Leu Gly Asp Thr Ser
    5450                5455                5460

Val Ser Thr Ser Thr Pro Asn Ile Ser Gln Thr Asn Gln Ile Gln
    5465                5470                5475

Thr Glu Pro Thr Ala Ser Leu Ser Pro Arg Leu Arg Glu Ser Ser
    5480                5485                5490

Thr Ser Glu Lys Thr Ser Ser Thr Thr Glu Thr Asn Thr Ala Phe
    5495                5500                5505

Ser Tyr Val Pro Thr Gly Ala Ile Thr Gln Ala Ser Arg Thr Glu
    5510                5515                5520

Ile Ser Ser Arg Thr Ser Ile Ser Asp Leu Asp Arg Pro Thr
    5525                5530                5535

Ile Ala Pro Asp Ile Ser Thr Gly Met Ile Thr Arg Leu Phe Thr
    5540                5545                5550

Ser Pro Ile Met Thr Lys Ser Ala Glu Met Thr Val Thr Thr Gln
    5555                5560                5565

Thr Thr Thr Pro Gly Ala Thr Ser Gln Gly Ile Leu Pro Trp Asp
    5570                5575                5580

Thr Ser Thr Thr Leu Phe Gln Gly Gly Thr His Ser Thr Val Ser
    5585                5590                5595

Gln Gly Phe Pro His Ser Glu Ile Thr Thr Leu Arg Ser Arg Thr
    5600                5605                5610

Pro Gly Asp Val Ser Trp Met Thr Thr Pro Pro Val Glu Glu Thr
    5615                5620                5625

Ser Ser Gly Phe Ser Leu Met Ser Pro Ser Met Thr Ser Pro Ser
    5630                5635                5640

Pro Val Ser Ser Thr Ser Pro Glu Ser Ile Pro Ser Ser Pro Leu
    5645                5650                5655

Pro Val Thr Ala Leu Leu Thr Ser Val Leu Val Thr Thr Thr Asn
    5660                5665                5670

Val Leu Gly Thr Thr Ser Pro Glu Pro Val Thr Ser Ser Pro Pro
    5675                5680                5685

Asn Leu Ser Ser Pro Thr Gln Glu Arg Leu Thr Thr Tyr Lys Asp
    5690                5695                5700

Thr Ala His Thr Glu Ala Met His Ala Ser Met His Thr Asn Thr
    5705                5710                5715

Ala Val Ala Asn Val Gly Thr Ser Ile Ser Gly His Glu Ser Gln
    5720                5725                5730

Ser Ser Val Pro Ala Asp Ser His Thr Ser Lys Ala Thr Ser Pro
    5735                5740                5745

Met Gly Ile Thr Phe Ala Met Gly Asp Thr Ser Val Ser Thr Ser
```

```
                    5750                5755                5760
Thr Pro Ala Phe Phe Glu Thr Arg Ile Gln Thr Glu Ser Thr Ser
    5765                5770                5775
Ser Leu Ile Pro Gly Leu Arg Asp Thr Arg Thr Ser Glu Glu Ile
    5780                5785                5790
Asn Thr Val Thr Glu Thr Ser Thr Val Leu Ser Glu Val Pro Thr
    5795                5800                5805
Thr Thr Thr Thr Glu Val Ser Arg Thr Glu Val Ile Thr Ser Ser
    5810                5815                5820
Arg Thr Thr Ile Ser Gly Pro Asp His Ser Lys Met Ser Pro Tyr
    5825                5830                5835
Ile Ser Thr Glu Thr Ile Thr Arg Leu Ser Thr Phe Pro Phe Val
    5840                5845                5850
Thr Gly Ser Thr Glu Met Ala Ile Thr Asn Gln Thr Gly Pro Ile
    5855                5860                5865
Gly Thr Ile Ser Gln Ala Thr Leu Thr Leu Asp Thr Ser Ser Thr
    5870                5875                5880
Ala Ser Trp Glu Gly Thr His Ser Pro Val Thr Gln Arg Phe Pro
    5885                5890                5895
His Ser Glu Glu Thr Thr Thr Met Ser Arg Ser Thr Lys Gly Val
    5900                5905                5910
Ser Trp Gln Ser Pro Pro Ser Val Glu Glu Thr Ser Ser Pro Ser
    5915                5920                5925
Ser Pro Val Pro Leu Pro Ala Ile Thr Ser His Ser Ser Leu Tyr
    5930                5935                5940
Ser Ala Val Ser Gly Ser Ser Pro Thr Ser Ala Leu Pro Val Thr
    5945                5950                5955
Ser Leu Leu Thr Ser Gly Arg Arg Lys Thr Ile Asp Met Leu Asp
    5960                5965                5970
Thr His Ser Glu Leu Val Thr Ser Ser Leu Pro Ser Ala Ser Ser
    5975                5980                5985
Phe Ser Gly Glu Ile Leu Thr Ser Glu Ala Ser Thr Asn Thr Glu
    5990                5995                6000
Thr Ile His Phe Ser Glu Asn Thr Ala Glu Thr Asn Met Gly Thr
    6005                6010                6015
Thr Asn Ser Met His Lys Leu His Ser Ser Val Ser Ile His Ser
    6020                6025                6030
Gln Pro Ser Gly His Thr Pro Pro Lys Val Thr Gly Ser Met Met
    6035                6040                6045
Glu Asp Ala Ile Val Ser Ser Thr Pro Gly Ser Pro Glu Thr
    6050                6055                6060
Lys Asn Val Asp Arg Asp Ser Thr Ser Pro Leu Thr Pro Glu Leu
    6065                6070                6075
Lys Glu Asp Ser Thr Ala Leu Val Met Asn Ser Thr Thr Glu Ser
    6080                6085                6090
Asn Thr Val Phe Ser Ser Val Ser Leu Asp Ala Ala Thr Glu Val
    6095                6100                6105
Ser Arg Ala Glu Val Thr Tyr Tyr Asp Pro Thr Phe Met Pro Ala
    6110                6115                6120
Ser Ala Gln Ser Thr Lys Ser Pro Asp Ile Ser Pro Glu Ala Ser
    6125                6130                6135
Ser Ser His Ser Asn Ser Pro Pro Leu Thr Ile Ser Thr His Lys
    6140                6145                6150
```

-continued

```
Thr Ile Ala Thr Gln Thr Gly Pro Ser Gly Val Thr Ser Leu Gly
    6155            6160                6165
Gln Leu Thr Leu Asp Thr Ser Thr Ile Ala Thr Ser Ala Gly Thr
    6170            6175                6180
Pro Ser Ala Arg Thr Gln Asp Phe Val Asp Ser Glu Thr Thr Ser
    6185            6190                6195
Val Met Asn Asn Asp Leu Asn Asp Val Leu Lys Thr Ser Pro Phe
    6200            6205                6210
Ser Ala Glu Glu Ala Asn Ser Leu Ser Ser Gln Ala Pro Leu Leu
    6215            6220                6225
Val Thr Thr Ser Pro Ser Pro Val Thr Ser Thr Leu Gln Glu His
    6230            6235                6240
Ser Thr Ser Ser Leu Val Ser Val Thr Ser Val Pro Thr Pro Thr
    6245            6250                6255
Leu Ala Lys Ile Thr Asp Met Asp Thr Asn Leu Glu Pro Val Thr
    6260            6265                6270
Arg Ser Pro Gln Asn Leu Arg Asn Thr Leu Ala Thr Ser Glu Ala
    6275            6280                6285
Thr Thr Asp Thr His Thr Met His Pro Ser Ile Asn Thr Ala Val
    6290            6295                6300
Ala Asn Val Gly Thr Thr Ser Ser Pro Asn Glu Phe Tyr Phe Thr
    6305            6310                6315
Val Ser Pro Asp Ser Asp Pro Tyr Lys Ala Thr Ser Ala Val Val
    6320            6325                6330
Ile Thr Ser Thr Ser Gly Asp Ser Ile Val Ser Thr Ser Met Pro
    6335            6340                6345
Arg Ser Ser Ala Met Lys Lys Ile Glu Ser Glu Thr Thr Phe Ser
    6350            6355                6360
Leu Ile Phe Arg Leu Arg Glu Thr Ser Thr Ser Gln Lys Ile Gly
    6365            6370                6375
Ser Ser Ser Asp Thr Ser Thr Val Phe Asp Lys Ala Phe Thr Ala
    6380            6385                6390
Ala Thr Thr Glu Val Ser Arg Thr Glu Leu Thr Ser Ser Ser Arg
    6395            6400                6405
Thr Ser Ile Gln Gly Thr Glu Lys Pro Thr Met Ser Pro Asp Thr
    6410            6415                6420
Ser Thr Arg Ser Val Thr Met Leu Ser Thr Phe Ala Gly Leu Thr
    6425            6430                6435
Lys Ser Glu Glu Arg Thr Ile Ala Thr Gln Thr Gly Pro His Arg
    6440            6445                6450
Ala Thr Ser Gln Gly Thr Leu Thr Trp Asp Thr Ser Ile Thr Thr
    6455            6460                6465
Ser Gln Ala Gly Thr His Ser Ala Met Thr His Gly Phe Ser Gln
    6470            6475                6480
Leu Asp Leu Ser Thr Leu Thr Ser Arg Val Pro Glu Tyr Ile Ser
    6485            6490                6495
Gly Thr Ser Pro Pro Ser Val Glu Lys Thr Ser Ser Ser Ser Ser
    6500            6505                6510
Leu Leu Ser Leu Pro Ala Ile Thr Ser Pro Ser Pro Val Pro Thr
    6515            6520                6525
Thr Leu Pro Glu Ser Arg Pro Ser Ser Pro Val His Leu Thr Ser
    6530            6535                6540
```

| | | | | | | | | | | | |
|---|---|---|---|---|---|---|---|---|---|---|---|
| Leu | Pro 6545 | Thr | Ser | Gly | Leu 6550 | Val | Lys | Thr | Thr 6555 | Asp | Met | Leu | Ala | Ser |
| Val | Ala 6560 | Ser | Leu | Pro | Pro 6565 | Asn | Leu | Gly | Ser 6570 | Thr | Ser | His | Lys | Ile |
| Pro | Thr 6575 | Thr | Ser | Glu | Asp 6580 | Ile | Lys | Asp | Thr 6585 | Glu | Lys | Met | Tyr | Pro |
| Ser | Thr 6590 | Asn | Ile | Ala | Val 6595 | Thr | Asn | Val | Gly 6600 | Thr | Thr | Thr | Ser | Glu |
| Lys | Glu 6605 | Ser | Tyr | Ser | Ser 6610 | Val | Pro | Ala | Tyr 6615 | Ser | Glu | Pro | Pro | Lys |
| Val | Thr 6620 | Ser | Pro | Met | Val 6625 | Thr | Ser | Phe | Asn 6630 | Ile | Arg | Asp | Thr | Ile |
| Val | Ser 6635 | Thr | Ser | Met | Pro 6640 | Gly | Ser | Ser | Glu 6645 | Ile | Thr | Arg | Ile | Glu |
| Met | Glu 6650 | Ser | Thr | Phe | Ser 6655 | Leu | Ala | His | Gly 6660 | Leu | Lys | Gly | Thr | Ser |
| Thr | Ser 6665 | Gln | Asp | Pro | Ile 6670 | Val | Ser | Thr | Glu 6675 | Lys | Ser | Ala | Val | Leu |
| His | Lys 6680 | Leu | Thr | Thr | Gly 6685 | Ala | Thr | Glu | Thr 6690 | Ser | Arg | Thr | Glu | Val |
| Ala | Ser 6695 | Ser | Arg | Arg | Thr 6700 | Ser | Ile | Pro | Gly 6705 | Pro | Asp | His | Ser | Thr |
| Glu | Ser 6710 | Pro | Asp | Ile | Ser 6715 | Thr | Glu | Val | Ile 6720 | Pro | Ser | Leu | Pro | Ile |
| Ser | Leu 6725 | Gly | Ile | Thr | Glu 6730 | Ser | Ser | Asn | Met 6735 | Thr | Ile | Ile | Thr | Arg |
| Thr | Gly 6740 | Pro | Pro | Leu | Gly 6745 | Ser | Thr | Ser | Gln 6750 | Gly | Thr | Phe | Thr | Leu |
| Asp | Thr 6755 | Pro | Thr | Thr | Ser 6760 | Ser | Arg | Ala | Gly 6765 | Thr | His | Ser | Met | Ala |
| Thr | Gln 6770 | Glu | Phe | Pro | His 6775 | Ser | Glu | Met | Thr 6780 | Thr | Val | Met | Asn | Lys |
| Asp | Pro 6785 | Glu | Ile | Leu | Ser 6790 | Trp | Thr | Ile | Pro 6795 | Pro | Ser | Ile | Glu | Lys |
| Thr | Ser 6800 | Phe | Ser | Ser | Ser 6805 | Leu | Met | Pro | Ser 6810 | Pro | Ala | Met | Thr | Ser |
| Pro | Pro 6815 | Val | Ser | Ser | Thr 6820 | Leu | Pro | Lys | Thr 6825 | Ile | His | Thr | Thr | Pro |
| Ser | Pro 6830 | Met | Thr | Ser | Leu 6835 | Leu | Thr | Pro | Ser 6840 | Leu | Val | Met | Thr | Thr |
| Asp | Thr 6845 | Leu | Gly | Thr | Ser 6850 | Pro | Glu | Pro | Thr 6855 | Thr | Ser | Ser | Pro | Pro |
| Asn | Leu 6860 | Ser | Ser | Thr | Ser 6865 | His | Glu | Ile | Leu 6870 | Thr | Thr | Asp | Glu | Asp |
| Thr | Thr 6875 | Ala | Ile | Glu | Ala 6880 | Met | His | Pro | Ser 6885 | Thr | Ser | Thr | Ala | Ala |
| Thr | Asn 6890 | Val | Glu | Thr | Thr 6895 | Ser | Ser | Gly | His 6900 | Gly | Ser | Gln | Ser | Ser |
| Val | Leu 6905 | Ala | Asp | Ser | Glu 6910 | Lys | Thr | Lys | Ala 6915 | Thr | Ala | Pro | Met | Asp |
| Thr | Thr 6920 | Ser | Thr | Met | Gly 6925 | His | Thr | Thr | Val 6930 | Ser | Thr | Ser | Met | Ser |
| Val | Ser | Ser | Glu | Thr | Thr | Lys | Ile | Lys | Arg | Glu | Ser | Thr | Tyr | Ser |

```
                6935                6940                6945
Leu Thr Pro Gly Leu Arg Glu Thr Ser Ile Ser Gln Asn Ala Ser
                6950                6955                6960
Phe Ser Thr Asp Thr Ser Ile Val Leu Ser Glu Val Pro Thr Gly
                6965                6970                6975
Thr Thr Ala Glu Val Ser Arg Thr Glu Val Thr Ser Ser Gly Arg
                6980                6985                6990
Thr Ser Ile Pro Gly Pro Ser Gln Ser Thr Val Leu Pro Glu Ile
                6995                7000                7005
Ser Thr Arg Thr Met Thr Arg Leu Phe Ala Ser Pro Thr Met Thr
                7010                7015                7020
Glu Ser Ala Glu Met Thr Ile Pro Thr Gln Thr Gly Pro Ser Gly
                7025                7030                7035
Ser Thr Ser Gln Asp Thr Leu Thr Leu Asp Thr Ser Thr Thr Lys
                7040                7045                7050
Ser Gln Ala Lys Thr His Ser Thr Leu Thr Gln Arg Phe Pro His
                7055                7060                7065
Ser Glu Met Thr Thr Leu Met Ser Arg Gly Pro Gly Asp Met Ser
                7070                7075                7080
Trp Gln Ser Ser Pro Ser Leu Glu Asn Pro Ser Ser Leu Pro Ser
                7085                7090                7095
Leu Leu Ser Leu Pro Ala Thr Thr Ser Pro Pro Ile Ser Ser
                7100                7105                7110
Thr Leu Pro Val Thr Ile Ser Ser Ser Pro Leu Pro Val Thr Ser
                7115                7120                7125
Leu Leu Thr Ser Ser Pro Val Thr Thr Thr Asp Met Leu His Thr
                7130                7135                7140
Ser Pro Glu Leu Val Thr Ser Ser Pro Pro Lys Leu Ser His Thr
                7145                7150                7155
Ser Asp Glu Arg Leu Thr Thr Gly Lys Asp Thr Thr Asn Thr Glu
                7160                7165                7170
Ala Val His Pro Ser Thr Asn Thr Ala Ala Ser Asn Val Glu Ile
                7175                7180                7185
Pro Ser Ser Gly His Glu Ser Pro Ser Ser Ala Leu Ala Asp Ser
                7190                7195                7200
Glu Thr Ser Lys Ala Thr Ser Pro Met Phe Ile Thr Ser Thr Gln
                7205                7210                7215
Glu Asp Thr Thr Val Ala Ile Ser Thr Pro His Phe Leu Glu Thr
                7220                7225                7230
Ser Arg Ile Gln Lys Glu Ser Ile Ser Ser Leu Ser Pro Lys Leu
                7235                7240                7245
Arg Glu Thr Gly Ser Ser Val Glu Thr Ser Ser Ala Ile Glu Thr
                7250                7255                7260
Ser Ala Val Leu Ser Glu Val Ser Ile Gly Ala Thr Thr Glu Ile
                7265                7270                7275
Ser Arg Thr Glu Val Thr Ser Ser Ser Arg Thr Ser Ile Ser Gly
                7280                7285                7290
Ser Ala Glu Ser Thr Met Leu Pro Glu Ile Ser Thr Thr Arg Lys
                7295                7300                7305
Ile Ile Lys Phe Pro Thr Ser Pro Ile Leu Ala Glu Ser Ser Glu
                7310                7315                7320
Met Thr Ile Lys Thr Gln Thr Ser Pro Pro Gly Ser Thr Ser Glu
                7325                7330                7335
```

```
Ser Thr Phe Thr Leu Asp Thr Ser Thr Pro Ser Leu Val Ile
    7340            7345            7350

Thr His Ser Thr Met Thr Gln Arg Leu Pro His Ser Glu Ile Thr
    7355            7360            7365

Thr Leu Val Ser Arg Gly Ala Gly Asp Val Pro Arg Pro Ser Ser
    7370            7375            7380

Leu Pro Val Glu Glu Thr Ser Pro Pro Ser Ser Gln Leu Ser Leu
    7385            7390            7395

Ser Ala Met Ile Ser Pro Pro Val Ser Ser Thr Leu Pro Ala
    7400            7405            7410

Ser Ser His Ser Ser Ser Ala Ser Val Thr Ser Leu Leu Thr Pro
    7415            7420            7425

Gly Gln Val Lys Thr Thr Glu Val Leu Asp Ala Ser Ala Glu Pro
    7430            7435            7440

Glu Thr Ser Ser Pro Pro Ser Leu Ser Ser Thr Ser Val Glu Ile
    7445            7450            7455

Leu Ala Thr Ser Glu Val Thr Thr Asp Thr Glu Lys Ile His Pro
    7460            7465            7470

Phe Ser Asn Thr Ala Val Thr Lys Val Gly Thr Ser Ser Ser Gly
    7475            7480            7485

His Glu Ser Pro Ser Ser Val Leu Pro Asp Ser Glu Thr Thr Lys
    7490            7495            7500

Ala Thr Ser Ala Met Gly Thr Ile Ser Ile Met Gly Asp Thr Ser
    7505            7510            7515

Val Ser Thr Leu Thr Pro Ala Leu Ser Asn Thr Arg Lys Ile Gln
    7520            7525            7530

Ser Glu Pro Ala Ser Ser Leu Thr Thr Arg Leu Arg Glu Thr Ser
    7535            7540            7545

Thr Ser Glu Glu Thr Ser Leu Ala Thr Glu Ala Asn Thr Val Leu
    7550            7555            7560

Ser Lys Val Ser Thr Gly Ala Thr Thr Glu Val Ser Arg Thr Glu
    7565            7570            7575

Ala Ile Ser Phe Ser Arg Thr Ser Met Ser Gly Pro Glu Gln Ser
    7580            7585            7590

Thr Met Ser Gln Asp Ile Ser Ile Gly Thr Ile Pro Arg Ile Ser
    7595            7600            7605

Ala Ser Ser Val Leu Thr Glu Ser Ala Lys Met Thr Ile Thr Thr
    7610            7615            7620

Gln Thr Gly Pro Ser Glu Ser Thr Leu Glu Ser Thr Leu Asn Leu
    7625            7630            7635

Asn Thr Ala Thr Thr Pro Ser Trp Val Glu Thr His Ser Ile Val
    7640            7645            7650

Ile Gln Gly Phe Pro His Pro Glu Met Thr Thr Ser Met Gly Arg
    7655            7660            7665

Gly Pro Gly Gly Val Ser Trp Pro Ser Pro Pro Phe Val Lys Glu
    7670            7675            7680

Thr Ser Pro Pro Ser Ser Pro Leu Ser Leu Pro Ala Val Thr Ser
    7685            7690            7695

Pro His Pro Val Ser Thr Thr Phe Leu Ala His Ile Pro Pro Ser
    7700            7705            7710

Pro Leu Pro Val Thr Ser Leu Leu Thr Ser Gly Pro Ala Thr Thr
    7715            7720            7725
```

-continued

```
Thr Asp Ile Leu Gly Thr Ser Thr Glu Pro Gly Thr Ser Ser Ser
    7730                7735                7740

Ser Ser Leu Ser Thr Thr Ser His Glu Arg Leu Thr Thr Tyr Lys
    7745                7750                7755

Asp Thr Ala His Thr Glu Ala Val His Pro Ser Thr Asn Thr Gly
    7760                7765                7770

Gly Thr Asn Val Ala Thr Thr Ser Ser Gly Tyr Lys Ser Gln Ser
    7775                7780                7785

Ser Val Leu Ala Asp Ser Ser Pro Met Cys Thr Thr Ser Thr Met
    7790                7795                7800

Gly Asp Thr Ser Val Leu Thr Ser Thr Pro Ala Phe Leu Glu Thr
    7805                7810                7815

Arg Arg Ile Gln Thr Glu Leu Ala Ser Ser Leu Thr Pro Gly Leu
    7820                7825                7830

Arg Glu Ser Ser Gly Ser Glu Gly Thr Ser Ser Gly Thr Lys Met
    7835                7840                7845

Ser Thr Val Leu Ser Lys Val Pro Thr Gly Ala Thr Thr Glu Ile
    7850                7855                7860

Ser Lys Glu Asp Val Thr Ser Ile Pro Gly Pro Ala Gln Ser Thr
    7865                7870                7875

Ile Ser Pro Asp Ile Ser Thr Arg Thr Val Ser Trp Phe Ser Thr
    7880                7885                7890

Ser Pro Val Met Thr Glu Ser Ala Glu Ile Thr Met Asn Thr His
    7895                7900                7905

Thr Ser Pro Leu Gly Ala Thr Thr Gln Gly Thr Ser Thr Leu Asp
    7910                7915                7920

Thr Ser Ser Thr Thr Ser Leu Thr Met Thr His Ser Thr Ile Ser
    7925                7930                7935

Gln Gly Phe Ser His Ser Gln Met Ser Thr Leu Met Arg Arg Gly
    7940                7945                7950

Pro Glu Asp Val Ser Trp Met Ser Pro Pro Leu Leu Glu Lys Thr
    7955                7960                7965

Arg Pro Ser Phe Ser Leu Met Ser Ser Pro Ala Thr Thr Ser Pro
    7970                7975                7980

Ser Pro Val Ser Ser Thr Leu Pro Glu Ser Ile Ser Ser Ser Pro
    7985                7990                7995

Leu Pro Val Thr Ser Leu Leu Thr Ser Gly Leu Ala Lys Thr Thr
    8000                8005                8010

Asp Met Leu His Lys Ser Ser Glu Pro Val Thr Asn Ser Pro Ala
    8015                8020                8025

Asn Leu Ser Ser Thr Ser Val Glu Ile Leu Ala Thr Ser Glu Val
    8030                8035                8040

Thr Thr Asp Thr Glu Lys Thr His Pro Ser Ser Asn Arg Thr Val
    8045                8050                8055

Thr Asp Val Gly Thr Ser Ser Ser Gly His Glu Ser Thr Ser Phe
    8060                8065                8070

Val Leu Ala Asp Ser Gln Thr Ser Lys Val Thr Ser Pro Met Val
    8075                8080                8085

Ile Thr Ser Thr Met Glu Asp Thr Ser Val Ser Thr Ser Thr Pro
    8090                8095                8100

Gly Phe Phe Glu Thr Ser Arg Ile Gln Thr Glu Pro Thr Ser Ser
    8105                8110                8115

Leu Thr Leu Gly Leu Arg Lys Thr Ser Ser Ser Glu Gly Thr Ser
```

```
                   8120                      8125                         8130

Leu  Ala  Thr  Glu  Met  Ser  Thr  Val  Leu  Ser  Gly  Val  Pro  Thr  Gly
                   8135                     8140                         8145

Ala  Thr  Ala  Glu  Val  Ser  Arg  Thr  Glu  Val  Thr  Ser  Ser  Ser  Arg
                   8150                     8155                         8160

Thr  Ser  Ile  Ser  Gly  Phe  Ala  Gln  Leu  Thr  Val  Ser  Pro  Glu  Thr
                   8165                     8170                         8175

Ser  Thr  Glu  Thr  Ile  Thr  Arg  Leu  Pro  Thr  Ser  Ser  Ile  Met  Thr
                   8180                     8185                         8190

Glu  Ser  Ala  Glu  Met  Met  Ile  Lys  Thr  Gln  Thr  Asp  Pro  Pro  Gly
                   8195                     8200                         8205

Ser  Thr  Pro  Glu  Ser  Thr  His  Thr  Val  Asp  Ile  Ser  Thr  Thr  Pro
                   8210                     8215                         8220

Asn  Trp  Val  Glu  Thr  His  Ser  Thr  Val  Thr  Gln  Arg  Phe  Ser  His
                   8225                     8230                         8235

Ser  Glu  Met  Thr  Thr  Leu  Val  Ser  Arg  Ser  Pro  Gly  Asp  Met  Leu
                   8240                     8245                         8250

Trp  Pro  Ser  Gln  Ser  Ser  Val  Glu  Glu  Thr  Ser  Ser  Ala  Ser  Ser
                   8255                     8260                         8265

Leu  Leu  Ser  Leu  Pro  Ala  Thr  Thr  Ser  Pro  Ser  Pro  Val  Ser  Ser
                   8270                     8275                         8280

Thr  Leu  Val  Glu  Asp  Phe  Pro  Ser  Ala  Ser  Leu  Pro  Val  Thr  Ser
                   8285                     8290                         8295

Leu  Leu  Asn  Pro  Gly  Leu  Val  Ile  Thr  Thr  Asp  Arg  Met  Gly  Ile
                   8300                     8305                         8310

Ser  Arg  Glu  Pro  Gly  Thr  Ser  Ser  Thr  Ser  Asn  Leu  Ser  Ser  Thr
                   8315                     8320                         8325

Ser  His  Glu  Arg  Leu  Thr  Thr  Leu  Glu  Asp  Thr  Val  Asp  Thr  Glu
                   8330                     8335                         8340

Asp  Met  Gln  Pro  Ser  Thr  His  Thr  Ala  Val  Thr  Asn  Val  Arg  Thr
                   8345                     8350                         8355

Ser  Ile  Ser  Gly  His  Glu  Ser  Gln  Ser  Ser  Val  Leu  Ser  Asp  Ser
                   8360                     8365                         8370

Glu  Thr  Pro  Lys  Ala  Thr  Ser  Pro  Met  Gly  Thr  Thr  Tyr  Thr  Met
                   8375                     8380                         8385

Gly  Glu  Thr  Ser  Val  Ser  Ile  Ser  Thr  Ser  Asp  Phe  Phe  Glu  Thr
                   8390                     8395                         8400

Ser  Arg  Ile  Gln  Ile  Glu  Pro  Thr  Ser  Ser  Leu  Thr  Ser  Gly  Leu
                   8405                     8410                         8415

Arg  Glu  Thr  Ser  Ser  Ser  Glu  Arg  Ile  Ser  Ser  Ala  Thr  Glu  Gly
                   8420                     8425                         8430

Ser  Thr  Val  Leu  Ser  Glu  Val  Pro  Ser  Gly  Ala  Thr  Thr  Glu  Val
                   8435                     8440                         8445

Ser  Arg  Thr  Glu  Val  Ile  Ser  Ser  Arg  Gly  Thr  Ser  Met  Ser  Gly
                   8450                     8455                         8460

Pro  Asp  Gln  Phe  Thr  Ile  Ser  Pro  Asp  Ile  Ser  Thr  Glu  Ala  Ile
                   8465                     8470                         8475

Thr  Arg  Leu  Ser  Thr  Ser  Pro  Ile  Met  Thr  Glu  Ser  Ala  Glu  Ser
                   8480                     8485                         8490

Ala  Ile  Thr  Ile  Glu  Thr  Gly  Ser  Pro  Gly  Ala  Thr  Ser  Glu  Gly
                   8495                     8500                         8505

Thr  Leu  Thr  Leu  Asp  Thr  Ser  Thr  Thr  Thr  Phe  Trp  Ser  Gly  Thr
                   8510                     8515                         8520
```

```
His Ser Thr Ala Ser Pro Gly Phe Ser His Ser Glu Met Thr Thr
    8525            8530            8535

Leu Met Ser Arg Thr Pro Gly Asp Val Pro Trp Pro Ser Leu Pro
    8540            8545            8550

Ser Val Glu Glu Ala Ser Ser Val Ser Ser Ser Leu Ser Ser Pro
    8555            8560            8565

Ala Met Thr Ser Thr Ser Phe Phe Ser Thr Leu Pro Glu Ser Ile
    8570            8575            8580

Ser Ser Ser Pro His Pro Val Thr Ala Leu Leu Thr Leu Gly Pro
    8585            8590            8595

Val Lys Thr Thr Asp Met Leu Arg Thr Ser Ser Glu Pro Glu Thr
    8600            8605            8610

Ser Ser Pro Pro Asn Leu Ser Ser Thr Ser Ala Glu Ile Leu Ala
    8615            8620            8625

Thr Ser Glu Val Thr Lys Asp Arg Glu Lys Ile His Pro Ser Ser
    8630            8635            8640

Asn Thr Pro Val Val Asn Val Gly Thr Val Ile Tyr Lys His Leu
    8645            8650            8655

Ser Pro Ser Ser Val Leu Ala Asp Leu Val Thr Thr Lys Pro Thr
    8660            8665            8670

Ser Pro Met Ala Thr Thr Ser Thr Leu Gly Asn Thr Ser Val Ser
    8675            8680            8685

Thr Ser Thr Pro Ala Phe Pro Glu Thr Met Met Thr Gln Pro Thr
    8690            8695            8700

Ser Ser Leu Thr Ser Gly Leu Arg Glu Ile Ser Thr Ser Gln Glu
    8705            8710            8715

Thr Ser Ser Ala Thr Glu Arg Ser Ala Ser Leu Ser Gly Met Pro
    8720            8725            8730

Thr Gly Ala Thr Thr Lys Val Ser Arg Thr Glu Ala Leu Ser Leu
    8735            8740            8745

Gly Arg Thr Ser Thr Pro Gly Pro Ala Gln Ser Thr Ile Ser Pro
    8750            8755            8760

Glu Ile Ser Thr Glu Thr Ile Thr Arg Ile Ser Thr Pro Leu Thr
    8765            8770            8775

Thr Thr Gly Ser Ala Glu Met Thr Ile Thr Pro Lys Thr Gly His
    8780            8785            8790

Ser Gly Ala Ser Ser Gln Gly Thr Phe Thr Leu Asp Thr Ser Ser
    8795            8800            8805

Arg Ala Ser Trp Pro Gly Thr His Ser Ala Ala Thr His Arg Ser
    8810            8815            8820

Pro His Ser Gly Met Thr Thr Pro Met Ser Arg Gly Pro Glu Asp
    8825            8830            8835

Val Ser Trp Pro Ser Arg Pro Ser Val Glu Lys Thr Ser Pro Pro
    8840            8845            8850

Ser Ser Leu Val Ser Leu Ser Ala Val Thr Ser Pro Ser Pro Leu
    8855            8860            8865

Tyr Ser Thr Pro Ser Glu Ser Ser His Ser Ser Pro Leu Arg Val
    8870            8875            8880

Thr Ser Leu Phe Thr Pro Val Met Met Lys Thr Thr Asp Met Leu
    8885            8890            8895

Asp Thr Ser Leu Glu Pro Val Thr Thr Ser Pro Pro Ser Met Asn
    8900            8905            8910
```

| | | | | | | | | | | |
|---|---|---|---|---|---|---|---|---|---|---|
|Ile|Thr|Ser|Asp|Glu|Ser|Leu|Ala|Thr|Ser|Lys|Ala|Thr|Met|Glu|
| |8915| | | |8920| | | |8925| | | | | |
|Thr|Glu|Ala|Ile|Gln|Leu|Ser|Glu|Asn|Thr|Ala|Val|Thr|Gln|Met|
| |8930| | | |8935| | | |8940| | | | | |
|Gly|Thr|Ile|Ser|Ala|Arg|Gln|Glu|Phe|Tyr|Ser|Ser|Tyr|Pro|Gly|
| |8945| | | |8950| | | |8955| | | | | |
|Leu|Pro|Glu|Pro|Ser|Lys|Val|Thr|Ser|Pro|Val|Val|Thr|Ser|Ser|
| |8960| | | |8965| | | |8970| | | | | |
|Thr|Ile|Lys|Asp|Ile|Val|Ser|Thr|Thr|Ile|Pro|Ala|Ser|Ser|Glu|
| |8975| | | |8980| | | |8985| | | | | |
|Ile|Thr|Arg|Ile|Glu|Met|Glu|Ser|Thr|Ser|Thr|Leu|Thr|Pro|Thr|
| |8990| | | |8995| | | |9000| | | | | |
|Pro|Arg|Glu|Thr|Ser|Thr|Ser|Gln|Glu|Ile|His|Ser|Ala|Thr|Lys|
| |9005| | | |9010| | | |9015| | | | | |
|Pro|Ser|Thr|Val|Pro|Tyr|Lys|Ala|Leu|Thr|Ser|Ala|Thr|Ile|Glu|
| |9020| | | |9025| | | |9030| | | | | |
|Asp|Ser|Met|Thr|Gln|Val|Met|Ser|Ser|Ser|Arg|Gly|Pro|Ser|Pro|
| |9035| | | |9040| | | |9045| | | | | |
|Asp|Gln|Ser|Thr|Met|Ser|Gln|Asp|Ile|Ser|Thr|Glu|Val|Ile|Thr|
| |9050| | | |9055| | | |9060| | | | | |
|Arg|Leu|Ser|Thr|Ser|Pro|Ile|Lys|Thr|Glu|Ser|Thr|Glu|Met|Thr|
| |9065| | | |9070| | | |9075| | | | | |
|Ile|Thr|Thr|Gln|Thr|Gly|Ser|Pro|Gly|Ala|Thr|Ser|Arg|Gly|Thr|
| |9080| | | |9085| | | |9090| | | | | |
|Leu|Thr|Leu|Asp|Thr|Ser|Thr|Thr|Phe|Met|Ser|Gly|Thr|His|Ser|
| |9095| | | |9100| | | |9105| | | | | |
|Thr|Ala|Ser|Gln|Gly|Phe|Ser|His|Ser|Gln|Met|Thr|Ala|Leu|Met|
| |9110| | | |9115| | | |9120| | | | | |
|Ser|Arg|Thr|Pro|Gly|Asp|Val|Pro|Trp|Leu|Ser|His|Pro|Ser|Val|
| |9125| | | |9130| | | |9135| | | | | |
|Glu|Glu|Ala|Ser|Ser|Ala|Ser|Phe|Ser|Leu|Ser|Ser|Pro|Val|Met|
| |9140| | | |9145| | | |9150| | | | | |
|Thr|Ser|Ser|Ser|Pro|Val|Ser|Ser|Thr|Leu|Pro|Asp|Ser|Ile|His|
| |9155| | | |9160| | | |9165| | | | | |
|Ser|Ser|Ser|Leu|Pro|Val|Thr|Ser|Leu|Leu|Thr|Ser|Gly|Leu|Val|
| |9170| | | |9175| | | |9180| | | | | |
|Lys|Thr|Thr|Glu|Leu|Leu|Gly|Thr|Ser|Ser|Glu|Pro|Glu|Thr|Ser|
| |9185| | | |9190| | | |9195| | | | | |
|Ser|Pro|Pro|Asn|Leu|Ser|Ser|Thr|Ser|Ala|Glu|Ile|Leu|Ala|Ile|
| |9200| | | |9205| | | |9210| | | | | |
|Thr|Glu|Val|Thr|Thr|Asp|Thr|Glu|Lys|Leu|Glu|Met|Thr|Asn|Val|
| |9215| | | |9220| | | |9225| | | | | |
|Val|Thr|Ser|Gly|Tyr|Thr|His|Glu|Ser|Pro|Ser|Ser|Val|Leu|Ala|
| |9230| | | |9235| | | |9240| | | | | |
|Asp|Ser|Val|Thr|Thr|Lys|Ala|Thr|Ser|Ser|Met|Gly|Ile|Thr|Tyr|
| |9245| | | |9250| | | |9255| | | | | |
|Pro|Thr|Gly|Asp|Thr|Asn|Val|Leu|Thr|Ser|Thr|Pro|Ala|Phe|Ser|
| |9260| | | |9265| | | |9270| | | | | |
|Asp|Thr|Ser|Arg|Ile|Gln|Thr|Lys|Ser|Lys|Leu|Ser|Leu|Thr|Pro|
| |9275| | | |9280| | | |9285| | | | | |
|Gly|Leu|Met|Glu|Thr|Ser|Ile|Ser|Glu|Glu|Thr|Ser|Ser|Ala|Thr|
| |9290| | | |9295| | | |9300| | | | | |
|Glu|Lys|Ser|Thr|Val|Leu|Ser|Ser|Val|Pro|Thr|Gly|Ala|Thr|Thr|

-continued

```
            9305                9310                9315
Glu Val Ser Arg Thr Glu Ala Ile Ser Ser Ser Arg Thr Ser Ile
            9320                9325                9330
Pro Gly Pro Ala Gln Ser Thr Met Ser Ser Asp Thr Ser Met Glu
            9335                9340                9345
Thr Ile Thr Arg Ile Ser Thr Pro Leu Thr Arg Lys Glu Ser Thr
            9350                9355                9360
Asp Met Ala Ile Thr Pro Lys Thr Gly Pro Ser Gly Ala Thr Ser
            9365                9370                9375
Gln Gly Thr Phe Thr Leu Asp Ser Ser Ser Thr Ala Ser Trp Pro
            9380                9385                9390
Gly Thr His Ser Ala Thr Thr Gln Arg Phe Pro Gln Ser Val Val
            9395                9400                9405
Thr Thr Pro Met Ser Arg Gly Pro Glu Asp Val Ser Trp Pro Ser
            9410                9415                9420
Pro Leu Ser Val Glu Lys Asn Ser Pro Pro Ser Ser Leu Val Ser
            9425                9430                9435
Ser Ser Ser Val Thr Ser Pro Ser Pro Leu Tyr Ser Thr Pro Ser
            9440                9445                9450
Gly Ser Ser His Ser Ser Pro Val Pro Val Thr Ser Leu Phe Thr
            9455                9460                9465
Ser Ile Met Met Lys Ala Thr Asp Met Leu Asp Ala Ser Leu Glu
            9470                9475                9480
Pro Glu Thr Thr Ser Ala Pro Asn Met Asn Ile Thr Ser Asp Glu
            9485                9490                9495
Ser Leu Ala Ala Ser Lys Ala Thr Thr Glu Thr Glu Ala Ile His
            9500                9505                9510
Val Phe Glu Asn Thr Ala Ala Ser His Val Glu Thr Thr Ser Ala
            9515                9520                9525
Thr Glu Glu Leu Tyr Ser Ser Ser Pro Gly Phe Ser Glu Pro Thr
            9530                9535                9540
Lys Val Ile Ser Pro Val Val Thr Ser Ser Ser Ile Arg Asp Asn
            9545                9550                9555
Met Val Ser Thr Thr Met Pro Gly Ser Ser Gly Ile Thr Arg Ile
            9560                9565                9570
Glu Ile Glu Ser Met Ser Ser Leu Thr Pro Gly Leu Arg Glu Thr
            9575                9580                9585
Arg Thr Ser Gln Asp Ile Thr Ser Ser Thr Glu Thr Ser Thr Val
            9590                9595                9600
Leu Tyr Lys Met Pro Ser Gly Ala Thr Pro Glu Val Ser Arg Thr
            9605                9610                9615
Glu Val Met Pro Ser Ser Arg Thr Ser Ile Pro Gly Pro Ala Gln
            9620                9625                9630
Ser Thr Met Ser Leu Asp Ile Ser Asp Glu Val Val Thr Arg Leu
            9635                9640                9645
Ser Thr Ser Pro Ile Met Thr Glu Ser Ala Glu Ile Thr Ile Thr
            9650                9655                9660
Thr Gln Thr Gly Tyr Ser Leu Ala Thr Ser Gln Val Thr Leu Pro
            9665                9670                9675
Leu Gly Thr Ser Met Thr Phe Leu Ser Gly Thr His Ser Thr Met
            9680                9685                9690
Ser Gln Gly Leu Ser His Ser Glu Met Thr Asn Leu Met Ser Arg
            9695                9700                9705
```

```
Gly Pro Glu Ser Leu Ser Trp Thr Ser Pro Arg Phe Val Glu Thr
    9710            9715            9720

Thr Arg Ser Ser Ser Ser Leu Thr Ser Leu Pro Leu Thr Thr Ser
    9725            9730            9735

Leu Ser Pro Val Ser Ser Thr Leu Leu Asp Ser Ser Pro Ser Ser
    9740            9745            9750

Pro Leu Pro Val Thr Ser Leu Ile Leu Pro Gly Leu Val Lys Thr
    9755            9760            9765

Thr Glu Val Leu Asp Thr Ser Ser Glu Pro Lys Thr Ser Ser Ser
    9770            9775            9780

Pro Asn Leu Ser Ser Thr Ser Val Glu Ile Pro Ala Thr Ser Glu
    9785            9790            9795

Ile Met Thr Asp Thr Glu Lys Ile His Pro Ser Ser Asn Thr Ala
    9800            9805            9810

Val Ala Lys Val Arg Thr Ser Ser Ser Val His Glu Ser His Ser
    9815            9820            9825

Ser Val Leu Ala Asp Ser Glu Thr Thr Ile Thr Ile Pro Ser Met
    9830            9835            9840

Gly Ile Thr Ser Ala Val Asp Asp Thr Thr Val Phe Thr Ser Asn
    9845            9850            9855

Pro Ala Phe Ser Glu Thr Arg Arg Ile Pro Thr Glu Pro Thr Phe
    9860            9865            9870

Ser Leu Thr Pro Gly Phe Arg Glu Thr Ser Thr Glu Glu Thr
    9875            9880            9885

Thr Ser Ile Thr Glu Thr Ser Ala Val Leu Tyr Gly Val Pro Thr
    9890            9895            9900

Ser Ala Thr Thr Glu Val Ser Met Thr Glu Ile Met Ser Ser Asn
    9905            9910            9915

Arg Ile His Ile Pro Asp Ser Asp Gln Ser Thr Met Ser Pro Asp
    9920            9925            9930

Ile Ile Thr Glu Val Ile Thr Arg Leu Ser Ser Ser Ser Met Met
    9935            9940            9945

Ser Glu Ser Thr Gln Met Thr Ile Thr Thr Gln Lys Ser Ser Pro
    9950            9955            9960

Gly Ala Thr Ala Gln Ser Thr Leu Thr Leu Ala Thr Thr Thr Ala
    9965            9970            9975

Pro Leu Ala Arg Thr His Ser Thr Val Pro Pro Arg Phe Leu His
    9980            9985            9990

Ser Glu Met Thr Thr Leu Met Ser Arg Ser Pro Glu Asn Pro Ser
    9995            10000           10005

Trp Lys Ser Ser Leu Phe Val Glu Lys Thr Ser Ser Ser Ser Ser
    10010           10015           10020

Leu Leu Ser Leu Pro Val Thr Thr Ser Pro Ser Val Ser Ser Thr
    10025           10030           10035

Leu Pro Gln Ser Ile Pro Ser Ser Ser Phe Ser Val Thr Ser Leu
    10040           10045           10050

Leu Thr Pro Gly Met Val Lys Thr Thr Asp Thr Ser Thr Glu Pro
    10055           10060           10065

Gly Thr Ser Leu Ser Pro Asn Leu Ser Gly Thr Ser Val Glu Ile
    10070           10075           10080

Leu Ala Ala Ser Glu Val Thr Thr Asp Thr Glu Lys Ile His Pro
    10085           10090           10095
```

-continued

| | | | | | | | | | | | |
|---|---|---|---|---|---|---|---|---|---|---|---|
| Ser | Ser | Ser | Met | Ala | Val | Thr | Asn | Val | Gly | Thr | Thr | Ser | Ser | Gly |
| | 10100 | | | | 10105 | | | | 10110 | | |
| His | Glu | Leu | Tyr | Ser | Ser | Val | Ser | Ile | His | Ser | Glu | Pro | Ser | Lys |
| | 10115 | | | | 10120 | | | | 10125 | | |
| Ala | Thr | Tyr | Pro | Val | Gly | Thr | Pro | Ser | Ser | Met | Ala | Glu | Thr | Ser |
| | 10130 | | | | 10135 | | | | 10140 | | |
| Ile | Ser | Thr | Ser | Met | Pro | Ala | Asn | Phe | Glu | Thr | Thr | Gly | Phe | Glu |
| | 10145 | | | | 10150 | | | | 10155 | | |
| Ala | Glu | Pro | Phe | Ser | His | Leu | Thr | Ser | Gly | Phe | Arg | Lys | Thr | Asn |
| | 10160 | | | | 10165 | | | | 10170 | | |
| Met | Ser | Leu | Asp | Thr | Ser | Ser | Val | Thr | Pro | Thr | Asn | Thr | Pro | Ser |
| | 10175 | | | | 10180 | | | | 10185 | | |
| Ser | Pro | Gly | Ser | Thr | His | Leu | Leu | Gln | Ser | Ser | Lys | Thr | Asp | Phe |
| | 10190 | | | | 10195 | | | | 10200 | | |
| Thr | Ser | Ser | Ala | Lys | Thr | Ser | Ser | Pro | Asp | Trp | Pro | Pro | Ala | Ser |
| | 10205 | | | | 10210 | | | | 10215 | | |
| Gln | Tyr | Thr | Glu | Ile | Pro | Val | Asp | Ile | Ile | Thr | Pro | Phe | Asn | Ala |
| | 10220 | | | | 10225 | | | | 10230 | | |
| Ser | Pro | Ser | Ile | Thr | Glu | Ser | Thr | Gly | Ile | Thr | Ser | Phe | Pro | Glu |
| | 10235 | | | | 10240 | | | | 10245 | | |
| Ser | Arg | Phe | Thr | Met | Ser | Val | Thr | Glu | Ser | Thr | His | His | Leu | Ser |
| | 10250 | | | | 10255 | | | | 10260 | | |
| Thr | Asp | Leu | Leu | Pro | Ser | Ala | Glu | Thr | Ile | Ser | Thr | Gly | Thr | Val |
| | 10265 | | | | 10270 | | | | 10275 | | |
| Met | Pro | Ser | Leu | Ser | Glu | Ala | Met | Thr | Ser | Phe | Ala | Thr | Thr | Gly |
| | 10280 | | | | 10285 | | | | 10290 | | |
| Val | Pro | Arg | Ala | Ile | Ser | Gly | Ser | Gly | Ser | Pro | Phe | Ser | Arg | Thr |
| | 10295 | | | | 10300 | | | | 10305 | | |
| Glu | Ser | Gly | Pro | Gly | Asp | Ala | Thr | Leu | Ser | Thr | Ile | Ala | Glu | Ser |
| | 10310 | | | | 10315 | | | | 10320 | | |
| Leu | Pro | Ser | Ser | Thr | Pro | Val | Pro | Phe | Ser | Ser | Ser | Thr | Phe | Thr |
| | 10325 | | | | 10330 | | | | 10335 | | |
| Thr | Thr | Asp | Ser | Ser | Thr | Ile | Pro | Ala | Leu | His | Glu | Ile | Thr | Ser |
| | 10340 | | | | 10345 | | | | 10350 | | |
| Ser | Ser | Ala | Thr | Pro | Tyr | Arg | Val | Asp | Thr | Ser | Leu | Gly | Thr | Glu |
| | 10355 | | | | 10360 | | | | 10365 | | |
| Ser | Ser | Thr | Thr | Glu | Gly | Arg | Leu | Val | Met | Val | Ser | Thr | Leu | Asp |
| | 10370 | | | | 10375 | | | | 10380 | | |
| Thr | Ser | Ser | Gln | Pro | Gly | Arg | Thr | Ser | Ser | Pro | Ile | Leu | Asp |
| | 10385 | | | | 10390 | | | | 10395 | | |
| Thr | Arg | Met | Thr | Glu | Ser | Val | Glu | Leu | Gly | Thr | Val | Thr | Ser | Ala |
| | 10400 | | | | 10405 | | | | 10410 | | |
| Tyr | Gln | Val | Pro | Ser | Leu | Ser | Thr | Arg | Leu | Thr | Arg | Thr | Asp | Gly |
| | 10415 | | | | 10420 | | | | 10425 | | |
| Ile | Met | Glu | His | Ile | Thr | Lys | Ile | Pro | Asn | Glu | Ala | Ala | His | Arg |
| | 10430 | | | | 10435 | | | | 10440 | | |
| Gly | Thr | Ile | Arg | Pro | Val | Lys | Gly | Pro | Gln | Thr | Ser | Thr | Ser | Pro |
| | 10445 | | | | 10450 | | | | 10455 | | |
| Ala | Ser | Pro | Lys | Gly | Leu | His | Thr | Gly | Gly | Thr | Lys | Arg | Met | Glu |
| | 10460 | | | | 10465 | | | | 10470 | | |
| Thr | Thr | Thr | Thr | Ala | Leu | Lys | Thr | Thr | Thr | Thr | Ala | Leu | Lys | Thr |
| | 10475 | | | | 10480 | | | | 10485 | | |
| Thr | Ser | Arg | Ala | Thr | Leu | Thr | Thr | Ser | Val | Tyr | Thr | Pro | Thr | Leu |

-continued

| | 10490 | | | | 10495 | | | | 10500 | | |
|---|---|---|---|---|---|---|---|---|---|---|---|
| Gly | Thr | Leu | Thr | Pro | Leu | Asn | Ala | Ser | Met | Gln | Met | Ala | Ser | Thr |
| | 10505 | | | | 10510 | | | | 10515 | | |
| Ile | Pro | Thr | Glu | Met | Met | Ile | Thr | Thr | Pro | Tyr | Val | Phe | Pro | Asp |
| | 10520 | | | | 10525 | | | | 10530 | | |
| Val | Pro | Glu | Thr | Thr | Ser | Ser | Leu | Ala | Thr | Ser | Leu | Gly | Ala | Glu |
| | 10535 | | | | 10540 | | | | 10545 | | |
| Thr | Ser | Thr | Ala | Leu | Pro | Arg | Thr | Thr | Pro | Ser | Val | Phe | Asn | Arg |
| | 10550 | | | | 10555 | | | | 10560 | | |
| Glu | Ser | Glu | Thr | Thr | Ala | Ser | Leu | Val | Ser | Arg | Ser | Gly | Ala | Glu |
| | 10565 | | | | 10570 | | | | 10575 | | |
| Arg | Ser | Pro | Val | Ile | Gln | Thr | Leu | Asp | Val | Ser | Ser | Ser | Glu | Pro |
| | 10580 | | | | 10585 | | | | 10590 | | |
| Asp | Thr | Thr | Ala | Ser | Trp | Val | Ile | His | Pro | Ala | Glu | Thr | Ile | Pro |
| | 10595 | | | | 10600 | | | | 10605 | | |
| Thr | Val | Ser | Lys | Thr | Thr | Pro | Asn | Phe | Phe | His | Ser | Glu | Leu | Asp |
| | 10610 | | | | 10615 | | | | 10620 | | |
| Thr | Val | Ser | Ser | Thr | Ala | Thr | Ser | His | Gly | Ala | Asp | Val | Ser | Ser |
| | 10625 | | | | 10630 | | | | 10635 | | |
| Ala | Ile | Pro | Thr | Asn | Ile | Ser | Pro | Ser | Glu | Leu | Asp | Ala | Leu | Thr |
| | 10640 | | | | 10645 | | | | 10650 | | |
| Pro | Leu | Val | Thr | Ile | Ser | Gly | Thr | Asp | Thr | Ser | Thr | Thr | Phe | Pro |
| | 10655 | | | | 10660 | | | | 10665 | | |
| Thr | Leu | Thr | Lys | Ser | Pro | His | Glu | Thr | Glu | Thr | Arg | Thr | Thr | Trp |
| | 10670 | | | | 10675 | | | | 10680 | | |
| Leu | Thr | His | Pro | Ala | Glu | Thr | Ser | Ser | Thr | Ile | Pro | Arg | Thr | Ile |
| | 10685 | | | | 10690 | | | | 10695 | | |
| Pro | Asn | Phe | Ser | His | His | Glu | Ser | Asp | Ala | Thr | Pro | Ser | Ile | Ala |
| | 10700 | | | | 10705 | | | | 10710 | | |
| Thr | Ser | Pro | Gly | Ala | Glu | Thr | Ser | Ser | Ala | Ile | Pro | Ile | Met | Thr |
| | 10715 | | | | 10720 | | | | 10725 | | |
| Val | Ser | Pro | Gly | Ala | Glu | Asp | Leu | Val | Thr | Ser | Gln | Val | Thr | Ser |
| | 10730 | | | | 10735 | | | | 10740 | | |
| Ser | Gly | Thr | Asp | Arg | Asn | Met | Thr | Ile | Pro | Thr | Leu | Thr | Leu | Ser |
| | 10745 | | | | 10750 | | | | 10755 | | |
| Pro | Gly | Glu | Pro | Lys | Thr | Ile | Ala | Ser | Leu | Val | Thr | His | Pro | Glu |
| | 10760 | | | | 10765 | | | | 10770 | | |
| Ala | Gln | Thr | Ser | Ser | Ala | Ile | Pro | Thr | Ser | Thr | Ile | Ser | Pro | Ala |
| | 10775 | | | | 10780 | | | | 10785 | | |
| Val | Ser | Arg | Leu | Val | Thr | Ser | Met | Val | Thr | Ser | Leu | Ala | Ala | Lys |
| | 10790 | | | | 10795 | | | | 10800 | | |
| Thr | Ser | Thr | Thr | Asn | Arg | Ala | Leu | Thr | Asn | Ser | Pro | Gly | Glu | Pro |
| | 10805 | | | | 10810 | | | | 10815 | | |
| Ala | Thr | Thr | Val | Ser | Leu | Val | Thr | His | Pro | Ala | Gln | Thr | Ser | Pro |
| | 10820 | | | | 10825 | | | | 10830 | | |
| Thr | Val | Pro | Trp | Thr | Thr | Ser | Ile | Phe | Phe | His | Ser | Lys | Ser | Asp |
| | 10835 | | | | 10840 | | | | 10845 | | |
| Thr | Thr | Pro | Ser | Met | Thr | Thr | Ser | His | Gly | Ala | Glu | Ser | Ser | Ser |
| | 10850 | | | | 10855 | | | | 10860 | | |
| Ala | Val | Pro | Thr | Pro | Thr | Val | Ser | Thr | Glu | Val | Pro | Gly | Val | Val |
| | 10865 | | | | 10870 | | | | 10875 | | |
| Thr | Pro | Leu | Val | Thr | Ser | Ser | Arg | Ala | Val | Ile | Ser | Thr | Thr | Ile |
| | 10880 | | | | 10885 | | | | 10890 | | |

```
Pro Ile Leu Thr Leu Ser Pro Gly Glu Pro Glu Thr    Thr Pro Ser
    10895            10900              10905

Met Ala Thr Ser His Gly Glu    Glu Ala Ser Ser Ala    Ile Pro Thr
    10910            10915              10920

Pro Thr Val Ser Pro Gly Val    Pro Gly Val Val Thr    Ser Leu Val
    10925            10930              10935

Thr Ser Ser Arg Ala Val Thr    Ser Thr Thr Ile Pro    Ile Leu Thr
    10940            10945              10950

Phe Ser Leu Gly Glu Pro Glu    Thr Thr Pro Ser Met    Ala Thr Ser
    10955            10960              10965

His Gly Thr Glu Ala Gly Ser    Ala Val Pro Thr Val    Leu Pro Glu
    10970            10975              10980

Val Pro Gly Met Val Thr Ser    Leu Val Ala Ser Ser    Arg Ala Val
    10985            10990              10995

Thr Ser Thr Thr Leu Pro Thr    Leu Thr Leu Ser Pro    Gly Glu Pro
    11000            11005              11010

Glu Thr Thr Pro Ser Met Ala    Thr Ser His Gly Ala    Glu Ala Ser
    11015            11020              11025

Ser Thr Val Pro Thr Val Ser    Pro Glu Val Pro Gly    Val Val Thr
    11030            11035              11040

Ser Leu Val Thr Ser Ser Ser    Gly Val Asn Ser Thr    Ser Ile Pro
    11045            11050              11055

Thr Leu Ile Leu Ser Pro Gly    Glu Leu Glu Thr Thr    Pro Ser Met
    11060            11065              11070

Ala Thr Ser His Gly Ala Glu    Ala Ser Ser Ala Val    Pro Thr Pro
    11075            11080              11085

Thr Val Ser Pro Gly Val Ser    Gly Val Val Thr Pro    Leu Val Thr
    11090            11095              11100

Ser Ser Arg Ala Val Thr Ser    Thr Thr Ile Pro Ile    Leu Thr Leu
    11105            11110              11115

Ser Ser Ser Glu Pro Glu Thr    Thr Pro Ser Met Ala    Thr Ser His
    11120            11125              11130

Gly Val Glu Ala Ser Ser Ala    Val Leu Thr Val Ser    Pro Glu Val
    11135            11140              11145

Pro Gly Met Val Thr Ser Leu    Val Thr Ser Ser Arg    Ala Val Thr
    11150            11155              11160

Ser Thr Thr Ile Pro Thr Leu    Thr Ile Ser Ser Asp    Glu Pro Glu
    11165            11170              11175

Thr Thr Thr Ser Leu Val Thr    His Ser Glu Ala Lys    Met Ile Ser
    11180            11185              11190

Ala Ile Pro Thr Leu Ala Val    Ser Pro Thr Val Gln    Gly Leu Val
    11195            11200              11205

Thr Ser Leu Val Thr Ser Ser    Gly Ser Glu Thr Ser    Ala Phe Ser
    11210            11215              11220

Asn Leu Thr Val Ala Ser Ser    Gln Pro Glu Thr Ile    Asp Ser Trp
    11225            11230              11235

Val Ala His Pro Gly Thr Glu    Ala Ser Ser Val Val    Pro Thr Leu
    11240            11245              11250

Thr Val Ser Thr Gly Glu Pro    Phe Thr Asn Ile Ser    Leu Val Thr
    11255            11260              11265

His Pro Ala Glu Ser Ser Ser    Thr Leu Pro Arg Thr    Thr Ser Arg
    11270            11275              11280
```

```
Phe Ser His Ser Glu Leu Asp Thr Met Pro Ser Thr Val Thr Ser
    11285             11290             11295

Pro Glu Ala Glu Ser Ser Ala Ile Ser Thr Thr Ile Ser Pro
    11300             11305             11310

Gly Ile Pro Gly Val Leu Thr Ser Leu Val Thr Ser Ser Gly Arg
    11315             11320             11325

Asp Ile Ser Ala Thr Phe Pro Thr Val Pro Glu Ser Pro His Glu
    11330             11335             11340

Ser Glu Ala Thr Ala Ser Trp Val Thr His Pro Ala Val Thr Ser
    11345             11350             11355

Thr Thr Val Pro Arg Thr Thr Pro Asn Tyr Ser His Ser Glu Pro
    11360             11365             11370

Asp Thr Thr Pro Ser Ile Ala Thr Ser Pro Gly Ala Glu Ala Thr
    11375             11380             11385

Ser Asp Phe Pro Thr Ile Thr Val Ser Pro Asp Val Pro Asp Met
    11390             11395             11400

Val Thr Ser Gln Val Thr Ser Ser Gly Thr Asp Thr Ser Ile Thr
    11405             11410             11415

Ile Pro Thr Leu Thr Leu Ser Ser Gly Glu Pro Glu Thr Thr Thr
    11420             11425             11430

Ser Phe Ile Thr Tyr Ser Glu Thr His Thr Ser Ser Ala Ile Pro
    11435             11440             11445

Thr Leu Pro Val Ser Pro Gly Ala Ser Lys Met Leu Thr Ser Leu
    11450             11455             11460

Val Ile Ser Ser Gly Thr Asp Ser Thr Thr Thr Phe Pro Thr Leu
    11465             11470             11475

Thr Glu Thr Pro Tyr Glu Pro Glu Thr Thr Ala Ile Gln Leu Ile
    11480             11485             11490

His Pro Ala Glu Thr Asn Thr Met Val Pro Arg Thr Thr Pro Lys
    11495             11500             11505

Phe Ser His Ser Lys Ser Asp Thr Thr Leu Pro Val Ala Ile Thr
    11510             11515             11520

Ser Pro Gly Pro Glu Ala Ser Ser Ala Val Ser Thr Thr Thr Ile
    11525             11530             11535

Ser Pro Asp Met Ser Asp Leu Val Thr Ser Leu Val Pro Ser Ser
    11540             11545             11550

Gly Thr Asp Thr Ser Thr Thr Phe Pro Thr Leu Ser Glu Thr Pro
    11555             11560             11565

Tyr Glu Pro Glu Thr Thr Ala Thr Trp Leu Thr His Pro Ala Glu
    11570             11575             11580

Thr Ser Thr Thr Val Ser Gly Thr Ile Pro Asn Phe Ser His Arg
    11585             11590             11595

Gly Ser Asp Thr Ala Pro Ser Met Val Thr Ser Pro Gly Val Asp
    11600             11605             11610

Thr Arg Ser Gly Val Pro Thr Thr Ile Pro Pro Ser Ile Pro
    11615             11620             11625

Gly Val Val Thr Ser Gln Val Thr Ser Ser Ala Thr Asp Thr Ser
    11630             11635             11640

Thr Ala Ile Pro Thr Leu Thr Pro Ser Pro Gly Glu Pro Glu Thr
    11645             11650             11655

Thr Ala Ser Ser Ala Thr His Pro Gly Thr Gln Thr Gly Phe Thr
    11660             11665             11670

Val Pro Ile Arg Thr Val Pro Ser Ser Glu Pro Asp Thr Met Ala
```

-continued

```
              11675                  11680                   11685

Ser  Trp  Val  Thr  His  Pro  Pro  Gln  Thr  Ser  Thr  Pro  Val  Ser  Arg
         11690                  11695                   11700

Thr  Thr  Ser  Ser  Phe  Ser  His  Ser  Ser  Pro  Asp  Ala  Thr  Pro  Val
         11705                  11710                   11715

Met  Ala  Thr  Ser  Pro  Arg  Thr  Glu  Ala  Ser  Ser  Ala  Val  Leu  Thr
         11720                  11725                   11730

Thr  Ile  Ser  Pro  Gly  Ala  Pro  Glu  Met  Val  Thr  Ser  Gln  Ile  Thr
         11735                  11740                   11745

Ser  Ser  Gly  Ala  Ala  Thr  Ser  Thr  Thr  Val  Pro  Thr  Leu  Thr  His
         11750                  11755                   11760

Ser  Pro  Gly  Met  Pro  Glu  Thr  Thr  Ala  Leu  Leu  Ser  Thr  His  Pro
         11765                  11770                   11775

Arg  Thr  Glu  Thr  Ser  Lys  Thr  Phe  Pro  Ala  Ser  Thr  Val  Phe  Pro
         11780                  11785                   11790

Gln  Val  Ser  Glu  Thr  Thr  Ala  Ser  Leu  Thr  Ile  Arg  Pro  Gly  Ala
         11795                  11800                   11805

Glu  Thr  Ser  Thr  Ala  Leu  Pro  Thr  Gln  Thr  Thr  Ser  Ser  Leu  Phe
         11810                  11815                   11820

Thr  Leu  Leu  Val  Thr  Gly  Thr  Ser  Arg  Val  Asp  Leu  Ser  Pro  Thr
         11825                  11830                   11835

Ala  Ser  Pro  Gly  Val  Ser  Ala  Lys  Thr  Ala  Pro  Leu  Ser  Thr  His
         11840                  11845                   11850

Pro  Gly  Thr  Glu  Thr  Ser  Thr  Met  Ile  Pro  Thr  Ser  Thr  Leu  Ser
         11855                  11860                   11865

Leu  Gly  Leu  Leu  Glu  Thr  Thr  Gly  Leu  Leu  Ala  Thr  Ser  Ser  Ser
         11870                  11875                   11880

Ala  Glu  Thr  Ser  Thr  Ser  Thr  Leu  Thr  Leu  Thr  Val  Ser  Pro  Ala
         11885                  11890                   11895

Val  Ser  Gly  Leu  Ser  Ser  Ala  Ser  Ile  Thr  Thr  Asp  Lys  Pro  Gln
         11900                  11905                   11910

Thr  Val  Thr  Ser  Trp  Asn  Thr  Glu  Thr  Ser  Pro  Ser  Val  Thr  Ser
         11915                  11920                   11925

Val  Gly  Pro  Pro  Glu  Phe  Ser  Arg  Thr  Val  Thr  Gly  Thr  Thr  Met
         11930                  11935                   11940

Thr  Leu  Ile  Pro  Ser  Glu  Met  Pro  Thr  Pro  Pro  Lys  Thr  Ser  His
         11945                  11950                   11955

Gly  Glu  Gly  Val  Ser  Pro  Thr  Thr  Ile  Leu  Arg  Thr  Thr  Met  Val
         11960                  11965                   11970

Glu  Ala  Thr  Asn  Leu  Ala  Thr  Thr  Gly  Ser  Ser  Pro  Thr  Val  Ala
         11975                  11980                   11985

Lys  Thr  Thr  Thr  Thr  Phe  Asn  Thr  Leu  Ala  Gly  Ser  Leu  Phe  Thr
         11990                  11995                   12000

Pro  Leu  Thr  Thr  Pro  Gly  Met  Ser  Thr  Leu  Ala  Ser  Glu  Ser  Val
         12005                  12010                   12015

Thr  Ser  Arg  Thr  Ser  Tyr  Asn  His  Arg  Ser  Trp  Ile  Ser  Thr  Thr
         12020                  12025                   12030

Ser  Ser  Tyr  Asn  Arg  Arg  Tyr  Trp  Thr  Pro  Ala  Thr  Ser  Thr  Pro
         12035                  12040                   12045

Val  Thr  Ser  Thr  Phe  Ser  Pro  Gly  Ile  Ser  Thr  Ser  Ser  Ile  Pro
         12050                  12055                   12060

Ser  Ser  Thr  Ala  Ala  Thr  Val  Pro  Phe  Met  Val  Pro  Phe  Thr  Leu
         12065                  12070                   12075
```

```
Asn Phe Thr Ile Thr Asn Leu Gln Tyr Glu Glu Asp Met Arg His
    12080               12085               12090

Pro Gly Ser Arg Lys Phe Asn Ala Thr Glu Arg Glu Leu Gln Gly
    12095               12100               12105

Leu Leu Lys Pro Leu Phe Arg Asn Ser Ser Leu Glu Tyr Leu Tyr
    12110               12115               12120

Ser Gly Cys Arg Leu Ala Ser Leu Arg Pro Glu Lys Asp Ser Ser
    12125               12130               12135

Ala Thr Ala Val Asp Ala Ile Cys Thr His Arg Pro Asp Pro Glu
    12140               12145               12150

Asp Leu Gly Leu Asp Arg Glu Arg Leu Tyr Trp Glu Leu Ser Asn
    12155               12160               12165

Leu Thr Asn Gly Ile Gln Glu Leu Gly Pro Tyr Thr Leu Asp Arg
    12170               12175               12180

Asn Ser Leu Tyr Val Asn Gly Phe Thr His Arg Ser Ser Met Pro
    12185               12190               12195

Thr Thr Ser Thr Pro Gly Thr Ser Thr Val Asp Val Gly Thr Ser
    12200               12205               12210

Gly Thr Pro Ser Ser Ser Pro Ser Pro Thr Thr Ala Gly Pro Leu
    12215               12220               12225

Leu Met Pro Phe Thr Leu Asn Phe Thr Ile Thr Asn Leu Gln Tyr
    12230               12235               12240

Glu Glu Asp Met Arg Arg Thr Gly Ser Arg Lys Phe Asn Thr Met
    12245               12250               12255

Glu Ser Val Leu Gln Gly Leu Leu Lys Pro Leu Phe Lys Asn Thr
    12260               12265               12270

Ser Val Gly Pro Leu Tyr Ser Gly Cys Arg Leu Thr Leu Leu Arg
    12275               12280               12285

Pro Glu Lys Asp Gly Ala Ala Thr Gly Val Asp Ala Ile Cys Thr
    12290               12295               12300

His Arg Leu Asp Pro Lys Ser Pro Gly Leu Asn Arg Glu Gln Leu
    12305               12310               12315

Tyr Trp Glu Leu Ser Lys Leu Thr Asn Asp Ile Glu Glu Leu Gly
    12320               12325               12330

Pro Tyr Thr Leu Asp Arg Asn Ser Leu Tyr Val Asn Gly Phe Thr
    12335               12340               12345

His Gln Ser Ser Val Ser Thr Thr Ser Thr Pro Gly Thr Ser Thr
    12350               12355               12360

Val Asp Leu Arg Thr Ser Gly Thr Pro Ser Ser Leu Ser Ser Pro
    12365               12370               12375

Thr Ile Met Ala Ala Gly Pro Leu Leu Val Pro Phe Thr Leu Asn
    12380               12385               12390

Phe Thr Ile Thr Asn Leu Gln Tyr Gly Glu Asp Met Gly His Pro
    12395               12400               12405

Gly Ser Arg Lys Phe Asn Thr Thr Glu Arg Val Leu Gln Gly Leu
    12410               12415               12420

Leu Gly Pro Ile Phe Lys Asn Thr Ser Val Gly Pro Leu Tyr Ser
    12425               12430               12435

Gly Cys Arg Leu Thr Ser Leu Arg Ser Glu Lys Asp Gly Ala Ala
    12440               12445               12450

Thr Gly Val Asp Ala Ile Cys Ile His His Leu Asp Pro Lys Ser
    12455               12460               12465
```

```
Pro Gly Leu Asn Arg Glu Arg     Leu Tyr Trp Glu Leu     Ser Gln Leu
    12470               12475                   12480

Thr Asn Gly Ile Lys Glu Leu     Gly Pro Tyr Thr Leu     Asp Arg Asn
    12485               12490                   12495

Ser Leu Tyr Val Asn Gly Phe     Thr His Arg Thr Ser     Val Pro Thr
    12500               12505                   12510

Ser Ser Thr Pro Gly Thr Ser     Thr Val Asp Leu Gly     Thr Ser Gly
    12515               12520                   12525

Thr Pro Phe Ser Leu Pro Ser     Pro Ala Thr Ala Gly     Pro Leu Leu
    12530               12535                   12540

Val Leu Phe Thr Leu Asn Phe     Thr Ile Thr Asn Leu     Lys Tyr Glu
    12545               12550                   12555

Glu Asp Met His Arg Pro Gly     Ser Arg Lys Phe Asn     Thr Thr Glu
    12560               12565                   12570

Arg Val Leu Gln Thr Leu Leu     Gly Pro Met Phe Lys     Asn Thr Ser
    12575               12580                   12585

Val Gly Leu Leu Tyr Ser Gly     Cys Arg Leu Thr Leu     Leu Arg Ser
    12590               12595                   12600

Glu Lys Asp Gly Ala Ala Thr     Gly Val Asp Ala Ile     Cys Thr His
    12605               12610                   12615

Arg Leu Asp Pro Lys Ser Pro     Gly Val Asp Arg Glu     Gln Leu Tyr
    12620               12625                   12630

Trp Glu Leu Ser Gln Leu Thr     Asn Gly Ile Lys Glu     Leu Gly Pro
    12635               12640                   12645

Tyr Thr Leu Asp Arg Asn Ser     Leu Tyr Val Asn Gly     Phe Thr His
    12650               12655                   12660

Trp Ile Pro Val Pro Thr Ser     Ser Thr Pro Gly Thr     Ser Thr Val
    12665               12670                   12675

Asp Leu Gly Ser Gly Thr Pro     Ser Ser Leu Pro Ser     Pro Thr Thr
    12680               12685                   12690

Ala Gly Pro Leu Leu Val Pro     Phe Thr Leu Asn Phe     Thr Ile Thr
    12695               12700                   12705

Asn Leu Lys Tyr Glu Glu Asp     Met His Cys Pro Gly     Ser Arg Lys
    12710               12715                   12720

Phe Asn Thr Thr Glu Arg Val     Leu Gln Ser Leu Leu     Gly Pro Met
    12725               12730                   12735

Phe Lys Asn Thr Ser Val Gly     Pro Leu Tyr Ser Gly     Cys Arg Leu
    12740               12745                   12750

Thr Leu Leu Arg Ser Glu Lys     Asp Gly Ala Ala Thr     Gly Val Asp
    12755               12760                   12765

Ala Ile Cys Thr His Arg Leu     Asp Pro Lys Ser Pro     Gly Val Asp
    12770               12775                   12780

Arg Glu Gln Leu Tyr Trp Glu     Leu Ser Gln Leu Thr     Asn Gly Ile
    12785               12790                   12795

Lys Glu Leu Gly Pro Tyr Thr     Leu Asp Arg Asn Ser     Leu Tyr Val
    12800               12805                   12810

Asn Gly Phe Thr His Gln Thr     Ser Ala Pro Asn Thr     Ser Thr Pro
    12815               12820                   12825

Gly Thr Ser Thr Val Asp Leu     Gly Thr Ser Gly Thr     Pro Ser Ser
    12830               12835                   12840

Leu Pro Ser Pro Thr Ser Ala     Gly Pro Leu Leu Val     Pro Phe Thr
    12845               12850                   12855

Leu Asn Phe Thr Ile Thr Asn     Leu Gln Tyr Glu Glu     Asp Met His
```

His Pro Gly Ser Arg Lys Phe Asn Thr Thr Glu Arg Val Leu Gln
    12860            12865              12870

Gly Leu Leu Gly Pro Met Phe Lys Asn Thr Ser Val Gly Leu Leu
    12875            12880              12885

Tyr Ser Gly Cys Arg Leu Thr Leu Leu Arg Pro Glu Lys Asn Gly
    12890            12895              12900

Ala Ala Thr Gly Met Asp Ala Ile Cys Ser His Arg Leu Asp Pro
    12905            12910              12915

Lys Ser Pro Gly Leu Asn Arg Glu Gln Leu Tyr Trp Glu Leu Ser
    12920            12925              12930

Gln Leu Thr His Gly Ile Lys Glu Leu Gly Pro Tyr Thr Leu Asp
    12935            12940              12945

Arg Asn Ser Leu Tyr Val Asn Gly Phe Thr His Arg Ser Ser Val
    12950            12955              12960

Ala Pro Thr Ser Thr Pro Gly Thr Ser Thr Val Asp Leu Gly Thr
    12965            12970              12975

Ser Gly Thr Pro Ser Ser Leu Pro Ser Pro Thr Thr Ala Val Pro
    12980            12985              12990

Leu Leu Val Pro Phe Thr Leu Asn Phe Thr Ile Thr Asn Leu Gln
    12995            13000              13005

Tyr Gly Glu Asp Met Arg His Pro Gly Ser Arg Lys Phe Asn Thr
    13010            13015              13020

Thr Glu Arg Val Leu Gln Gly Leu Leu Gly Pro Leu Phe Lys Asn
    13025            13030              13035

Ser Ser Val Gly Pro Leu Tyr Ser Gly Cys Arg Leu Ile Ser Leu
    13040            13045              13050

Arg Ser Glu Lys Asp Gly Ala Ala Thr Gly Val Asp Ala Ile Cys
    13055            13060              13065

Thr His His Leu Asn Pro Gln Ser Pro Gly Leu Asp Arg Glu Gln
    13070            13075              13080

Leu Tyr Trp Gln Leu Ser Gln Met Thr Asn Gly Ile Lys Glu Leu
    13085            13090              13095

Gly Pro Tyr Thr Leu Asp Arg Asn Ser Leu Tyr Val Asn Gly Phe
    13100            13105              13110

Thr His Arg Ser Ser Gly Leu Thr Thr Ser Thr Pro Trp Thr Ser
    13115            13120              13125

Thr Val Asp Leu Gly Thr Ser Gly Thr Pro Ser Pro Val Pro Ser
    13130            13135              13140

Pro Thr Thr Thr Gly Pro Leu Leu Val Pro Phe Thr Leu Asn Phe
    13145            13150              13155

Thr Ile Thr Asn Leu Gln Tyr Glu Glu Asn Met Gly His Pro Gly
    13160            13165              13170

Ser Arg Lys Phe Asn Ile Thr Glu Ser Val Leu Gln Gly Leu Leu
    13175            13180              13185

Lys Pro Leu Phe Lys Ser Thr Ser Val Gly Pro Leu Tyr Ser Gly
    13190            13195              13200

Cys Arg Leu Thr Leu Leu Arg Pro Glu Lys Asp Gly Val Ala Thr
    13205            13210              13215

Arg Val Asp Ala Ile Cys Thr His Arg Pro Asp Pro Lys Ile Pro
    13220            13225              13230

Gly Leu Asp Arg Gln Gln Leu Tyr Trp Glu Leu Ser Gln Leu Thr
    13235            13240              13245

His Ser Ile Thr Glu Leu Gly Pro Tyr Thr Leu Asp Arg Asp Ser
13265                13270                13275

Leu Tyr Val Asn Gly Phe Thr Gln Arg Ser Ser Val Pro Thr Thr
13280                13285                13290

Ser Thr Pro Gly Thr Phe Thr Val Gln Pro Glu Thr Ser Glu Thr
13295                13300                13305

Pro Ser Ser Leu Pro Gly Pro Thr Ala Thr Gly Pro Val Leu Leu
13310                13315                13320

Pro Phe Thr Leu Asn Phe Thr Ile Thr Asn Leu Gln Tyr Glu Glu
13325                13330                13335

Asp Met Arg Arg Pro Gly Ser Arg Lys Phe Asn Thr Thr Glu Arg
13340                13345                13350

Val Leu Gln Gly Leu Leu Met Pro Leu Phe Lys Asn Thr Ser Val
13355                13360                13365

Ser Ser Leu Tyr Ser Gly Cys Arg Leu Thr Leu Leu Arg Pro Glu
13370                13375                13380

Lys Asp Gly Ala Ala Thr Arg Val Asp Ala Val Cys Thr His Arg
13385                13390                13395

Pro Asp Pro Lys Ser Pro Gly Leu Asp Arg Glu Arg Leu Tyr Trp
13400                13405                13410

Lys Leu Ser Gln Leu Thr His Gly Ile Thr Glu Leu Gly Pro Tyr
13415                13420                13425

Thr Leu Asp Arg His Ser Leu Tyr Val Asn Gly Phe Thr His Gln
13430                13435                13440

Ser Ser Met Thr Thr Thr Arg Thr Pro Asp Thr Ser Thr Met His
13445                13450                13455

Leu Ala Thr Ser Arg Thr Pro Ala Ser Leu Ser Gly Pro Met Thr
13460                13465                13470

Ala Ser Pro Leu Leu Val Leu Phe Thr Ile Asn Phe Thr Ile Thr
13475                13480                13485

Asn Leu Arg Tyr Glu Glu Asn Met His His Pro Gly Ser Arg Lys
13490                13495                13500

Phe Asn Thr Thr Glu Arg Val Leu Gln Gly Leu Leu Arg Pro Val
13505                13510                13515

Phe Lys Asn Thr Ser Val Gly Pro Leu Tyr Ser Gly Cys Arg Leu
13520                13525                13530

Thr Leu Leu Arg Pro Lys Lys Asp Gly Ala Ala Thr Lys Val Asp
13535                13540                13545

Ala Ile Cys Thr Tyr Arg Pro Asp Pro Lys Ser Pro Gly Leu Asp
13550                13555                13560

Arg Glu Gln Leu Tyr Trp Glu Leu Ser Gln Leu Thr His Ser Ile
13565                13570                13575

Thr Glu Leu Gly Pro Tyr Thr Leu Asp Arg Asp Ser Leu Tyr Val
13580                13585                13590

Asn Gly Phe Thr Gln Arg Ser Ser Val Pro Thr Thr Ser Ile Pro
13595                13600                13605

Gly Thr Pro Thr Val Asp Leu Gly Thr Ser Gly Thr Pro Val Ser
13610                13615                13620

Lys Pro Gly Pro Ser Ala Ala Ser Pro Leu Leu Val Leu Phe Thr
13625                13630                13635

Leu Asn Phe Thr Ile Thr Asn Leu Arg Tyr Glu Glu Asn Met Gln
13640                13645                13650

```
His Pro Gly Ser Arg Lys Phe Asn Thr Thr Glu Arg Val Leu Gln
    13655               13660               13665

Gly Leu Leu Arg Ser Leu Phe Lys Ser Thr Ser Val Gly Pro Leu
    13670               13675               13680

Tyr Ser Gly Cys Arg Leu Thr Leu Leu Arg Pro Glu Lys Asp Gly
    13685               13690               13695

Thr Ala Thr Gly Val Asp Ala Ile Cys Thr His His Pro Asp Pro
    13700               13705               13710

Lys Ser Pro Arg Leu Asp Arg Glu Gln Leu Tyr Trp Glu Leu Ser
    13715               13720               13725

Gln Leu Thr His Asn Ile Thr Glu Leu Gly Pro Tyr Ala Leu Asp
    13730               13735               13740

Asn Asp Ser Leu Phe Val Asn Gly Phe Thr His Arg Ser Ser Val
    13745               13750               13755

Ser Thr Thr Ser Thr Pro Gly Thr Pro Thr Val Tyr Leu Gly Ala
    13760               13765               13770

Ser Lys Thr Pro Ala Ser Ile Phe Gly Pro Ser Ala Ala Ser His
    13775               13780               13785

Leu Leu Ile Leu Phe Thr Leu Asn Phe Thr Ile Thr Asn Leu Arg
    13790               13795               13800

Tyr Glu Glu Asn Met Trp Pro Gly Ser Arg Lys Phe Asn Thr Thr
    13805               13810               13815

Glu Arg Val Leu Gln Gly Leu Leu Arg Pro Leu Phe Lys Asn Thr
    13820               13825               13830

Ser Val Gly Pro Leu Tyr Ser Gly Cys Arg Leu Thr Leu Leu Arg
    13835               13840               13845

Pro Glu Lys Asp Gly Glu Ala Thr Gly Val Asp Ala Ile Cys Thr
    13850               13855               13860

His Arg Pro Asp Pro Thr Gly Pro Gly Leu Asp Arg Glu Gln Leu
    13865               13870               13875

Tyr Leu Glu Leu Ser Gln Leu Thr His Ser Ile Thr Glu Leu Gly
    13880               13885               13890

Pro Tyr Thr Leu Asp Arg Asp Ser Leu Tyr Val Asn Gly Phe Thr
    13895               13900               13905

His Arg Ser Ser Val Pro Thr Thr Ser Thr Gly Val Val Ser Glu
    13910               13915               13920

Glu Pro Phe Thr Leu Asn Phe Thr Ile Asn Asn Leu Arg Tyr Met
    13925               13930               13935

Ala Asp Met Gly Gln Pro Gly Ser Leu Lys Phe Asn Ile Thr Asp
    13940               13945               13950

Asn Val Met Gln His Leu Leu Ser Pro Leu Phe Gln Arg Ser Ser
    13955               13960               13965

Leu Gly Ala Arg Tyr Thr Gly Cys Arg Val Ile Ala Leu Arg Ser
    13970               13975               13980

Val Lys Asn Gly Ala Glu Thr Arg Val Asp Leu Leu Cys Thr Tyr
    13985               13990               13995

Leu Gln Pro Leu Ser Gly Pro Gly Leu Pro Ile Lys Gln Val Phe
    14000               14005               14010

His Glu Leu Ser Gln Gln Thr His Gly Ile Thr Arg Leu Gly Pro
    14015               14020               14025

Tyr Ser Leu Asp Lys Asp Ser Leu Tyr Leu Asn Gly Tyr Asn Glu
    14030               14035               14040

Pro Gly Pro Asp Glu Pro Pro Thr Thr Pro Lys Pro Ala Thr Thr
```

|  |  |  |  |  |  |  |  |  |  |
|---|---|---|---|---|---|---|---|---|---|
| 14045 | | | | 14050 | | | | 14055 | |
| Phe | Leu | Pro | Pro | Leu | Ser | Glu | Ala | Thr | Thr | Ala | Met | Gly | Tyr | His |
| 14060 | | | | 14065 | | | | 14070 | |
| Leu | Lys | Thr | Leu | Thr | Leu | Asn | Phe | Thr | Ile | Ser | Asn | Leu | Gln | Tyr |
| 14075 | | | | 14080 | | | | 14085 | |
| Ser | Pro | Asp | Met | Gly | Lys | Gly | Ser | Ala | Thr | Phe | Asn | Ser | Thr | Glu |
| 14090 | | | | 14095 | | | | 14100 | |
| Gly | Val | Leu | Gln | His | Leu | Leu | Arg | Pro | Leu | Phe | Gln | Lys | Ser | Ser |
| 14105 | | | | 14110 | | | | 14115 | |
| Met | Gly | Pro | Phe | Tyr | Leu | Gly | Cys | Gln | Leu | Ile | Ser | Leu | Arg | Pro |
| 14120 | | | | 14125 | | | | 14130 | |
| Glu | Lys | Asp | Gly | Ala | Ala | Thr | Gly | Val | Asp | Thr | Thr | Cys | Thr | Tyr |
| 14135 | | | | 14140 | | | | 14145 | |
| His | Pro | Asp | Pro | Val | Gly | Pro | Gly | Leu | Asp | Ile | Gln | Gln | Leu | Tyr |
| 14150 | | | | 14155 | | | | 14160 | |
| Trp | Glu | Leu | Ser | Gln | Leu | Thr | His | Gly | Val | Thr | Gln | Leu | Gly | Phe |
| 14165 | | | | 14170 | | | | 14175 | |
| Tyr | Val | Leu | Asp | Arg | Asp | Ser | Leu | Phe | Ile | Asn | Gly | Tyr | Ala | Pro |
| 14180 | | | | 14185 | | | | 14190 | |
| Gln | Asn | Leu | Ser | Ile | Arg | Gly | Glu | Tyr | Gln | Ile | Asn | Phe | His | Ile |
| 14195 | | | | 14200 | | | | 14205 | |
| Val | Asn | Trp | Asn | Leu | Ser | Asn | Pro | Asp | Pro | Thr | Ser | Ser | Glu | Tyr |
| 14210 | | | | 14215 | | | | 14220 | |
| Ile | Thr | Leu | Leu | Arg | Asp | Ile | Gln | Asp | Lys | Val | Thr | Thr | Leu | Tyr |
| 14225 | | | | 14230 | | | | 14235 | |
| Lys | Gly | Ser | Gln | Leu | His | Asp | Thr | Phe | Arg | Phe | Cys | Leu | Val | Thr |
| 14240 | | | | 14245 | | | | 14250 | |
| Asn | Leu | Thr | Met | Asp | Ser | Val | Leu | Val | Thr | Val | Lys | Ala | Leu | Phe |
| 14255 | | | | 14260 | | | | 14265 | |
| Ser | Ser | Asn | Leu | Asp | Pro | Ser | Leu | Val | Glu | Gln | Val | Phe | Leu | Asp |
| 14270 | | | | 14275 | | | | 14280 | |
| Lys | Thr | Leu | Asn | Ala | Ser | Phe | His | Trp | Leu | Gly | Ser | Thr | Tyr | Gln |
| 14285 | | | | 14290 | | | | 14295 | |
| Leu | Val | Asp | Ile | His | Val | Thr | Glu | Met | Glu | Ser | Ser | Val | Tyr | Gln |
| 14300 | | | | 14305 | | | | 14310 | |
| Pro | Thr | Ser | Ser | Ser | Ser | Thr | Gln | His | Phe | Tyr | Leu | Asn | Phe | Thr |
| 14315 | | | | 14320 | | | | 14325 | |
| Ile | Thr | Asn | Leu | Pro | Tyr | Ser | Gln | Asp | Lys | Ala | Gln | Pro | Gly | Thr |
| 14330 | | | | 14335 | | | | 14340 | |
| Thr | Asn | Tyr | Gln | Arg | Asn | Lys | Arg | Asn | Ile | Glu | Asp | Ala | Leu | Asn |
| 14345 | | | | 14350 | | | | 14355 | |
| Gln | Leu | Phe | Arg | Asn | Ser | Ser | Ile | Lys | Ser | Tyr | Phe | Ser | Asp | Cys |
| 14360 | | | | 14365 | | | | 14370 | |
| Gln | Val | Ser | Thr | Phe | Arg | Ser | Val | Pro | Asn | Arg | His | His | Thr | Gly |
| 14375 | | | | 14380 | | | | 14385 | |
| Val | Asp | Ser | Leu | Cys | Asn | Phe | Ser | Pro | Leu | Ala | Arg | Arg | Val | Asp |
| 14390 | | | | 14395 | | | | 14400 | |
| Arg | Val | Ala | Ile | Tyr | Glu | Glu | Phe | Leu | Arg | Met | Thr | Arg | Asn | Gly |
| 14405 | | | | 14410 | | | | 14415 | |
| Thr | Gln | Leu | Gln | Asn | Phe | Thr | Leu | Asp | Arg | Ser | Ser | Val | Leu | Val |
| 14420 | | | | 14425 | | | | 14430 | |
| Asp | Gly | Tyr | Ser | Pro | Asn | Arg | Asn | Glu | Pro | Leu | Thr | Gly | Asn | Ser |
| 14435 | | | | 14440 | | | | 14445 | |

Asp Leu    Pro Phe Trp Ala Val    Ile Leu Ile Gly Leu    Ala Gly Leu
       14450              14455              14460

Leu Gly    Val Ile Thr Cys Leu    Ile Cys Gly Val Leu    Val Thr Thr
       14465              14470              14475

Arg Arg    Arg Lys Lys Glu Gly    Glu Tyr Asn Val Gln    Gln Gln Cys
       14480              14485              14490

Pro Gly    Tyr Tyr Gln Ser His    Leu Asp Leu Glu Asp    Leu Gln
       14495              14500              14505

<210> SEQ ID NO 14
<211> LENGTH: 24
<212> TYPE: PRT
<213> ORGANISM: Artificial Sequence
<220> FEATURE:
<223> OTHER INFORMATION: Synthetic

<400> SEQUENCE: 14

Phe Trp Ala Val Ile Leu Ile Gly Leu Ala Gly Leu Leu Gly Leu Ile
1               5                   10                  15

Thr Cys Leu Ile Cys Gly Val Leu
            20

<210> SEQ ID NO 15
<211> LENGTH: 32
<212> TYPE: PRT
<213> ORGANISM: Artificial Sequence
<220> FEATURE:
<223> OTHER INFORMATION: Synthetic

<400> SEQUENCE: 15

Lys Ser Tyr Phe Ser Asp Cys Gln Val Ser Thr Phe Arg Ser Val Pro
1               5                   10                  15

Asn Arg His His Thr Gly Val Asp Ser Leu Cys Asn Phe Ser Pro Leu
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Synthetic

<400> SEQUENCE: 16

Val Thr Thr Arg Arg Lys Lys Glu Gly Glu Tyr Asn Val Gln Gln Gln
1               5                   10                  15

Gln Cys Pro Gly Tyr Tyr Gln Ser His Leu Asp Leu Glu Asp Leu Gln
            20                  25                  30

<210> SEQ ID NO 17
<211> LENGTH: 58
<212> TYPE: PRT
<213> ORGANISM: Artificial Sequence
<220> FEATURE:
<223> OTHER INFORMATION: Synthetic

<400> SEQUENCE: 17

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

```
Glu Pro Leu Thr Gly Asn Ser Asp Leu Pro
    50                  55

<210> SEQ ID NO 18
<211> LENGTH: 17
<212> TYPE: PRT
<213> ORGANISM: Artificial Sequence
<220> FEATURE:
<223> OTHER INFORMATION: Synthetic

<400> SEQUENCE: 18

Val Thr Thr Arg Arg Lys Lys Glu Gly Glu Tyr Asn Val Gln Gln
1               5                   10                  15

Gln

<210> SEQ ID NO 19
<211> LENGTH: 21
<212> TYPE: PRT
<213> ORGANISM: Artificial Sequence
<220> FEATURE:
<223> OTHER INFORMATION: Synthetic

<400> SEQUENCE: 19

Cys Gln Val Ser Thr Phe Arg Ser Val Pro Asn Arg His His Thr Gly
1               5                   10                  15

Val Asp Ser Leu Cys
            20

<210> SEQ ID NO 20
<211> LENGTH: 18
<212> TYPE: PRT
<213> ORGANISM: Artificial Sequence
<220> FEATURE:
<223> OTHER INFORMATION: Synthetic

<400> SEQUENCE: 20

Leu Val Thr Thr Arg Arg Arg Lys Lys Glu Gly Glu Tyr Asn Val Gln
1               5                   10                  15

Gln Gln

<210> SEQ ID NO 21
<211> LENGTH: 18
<212> TYPE: PRT
<213> ORGANISM: Mus musculus

<400> SEQUENCE: 21

Thr Leu Asp Arg Lys Ser Val Phe Val Asp Gly Tyr Ser Gln Asn Arg
1               5                   10                  15

Asp Asp

<210> SEQ ID NO 22
<211> LENGTH: 33
<212> TYPE: PRT
<213> ORGANISM: Mus musculus

<400> SEQUENCE: 22

Lys Ser Tyr Phe Ser Asp Cys Gln Val Leu Ala Phe Arg Ser Val Ser
1               5                   10                  15

Asn Asn Asn Asn His Thr Gly Val Asp Ser Leu Cys Asn Phe Ser Pro
                20                  25                  30

Leu
```

<210> SEQ ID NO 23
<211> LENGTH: 31
<212> TYPE: PRT
<213> ORGANISM: Mus musculus

<400> SEQUENCE: 23

Ser Leu Tyr Ser Asn Cys Arg Leu Ala Ser Leu Arg Pro Lys Lys Asn
1               5                   10                  15

Gly Thr Ala Thr Gly Val Asn Ala Ile Cys Ser Tyr His Gln Asn
            20                  25                  30

<210> SEQ ID NO 24
<211> LENGTH: 402
<212> TYPE: PRT
<213> ORGANISM: Mus musculus

<400> SEQUENCE: 24

His Leu Ile Arg Pro Leu Val Gln Asn Glu Ser Leu Tyr Ser Asn Cys
1               5                   10                  15

Arg Leu Ala Ser Leu Arg Pro Lys Lys Asn Gly Thr Ala Thr Gly Val
            20                  25                  30

Asn Ala Ile Cys Ser Tyr His Gln Asn Pro Asp His Pro Glu Leu Asp
        35                  40                  45

Thr Gln Glu Leu Tyr Thr Lys Leu Thr Gln Leu Thr Gln Gly Val Thr
    50                  55                  60

Gln Leu Gly Ser Tyr Met Leu Asp Gln Asn Ser Ile Tyr Val Asn Gly
65                  70                  75                  80

Tyr Val Pro Leu Asn Ile Thr Ile Gln Gly Lys Tyr Gln Leu Asn Phe
                85                  90                  95

Cys Ile Ile Asn Trp Asn Leu Asn Asn Thr Asp Pro Thr Ser Ser Glu
            100                 105                 110

Tyr Ile Thr Leu Glu Arg Asp Ile Glu Asp Lys Val Thr Thr Leu Tyr
        115                 120                 125

Thr Gly Ser Gln Leu Lys Glu Val Phe Gln Ser Cys Leu Val Thr Asn
    130                 135                 140

Met Thr Ser Gly Ser Thr Val Val Thr Leu Glu Ala Leu Phe Ser Ser
145                 150                 155                 160

His Leu Asp Pro Asn Leu Val Lys Gln Val Phe Leu Asn Lys Thr Leu
                165                 170                 175

Asn Ala Ser Ser His Trp Leu Gly Ala Thr Tyr Gln Leu Lys Asp Leu
            180                 185                 190

His Val Ile Asp Met Lys Thr Ser Ile Leu Pro Ala Glu Ile Pro
        195                 200                 205

Thr Thr Ser Ser Ser Gln His Phe Asn Leu Asn Phe Thr Ile Thr
    210                 215                 220

Asn Leu Pro Tyr Ser Gln Asp Ile Ala Gln Pro Ser Thr Lys Tyr
225                 230                 235                 240

Gln Gln Thr Lys Arg Ser Ile Glu Asn Ala Leu Asn Gln Leu Phe Arg
                245                 250                 255

Asn Ser Ser Ile Lys Ser Tyr Phe Ser Asp Cys Gln Val Leu Ala Phe
            260                 265                 270

Arg Ser Val Ser Asn Asn Asn His Thr Gly Val Asp Ser Leu Cys
        275                 280                 285

Asn Phe Ser Pro Leu Ala Arg Arg Val Asp Arg Val Ala Ile Tyr Glu
    290                 295                 300

```
Glu Phe Leu Arg Met Thr His Asn Gly Thr Gln Leu Leu Asn Phe Thr
305                 310                 315                 320

Leu Asp Arg Lys Ser Val Phe Val Asp Gly Tyr Ser Gln Asn Arg Asp
            325                 330                 335

Asp Asp Val Met Lys Asn Ser Gly Leu Pro Phe Trp Ala Ile Ile Leu
            340                 345                 350

Ile Cys Leu Ala Val Leu Leu Val Leu Ile Thr Cys Leu Met Cys Cys
            355                 360                 365

Phe Leu Val Thr Val Cys Arg Arg Lys Lys Glu Gly Asp Tyr Gln Val
            370                 375                 380

Gln Arg His Arg Leu Ala Tyr Tyr Leu Ser His Leu Asp Leu Arg Lys
385                 390                 395                 400

Leu Gln

<210> SEQ ID NO 25
<211> LENGTH: 400
<212> TYPE: PRT
<213> ORGANISM: Homo sapiens

<400> SEQUENCE: 25

His Leu Leu Arg Pro Leu Phe Gln Lys Ser Met Gly Pro Phe Tyr
1               5                   10                  15

Leu Gly Cys Gln Leu Ile Ser Leu Arg Pro Glu Lys Asp Gly Ala Ala
            20                  25                  30

Thr Gly Val Asp Thr Thr Cys Thr Tyr His Pro Asp Pro Val Gly Pro
            35                  40                  45

Gly Leu Asp Ile Gln Gln Leu Tyr Trp Glu Leu Ser Gln Leu Thr His
    50                  55                  60

Gly Val Thr Gln Leu Gly Phe Tyr Val Leu Asp Arg Asp Ser Leu Phe
65                  70                  75                  80

Ile Asn Gly Tyr Ala Pro Gln Asn Leu Ser Ile Arg Gly Glu Tyr Gln
                85                  90                  95

Ile Asn Phe His Ile Val Asn Trp Asn Leu Ser Asn Pro Asp Pro Thr
            100                 105                 110

Ser Ser Glu Tyr Ile Thr Leu Leu Arg Asp Ile Gln Asp Lys Val Thr
        115                 120                 125

Thr Leu Tyr Lys Gly Ser Gln Leu His Asp Thr Phe Arg Phe Cys Leu
130                 135                 140

Val Thr Asn Leu Thr Met Asp Ser Val Leu Val Thr Val Lys Ala Leu
145                 150                 155                 160

Phe Ser Ser Asn Leu Asp Pro Ser Leu Val Glu Gln Val Phe Leu Asp
                165                 170                 175

Lys Thr Leu Asn Ala Ser Phe His Trp Leu Gly Ser Thr Tyr Gln Leu
            180                 185                 190

Val Asp Ile His Val Thr Glu Met Glu Ser Ser Val Tyr Gln Pro Thr
        195                 200                 205

Ser Ser Ser Ser Thr Gln His Phe Tyr Leu Asn Phe Thr Ile Thr Asn
    210                 215                 220

Leu Pro Tyr Ser Gln Asp Lys Ala Gln Pro Gly Thr Thr Asn Tyr Gln
225                 230                 235                 240

Arg Asn Lys Arg Asn Ile Glu Asp Ala Leu Asn Gln Leu Phe Arg Asn
                245                 250                 255

Ser Ser Ile Lys Ser Tyr Phe Ser Asp Cys Gln Val Ser Thr Phe Arg
            260                 265                 270
```

```
Ser Val Pro Asn Arg His His Thr Gly Val Asp Ser Leu Cys Asn Phe
        275                 280                 285
Ser Pro Leu Ala Arg Arg Val Asp Arg Val Ala Ile Tyr Glu Glu Phe
        290                 295                 300
Leu Arg Met Thr Arg Asn Gly Thr Gln Leu Gln Asn Phe Thr Leu Asp
305                 310                 315                 320
Arg Ser Ser Val Leu Val Asp Gly Tyr Ser Pro Asn Arg Asn Glu Pro
                325                 330                 335
Leu Thr Gly Asn Ser Asp Leu Pro Phe Trp Ala Val Ile Leu Ile Gly
                340                 345                 350
Leu Ala Gly Leu Leu Gly Val Ile Thr Cys Leu Ile Cys Gly Val Leu
            355                 360                 365
Val Thr Thr Arg Arg Arg Lys Lys Glu Gly Glu Tyr Asn Val Gln Gln
370                 375                 380
Gln Cys Pro Gly Tyr Tyr Gln Ser His Leu Asp Leu Glu Asp Leu Gln
385                 390                 395                 400

<210> SEQ ID NO 26
<211> LENGTH: 360
<212> TYPE: DNA
<213> ORGANISM: Artificial Sequence
<220> FEATURE:
<223> OTHER INFORMATION: Synthetic

<400> SEQUENCE: 26
gaggtgaagc tggaggagtc aggtggagga ttggtgcagc ctaaaggatc attgaaactc      60
tcatgtgccg cctctggttt caccttcaat acctatgccg tgcactgggt ccgccaggct     120
ccaggaaagg gtatggaatg ggttgctcgc ataagaagta aaagtggaaa ttatgcaaca     180
tattatgccg attcagtgaa agacagattc accatctcca gaaatgattc acagagcatg     240
ctctatctgc aaatgaacaa cctgaaaact gaggacacag ccatatatta ctgtgtgaga     300
gcgggtaaca acgggccctt ccttactggg gccaaggga ccacggtcac cgtctcctca     360

<210> SEQ ID NO 27
<211> LENGTH: 120
<212> TYPE: PRT
<213> ORGANISM: Artificial Sequence
<220> FEATURE:
<223> OTHER INFORMATION: Synthetic

<400> SEQUENCE: 27

Glu Val Lys Leu Glu Glu Ser Gly Gly Gly Leu Val Gln Pro Lys Gly
1               5                   10                  15
Ser Leu Lys Leu Ser Cys Ala Ala Ser Gly Phe Thr Phe Asn Thr Tyr
            20                  25                  30
Ala Val His Trp Val Arg Gln Ala Pro Gly Lys Gly Met Glu Trp Val
        35                  40                  45
Ala Arg Ile Arg Ser Lys Ser Gly Asn Tyr Ala Thr Tyr Tyr Ala Asp
    50                  55                  60
Ser Val Lys Asp Arg Phe Thr Ile Ser Arg Asn Asp Ser Gln Ser Met
65                  70                  75                  80
Leu Tyr Leu Gln Met Asn Asn Leu Lys Thr Glu Asp Thr Ala Ile Tyr
                85                  90                  95
Tyr Cys Val Arg Ala Gly Asn Asn Gly Ala Phe Pro Tyr Trp Gly Gln
            100                 105                 110
Gly Thr Thr Val Thr Val Ser Ser
        115                 120
```

<210> SEQ ID NO 28
<211> LENGTH: 330
<212> TYPE: DNA
<213> ORGANISM: Artificial Sequence
<220> FEATURE:
<223> OTHER INFORMATION: Synthetic

<400> SEQUENCE: 28

```
gacattgagc tcacccagtc tccatcctca ctgtctgcat ctctgggagg cagagtcacc      60
atcacttgca aggctagcca agatattaag aagtatatag cttggtacca acacaagcct     120
ggaaaaactc ctcgactact catacatttc acatctacat tacagacagg catcccatca     180
aggttcagtg acgtgggtc tgggagagac tattccttca gcatcagcaa cctggagtct      240
gaagatattg caacttatta ttgtctacag tatgatagtc tgtacacgtt cggagggggg     300
accaagctgg agatcaaacg ggcggccgca                                      330
```

<210> SEQ ID NO 29
<211> LENGTH: 110
<212> TYPE: PRT
<213> ORGANISM: Artificial Sequence
<220> FEATURE:
<223> OTHER INFORMATION: Synthetic

<400> SEQUENCE: 29

```
Asp Ile Glu Leu Thr Gln Ser Pro Ser Ser Leu Ser Ala Ser Leu Gly
1               5                   10                  15

Gly Arg Val Thr Ile Thr Cys Lys Ala Ser Gln Asp Ile Lys Lys Tyr
            20                  25                  30

Ile Ala Trp Tyr Gln His Lys Pro Gly Lys Thr Pro Arg Leu Leu Ile
        35                  40                  45

His Phe Thr Ser Thr Leu Gln Thr Gly Ile Pro Ser Arg Phe Ser Gly
    50                  55                  60

Arg Gly Ser Gly Arg Asp Tyr Ser Phe Ser Ile Ser Asn Leu Glu Ser
65                  70                  75                  80

Glu Asp Ile Ala Thr Tyr Tyr Cys Leu Gln Tyr Asp Ser Leu Tyr Thr
                85                  90                  95

Phe Gly Gly Gly Thr Lys Leu Glu Ile Lys Arg Ala Ala Ala
            100                 105                 110
```

<210> SEQ ID NO 30
<211> LENGTH: 14
<212> TYPE: PRT
<213> ORGANISM: Artificial Sequence
<220> FEATURE:
<223> OTHER INFORMATION: Synthetic

<400> SEQUENCE: 30

```
Lys Ser Tyr Phe Ser Asp Cys Gln Val Asn Asn Phe Arg Ser
1               5                   10
```

<210> SEQ ID NO 31
<211> LENGTH: 18
<212> TYPE: PRT
<213> ORGANISM: Artificial Sequence
<220> FEATURE:
<223> OTHER INFORMATION: Synthetic

<400> SEQUENCE: 31

```
Thr Leu Asp Arg Ser Ser Val Leu Val Asp Gly Tyr Ser Gln Asn Arg
1               5                   10                  15
```

Asp Asp

<210> SEQ ID NO 32
<211> LENGTH: 57
<212> TYPE: DNA
<213> ORGANISM: Artificial Sequence
<220> FEATURE:
<223> OTHER INFORMATION: CD8 leader sequence

<400> SEQUENCE: 32
atggctctcc cagtgactgc cctactgctt cccctagcgc ttctcctgca tgcagag    57

<210> SEQ ID NO 33
<211> LENGTH: 335
<212> TYPE: DNA
<213> ORGANISM: Artificial Sequence
<220> FEATURE:
<223> OTHER INFORMATION: CD3 zeta chain intracellular domain

<400> SEQUENCE: 33
agagtgaagt tcagcaggag cgcagagccc ccgcgtacc agcagggcca gaaccagctc    60
tataacgagc tcaatctagg acgaagagag gagtacgatg ttttggacaa gagacgtggc    120
cgggaccctg agatgggggg aaagccgaga aggaagaacc ctcaggaagg cctgtacaat    180
gaactgcaga agataagat ggcggaggcc tacagtgaga ttgggatgaa aggcgagcgc    240
cggaggggca aggggcacga tggcctttac cagggtctca gtacagccac caaggacacc    300
tacgacgccc ttcacatgca ggccctgccc cctcg                              335

<210> SEQ ID NO 34
<211> LENGTH: 45
<212> TYPE: DNA
<213> ORGANISM: Artificial Sequence
<220> FEATURE:
<223> OTHER INFORMATION: (G4S)3 serine-glycine linker

<400> SEQUENCE: 34
ggtggaggtg gatcaggtgg aggtggatct ggtggaggtg gatct                    45

<210> SEQ ID NO 35
<211> LENGTH: 225
<212> TYPE: DNA
<213> ORGANISM: Artificial Sequence
<220> FEATURE:
<223> OTHER INFORMATION: CD8 transmembrane domain

<400> SEQUENCE: 35
gcggccgcac ccaccacgac gccagcgccg cgaccaccaa ccccggcgcc cacgatcgcg    60
tcgcagcccc tgtccctgcg cccagaggcg tgccggccag cggcgggggg cgcagtgcac    120
acgagggggc tggacttcgc ctgtgatatc tacatctggg cgcccttggc cgggacttgt    180
ggggtccttc tcctgtcact ggttatcacc ctttactgca accac                    225

<210> SEQ ID NO 36
<211> LENGTH: 223
<212> TYPE: DNA
<213> ORGANISM: Artificial Sequence
<220> FEATURE:
<223> OTHER INFORMATION: CD28 transmembrane + intracellular domains
      (-STOP)

<400> SEQUENCE: 36
caattgaagt tatgtatcct cctccttacc tagacaatga gaagagcaat ggaaccatta    60

```
tccatgtgaa agggaaacac ctttgtccaa gtccctatt tcccggacct tctaagccct    120
tttgggtgct ggtggtggtt ggtggagtcc tggcttgcta tagcttgcta gtaacagtgg    180
cctttattat tttctgggtg aggagtaaga ggagcaggct cct                     223
```

<210> SEQ ID NO 37
<211> LENGTH: 7726
<212> TYPE: DNA
<213> ORGANISM: Artificial Sequence
<220> FEATURE:
<223> OTHER INFORMATION: SFG_4H11z forward sequence

<400> SEQUENCE: 37

```
ggatccggat tagtccaatt tgttaaagac aggatatcag tggtccaggc tctagttttg     60
actcaacaat atcaccagct gaagcctata gagtacgagc catagataaa ataaaagatt    120
ttatttagtc tccagaaaaa ggggggaatg aaagacccca cctgtaggtt tggcaagcta    180
gcttaagtaa cgccattttg caaggcatgg aaaaatacat aactgagaat agagaagttc    240
agatcaaggt caggaacaga tggaacagct gaatatgggc caaacaggat atctgtggta    300
agcagttcct gccccggctc agggccaaga acagatggaa cagctgaata tgggccaaac    360
aggatatctg tggtaagcag ttcctgcccc ggctcagggc caagaacaga tggtccccag    420
atgcggtcca gccctcagca gtttctagag aaccatcaga tgtttccagg gtgccccaag    480
gacctgaaat gaccctgtgc cttatttgaa ctaaccaatc agttcgcttc tcgcttctgt    540
tcgcgcgctt ctgctcccg agctcaataa aagagcccac aaccctcac tcggggcgcc    600 agtcctccga ttgactgagt cgcccgggta cccgtgtatc aataaaccc tcttgcagtt    660 gcatccgact tgtggtctcg ctgttccttg ggagggtctc ctctgagtga ttgactaccc    720
gtcagcgggg gtcttcaca catgcagcat gtatcaaaat taatttggtt ttttttctta    780
agtatttaca ttaaatggcc atagtactta aagttacatt ggcttccttg aaataaacat    840
ggagtattca gaatgtgtca taaatatttc taattttaag atagtatctc cattggcttt    900 ctacttttc ttttattttt ttttgtcctc tgtcttccat ttgttgttgt tgttgtttgt    960
ttgtttgttt gttggttggt tggttaattt ttttttaaag atcctacact atagttcaag   1020
ctagactatt agctactctg taacccaggg tgaccttgaa gtcatgggta gcctgctgtt   1080
ttagccttcc cacatctaag attacaggta tgagctatca ttttttggtat attgattgat   1140 tgattgattg atgtgtgtgt gtgtgattgt gtttgtgtgt gtgactgtga aaatgtgtgt   1200
atgggtgtgt gtgaatgtgt gtatgtatgt gtgtgtgtga gtgtgtgtgt gtgtgtgtgc   1260
atgtgtgtgt gtgtgactgt gtctatgtgt atgactgtgt gtgtgtgtgt gtgtgtgtgt   1320
gtgtgtgtgt gtgtgtgtgt gttgtgaaaa aatattctat ggtagtgaga gccaacgctc   1380
cggctcaggt gtcaggttgg ttttgagac agagtctttc acttagcttg gaattcactg   1440
gccgtcgttt tacaacgtcg tgactgggaa accctggcg ttacccaact taatcgcctt   1500
gcagcacatc cccctttcgc cagctggcgt aatagcgaag aggcccgcac cgatcgccct   1560
tcccaacagt tgcgcagcct gaatggcgaa tggcgcctga tcggtatttt tctccttacg   1620
catctgtgcg gtatttcaca ccgcatatgg tgcactctca gtacaatctg ctctgatgcc   1680
gcatagttaa gccagccccg acacccgcca cacccgctg acgcgccctg acgggcttgt   1740 ctgctccccgg catccgctta cagacaagct gtgaccgtct ccgggagctg catgtgtcag   1800
aggttttcac cgtcatcacc gaaacgcgcg atgacgaaag gcctcgtga tacgcctatt   1860
```

```
tttataggtt aatgtcatga taataatggt ttcttagacg tcaggtggca cttttcgggg    1920
aaatgtgcgc ggaacccta tttgtttatt tttctaaata cattcaaata tgtatccgct    1980
catgagacaa taaccctgat aaatgcttca ataatattga aaaggaaga gtatgagtat    2040 tcaacatttc cgtgtcgccc ttattccctt ttttgcggca ttttgccttc ctgtttttgc    2100
tcacccagaa acgctggtga agtaaaaga tgctgaagat cagttgggtg cacgagtggg    2160
ttacatcgaa ctggatctca acagcggtaa gatccttgag agttttcgcc ccgaagaacg    2220
ttttccaatg atgagcactt ttaaagttct gctatgtggc gcggtattat cccgtattga    2280
cgccgggcaa gagcaactcg gtcgccgcat acactattct cagaatgact tggttgagta    2340
ctcaccagtc acagaaaagc atcttacgga tggcatgaca gtaagagaat tatgcagtgc    2400
tgccataacc atgagtgata acactgcggc caacttactt ctgacaacga tcggaggacc    2460
gaaggagcta accgcttttt tgcacaacat ggggatcat gtaactcgcc ttgatcgttg    2520
ggaaccggag ctgaatgaag ccataccaaa cgacgagcgt gacaccacga tgcctgtagc    2580
aatggcaaca acgttgcgca aactattaac tggcgaacta cttactctag cttcccggca    2640
acaattaata gactggatgg aggcggataa agttgcagga ccacttctgc gctcggccct    2700
tccggctggc tggtttattg ctgataaatc tggagccggt gagcgtgggt ctcgcggtat    2760
cattgcagca ctggggccag atggtaagcc ctcccgtatc gtagttatct acacgacggg    2820
gagtcaggca actatggatg aacgaaatag acagatcgct gagataggtg cctcactgat    2880
taagcattgg taactgtcag accaagttta ctcatatata ctttagattg atttaaaact    2940 tcattttaa tttaaaagga tctaggtgaa gatccttttt gataatctca tgaccaaaat    3000
cccttaacgt gagttttcgt tccactgagc gtcagacccc gtagaaaaga tcaaaggatc    3060
ttcttgagat cctttttttc tgcgcgtaat ctgctgcttg caaacaaaaa aaccaccgct    3120
accagcggtg gtttgtttgc cggatcaaga gctaccaact cttttttccga aggtaactgg    3180 cttcagcaga gcgcagatac caaatactgt ccttctagtg tagccgtagt taggccacca    3240
cttcaagaac tctgtagcac cgcctacata cctcgctctg ctaatcctgt taccagtggc    3300
tgctgccagt ggcgataagt cgtgtcttac cgggttggac tcaagacgat agttaccgga    3360
taaggcgcag cggtcgggct gaacggggggg ttcgtgcaca cagcccagct tggagcgaac    3420
gacctacacc gaactgagat acctacagcg tgagcattga aaagcgcca cgcttcccga    3480 agggagaaag gcggacaggt atccggtaag cggcagggtc ggaacaggag agcgcacgag    3540
ggagcttcca gggggaaacg cctggtatct ttatagtcct gtcgggtttc gccacctctg    3600
acttgagcgt cgatttttgt gatgctcgtc aggggggcgg agcctatgga aaaacgccag    3660
caacgcggcc ttttttacggt tcctggcctt ttgctggcct tttgctcaca tgttctttcc    3720
tgcgttatcc cctgattctg tggataaccg tattaccgcc tttgagtgag ctgataccgc    3780
tcgccgcagc cgaacgaccg agcgcagcga gtcagtgagc gaggaagcgg aagagcgccc    3840
aatacgcaaa ccgcctctcc ccgcgcgttg gccgattcat taatgcagct ggcacgacag    3900
gtttcccgac tggaaagcgg gcagtgagcg caacgcaatt aatgtgagtt agctcactca    3960
ttaggcaccc caggctttac actttatgct tccggctcgt atgttgtgtg gaattgtgag    4020
cggataacaa tttcacacag gaaacagcta tgaccatgat tacgccaagc tttgctctta    4080
ggagtttcct aatacatccc aaactcaaat atataaagca tttgacttgt tctatgccct    4140 aggggggcggg gggaagctaa gccagctttt tttaacattt aaaatgttaa ttccatttta    4200
aatgcacaga tgtttttatt tcataagggt ttcaatgtgc atgaatgctg caatattcct    4260
```

-continued

```
gttaccaaag ctagtataaa taaaaataga taaacgtgga aattacttag agtttctgtc    4320
attaacgttt ccttcctcag ttgacaacat aaatgcgctg ctgagcaagc cagtttgcat    4380
ctgtcaggat caatttccca ttatgccagt catattaatt actagtcaat tagttgattt    4440
ttatttttga catatacatg tgaatgaaag accccacctg taggtttggc aagctagctt    4500
aagtaacgcc attttgcaag gcatggaaaa atacataact gagaatagaa aagttcagat    4560
caaggtcagg aacagatgga acagctgaat atgggccaaa caggatatct gtggtaagca    4620
gttcctgccc cggctcaggg ccaagaacag atggaacagc tgaatatggg ccaaacagga    4680
tatctgtggt aagcagttcc tgccccggct cagggccaag aacagatggt ccccagatgc    4740
ggtccagccc tcagcagttt ctagagaacc atcagatgtt tccagggtgc cccaaggacc    4800
tgaaatgacc ctgtgcctta tttgaactaa ccaatcagtt cgcttctcgc ttctgttcgc    4860
gcgcttatgc tccccgagct caataaaaga gcccacaacc cctcactcgg ggcgccagtc    4920
ctccgattga ctgagtcgcc cgggtacccg tgtatccaat aaaccctctt gcagttgcat    4980
ccgacttgtg gtctcgctgt tccttgggag ggtctcctct gagtgattga ctacccgtca    5040
gcgggggtct ttcatttggg ggctcgtccg ggatcgggag accctgccc agggaccacc    5100
gacccaccac cgggaggtaa gctggccagc aacttatctg tgtctgtccg attgtctagt    5160
gtctatgact gattttatgc gcctgcgtcg gtactagtta gctaactagc tctgtatctg    5220
gcggacccgt ggtggaactg acgagttcgg aacacccggc cgcaaccctg ggagacgtcc    5280
cagggacttc gggggccgtt tttgtggccc gacctgagtc ctaaaatccc gatcgtttag    5340
gactctttgg tgcacccccc ttagaggagg gatatgtggt tctggtagga gacgagaacc    5400
taaaacagtt cccgcctccg tctgaatttt tgctttcggt ttgggaccga agccgcgccg    5460
cgcgtcttgt ctgctgcagc atcgttctgt gttgtctctg tctgactgtg tttctgtatt    5520
tgtctgaaaa tatgggcccg ggctagactg ttaccactcc cttaagtttg accttaggtc    5580
actggaaaga tgtcgagcgg atcgctcaca accagtcggt agatgtcaag aagagacgtt    5640
gggttacctt ctgctctgca gaatggccaa cctttaacgt cggatggccg cgagacggca    5700
cctttaaccg agacctcatc acccaggtta agatcaaggt cttttcacct ggcccgcatg    5760
gacacccaga ccaggtcccc tacatcgtga cctgggaagc cttggctttt gacccccctc    5820
cctgggtcaa gccctttgta caccctaagc ctccgcctcc tcttcctcca tccgccccgt    5880
ctctcccct tgaacctcct cgttcgaccc cgcctcgatc ctcctttat ccagccctca    5940
ctccttctct aggcgccccc atatggccat atgagatctt atatgggca ccccgcccc    6000
ttgtaaactt ccctgaccct gacatgacaa gagttactaa cagcccctct ctccaagctc    6060
acttacaggc tctctactta gtccagcacg aagtctggag acctctggcg gcagcctacc    6120
aagaacaact ggaccgaccg gtggtacctc acccttaccg agtcggcgac acagtgtggg    6180
tccgccgaca ccagactaag aacctagaac ctcgctggaa aggaccttac acagtcctgc    6240
tgaccacccc caccgccctc aaagtagacg gcatcgcagc ttggatacac gccgcccacg    6300
tgaaggctgc cgaccccggg ggtgaccat cctctagact gccatggctc tcccagtgac    6360
tgccctactg cttcccctag cgcttctcct gcatgcagag gtgaagctgc aggagtcagg    6420
gggaggcttc gtgaagcctg gagggtccct caaagtctcc tgtgcagcct ctggattcac    6480
tttcagtagc tatgccatgt cctgggttcg cctgagtccg gagatgaggc tggagtgggt    6540
cgcaaccatt agcagtgctg gtggttacat cttctattct gacagtgtgc agggacgatt    6600
```

```
caccatttcc agagacaatg ccaagaacac cctgcacctg caaatgggca gtctgaggtc    6660
tggggacacg gccatgtatt actgtgcaag gcagggattt ggtaactacg gtgattacta    6720
tgctatggac tactggggcc aagggaccac ggtcaccgtc tcctcaggtg gaggtggatc    6780
aggtggaggt ggatctggtg gaggtggatc tgacattgag ctcacccagt ctccatcctc    6840
cctggctgtg tcagcaggag agaaggtcac tatgagctgc aaatccagtc agagtctgct    6900
caacagtaga acccgaaaga accagttggc ttggtaccag caaaaaccag acagtctcc    6960 tgaactgctg atctactggg catccactag gcaatctgga gtccctgatc gcttcacagg    7020
cagtggatct gggacagatt tcactctcac catcagcagt gtgcaggctg aagacctggc    7080
agtttattac tgccagcaat cttataatct actcacgttc ggtcctggga ccaagctgga    7140
gatcaaacgg gcggccgcac ccaccacgac gccagcgccg cgaccaccaa ccccggcgcc    7200
cacgatcgcg tcgcagcccc tgtccctgcg cccagaggcg tgccggccag cggcgggggg    7260
cgcagtgcac acgagggggc tggacttcgc ctgtgatatc tacatctggg cgccttggc    7320 cgggacttgt ggggtccttc tcctgtcact ggttatcacc ctttactgca accacagagt    7380
gaagttcagc aggagcgcag agccccccgc gtaccagcag gccagaacc agctctataa    7440 cgagctcaat ctaggacgaa gagaggagta cgatgttttg acaagagac gtggccggga    7500 ccctgagatg gggggaaagc cgagaaggaa gaaccctcag gaaggcctgt acaatgaact    7560
gcagaaagat aagatggcgg aggcctacag tgagattggg atgaaaggcg agcgccggag    7620
gggcaagggg cacgatggcc tttaccaggg tctcagtaca gccaccaagg acacctacga    7680
cgcccttcac atgcaggccc tgccccctcg ctaacagcca ctcgag                  7726

<210> SEQ ID NO 38
<211> LENGTH: 7726
<212> TYPE: DNA
<213> ORGANISM: Artificial Sequence
<220> FEATURE:
<223> OTHER INFORMATION: SFG_4H11z reverse sequence

<400> SEQUENCE: 38
cctaggccta atcaggttaa acaatttctg tcctatagtc accaggtccg agatcaaaac     60
tgagttgtta tagtggtcga cttcggatat ctcatgctcg gtatctattt tatttttctaa   120 aataaatcag aggtcttttt cccccttac tttctggggt ggacatccaa accgttcgat    180
cgaattcatt gcggtaaaac gttccgtacc tttttatgta ttgactctta tctcttcaag    240
tctagttcca gtccttgtct accttgtcga cttatacccg gtttgtccta tagacaccat    300
tcgtcaagga cggggccgag tcccggttct tgtctacctt gtcgacttat acccggtttg   360
tcctatagac accattcgtc aaggacgggg ccgagtcccg gttcttgtct accagggggtc   420 tacgccaggt cgggagtcgt caaagatctc ttggtagtct acaaaggtcc cacggggttc    480
ctggacttta ctgggacacg gaataaactt gattggttag tcaagcgaag agcgaagaca    540
agcgcgcgaa gacgaggggc tcgagttatt ttctcgggtg ttggggagtg agcccgcgg    600 tcaggaggct aactgactca gcgggcccat gggcacatag gttatttggg agaacgtcaa    660
cgtaggctga acaccagagc gacaaggaac cctcccagag gagactcact aactgatggg    720
cagtcgcccc cagaaagtgt gtacgtcgta catagtttta attaaaccaa aaaaaagaat    780
tcataaatgt aatttaccgg tatcatgaat ttcaatgtaa ccgaaggaac tttatttgta    840
cctcataagt cttacacagt atttataaag attaaaattc tatcatagag gtaaccgaaa    900
gatgaaaaag aaaataaaaa aaacaggag acagaaggta aacaacaaca acaacaaaca    960
```

```
aacaaacaaa caaccaacca accaattaaa aaaaaatttc taggatgtga tatcaagttc    1020
gatctgataa tcgatgagac attgggtccc actggaactt cagtacccat cggacgacaa    1080
aatcggaagg gtgtagattc taatgtccat actcgatagt aaaaaccata taactaacta    1140
actaactaac tacacacaca cacactaaca caaacacaca cactgacact tttacacaca    1200
tacccacaca cacttacaca catacataca cacacacact cacacacaca cacacacacg    1260
tacacacaca cacactgaca cagatacaca tactgacaca cacacacaca cacacacaca    1320
cacacacaca cacacacaca caacactttt ttataagata ccatcactct cggttgcgag    1380
gccgagtcca cagtccaacc aaaaactctg tctcagaaag tgaatcgaac cttaagtgac    1440
cggcagcaaa atgttgcagc actgacccct ttgggaccgc aatgggttga attagcggaa    1500
cgtcgtgtag ggggaaagcg gtcgaccgca ttatcgcttc tccgggcgtg gctagcggga    1560
agggttgtca acgcgtcgga cttaccgctt accgcggact acgccataaa agaggaatgc    1620
gtagacacgc cataaagtgt ggcgtatacc acgtgagagt catgttagac gagactacgg    1680
cgtatcaatt cggtcggggc tgtgggcggt tgtgggcgac tgcgcgggac tgcccgaaca    1740
gacgagggcc gtaggcgaat gtctgttcga cactggcaga ggccctcgac gtacacagtc    1800
tccaaaagtg gcagtagtgg cttttgcgcgc tactgctttc ccggagcact atgcggataa    1860
aaatatccaa ttacagtact attattacca aagaatctgc agtccaccgt gaaaagcccc    1920
tttacacgcg ccttggggat aaacaaataa aaagatttat gtaagtttat acataggcga    1980
gtactctgtt attgggacta tttacgaagt tattataact ttttccttct catactcata    2040
agttgtaaag gcacagcggg aataagggaa aaaacgccgt aaaacggaag gacaaaaacg    2100
agtgggtctt tgcgaccact ttcattttct acgacttcta gtcaacccac gtgctcaccc    2160
aatgtagctt gacctagagt tgtcgccatt ctaggaactc tcaaaagcgg ggcttcttgc    2220
aaaaggttac tactcgtgaa aatttcaaga cgatacaccg cgccataata gggcataact    2280
gcggcccgtt ctcgttgagc cagcggcgta tgtgataaga gtcttactga accaactcat    2340
gagtggtcag tgtctttttcg tagaatgcct accgtactgt cattctctta atacgtcacg    2400
acggtattgg tactcactat tgtgacgccg gttaatgaa gactgttgct agcctcctgg    2460
cttcctcgat tggcgaaaaa acgtgttgta cccctagta cattgagcgg aactagcaac    2520
ccttggcctc gacttacttc ggtatggttt gctgctcgca ctgtggtgct acggacatcg    2580
ttaccgttgt tgcaacgcgt ttgataattg accgcttgat gaatgagatc gaagggccgt    2640
tgttaattat ctgacctacc tccgcctatt tcaacgtcct ggtgaagacg cgagccggga    2700
aggccgaccg accaaataac gactatttag acctcggcca ctcgcaccca gagcgccata    2760
gtaacgtcgt gaccccggtc taccattcgg gagggcatag catcaataga tgtgctgccc    2820
ctcagtccgt tgatacctac ttgctttatc tgtctagcga ctctatccac ggagtgacta    2880
attcgtaacc attgacagtc tggttcaaat gagtatatat gaaatctaac taaattttga    2940
agtaaaaatt aaattttcct agatccactt ctaggaaaaa ctattagagt actggtttta    3000
gggaattgca ctcaaaagca aggtgactcg cagtctgggg catcttttct agtttcctag    3060
aagaactcta ggaaaaaaag acgcgcatta gacgacgaac gtttgttttt ttggtggcga    3120
tggtcgccac caaacaaacg gcctagttct cgatggttga gaaaaaggct tccattgacc    3180
gaagtcgtct cgcgtctatg gtttatgaca ggaagatcac atcggcatca atccggtggt    3240
gaagttcttg agacatcgtg gcggatgtat ggagcgagac gattaggaca atggtcaccg    3300
```

```
acgacggtca ccgctattca gcacagaatg gcccaacctg agttctgcta tcaatggcct    3360
attccgcgtc gccagcccga cttgccccccc aagcacgtgt gtcgggtcga acctcgcttg    3420
ctggatgtgg cttgactcta tggatgtcgc actcgtaact cttcgcggt gcgaagggct    3480 tccctctttc cgcctgtcca taggccattc gccgtcccag ccttgtcctc tcgcgtgctc    3540
cctcgaaggt ccccctttgc ggaccataga aatatcagga cagcccaaag cggtggagac    3600
tgaactcgca gctaaaaaca ctacgagcag tccccccgcc tcggatacct tttttgcggtc    3660 gttgcgccgg aaaaatgcca aggaccggaa aacgaccgga aaacgagtgt acaagaaagg    3720
acgcaatagg ggactaagac acctattggc ataatggcgg aaactcactc gactatggcg    3780
agcggcgtcg gcttgctggc tcgcgtcgct cagtcactcg ctccttcgcc ttctcgcggg    3840
ttatgcgttt ggcggagagg ggcgcgcaac cggctaagta attacgtcga ccgtgctgtc    3900
caaagggctg acctttcgcc cgtcactcgc gttgcgttaa ttacactcaa tcgagtgagt    3960
aatccgtggg gtccgaaatg tgaaatacga aggccgagca tacaacacac cttaacactc    4020
gcctattgtt aaagtgtgtc ctttgtcgat actggtacta atgcggttcg aaacgagaat    4080
cctcaaagga ttatgtaggg tttgagttta tatatttcgt aaactgaaca agatacggga    4140 tccccccgccc cccttcgatt cggtcgaaaa aaattgtaaa ttttacaatt aaggtaaaat    4200
ttacgtgtct acaaaaataa agtattccca aagttacacg tacttacgac gttataagga    4260
caatggtttc gatcatattt attttatct atttgcacct ttaatgaatc tcaaagacag    4320
taattgcaaa ggaaggagtc aactgttgta tttacgcgac gactcgttcg gtcaaacgta    4380
gacagtccta gttaaagggt aatacggtca gtataattaa tgatcagtta atcaactaaa    4440
aataaaaact gtatatgtac acttactttc tggggtggac atccaaaccg ttcgatcgaa    4500
ttcattgcgg taaaacgttc cgtaccttt tatgtattga ctcttatctt ttcaagtcta    4560
gttccagtcc ttgtctacct tgtcgactta tacccggttt gtcctataga caccattcgt    4620
caaggacggg gccgagtccc ggttcttgtc taccttgtcg acttataccc ggtttgtcct    4680
atagacacca ttcgtcaagg acggggccga gtcccggttc ttgtctacca ggggtctacg    4740 ccaggtcgg agtcgtcaaa gatctcttgg tagtctacaa aggtcccacg gggttcctgg    4800
actttactgg gacacggaat aaacttgatt ggttagtcaa gcgaagagcg aagacaagcg    4860
cgcgaatacg aggggctcga gttattttct cgggtgttgg ggagtgagcc ccgcggtcag    4920
gaggctaact gactcagcgg gcccatgggc acataggtta tttgggagaa cgtcaacgta    4980
ggctgaacac cagagcgaca aggaaccctc ccagaggaga ctcactaact gatgggcagt    5040
cgcccccaga aagtaaaccc ccgagcaggc cctagccctc tggggacggg tccctggtgg    5100
ctgggtggtg gccctccatt cgaccggtcg ttgaatagac acagacaggc taacagatca    5160
cagatactga ctaaaatacg cggacgcagc catgatcaat cgattgatcg agacatagac    5220
cgcctgggca ccaccttgac tgctcaagcc ttgtgggccg gcgttgggac cctctgcagg    5280
gtccctgaag ccccccggcaa aaacaccggg ctggactcag gattttaggg ctagcaaatc    5340
ctgagaaacc acgtgggggg aatctcctcc ctatacacca agaccatcct ctgctcttgg    5400
attttgtcaa gggcggaggc agacttaaaa acgaaagcca aaccctggct tcggcgcggc    5460
gcgcagaaca gacgacgtcg tagcaagaca caacagagac agactgacac aaagacataa    5520
acagactttt atacccgggc ccgatctgac aatggtgagg gaattcaaac tggaatccag    5580
tgacctttct acagctcgcc tagcgagtgt tggtcagcca tctacagttc ttctctgcaa    5640
cccaatggaa gacgagacgt cttaccggtt ggaaattgca gcctaccggc gctctgccgt    5700
```

```
ggaaattggc tctggagtag tgggtccaat tctagttcca gaaaagtgga ccgggcgtac   5760
ctgtgggtct ggtccagggg atgtagcact ggacccttcg gaaccgaaaa ctgggggag    5820
ggacccagtt cgggaaacat gtgggattcg gaggcggagg agaaggaggt aggcggggca   5880
gagaggggga acttggagga gcaagctggg gcggagctag gagggaaata ggtcgggagt   5940
gaggaagaga tccgcggggg tataccggta tactctagaa tatacccgt ggggggcgggg  6000
aacatttgaa gggactggga ctgtactgtt ctcaatgatt gtcggggaga gaggttcgag   6060
tgaatgtccg agagatgaat caggtcgtgc ttcagacctc tggagaccgc cgtcggatgg   6120
ttcttgttga cctggctggc caccatggag tgggaatggc tcagccgctg tgtcacaccc   6180
aggcggctgt ggtctgattc ttggatcttg gagcgacctt tcctggaatg tgtcaggacg   6240
actggtgggg gtggcgggag tttcatctgc cgtagcgtcg aacctatgtg cggcgggtgc   6300
acttccgacg gctggggccc ccacctggta ggagatctga cggtaccgag agggtcactg   6360
acgggatgac gaaggggatc gcgaagagga cgtacgtctc cacttcgacg tcctcagtcc   6420
ccctccgaag cacttcggac ctcccaggga gtttcagagg acacgtcgga gacctaagtg   6480
aaagtcatcg atacggtaca ggacccaagc ggactcaggc tctactccg acctcaccca    6540
gcgttggtaa tcgtcacgac caccaatgta gaagataaga ctgtcacacg tccctgctaa   6600
gtggtaaagg tctctgttac ggttcttgtg ggacgtggac gtttaccgt cagactccag    6660
accctgtgc cggtacataa tgacacgttc cgtccctaaa ccattgatgc cactaatgat    6720
acgatacctg atgaccccgg ttccctggtg ccagtggcag aggagtccac ctccacctag   6780
tccacctcca cctagaccac ctccacctag actgtaactc gagtgggtca gaggtaggag   6840
ggaccgacac agtcgtcctc tcttccagtg atactcgacg tttaggtcag tctcagacga   6900
gttgtcatct tgggctttct tggtcaaccg aaccatggtc gttttggtc ctgtcagagg    6960
acttgacgac tagatgaccc gtaggtgatc cgttagacct cagggactag cgaagtgtcc   7020
gtcacctaga ccctgtctaa agtgagagtg gtagtcgtca cacgtccgac ttctggaccg   7080
tcaaataatg acgtcgtta gaatattaga tgagtgcaag ccaggaccct ggttcgacct    7140
ctagtttgcc cgccggcgtg ggtggtgctg cggtcgcggc gctggtggtt ggggccgcgg   7200
gtgctagcgc agcgtcgggg acagggacgc gggtctccgc acggccggtc gccgcccccc   7260
gcgtcacgtg tgctcccccg acctgaagcg gacactatag atgtagaccc gcgggaaccg   7320
gccctgaaca ccccaggaag aggacagtga ccaatagtgg gaaatgacgt tggtgtctca   7380
cttcaagtcg tcctcgcgtc tcgggggggcg catggtcgtc ccggtcttgg tcgagatatt   7440
gctcgagtta gatcctgctt ctctcctcat gctacaaaac ctgttctctg caccggccct   7500
gggactctac ccccctttcg gctcttcctt cttgggagtc cttccggaca tgttacttga   7560
cgtctttcta ttctaccgcc tccggatgtc actctaaccc tactttccgc tcgcggcctc   7620
cccgttcccc gtgctaccgg aaatggtccc agagtcatgt cggtggttcc tgtggatgct   7680
gcgggaagtg tacgtccggg acgggggagc gattgtcggt gagctc               7726
```

<210> SEQ ID NO 39
<211> LENGTH: 7831
<212> TYPE: DNA
<213> ORGANISM: Artificial Sequence
<220> FEATURE:
<223> OTHER INFORMATION: SFG_4H11-28z forward sequence
<400> SEQUENCE: 39

```
ggatccggat tagtccaatt tgttaaagac aggatatcag tggtccaggc tctagttttg        60
actcaacaat atcaccagct gaagcctata gagtacgagc catagataaa ataaaagatt       120
ttatttagtc tccagaaaaa gggggggaatg aaagacccca cctgtaggtt tggcaagcta      180
gcttaagtaa cgccattttg caaggcatgg aaaaatacat aactgagaat agagaagttc       240
agatcaaggt caggaacaga tggaacagct gaatatgggc caaacaggat atctgtggta       300
agcagttcct gccccggctc agggccaaga acagatggaa cagctgaata tgggccaaac       360
aggatatctg tggtaagcag ttcctgcccc ggctcagggc caagaacaga tggtccccag       420
atgcggtcca gccctcagca gtttctagag aaccatcaga tgtttccagg gtgccccaag       480
gacctgaaat gaccctgtgc cttatttgaa ctaaccaatc agttcgcttc tcgcttctgt       540
tcgcgcgctt ctgctcccg agctcaataa aagagcccac aacccctcac tcggggcgcc        600
agtcctccga ttgactgagt cgcccgggta cccgtgtatc aataaacccc tcttgcagtt       660
gcatccgact tgtggtctcg ctgttccttg ggagggtctc ctctgagtga ttgactaccc       720
gtcagcgggg gtctttcaca catgcagcat gtatcaaaat taatttggtt tttttttctta     780 agtatttaca ttaaatggcc atagtactta aagttacatt ggcttccttg aaataaacat       840
ggagtattca gaatgtgtca taaatatttc taattttaag atagtatctc cattggcttt       900 ctacttttc ttttatttt ttttgtcctc tgtcttccat ttgttgttgt tgttgtttgt         960
ttgtttgttt gttggttggt tggttaattt tttttaaag atcctacact atagttcaag        1020
ctagactatt agctactctg taacccaggg tgaccttgaa gtcatgggta gcctgctgtt       1080
ttagccttcc cacatctaag attacaggta tgagctatca ttttggtat attgattgat        1140 tgattgattg atgtgtgtgt gtgtgattgt gtttgtgtgt gtgactgtga aaatgtgtgt      1200
atgggtgtgt gtgaatgtgt gtatgtatgt gtgtgtgtga gtgtgtgtgt gtgtgtgtgc      1260
atgtgtgtgt gtgtgactgt gtctatgtgt atgactgtgt gtgtgtgtgt gtgtgtgtgt      1320
gtgtgtgtgt gtgtgtgtgt gttgtgaaaa aatattctat ggtagtgaga gccaacgctc      1380
cggctcaggt gtcaggttgg tttttgagac agagtctttc acttagcttg gaattcactg      1440
gccgtcgttt tacaacgtcg tgactgggaa accctggcg ttacccaact taatcgcctt       1500
gcagcacatc cccctttcgc cagctggcgt aatagcgaag aggcccgcac cgatcgccct      1560
tcccaacagt tgcgcagcct gaatggcgaa tggcgcctga tgcggtattt tctccttacg      1620
catctgtgcg gtatttcaca ccgcatatgg tgcactctca gtacaatctg ctctgatgcc      1680
gcatagttaa gccagccccg acacccgcca cacccgctg acgcgccctg acgggcttgt       1740
ctgctcccgg catccgctta cagacaagct gtgaccgtct ccgggagctg catgtgtcag      1800
aggttttcac cgtcatcacc gaaacgcgcg atgacgaaag gcctcgtgat acgcctatt      1860 tttataggtt aatgtcatga taataatggt ttcttagacg tcaggtggca cttttcgggg     1920
aaatgtgcgc ggaacccctta tttgtttatt tttctaaata cattcaaata tgtatccgct    1980
catgagacaa taaccctgat aaatgcttca ataatattga aaaggaaga gtatgagtat      2040 tcaacatttc cgtgtcgccc ttattccctt ttttgcggca ttttgcttc ctgtttttgc       2100 tcacccagaa acgctggtga agtaaaaga tgctgaagat cagttgggtg cacgagtggg      2160
ttacatcgaa ctggatctca acagcggtaa gatccttgag agttttcgcc ccgaagaacg     2220
ttttccaatg atgagcactt ttaaagttct gctatgtggc gcggtattat cccgtattga    2280
cgccgggcaa gagcaactcg gtcgccgcat acactattct cagaatgact tggttgagta    2340
ctcaccagtc acagaaaagc atcttacgga tggcatgaca gtaagagaat tatgcagtgc    2400
```

```
tgccataacc atgagtgata acactgcggc caacttactt ctgacaacga tcggaggacc     2460
gaaggagcta accgcttttt tgcacaacat gggggatcat gtaactcgcc ttgatcgttg     2520
ggaaccggag ctgaatgaag ccataccaaa cgacgagcgt gacaccacga tgcctgtagc     2580 aatgcaaca acgttgcgca aactattaac tggcgaacta cttactctag cttcccggca     2640
acaattaata gactggatgg aggcggataa agttgcagga ccacttctgc gctcggccct     2700
tccggctggc tggtttattg ctgataaatc tggagccggt gagcgtgggt ctcgcggtat     2760
cattgcagca ctggggccag atggtaagcc ctcccgtatc gtagttatct acacgacggg     2820
gagtcaggca actatggatg aacgaaatag acagatcgct gagataggtg cctcactgat     2880
taagcattgg taactgtcag accaagttta ctcatatata ctttagattg atttaaaact     2940
tcatttttaa tttaaaagga tctaggtgaa gatcctttttt gataatctca tgaccaaaat     3000
cccttaacgt gagttttcgt tccactgagc gtcagacccc gtagaaaaga tcaaaggatc     3060
ttcttgagat cctttttttc tgcgcgtaat ctgctgcttg caaacaaaaa aaccaccgct     3120
accagcggtg gtttgtttgc cggatcaaga gctaccaact cttttttccga aggtaactgg     3180 cttcagcaga gcgcagatac caaatactgt ccttctagtg tagccgtagt taggccacca     3240
cttcaagaac tctgtagcac cgcctacata cctcgctctg ctaatcctgt taccagtggc     3300
tgctgccagt ggcgataagt cgtgtcttac cgggttggac tcaagacgat agttaccgga     3360
taaggcgcag cggtcgggct gaacggggggg ttcgtgcaca cagcccagct tggagcgaac     3420
gacctacacc gaactgagat acctacagcg tgagcattga gaaagcgcca cgcttcccga     3480
agggagaaag gcggacaggt atccggtaag cggcagggtc ggaacaggag agcgcacgag     3540
ggagcttcca gggggaaacg cctggtatct ttatagtcct gtcgggtttc gccacctctg     3600
acttgagcgt cgatttttgt gatgctcgtc aggggggcgg agcctatgga aaaacgccag     3660
caacgcggcc ttttacggt tcctggcctt ttgctggcct tttgctcaca tgttctttcc     3720
tgcgttatcc cctgattctg tggataaccg tattaccgcc tttgagtgag ctgataccgc     3780
tcgccgcagc cgaacgaccg agcgcagcga gtcagtgagc gaggaagcgg aagagcgccc     3840
aatacgcaaa ccgcctctcc ccgcgcgttg gccgattcat taatgcagct ggcacgacag     3900
gtttcccgac tggaaagcgg gcagtgagcg caacgcaatt aatgtgagtt agctcactca     3960
ttaggcaccc caggctttac actttatgct tccggctcgt atgttgtgtg gaattgtgag     4020
cggataacaa tttcacacag gaaacagcta tgaccatgat tacgccaagc tttgctctta     4080
ggagtttcct aatacatccc aaactcaaat atataaagca tttgacttgt tctatgccct     4140 aggggggcggg gggaagctaa gccagctttt tttaacattt aaaatgttaa ttccatttta     4200
aatgcacaga tgttttttatt tcataagggt ttcaatgtgc atgaatgctg caatattcct     4260
gttaccaaag ctagtataaa taaaaataga taaacgtgga aattacttag agtttctgtc     4320
attaacgttt ccttcctcag ttgacaacat aaatgcgctg ctgagcaagc cagtttgcat     4380
ctgtcaggat caatttccca ttatgccagt catattaatt actagtcaat tagttgattt     4440
ttatttttga catatacatg tgaatgaaag accccacctg taggtttggc aagctagctt     4500
aagtaacgcc attttgcaag gcatggaaaa atacataact gagaatagaa aagttcagat     4560
caaggtcagg aacagatgga acagctgaat atgggccaaa caggatatct gtggtaagca     4620
gttcctgccc cggctcaggg ccaagaacag atggaacagc tgaatatggg ccaaacagga     4680
tatctgtggt aagcagttcc tgccccggct cagggccaag aacagatggt ccccagatgc     4740
```

```
ggtccagccc tcagcagttt ctagagaacc atcagatgtt tccagggtgc cccaaggacc    4800
tgaaatgacc ctgtgcctta tttgaactaa ccaatcagtt cgcttctcgc ttctgttcgc    4860
gcgcttatgc tccccgagct caataaaaga gcccacaacc cctcactcgg ggcgccagtc    4920
ctccgattga ctgagtcgcc cgggtacccg tgtatccaat aaaccctctt gcagttgcat    4980
ccgacttgtg gtctcgctgt tccttgggag ggtctcctct gagtgattga ctacccgtca    5040 gcggggtct ttcatttggg ggctcgtccg ggatcgggag accccctgccc agggaccacc    5100 gacccaccac cgggaggtaa gctggccagc aacttatctg tgtctgtccg attgtctagt    5160
gtctatgact gattttatgc gcctgcgtcg gtactagtta gctaactagc tctgtatctg    5220
gcggacccgt ggtggaactg acgagttcgg aacacccggc cgcaaccctg ggagacgtcc    5280
cagggacttc gggggccgtt tttgtggccc gacctgagtc ctaaaatccc gatcgtttag    5340
gactctttgg tgcacccccc ttagaggagg gatatgtggt tctggtagga gacgagaacc    5400
taaaacagtt cccgcctccg tctgaatttt tgctttcggt ttgggaccga gccgcgccg    5460 cgcgtcttgt ctgctgcagc atcgttctgt gttgtctctg tctgactgtg tttctgtatt    5520
tgtctgaaaa tatgggcccg ggctagactg ttaccactcc cttaagtttg accttaggtc    5580
actgaaagat gtcgagcgg atcgctcaca accagtcggg agatgtcaag aagagacgtt    5640
gggttacctt ctgctctgca gaatggccaa cctttaacgt cggatggccg cgagacggca    5700
cctttaaccg agacctcatc acccaggtta agatcaaggt cttttcacct ggcccgcatg    5760
gacacccaga ccaggtcccc tacatcgtga cctgggaagc cttggctttt gacccccctc    5820
cctgggtcaa gcccttttgta cacccctaagc ctccgcctcc tcttcctcca tccgcccgt    5880 ctctcccct tgaacctcct cgttcgaccc cgcctcgatc ctcccttttat ccagccctca    5940 ctccttctct aggcgccccc atatggccat atgagatctt atatgggca ccccgcccc    6000 ttgtaaactt ccctgaccct gacatgacaa gagttactaa cagccctct ctccaagctc    6060 acttacaggc tctctactta gtccagcacg aagtctggag acctctggcg gcagcctacc    6120
aagaacaact ggaccgaccg gtggtacctc accccttaccg agtcggcgac acagtgtggg    6180
tccgccgaca ccagactaag aacctagaac ctcgctggaa aggaccttac acagtcctgc    6240
tgaccacccc caccgccctc aaagtagacg gcatcgcagc ttggatacac gccgcccacg    6300
tgaaggctgc cgaccccggg ggtggaccat cctctagact gccatggctc tcccagtgac    6360
tgccctactg cttcccctag cgcttctcct gcatgcagag gtgaagctgc aggagtcagg    6420
gggaggcttc gtgaagcctg gagggtccct caaagtctcc tgtgcagcct ctggattcac    6480
tttcagtagc tatgccatgt cctgggttcg cctgagtccg gagatgaggc tggagtgggt    6540
cgcaaccatt agcagtgctg gtggttacat cttctattct gacagtgtgc agggacgatt    6600
caccatttcc agagacaatg ccaagaacac cctgcacctg caaatgggca gtctgaggtc    6660
tggggacacg gccatgtatt actgtgcaag gcagggattt ggtaactacg gtgattacta    6720
tgctatggac tactggggcc aagggaccac ggtcaccgtc tcctcaggtg aggtggatc    6780 aggtggaggt ggatctggtg gaggtggatc tgacattgag ctcacccagt ctccatcctc    6840
cctggctgtg tcagcaggag agaaggtcac tatgagctgc aaatccagtc agagtctgct    6900
caacagtaga acccgaaaga accagttggc ttggtaccag caaaaaccag acagtctcc    6960 tgaactgctg atctactggg catccactag gcaatctgga gtccctgatc gcttcacagg    7020
cagtggatct gggacagatt tcactctcac catcagcagt gtgcaggctg aagacctggc    7080
agtttattac tgccagcaat cttataatct actcacgttc ggtcctggga ccaagctgga    7140
```

```
gatcaaacgg gcggccgcaa ttgaagttat gtatcctcct ccttacctag acaatgagaa    7200
gagcaatgga accattatcc atgtgaaagg gaaacacctt tgtccaagtc ccctatttcc    7260
cggaccttct aagccctttt gggtgctggt ggtggttggt ggagtcctgg cttgctatag    7320
cttgctagta acagtggcct ttattatttt ctgggtgagg agtaagagga gcaggctcct    7380
gcacagtgac tacatgaaca tgactccccg ccgccccggg cccacccgca agcattacca    7440
gccctatgcc ccaccacgcg acttcgcagc ctatcgctcc agagtgaagt tcagcaggag    7500
cgcagagccc cccgcgtacc agcagggcca gaaccagctc tataacgagc tcaatctagg    7560
acgaagagag gagtacgatg tttttggaca gagacgtggc cgggaccctg agatgggggg    7620
aaagccgaga aggaagaacc ctcaggaagg cctgtacaat gaactgcaga aagataagat    7680
ggcggaggcc tacagtgaga ttgggatgaa aggcgagcgc cggaggggca aggggcacga    7740
tggcctttac cagggtctca gtacagccac caaggacacc tacgacgccc ttcacatgca    7800
ggccctgccc cctcgctaac agccactcga g                                    7831

<210> SEQ ID NO 40
<211> LENGTH: 7831
<212> TYPE: DNA
<213> ORGANISM: Artificial Sequence
<220> FEATURE:
<223> OTHER INFORMATION: SFG_4H11-28z reverse sequence

<400> SEQUENCE: 40
cctaggccta atcaggttaa acaatttctg tcctatagtc accaggtccg agatcaaaac      60
tgagttgtta tagtggtcga cttcggatat ctcatgctcg gtatctattt tattttctaa     120
aataaatcag aggtctttt ccccccttac tttctgggt ggacatccaa accgttcgat       180
cgaattcatt gcggtaaaac gttccgtacc tttttatgta ttgactctta tctcttcaag     240
tctagttcca gtccttgtct accttgtcga cttatacccg gtttgtccta tagacaccat     300
tcgtcaagga cggggccgag tcccggttct tgtctacctt gtcgacttat acccggtttg    360
tcctatagac accattcgtc aaggacgggg ccgagtcccg gttcttgtct accaggggtc    420
tacgccaggt cgggagtcgt caaagatctc ttggtagtct acaaaggtcc cacggggttc    480
ctggacttta ctgggacacg gaataaactt gattggttag tcaagcgaag agcgaagaca    540
agcgcgcgaa gacgagggc tcgagttatt ttctcgggtg ttggggagtg agccccgcgg    600
tcaggaggct aactgactca gcgggcccat gggcacatag gttatttggg agaacgtcaa    660
cgtaggctga acaccagagc gacaaggaac cctcccagag gagactcact aactgatggg    720
cagtcgcccc cagaaagtgt gtacgtcgta catagttta attaaccaa aaaaagaat      780 tcataaatgt aatttaccgg tatcatgaat ttcaatgtaa ccgaaggaac tttatttgta    840
cctcataagt cttacacagt atttataaag attaaaattc tatcatagag gtaaccgaaa    900
gatgaaaaag aaaataaaaa aaacaggag acagaaggta aacaacaaca acaacaaaca     960
aacaaacaaa caaccaacca accaattaaa aaaaatttc taggatgtga tatcaagttc   1020
gatctgataa tcgatgagac attgggtccc actggaactt cagtaccat cggacgacaa    1080 aatcggaagg gtgtagattc taatgtccat actcgatagt aaaaaccata taactaacta    1140
actaactaac tacacacaca cactaacaa caacacaca cactgacact tttacacaca    1200
tacccacaca cacttacaca catacataca cacacacact cacacacaca cacacacacg    1260
tacacacaca cacactgaca cagatacaca tactgacaca cacacacaca cacacacaca    1320
```

-continued

```
cacacacaca cacacacaca caacactttt ttataagata ccatcactct cggttgcgag    1380
gccgagtcca cagtccaacc aaaaactctg tctcagaaag tgaatcgaac cttaagtgac    1440
cggcagcaaa atgttgcagc actgacgcct ttgggaccgc aatgggttga attagcggaa    1500
cgtcgtgtag ggggaaagcg gtcgaccgca ttatcgcttc tccgggcgtg gctagcggga    1560
agggttgtca acgcgtcgga cttaccgctt accgcggact acgccataaa agaggaatgc    1620
gtagacacgc cataaagtgt ggcgtatacc acgtgagagt catgttagac gagactacgg    1680
cgtatcaatt cggtcggggc tgtgggcggt tgtgggcgac tgcgcgggac tgcccgaaca    1740
gacgagggcc gtaggcgaat gtctgttcga cactggcaga ggccctcgac gtacacagtc    1800
tccaaaagtg gcagtagtgg ctttgcgcgc tactgctttc ccggagcact atgcggataa    1860
aaatatccaa ttacagtact attattacca aagaatctgc agtccaccgt gaaaagcccc    1920
tttacacgcg ccttggggat aaacaaataa aaagatttat gtaagtttat acataggcga    1980
gtactctgtt attgggacta tttacgaagt tattataact ttttccttct catactcata    2040
agttgtaaag gcacagcggg aataagggaa aaaacgccgt aaaacggaag acaaaaacg    2100
agtgggtctt tgcgaccact ttcattttct acgacttcta gtcaacccac gtgctcaccc    2160
aatgtagctt gacctagagt tgtcgccatt ctaggaactc tcaaaagcgg ggcttcttgc    2220
aaaaggttac tactcgtgaa aatttcaaga cgatacaccg cgccataata gggcataact    2280
gcggcccgtt ctcgttgagc cagcggcgta tgtgataaga gtcttactga accaactcat    2340
gagtggtcag tgtcttttcg tagaatgcct accgtactgt cattctctta atacgtcacg    2400
acggtattgg tactcactat tgtgacgccg gttaatgaa gactgttgct agcctcctgg     2460
cttcctcgat tggcgaaaaa acgtgttgta ccccctagta cattgagcgg aactagcaac    2520
ccttggcctc gacttacttc ggtatggttt gctgctcgca ctgtggtgct acggacatcg    2580
ttaccgttgt tgcaacgcgt ttgataattg accgcttgat gaatgagatc gaagggccgt    2640
tgttaattat ctgacctacc tccgccgatt tcaacgtcct ggtgaagacg cgagccggga    2700
aggccgaccg accaaataac gactatttag acctcggcca ctcgcaccca gagcgccata    2760
gtaacgtcgt gaccccggtc taccattcgg gagggcatag catcaataga tgtgctgccc    2820
ctcagtccgt tgatacctac ttgctttatc tgtctagcga ctctatccac ggagtgacta    2880
attcgtaacc attgacagtc tggttcaaat gagtatatat gaaatctaac taaattttga    2940
agtaaaaatt aaattttcct agatccactt ctaggaaaaa ctattagagt actggttta    3000
gggaattgca ctcaaaagca aggtgactcg cagtctgggg catcttttct agtttcctag    3060
aagaactcta ggaaaaaaag acgcgcatta gacgacgaac gtttgttttt ttggtggcga    3120
tggtcgccac caaacaaacg gcctagttct cgatggttga gaaaaaggct tccattgacc    3180
gaagtcgtct cgcgtctatg gtttatgaca ggaagatcac atcggcatca atccggtggt    3240
gaagttcttg agacatcgtg gcggatgtat ggagcgagac gattaggaca atggtcaccg    3300
acgacggtca ccgctattca gcacagaatg gcccaacctg agttctgcta tcaatggcct    3360
attccgcgtc gccagcccga cttgcccccc aagcacgtgt gtcgggtcga acctcgcttg    3420
ctggatgtgg cttgactcta tggatgtcgc actcgtaact ctttcgcggt gcgaagggct    3480
tccctctttc cgcctgtcca taggccattc gccgtcccag ccttgtcctc tcgcgtgctc    3540
cctcgaaggt cccccttgc ggaccataga aatatcagga cagcccaaag cggtggagac    3600
tgaactcgca gctaaaaaca ctacgagcag tcccccgcc tcggatacct ttttgcggtc    3660
gttgcgccgg aaaaatgcca aggaccggaa aacgaccgga aaacgagtgt acaagaaagg    3720
```

```
acgcaataqg ggactaagac acctattggc ataatggcgg aaactcactc gactatggcg    3780
agcggcgtcg gcttgctggc tcgcgtcgct cagtcactcg ctccttcgcc ttctcgcggg    3840
ttatgcgttt ggcggagagg ggcgcgcaac cggctaagta attacgtcga ccgtgctgtc    3900
caaagggctg acctttcgcc cgtcactcgc gttgcgttaa ttacactcaa tcgagtgagt    3960
aatccgtggg gtccgaaatg tgaaatacga aggccgagca tacaacacac cttaacactc    4020
gcctattgtt aaagtgtgtc ctttgtcgat actggtacta atgcggttcg aaacgagaat    4080
cctcaaagga ttatgtaggg tttgagttta tatatttcgt aaactgaaca agatacggga    4140
tcccccgccc cccttcgatt cggtcgaaaa aaattgtaaa ttttacaatt aaggtaaaat    4200
ttacgtgtct acaaaaataa agtattccca aagttacacg tacttacgac gttataagga    4260
caatggtttc gatcatattt atttttatct atttgcacct ttaatgaatc tcaaagacag    4320
taattgcaaa ggaaggagtc aactgttgta tttacgcgac gactcgttcg gtcaaacgta    4380
gacagtccta gttaaagggt aatacggtca gtataattaa tgatcagtta atcaactaaa    4440
aataaaaact gtatatgtac acttactttc tggggtggac atccaaaccg ttcgatcgaa    4500
ttcattgcgg taaaacgttc cgtaccttt tatgtattga ctcttatctt ttcaagtcta    4560
gttccagtcc ttgtctacct tgtcgactta tacccggttt gtcctataga caccattcgt    4620
caaggacggg gccgagtccc ggttcttgtc taccttgtcg acttataccc ggtttgtcct    4680
atagacacca ttcgtcaagg acggggccga gtccggttc ttgtctacca ggggtctacg    4740
ccaggtcgag agtcgtcaaa gatctcttgg tagtctacaa aggtcccacg gggttcctgg    4800
actttactgg gacacggaat aaacttgatt ggttagtcaa gcgaagagcg aagacaagcg    4860
cgcgaatacg aggggctcga gttatttct cgggtgttgg ggagtgagcc ccgcggtcag    4920
gaggctaact gactcagcgg gcccatgggc acataggtta tttgggagaa cgtcaacgta    4980
ggctgaacac cagagcgaca aggaaccctc ccagaggaga ctcactaact gatgggcagt    5040
cgcccccaga aagtaaaccc ccgagcaggc cctagccctc tggggacggg tccctggtgg    5100
ctgggtggtg gccctccatt cgaccggtcg ttgaatagac acagacaggc taacagatca    5160
cagatactga ctaaaatacg cggacgcagc catgatcaat cgattgatcg agacatagac    5220
cgcctgggca ccaccttgac tgctcaagcc ttgtgggccg gcgttgggac cctctgcagg    5280
gtccctgaag cccccggcaa aaacaccggg ctggactcag gattttaggg ctagcaaatc    5340
ctgagaaacc acgtgggggg aatctcctcc ctatacacca agaccatcct ctgctcttgg    5400
attttgtcaa gggcggaggc agacttaaaa acgaaagcca aaccctggct tcggcgcggc    5460
gcgcagaaca gacgacgtcg tagcaagaca caacagagac agactgacac aaagacataa    5520
acagactttt ataccccggc ccgatctgac aatggtgagg gaattcaaac tggaatccag    5580
tgacctttct acagctcgcc tagcgagtgt tggtcagcca tctacagttc ttctctgcaa    5640
cccaatggaa gacgagacgt cttaccggtt ggaaattgca gcctaccggc gctctgccgt    5700
ggaaattggc tctggagtag tgggtccaat tctagttcca gaaaagtgga ccgggcgtac    5760
ctgtgggtct ggtccagggg atgtagcact ggacccttcg gaaccgaaaa ctggggggag    5820
ggacccagtt cgggaaacat gtgggattcg gaggcggagg agaaggaggt aggcggggca    5880
gagaggggga acttggagga gcaagctggg gcggagctag gagggaaata ggtcgggagt    5940
gaggaagaga tccgcggggg tataccggta tactctagaa tataccccgt ggggcgggg    6000 aacatttgaa gggactggga ctgtactgtt ctcaatgatt gtcggggaga gaggttcgag    6060
```

-continued

```
tgaatgtccg agagatgaat caggtcgtgc ttcagacctc tggagaccgc cgtcggatgg    6120
ttcttgttga cctggctggc caccatggag tgggaatggc tcagccgctg tgtcacaccc    6180
aggcggctgt ggtctgattc ttggatcttg gagcgacctt tcctggaatg tgtcaggacg    6240
actggtgggg gtggcgggag tttcatctgc cgtagcgtcg aacctatgtg cggcgggtgc    6300
acttccgacg gctggggccc ccacctggta ggagatctga cggtaccgag agggtcactg    6360
acggatgac gaaggggatc gcgaagagga cgtacgtctc cacttcgacg tcctcagtcc     6420
ccctccgaag cacttcggac ctcccaggga gtttcagagg acacgtcgga gacctaagtg    6480
aaagtcatcg atacggtaca ggacccaagc ggactcaggc ctctactccg acctcaccca    6540
gcgttggtaa tcgtcacgac caccaatgta gaagataaga ctgtcacacg tccctgctaa    6600
gtggtaaagg tctctgttac ggttcttgtg ggacgtggac gtttacccgt cagactccag    6660
acccctgtgc cggtacataa tgacacgttc cgtccctaaa ccattgatgc cactaatgat    6720
acgatacctg atgaccccgg ttccctggtg ccagtggcag aggagtccac ctccacctag    6780
tccacctcca cctagaccac ctccacctag actgtaactc gagtgggtca gaggtaggag    6840
ggaccgacac agtcgtcctc tcttccagtg atactcgacg tttaggtcag tctcagacga    6900
gttgtcatct tgggctttct tggtcaaccg aaccatggtc gttttggtc ctgtcagagg     6960
acttgacgac tagatgaccc gtaggtgatc cgttagacct cagggactag cgaagtgtcc    7020
gtcacctaga ccctgtctaa agtgagagtg gtagtcgtca cacgtccgac ttctggaccg    7080
tcaaataatg acggtcgtta gaatattaga tgagtgcaag ccaggaccct ggttcgacct    7140
ctagtttgcc cgccggcgtt aacttcaata cataggagga ggaatggatc tgttactctt    7200
ctcgttacct tggtaatagg tacactttcc ctttgtggaa acaggttcag gggataaagg    7260
gcctggaaga ttcgggaaaa cccacgacca ccaccaacca cctcaggacc gaacgatatc    7320
gaacgatcat tgtcaccgga ataataaaa gacccactcc tcattctcct cgtccgagga    7380
cgtgtcactg atgtacttgt actgaggggc ggcggggccc gggtgggcgt tcgtaatggt    7440
cgggatacgg ggtggtgcgc tgaagcgtcg gatagcgagg tctcacttca agtcgtcctc    7500
gcgtctcggg gggcgcatgg tcgtcccggt cttggtcgag atattgctcg agttagatcc    7560
tgcttctctc ctcatgctac aaaacctgtt tctgcaccg gccctgggac tctacccccc     7620
tttcggctct tccttcttgg gagtccttcc ggacatgtta cttgacgtct ttctattcta    7680
ccgcctccgg atgtcactct aaccctactt tccgctcgcg gcctcccgt tccccgtgct     7740
accggaaatg gtcccagagt catgtcggtg gttcctgtgg atgctgcggg aagtgtacgt    7800
ccgggacggg ggagcgattg tcggtgagct c                                   7831
```